(12) United States Patent
Weisskoff et al.

(10) Patent No.: US 7,412,279 B2
(45) Date of Patent: Aug. 12, 2008

(54) SYSTEMS AND METHODS FOR TARGETED MAGNETIC RESONANCE IMAGING OF THE VASCULAR SYSTEM

(75) Inventors: Robert M. Weisskoff, Lexington, MA (US); Peter D. Caravan, Cambridge, MA (US); Sonia Witte, Roslindale, MA (US); Randall B. Lauffer, Brookline, MA (US); Alan P. Carpenter, Jr., Carlisle, MA (US)

(73) Assignee: Epix Pharmaceuticals, Inc., Lexington, MA (US)

( * ) Notice: Subject to any disclaimer, the term of this patent is extended or adjusted under 35 U.S.C. 154(b) by 884 days.

(21) Appl. No.: 10/209,416

(22) Filed: Jul. 30, 2002

(65) Prior Publication Data

US 2003/0028101 A1    Feb. 6, 2003

Related U.S. Application Data

(60) Provisional application No. 60/308,690, filed on Jul. 30, 2001.

(51) Int. Cl.
*A61B 5/05* (2006.01)
(52) U.S. Cl. .................. 600/420; 424/9.3; 600/431; 600/419; 600/410
(58) Field of Classification Search .......... 600/420, 600/410, 411, 424, 419, 431; 424/9.3
See application file for complete search history.

(56) References Cited

U.S. PATENT DOCUMENTS

| | | | |
|---|---|---|---|
| 4,777,957 A | 10/1988 | Wehrli et al. | |
| 4,880,008 A | 11/1989 | Lauffer | |
| 5,128,121 A | * 7/1992 | Berg et al. | 424/9.32 |
| 5,155,215 A | * 10/1992 | Ranney | 534/16 |
| 5,364,614 A | 11/1994 | Platzek et al. | |

(Continued)

FOREIGN PATENT DOCUMENTS

NZ    28 44 13    8/1998

(Continued)

OTHER PUBLICATIONS

Wiessleder et al., American Journal of Roentgenology, vol. 150, p. 561-566, 1998.*

(Continued)

*Primary Examiner*—Brian L. Casler
*Assistant Examiner*—Jacqueline Cheng
(74) *Attorney, Agent, or Firm*—Fish & Richardson P.C.

(57) ABSTRACT

This invention relates to MRI-based methods and systems useful for diagnosing and clinically assessing the presence, location, and size of cardiovascular disease-associated stationary targets, e.g., thrombi and atherosclerotic lesions, within the vascular system. Methods and systems of the invention allow for improved anatomical information to be obtained from MRI images and allow the clinician to develop more effective treatment plans. In one aspect, the invention provides a method of determining the presence or absence of a stationary target within the vascular system of a mammal wherein two MRI data sets representing images of the vascular system and the stationary target are acquired after administration of a targeted MRI contrast agent. In another embodiment, both a targeted MRI contrast agent and a vascular MRI contrast agent are administered to a mammal, and both a vascular MRI and a targeted MRI data set are acquired.

71 Claims, 7 Drawing Sheets

U.S. PATENT DOCUMENTS

| | | | |
|---|---|---|---|
| 5,368,033 A | 11/1994 | Moshfeghi | |
| 5,401,493 A | 3/1995 | Lohrmann et al. | |
| 5,417,213 A | 5/1995 | Prince | |
| 5,466,438 A | 11/1995 | Unger et al. | |
| 5,522,390 A * | 6/1996 | Tuithof et al. | 600/410 |
| 5,573,752 A | 11/1996 | Ranganathan et al. | |
| 5,579,767 A | 12/1996 | Prince | |
| 5,637,759 A | 6/1997 | Hearst et al. | |
| 5,649,537 A | 7/1997 | Anelli et al. | |
| 5,650,133 A | 7/1997 | Carvalho et al. | |
| 5,650,136 A | 7/1997 | Platzek et al. | |
| 5,681,543 A | 10/1997 | Schmitt-Willich et al. | |
| 5,695,739 A | 12/1997 | Schmitt-Willich et al. | |
| 5,733,528 A | 3/1998 | Felder et al. | |
| 5,759,518 A | 6/1998 | Schmitt-Willich et al. | |
| 5,798,092 A | 8/1998 | Schmitt-Willich et al. | |
| 5,820,849 A | 10/1998 | Schmitt-Willich et al. | |
| 5,869,023 A * | 2/1999 | Ericcson et al. | 424/9.36 |
| 5,876,698 A | 3/1999 | Schmitt-Willich et al. | |
| 5,888,576 A | 3/1999 | Nagano | |
| 5,914,095 A | 6/1999 | Watson | |
| 5,977,064 A | 11/1999 | Dean et al. | |
| 6,061,587 A | 5/2000 | Kucharczyk et al. | |
| 6,073,042 A * | 6/2000 | Simonetti | 600/420 |
| 6,112,112 A * | 8/2000 | Gilhuijs et al. | 600/425 |
| 6,219,572 B1 | 4/2001 | Young | |
| 6,248,306 B1 | 6/2001 | Schmitt-Willich et al. | |
| 6,342,598 B1 | 1/2002 | Anelli et al. | |
| 6,372,194 B1 | 4/2002 | Akaike et al. | |
| 6,459,264 B1 | 10/2002 | Fain et al. | |
| 6,638,508 B2 | 10/2003 | Schechter et al. | |
| 6,652,834 B2 | 11/2003 | Anelli et al. | |
| 6,972,122 B2 | 12/2005 | Haroon et al. | |
| 2002/0009416 A1* | 1/2002 | Schechter et al. | 424/9.1 |
| 2002/0065467 A1* | 5/2002 | Schutt | 600/454 |
| 2002/0113589 A1* | 8/2002 | Fain et al. | 324/307 |
| 2002/0136692 A1* | 9/2002 | Haroon et al. | 424/9.34 |
| 2004/0204561 A1 | 10/2004 | Ellison | |
| 2005/0261472 A1* | 11/2005 | Wescott et al. | 530/328 |

FOREIGN PATENT DOCUMENTS

| | | |
|---|---|---|
| NZ | 29 68 23 | 10/1999 |
| WO | WO 88/01178 | 2/1988 |
| WO | WO 88/01179 | 2/1988 |
| WO | WO 88/01180 | 2/1988 |
| WO | WO 91/05762 | 5/1991 |
| WO | WO 93/06868 | 5/1993 |
| WO | WO 95/02831 | 1/1995 |
| WO | WO 95/07270 | 3/1995 |
| WO | WO 95/09848 | 4/1995 |
| WO | WO 95/17451 | 6/1995 |
| WO | WO 96/22321 | 7/1995 |
| WO | WO 95/25761 | 9/1995 |
| WO | WO 95/28179 | 10/1995 |
| WO | WO 95/28966 | 11/1995 |
| WO | WO 95/32741 | 12/1995 |
| WO | WO 96/01655 | 1/1996 |
| WO | WO 96/09840 | 4/1996 |
| WO | WO 96/23526 | 8/1996 |
| WO | WO 96/35456 | 11/1996 |
| WO | WO 96/41830 | 12/1996 |
| WO | WO 97/02051 | 1/1997 |
| WO | WO 97/06833 | 2/1997 |
| WO | WO 97/10281 | 3/1997 |
| WO | WO 97/25073 | 7/1997 |
| WO | WO 97/32862 | 9/1997 |
| WO | WO 97/36619 | 10/1997 |
| WO | WO 97/41856 | 11/1997 |
| WO | WO 98/05625 | 2/1998 |
| WO | WO 98/05626 | 2/1998 |
| WO | WO 98/38738 | 9/1998 |
| WO | WO 98/41241 | 12/1998 |
| WO | WO 99/02193 | 1/1999 |
| WO | WO 99/17809 | 4/1999 |
| WO | WO 99/25389 | 6/1999 |
| WO | WO 99/64595 | 12/1999 |
| WO | WO 00/09170 | 2/2000 |
| WO | WO 00/30688 | 6/2000 |
| WO | WO 00/34231 | 6/2000 |
| WO | WO 00/34296 | 6/2000 |
| WO | WO 01/08712 | 2/2001 |
| WO | WO 01/09188 | 2/2001 |
| WO | WO02/062220 | 8/2002 |

OTHER PUBLICATIONS

U.S. Appl. No. 10/209,183, filed Sep. 25, 2003, Zhang et al.

Caravan et al., "Gadolinium(III) Chelates as MRI Contrast Agents: Structure, Dynamics, and Applications," *Chem. Rev.*, 1999, 99:2293-2352.

Johansson et al., "A Targeted Contrast Agent for Magnetic Resonance Imaging of Thrombus: Implications of Spatial Resolution," *J. Mag. Res. Imaging*, 2001, 13:615-618.

Kornguth et al., "Magnetic resonance imaging of gadolinium-labeled monoclonal antibody polymers directed at human T lymphocytes implanted in canine brain," *J. Neurosurg.*, 1987, 66:898-906.

Kroft and Roos, "Blood Pool Contrast Agents for Cardiovascular MR Imaging," *J. Mag. Res. Imaging*, 1999, 10:395-403.

Lanza et al., "Enhanced Detection of Thrombi with a Novel Fibrin-targeted Magnetic Resonance Imaging Agent," *Acad. Radiol.*, 1998, 5(Suppl. 1):S173-S176.

Moore et al., "Uptake of Dextran-Coated Monocrystalline Iron Oxides in Tumor Cells and Macrophages," *JMRI*, 1997, 7:1140-1145.

Mühler, "The Future of Contrast-Enhanced Magnetic Resonance Angiography," *Invest. Radiol.*, 1998, 33(9):709-714.

Ruehm et al., "Magnetic Resonance Imaging of Atherosclerotic Plaque With Ultrasmall Superparamagnetic Particles of Iron Oxide in Hyperlipidemic Rabbits," *Circulation*, 2001, 103:415-422.

Schmitz et al., "Superparamagnetic Iron Oxide-Enhanced MRI of Atherosclerotic Plaques in Watanabe Hereditable Hyperlipidemic Rabbits," *Invest. Radiol.*, 2000, 35(8):460-471.

Sipkins et al., "Detection of tumor angiogenesis in vivo by $\alpha_v\beta_3$-targeted magnetic resonance imaging," *Nature Medicine*, 1998, 4(5):623-626.

Sipkins et al., "ICAM-1 expression in autoimmune encephalitis visualized using magnetic resonance imaging," *J. Neuroimmunol.*, 2000, 104:1-9.

Weissleder et al., "Polyclonal Human Immunoglobulin G Labeled with Polymeric Iron Oxide: Antibody MR Imaging," *Radiology*, 1991, 181:245-249.

Woods et al., "Rapid Automated Algorithm for Aligning and Reslicing PET Images," *J. Computer Assisted Tomography*, 1992, 16(4):620-633.

Yu et al., "High-Resolution MRI Characterization of Human Thrombus Using a Novel Fibrin-Targeted Paramagnetic Nanoparticle Contrast Agent," *Magnetic Resonance in Medicine*, 2000, 44:867-872.

Aime et al., "Synthesis, Characterization and $1/T_1$ NMRD Profiles of Gadolinium (III) Complexes of Monoamide Derivatives of DOTA-like Ligands. X-ray Structure of the 10-[-2-[[2-Hydroxy-1-(hydroxymethyl)ethyl]-1-[(phenylmethoxy)methyl]-2-oxo-ethyl]-1,4,7,10-tetraazacyclododecane-1,4,7,10-triacetic Acid-Gadolinium(III) Complex," *Inorg. Chem.*, 1992, 31:2422-2428.

Aime et al., "Multinuclear and multifrequency NMR study of gadolinium(III) complexes with bis-amide derivatives of ethylenedioxydiethylene-dinitrilotetraacetic acid," *J. Chem. Soc.*, 2000, 19:3435-3440.

Alexander et al., "Intracranial Black-Blood MR Angiography with High-Resolution 3D Fast Spin Echo," *MRM*, 1998, 40:298-310.

Amedio et al., "A Practical Manufacturing Synthesis of 1-(R)-Hydroxymethyl-DPTA: An Important Intermediate in the Synthesis of MRI Contrast Agents," *Synthetic Communications*, 1999, 29(14):2377-2391.

Amedio et al., "Preparation fo N,N-BIS[2-[N',N'-BIS[(Tert-Butoxycarbonyl)Methyl]-Amino]Ethyl-L-Aspartic Acid: An Intermediate in the Synthesis of MRI Contrast Agents," *Synthetic Communications*, 2000, 30(20):3755-3763.

Augustijns et al., "Peptidyl Dipeptidase A-Catalyzed Metabolism of Delta Sleep-Inducing Peptide in Bovine Brain Microvessel Endothelial Cells: A Cell Culture Model of the Blood Brain Barrier," *Biochem. Biophys. Res. Comm.*, 1995, 210:987-994.

Bard et al., "BisMSH-DTPA: A Potential Imaging Agent for Malignant Melanoma," *Ann. NY Acad. Sci.*, 1993, 680:451-453.

Bligh et al., "Neutral Gadolinium(III) Complexes of Bulky Octadentate dtpa Derivatives as Potential Contrast Agents for Magnetic Resonance Imaging," *Polyhedron*, 1994, 14: 567-569.

Brasch, "Rationale and Applications for Macromolecular Gd-Based Contrast Agents," *Magnetic Resonance in Medicine*, 1991, 22:282-287.

Clackson et al., "Redesigning an FKBP-ligand interface to generate chemical dimerizers with novel specificity," *Proc. Natl. Acad. Sci. USA*, 1998, 95:10437-10442.

Deacon et al., "Degradation of Glucagon-Like Peptide-1 by Human Plasma in Vitro Yields an N-Terminally Truncated Peptide that is a Major Endogenous Metabolite in Vivo," *J. Clin. Endocrin. Metab.*, 1995, 80:952-957.

Edelman et al., "Extracranial Carotid Arteries: Evaluation with "Black Blood" MR Angiography," *Radiology*, 1990, 177:45-50.

Huber et al., "Fluorescently Detectable Magnetic Resonance Imaging Agents," *Bioconjugate Chem.*, 1998, 9:242-249.

Kolc, Amino Acids and Peptides. LXXXIX. Synthesis of L-4-Azalysine, D-4-Azalysine, and L-4-Azalysine-[6-$^{14}$C,], *Collection Czechoslov. Chem. Commun.*, 1969, 34:630-634.

Konings et al., "Gadolinium Complexation by a New DPTA-Amide Ligand. Amide Oxygen Coordination," *Inorg. Chem.*, 1990, 29:1488-1491.

Kramer et al., "Spanning binding sites on allosteric proteins with polymer-linked ligand dimers," *Nature*, 395:710-713, no date.

Krieter et al., "In Vivo Metabolism of Atrial Natriuretic Peptide: Identification of Plasma Metabolites and Enzymes Responsible for Their Generation," *J. Pharmacol. Exp. Thera.*, 1989, 249:411-417.

Lauffer, "Paramagnetic Metal Complexes as Water Proton Relaxation Agents for NMR Imaging: Theory and Design," *Chem. Rev.* 1987, 87:901-927.

Lee et al., "Multivalent Ligand Binding by Serum Mannose-Binding Protein," *Arch. Biochem. Biophys.*, 1992, 299:129-136.

Liu et al., "Tc-Labeled Small Peptides as Diagnostic Radiopharmaceuticals," *Chem. Rev.*, 1999, 99:2235-2268.

Mann et al., "Probing Low Affinity and Multivalent Interactions with Surface Plasmon Resonance: Ligands for Concanavalin A," *J. Am. Chem. Soc.*, 1998, 120:10575-10582.

Martin et al., "Gadolinium (III) di- and tetrachelates designed for in vivo noncovalent complexation with plasma proteins: A novel molecular design for blood pool MRI contrast enhancing agents," *Biochem. Conj.*, 1995, 6: 616-623.

Melhem et al., "Black Blood MR angiography using multislab three dimensional T1-weighted turbo spin-echo," *AJR*, 1997: 169.

Moats et al., "A 'Smart' Magnetic Resonance Imaging Agent That Reports on Specific Enzymatic Activity," *Angew. Chem. Int. Ed. Engl.*, 1997, 36:726-728.

Muller et al., "Metabolism of Dynorphin A 1-13 in Human Blood and Plasma," *Pharmaceutical Res.*, 1995, 12:1165-1170.

Muller et al., "Assessment of Complex Peptide Degradation Pathways via Structured Multicompartmental Modeling Approaches: The Metabolism of Dynorphin A1-13 and Related Fragments in Human Plasma," *J. Pharmaceut. Sci.*, 1999, 88:938-944.

Muller et al., "Physicochemical Characterization of MS-325, a New Gadolinium Complex, by Multinuclear Rexaxometry," *Eur. J. Inorg. Chem.*, 1999, 1999:1949-1955.

Muller et al., "Interspecies comparison of in vitro plasma degradation of dynorphin A 1-13," *Pharmazie*, 1996, 51:581-585.

Murphey et al., "Metabolism of Bradykinin In Vivo in Humans: Identification of BK1-5 as a Stable Plasma Peptide Metabolite," *J. Pharmacol. Exp. Thera.*, 2000, 29:263-269.

Peltier et al., "Radioimmunodetection of Medullary Thyroid Cancer Using a Bispecific Anti-CEA/Anti-Indium-DTPA Antibody and an Indium-111-Labeled DTPA Dimer," *J. Nucl. Med.*, 1993, 34:1267-1273.

Powell et al., "Structural and Dynamic Parameters Obtained from $^{17}O$ NMR, EPR, and NMRD Studies of Monomeric and Dimeric $Gd^{3+}$ Complexes of Interest in Magnetic Resonance Imaging: An Integrated and Theoretically Self-Consistent Approach," *J. Am. Chem. Soc.*, 1996, 118:9333-9346.

Powell et al., "Peptide Stability in Drug Development. II. Effect of Single Amino Acid Substitution and Glycosylation on Peptide Reactivity in Human Serum," *Pharmaceutical Research*, 1993, 10(9):1268-1273.

Powell, "Peptide Stability in Drug Development: In Vitro Peptide Degradation in Plasma and Serum," *Annual Reports in Medicinal Chemistry*, 1993, 28:285-294.

Ranganathan et al., "New Multimeric Magnetic Resonance Imaging Agents," *Investigative Radiology*, 1998, 33(11):779-797.

Rao et al., "A Trivalent System from Vancomycin D-Ala-D-Ala with Higher Affinity Than Avidin-Biotin," *Science*, 1998, 280:708-711.

Shukla et al., "Alteration of Electronic Relaxation In MR Contrast Agents Through De-Novo Ligand Design," *Acta Radiologica*, 1998, 38 Suppl. 412:121-123.

Shukla et al., "Design of Conformationally Rigid Dimeric MRI Agents," *Mag. Reson. Med.*, 1996, 35:928-931.

Spevak et al., "Carbohydrates in an Acidic Multivalent Assembly: Nanomolar P-Selectin Inhibitors," *J. Med. Chem.*, 1996, 39:1018-1020.

Swanson et al., "Laminin Peptide Fragments for Malignant Tumor Detection," *J. Nucl. Med.*, 1993, 34(5 suppl.):231P.

Toth et al., "Tuning water-exchange rates on (carboxymethyl)iminobis-ethylenenitrilo)tetraacetate (dtpa)-type gadolinium (III) complexes," *J. Chem. Soc.*, 1997, 9:1587-1594.

Villringer et al., "Dynamic Imaging with Lanthanide Chelates in Normal Brain: Contrast Due to Magnetic Susceptibility Effects," *Magnetic Resonance in Medicine*, 1988, 6:164-174.

Wettergren et al., "Amidated and non-amidated glucagon-like peptide-1 (GLP-1): non-pancreatic effects (cephalic phase acid secretion) and stability in plasma in humans," *Regulatory Peptides*, 1988, 77:83-87.

Wolff et al., "Magnetization transfer imaging: practical aspects and clinical applications," *Radiology*, 1994, 192: 593-599.

Zhao et al., "Oxidation of Primary Alcohols to Carboxylic Acids with Sodium Chlorite Catalyzed by TEMPO and Bleach," *J. Org. Chem.*, 1999, 64:2564-2566.

\* cited by examiner

SYSTEMS AND METHODS FOR TARGETED MAGNETIC RESONANCE IMAGING OF THE VASCULAR SYSTEM

RELATED APPLICATION DATA

This application claims priority under 35 U.S.C. §119(e)(1) to U.S. Provisional Application Ser. No. 60/308,690, entitled "Systems and Methods for Targeted Magnetic Resonance Imaging of the Vasculature," filed Jul. 30, 2001.

TECHNICAL FIELD

This invention relates to magnetic resonance imaging of the vascular system and of cardiovascular disease states, and more particularly to systems and methods for improved detection, localization, and clinical assessment of a stationary target, such as a thrombus or atherosclerotic lesion, in the vascular system.

BACKGROUND

Cardiovascular diseases (CVDs), such as high blood pressure, heart attack, stroke, angina pectoris, atherosclerosis, and arteriosclerosis, affect millions of people and are a leading cause of death in the world today. CVDs mainly consist of a progressive narrowing of the arteries that nourish an organ or tissue, e.g., the heart. The narrowing is caused by an excessive buildup of fatty plaque along artery walls. The plaque buildup can lead to aneurism and thrombi, i.e., blood clots, and thrombi in turn can result in thrombosis, heart attack, and stroke.

The key to CVD therapy is early detection and diagnosis so that the proper treatment can be initiated. Accurately identifying the presence, location, and size of a CVD, such as a thrombus or atherosclerotic lesion, within the vascular system is diagnostically significant to establish a proper course of treatment, the need for surgical intervention, and the site of surgery or therapy.

Effective detection and diagnosis of plaque build-up, aneurism, thrombus, and other injuries or disease processes often require the use of imaging techniques to visualize the patient's vascular system. Such imaging techniques include x-ray angiography, computed tomography (CT) and spiral CT angiography, and magnetic resonance imaging (MRI). The use of magnetic resonance angiography (MRA) to diagnose CVDs has become increasingly popular because it is generally perceived to be cost-effective, convenient, and safe. MRA is a non-invasive MRI technique that uses short magnetic pulses to provide three-dimensional ("3D") images of the arteries and blood vessels that supply blood to the heart and other vital organs.

Contrast agents may be administered during an MRA exam to improve the visualization of the vascular system. A contrast agent is a substance that, when administered to a subject, increases the image contrast (e.g., provides contrast enhancement) between a chosen target, tissue, or organ and the rest of the field of the image (e.g., the remaining areas of the body). "Vascular" contrast agents can improve the visualization of the vascular system by altering the contrast of the vascular system relative to the surrounding tissues, usually by brightening (hyper-intensifying) the vascular system (e.g., the blood).

Injecting a vascular contrast agent into a patient's blood stream provides contrast enhancement to the vascular system image and may allow clinicians to visualize and measure the diameter of blood vessels, including those that are very small. Accurately defining vessel size and diameter is important to CVD diagnosis because the diameter of the vessels indicates the presence of stenoses, characterized by a narrowing of the blood vessels, and aneurisms, characterized by a widening of the vessels. Other types of CVDs may also be indirectly detected through use of a vascular contrast agent during an MRI exam. For example, thrombi and atherosclerotic lesions may be indirectly detected as these displace blood, causing the blood vessels to appear blocked or narrowed in contrast-enhanced images.

Despite the use of vascular contrast agents, the diagnosis of CVDs in the vascular system remains difficult. For example, the physician must seek out dark areas (e.g., areas of negative contrast) of the vascular image, within the bright (e.g., enhanced) vascular system. In addition, the use of vascular contrast agents typically does not allow a physician to distinguish between a vessel that contains a thrombus within the vessel interior and some other type of blockage (e.g., a blockage within the vessel wall).

Another class of contrast agents, referred to herein as "targeted" contrast agents, can function by binding to a particular target that may be present within the vascular system. For example, the targeted agent may bind to a CVD target, e.g., a thrombus, present within a blood vessel. Thus, the targeted agent may enhance the contrast between the target and background tissue and blood by, for example, hyper-intensifying the target relative to background tissue and blood. The use of such targeted agents, however, does not indicate whether the contrast-enhanced target is indeed within a blood vessel, nor does it identify the location or size of the target within the vascular system itself. Thus, a targeted image often lacks important anatomic information required for effective diagnosis and therapy of CVDs.

It would be useful for the clinician to be able to identify accurately the presence, location, and size of CVD targets within the vascular system using a method that is cost-efficient, safe, and convenient. It would be further useful for the clinician to have methods to distinguish a chosen target (e.g., a CVD) and the vascular system one from the other and also from the remaining background tissues in the field of view.

SUMMARY

This invention relates to MRI-based methods and systems useful for diagnosing and clinically assessing the presence, location, and size of CVDs, e.g., thrombi and atherosclerotic lesions, within the vascular system. The use of the methods and systems of the present invention allows for improved anatomical information concerning CVDs to be obtained from vascular and targeted MRI images and allows greater flexibility in such studies, facilitating proper patient management.

Accordingly, it is one aspect of the invention to provide a method of determining the presence or absence of a stationary target within a vascular system of a mammal. The stationary target within the vascular system can be, for example, a tissue, a biological structure, a cell, a cell surface, and a biopolymer. Examples of biological structures include CVDs, such as a thrombus, an atherosclerotic plaque, an atherosclerotic lesion, a tumor, and a thromboembolism. Alternatively, the stationary target can be a biopolymer. Examples of biopolymers include lipids, lipoproteins, proteins, polypeptides, and polysaccharides. If the biopolymer is a protein, it can be a protein typically present at higher concentrations in CVDs, including, for example, fibrin and collagen.

According to one embodiment of the method, a targeted MRI contrast agent is administered to a mammal. The targeted MRI contrast agent has a specific affinity for the stationary target, and the targeted MRI contrast agent also is capable of providing contrast enhancement of both the stationary target and the vascular system of the mammal.

In one embodiment, the targeted MRI contrast agent's specific affinity for the stationary target, expressed as a dissociation constant, is less than 50 μM. Alternatively, the targeted MRI contrast agent's specific affinity for the stationary target, expressed as a dissociation constant, is less than 5 μM, or less than 0.5 μM.

In principle, any contrast agent that exhibits specific affinity for a stationary target may be employed in the methods of the present invention. Some structures of targeted MRI contrast agents for use in the present invention include:

Structure I:

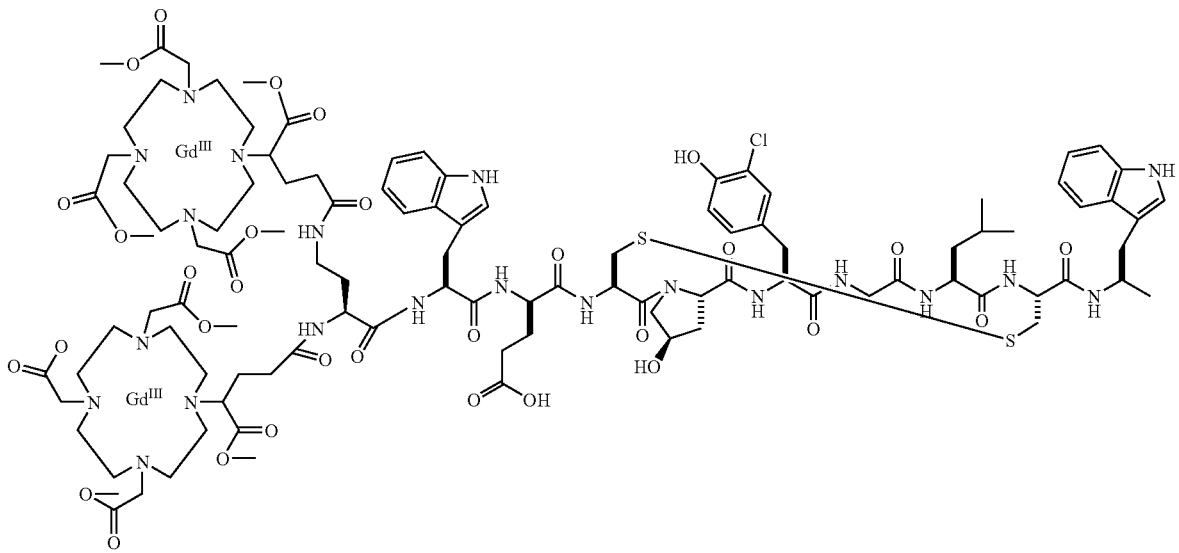

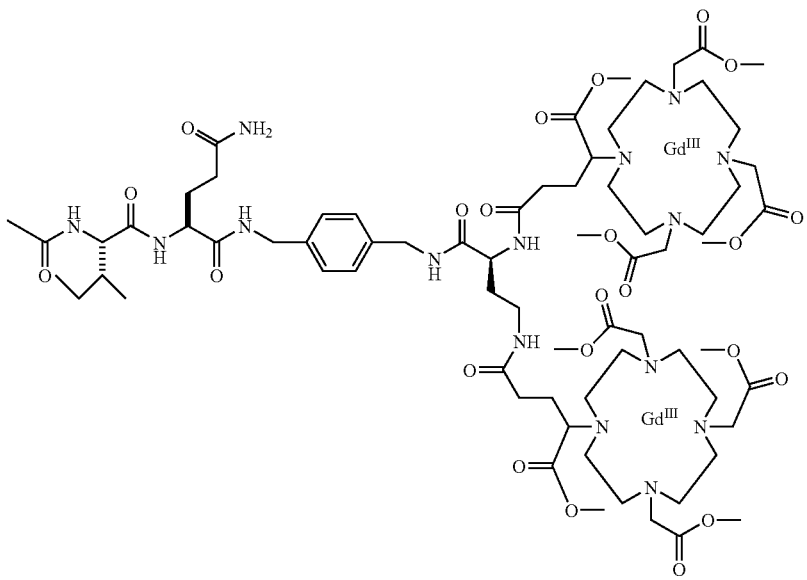

Structure II:
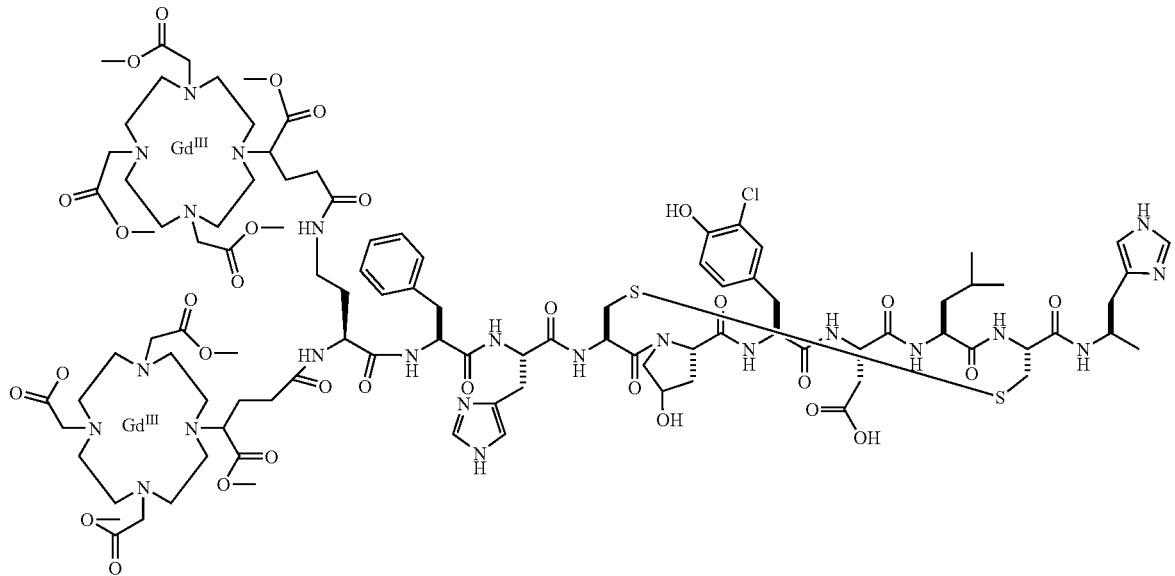
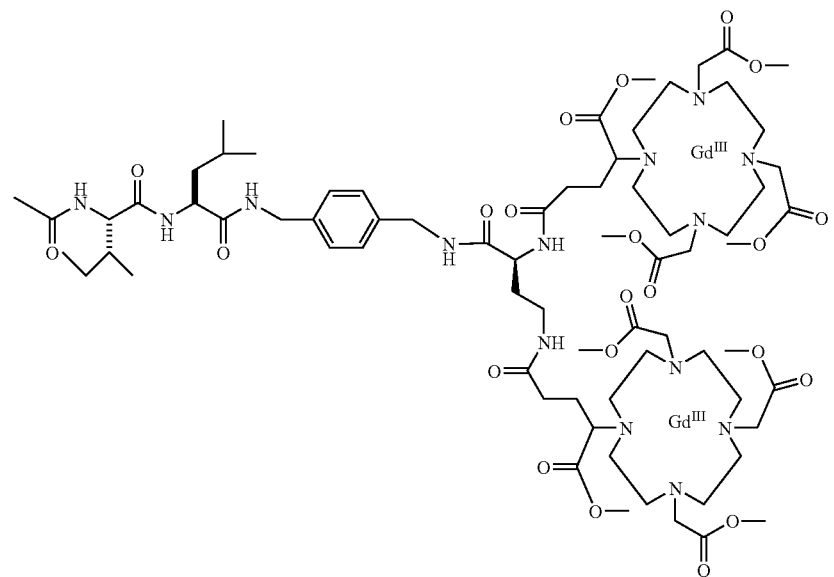

Structure III:
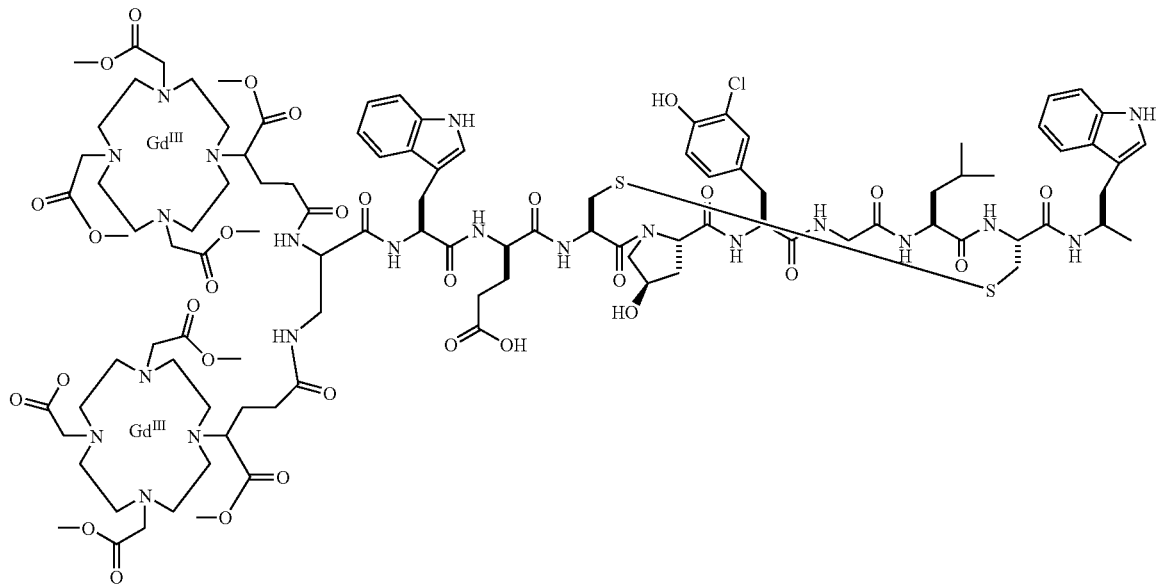
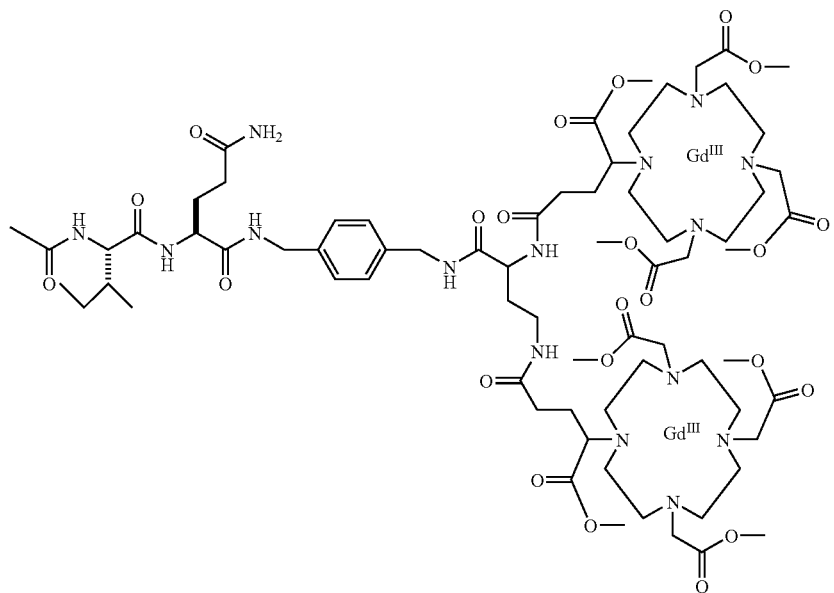

Structure IV:
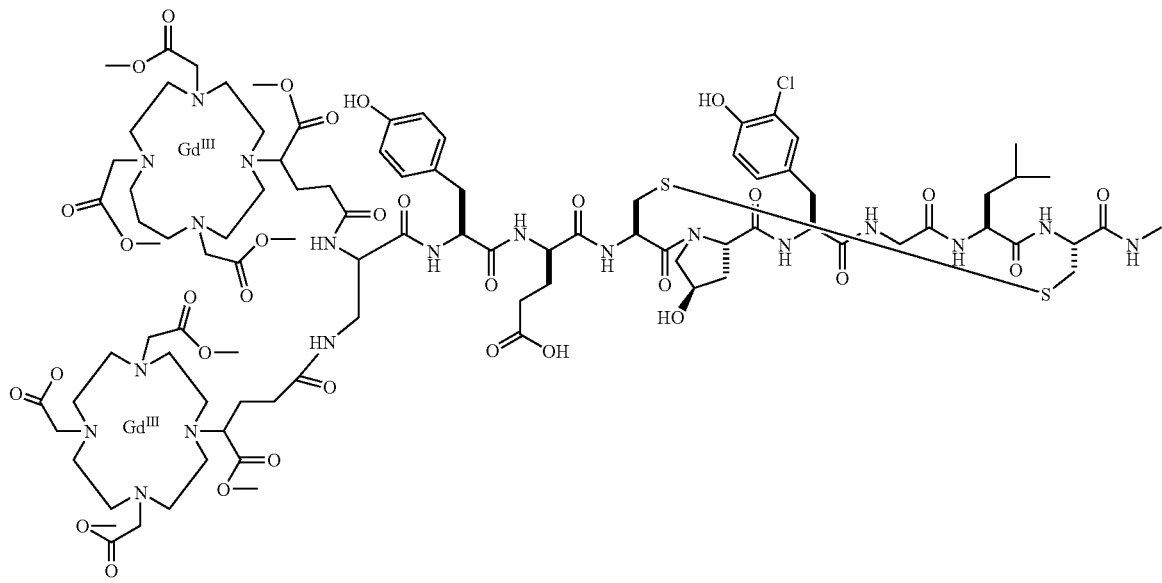
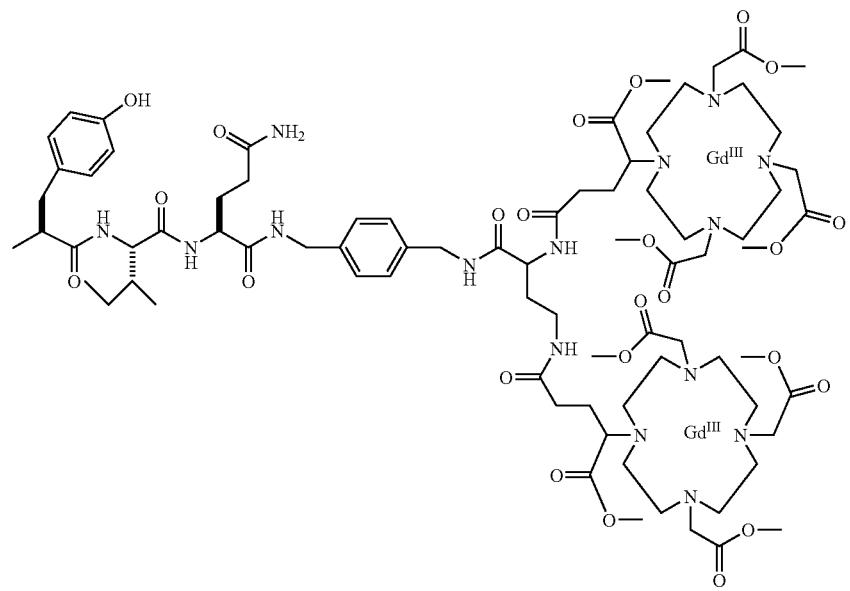

Structure V:
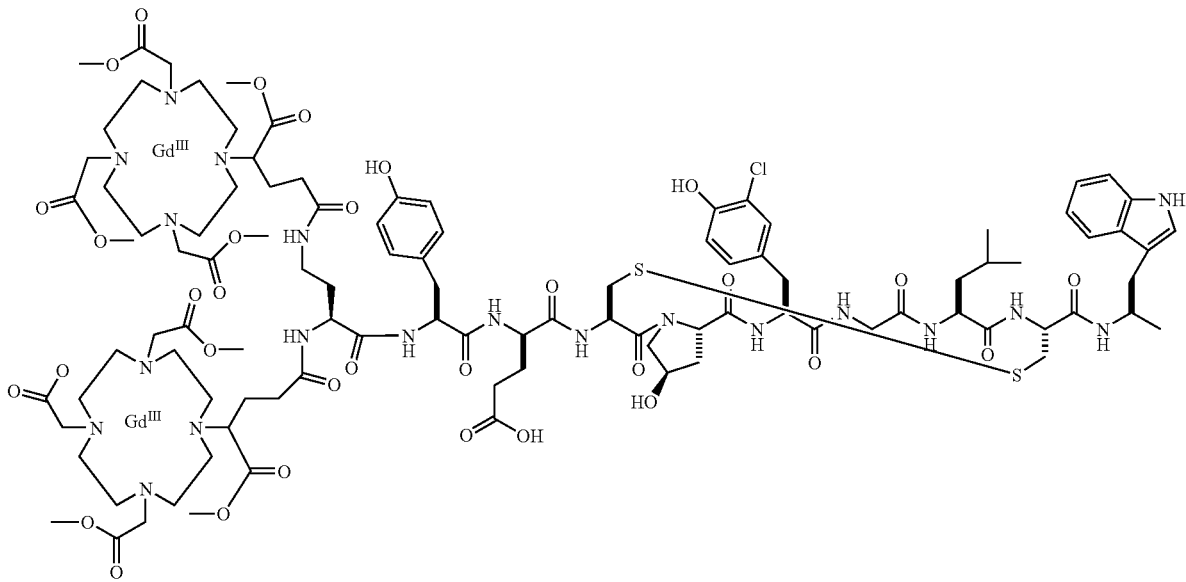
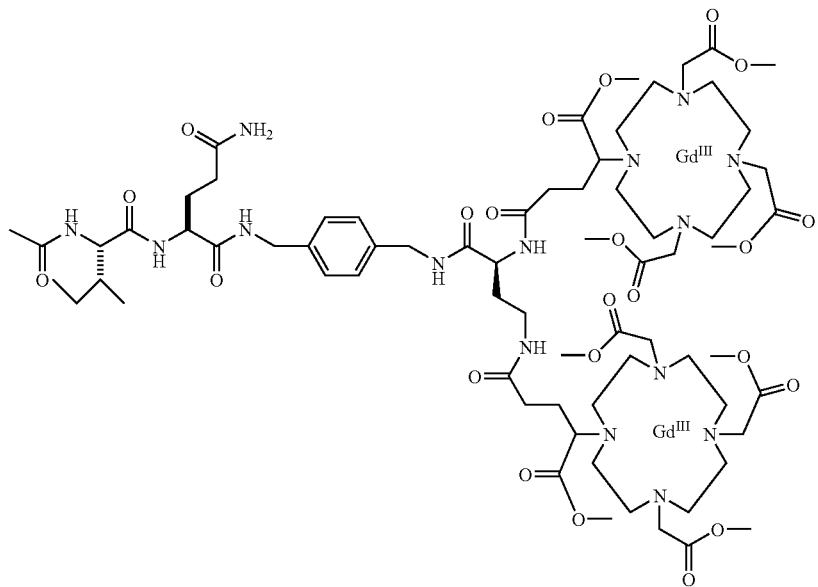

Structure VI:
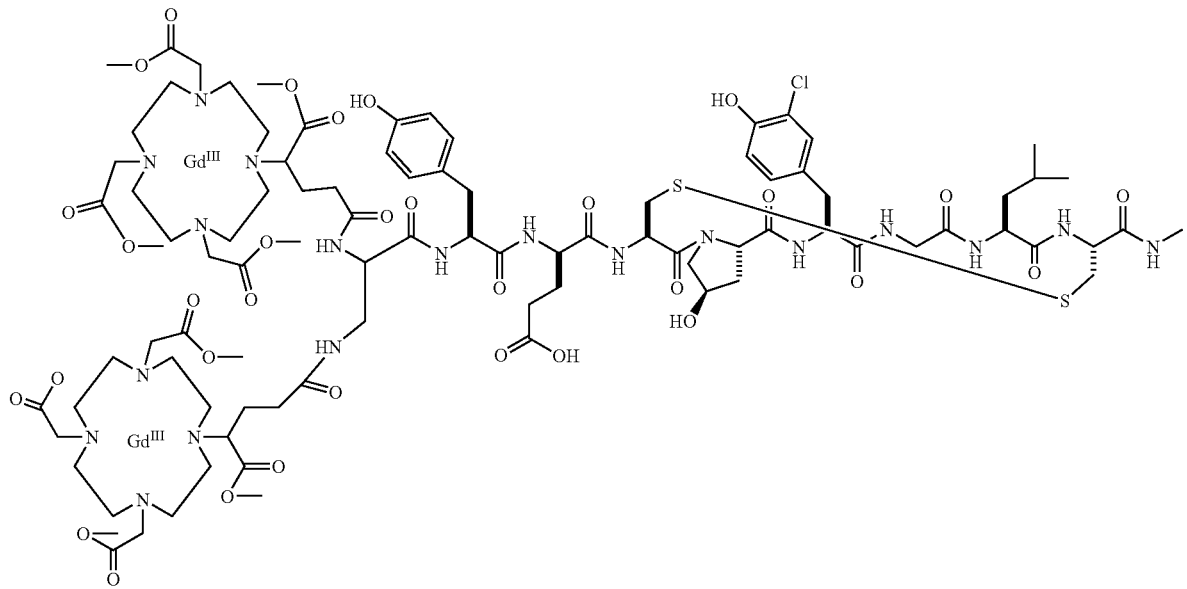
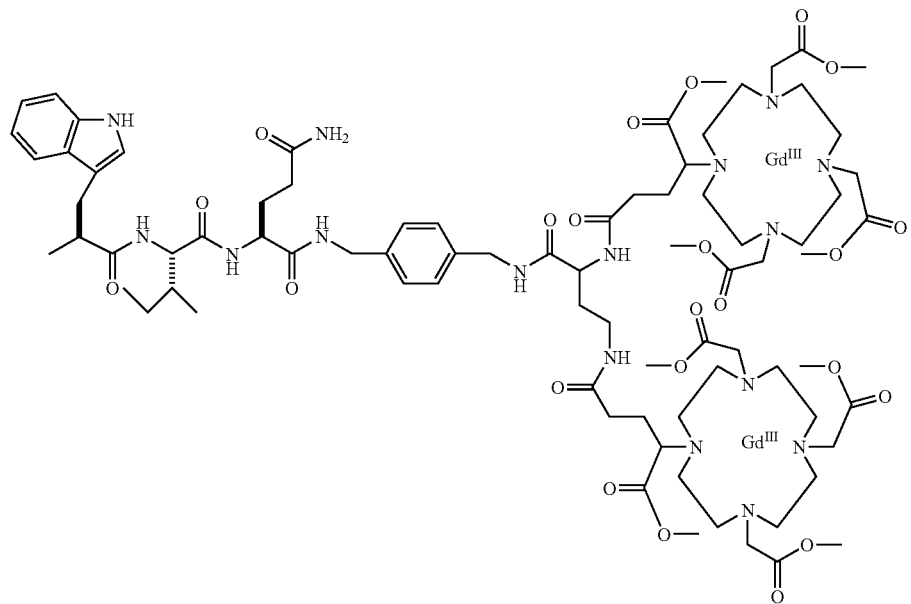

Structure VII:
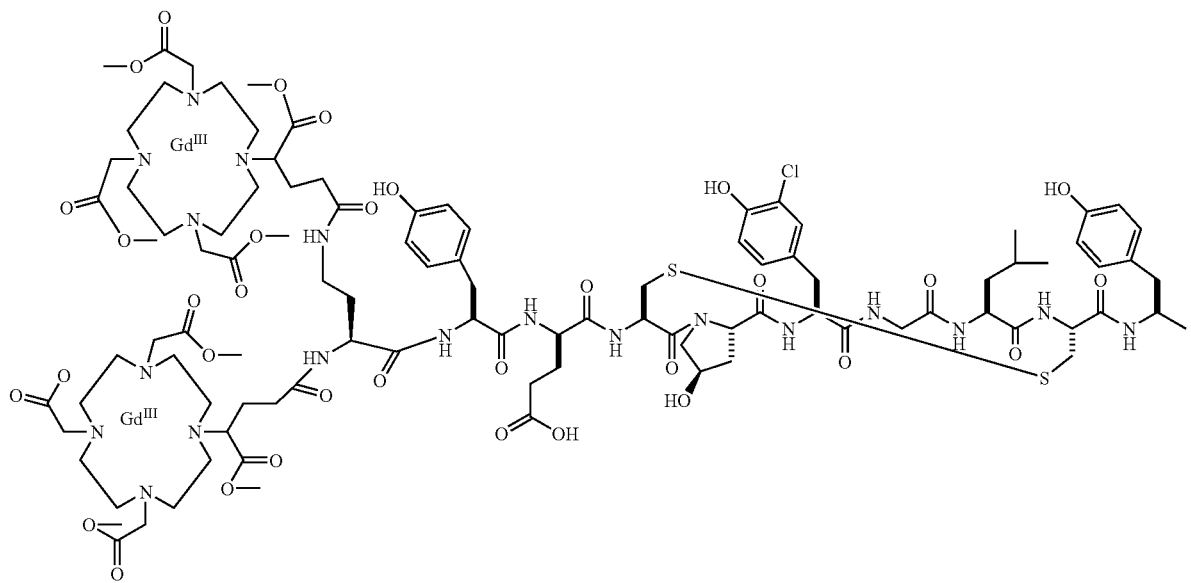
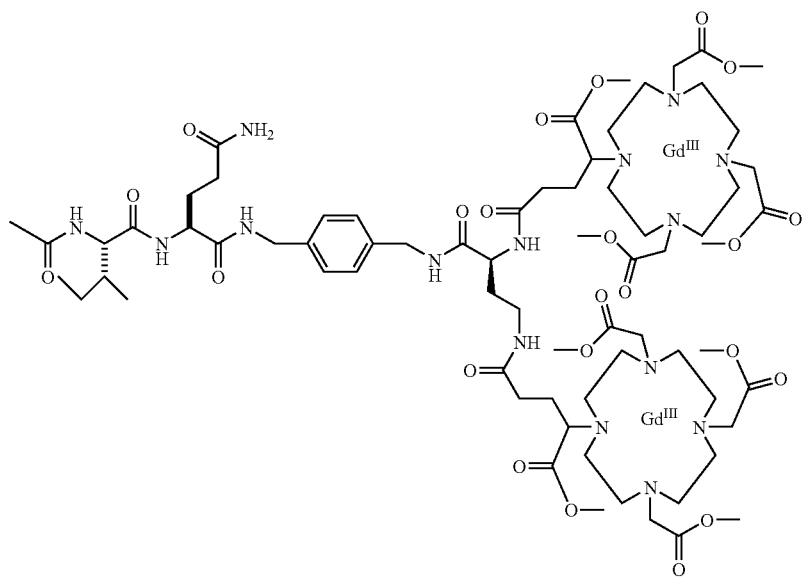

Structure VIII:
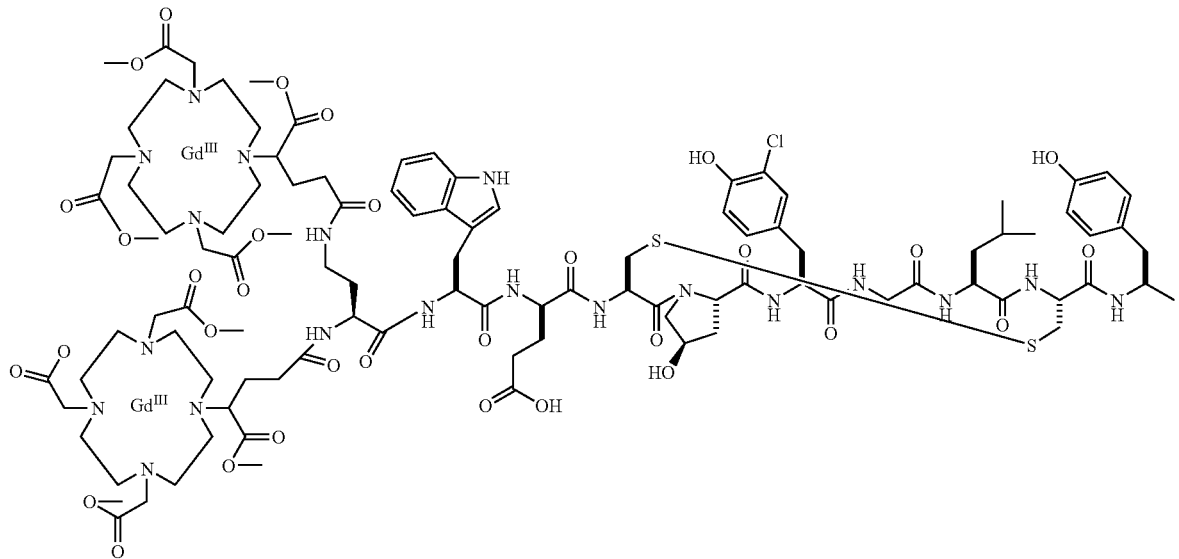
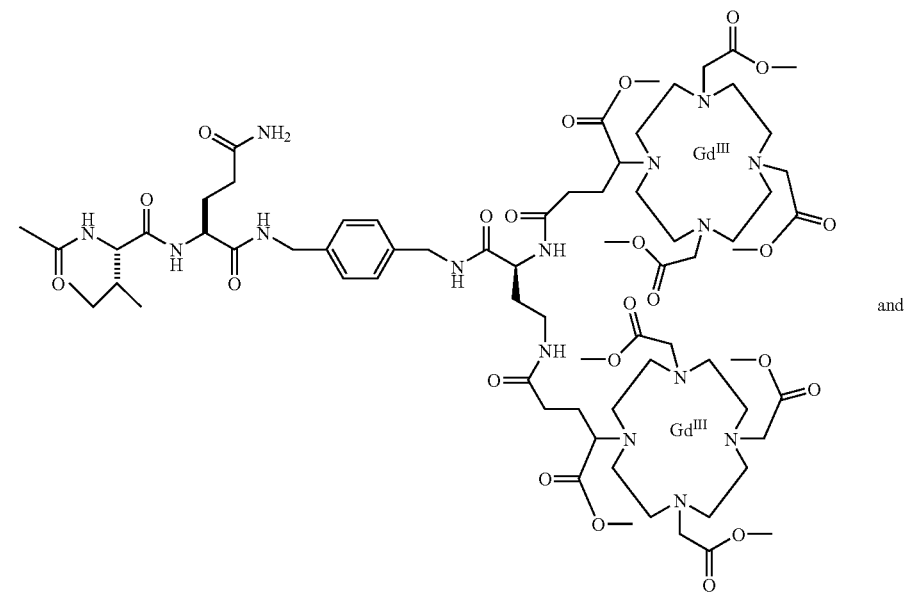
and

Structure IX:

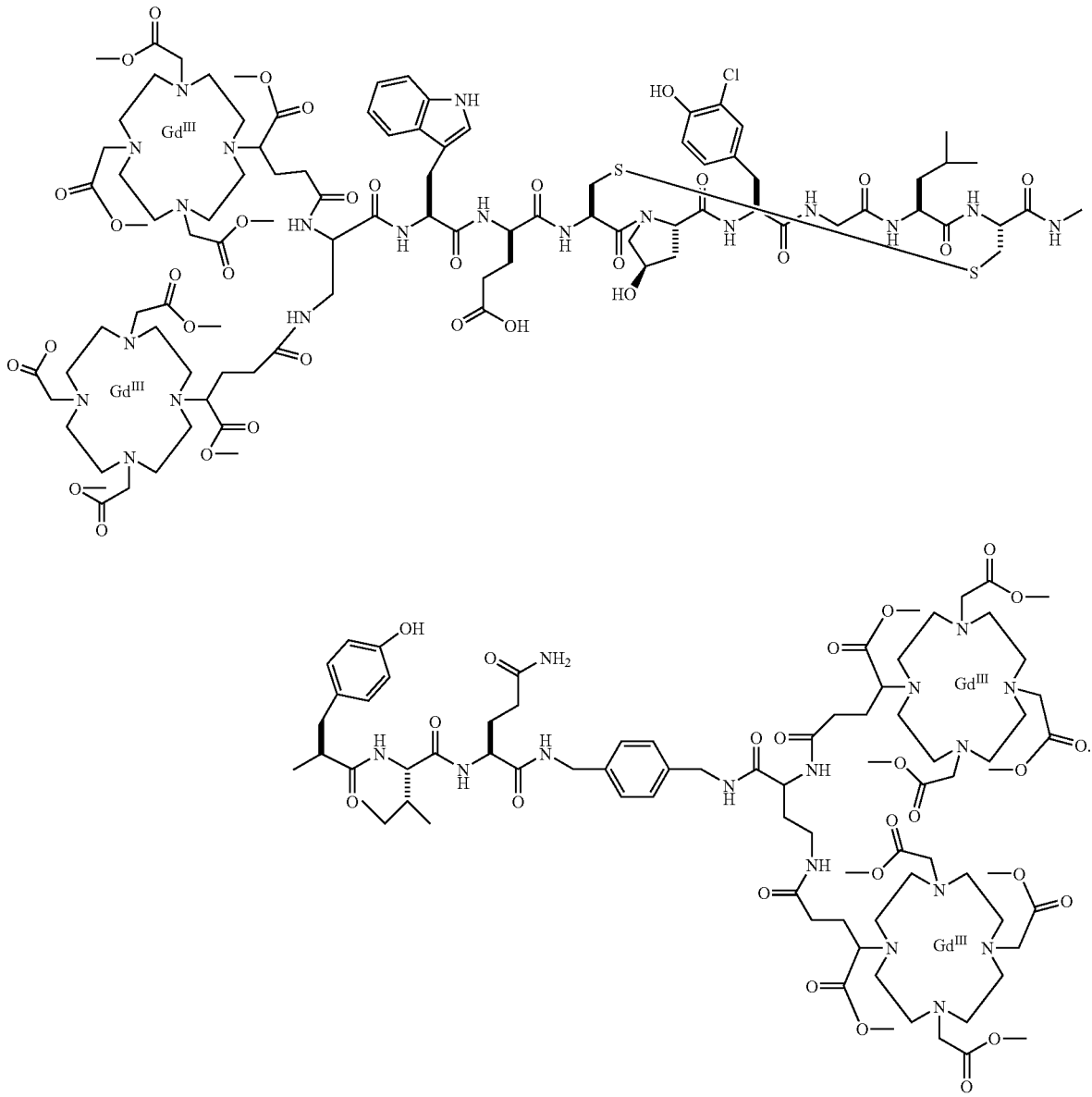

Additional information on Structures I-IX above is set forth in U.S. Provisional Application "Peptide-Based Multimeric Targeted Contrast Agents," by Zhang et al., filed Jul. 30, 2001, Ser. No. 60/308,721, and in "Peptide-Based Multimeric Targeted Contrast Agents" by Zhang et al., filed concurrently herewith, U.S. Ser. No. 11/564,648, both of which are incorporated by reference herein in their entirety.

In one embodiment, the targeted MRI contrast agent can be administered at a dose sufficient to result in a blood $T_1$ after administration of less than 500 ms. Alternatively, the targeted MRI contrast agent is administered at a dose sufficient to result in a blood $T_1$ after administration of less than 300 ms, or at a dose sufficient to result in a blood $T_1$ after administration of less than 175 ms. Typically, the targeted MRI contrast agent is administered at a dose from about 0.001 to about 500 μmol/kg. In other embodiments, the dose is from about 0.001 to about 50 μmol/kg, or from about 0.001. to about 5 μmol/kg.

A first MRI data set of an image of the vascular system is acquired. Subsequently, a second MRI data set of an image of the stationary target is acquired. The second MRI data set is acquired at a time appropriate to provide an observable level of contrast enhancement of the stationary target, if present, relative to background blood and tissue enhancement. The second MRI data set may be acquired using a spoiled gradient echo sequence.

In one embodiment, the targeted MRI contrast agent is administered at a dose sufficient to result in a $T_1$ of the stationary target of less than 500 ms. Alternatively, the targeted MRI contrast agent is administered at a dose sufficient to result in a $T_1$ of the stationary target of less than 300 ms, or at a dose sufficient to result in a $T_1$ of the stationary target of less than 100 ms.

The first and second MRI data sets may be acquired in a single MRI session. In one embodiment, the single MRI session lasts for less than 6 hours. Alternativley, the single MRI session can last for less than 4 hours, or for less than 2 hours, or for less than 1 hour.

The first and second MRI data sets are then compared to determine the presence of the stationary target within the vascular system, provided that the second MRI data set had indicated the presence of the stationary target. For example, the first and second MRI data sets can be combined to produce a third MRI data set that includes an image of both the stationary target and the vascular system. The third data set is capable of indicating the location of the stationary target, if present, within the vascular system. If desired, the third MRI data set may be displayed on a display device in order to indicate the location of the stationary target within the vascular system. The third MRI data set may also indicate the size of the stationary target within the vascular system.

The first and second MRI data sets may be combined by registering spatially the first and second MRI data sets with respect to one another. The combining step may further include interpolating the spatial resolution of the first or the second MRI data set so that the first and second MRI data set are of equivalent spatial resolution. For example, one can determine which of the first and second data sets has the higher spatial resolution and interpolate the spatial resolution of the corresponding other data set to the higher spatial resolution. In addition, one can combine the data sets with a direct calculation of modified image intensities resulting from a combination of individual values from the so registered, interpolated data elements from the first and second data sets. In this regard, the direct calculation of modified image intensities may include variably weighting the individual values of the registered, interpolated data elements from the first and second data sets.

In addition to its specific affinity for the stationary target, the targeted MRI contrast agent may also exhibit a specific affinity for a non-stationary biological component present within the mammal's vascular system. The non-stationary biological component present within the mammal's vascular system can be, for example, a protein present within the vascular blood pool, such as human serum albumin, fibrinogen, alpha acid glycoprotein, globulins, and lipoproteins.

It is another object of the invention to provide methods to determine the presence or absence of a stationary target within a vascular system of a mammal wherein both a targeted MRI contrast agent and a vascular MRI contrast agent are administered to a mammal. The method includes administering a targeted MRI contrast agent to the mammal. The targeted contrast agent has a specific affinity for the stationary target and the targeted contrast agent is capable of providing contrast enhancement of the stationary target.

The stationary target within the vascular system may be a tissue, a biological structure, a cell, a cell surface, and a biopolymer. In embodiments wherein the stationary target is a biological structure, the biological structure may be a structure associated with a CVD, e.g., such as a thrombus, an atherosclerotic plaque, an atherosclerotic lesion, a tumor, and a thromboembolism. Alternatively, the stationary target may be a biopolymer. Examples of biopolymers associated with CVDs are lipids, lipoproteins, proteins, polypeptides, and polysaccharides. If the stationary target is a biopolymer, the biopolymer is typically a protein present at high concentrations in CVDs, such as fibrin and collagen.

The targeted MRI contrast agent may be administered at a dose sufficient to result in a $T_1$ of the stationary target of less than 500 ms. In other embodiments, the targeted MRI contrast agent is administered at a dose sufficient to result in a $T_1$ of the stationary target of less than 300 ms, or of less than 100 ms.

The targeted MRI contrast agent exhibits a specific affinity for the stationary target. In some embodiments, the specific affinity of the targeted MRI contrast agent, expressed as a dissociation constant, is less than 50 μM. In other embodiments, the specific affinity is less than 5 μM. In still other embodiments, the specific affinity is less than 0.5 μM.

Examples of structures of targeted MRI contrast agents for use in the present invention include:

Structure I:

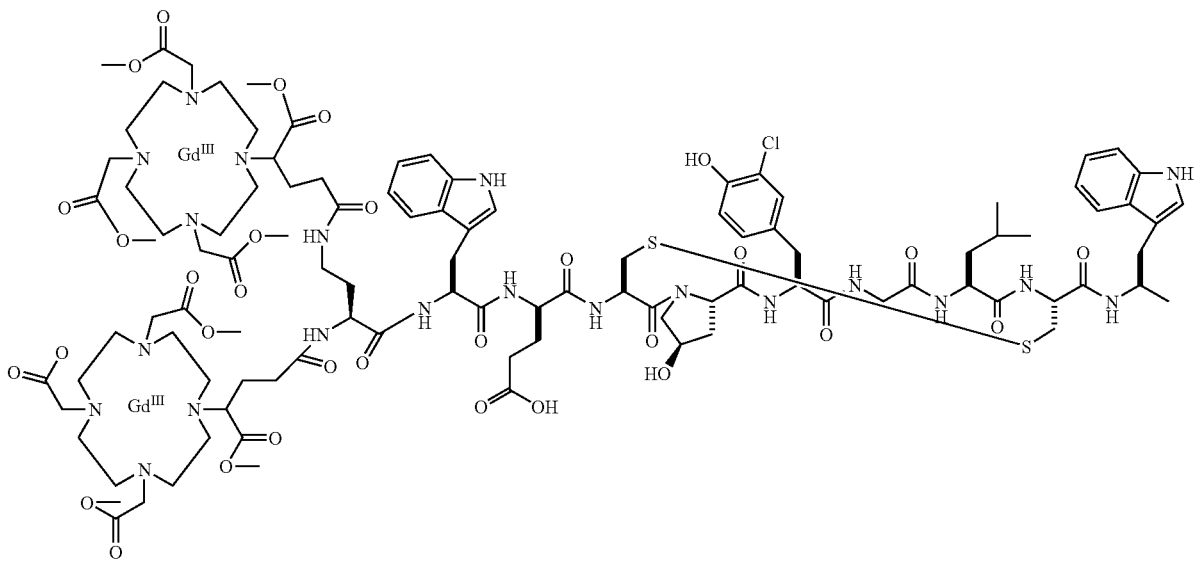

-continued
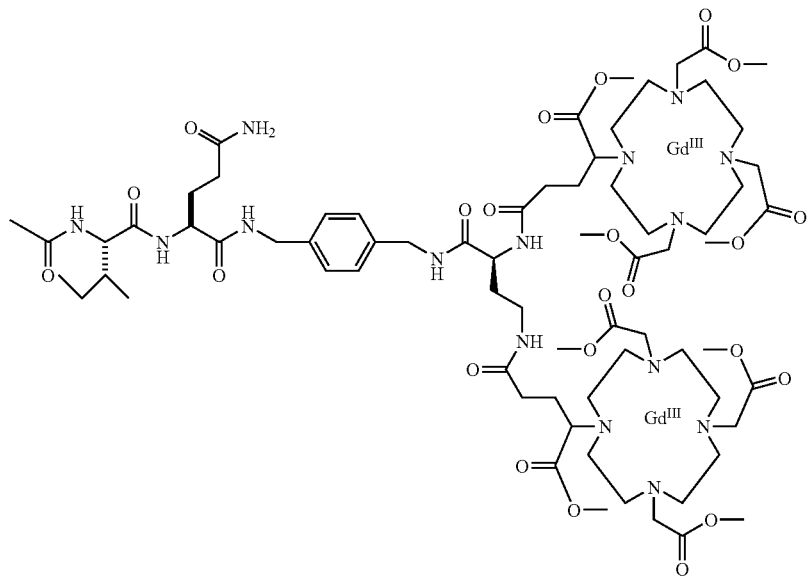
Structure II:
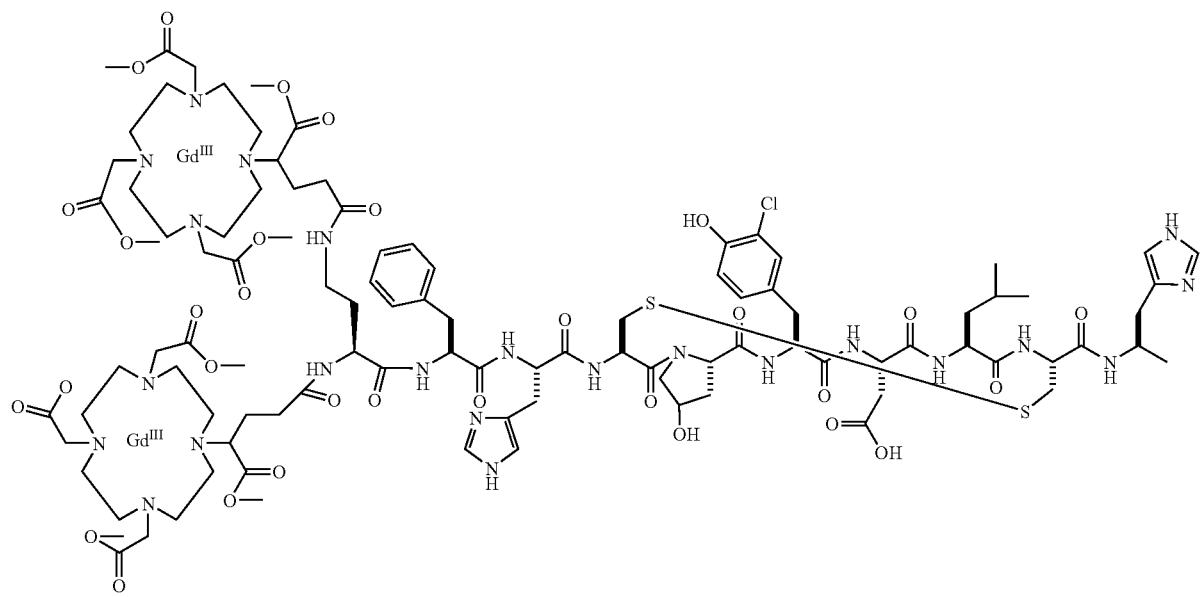

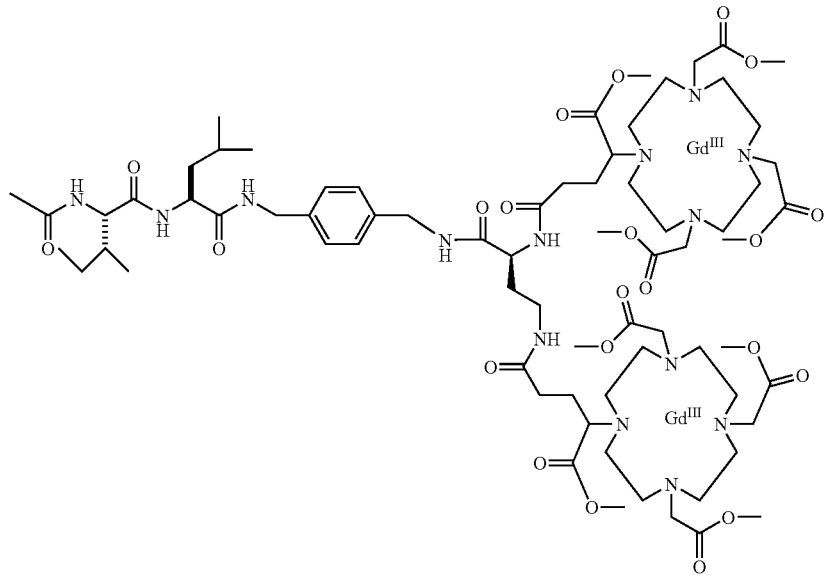
Structure III:
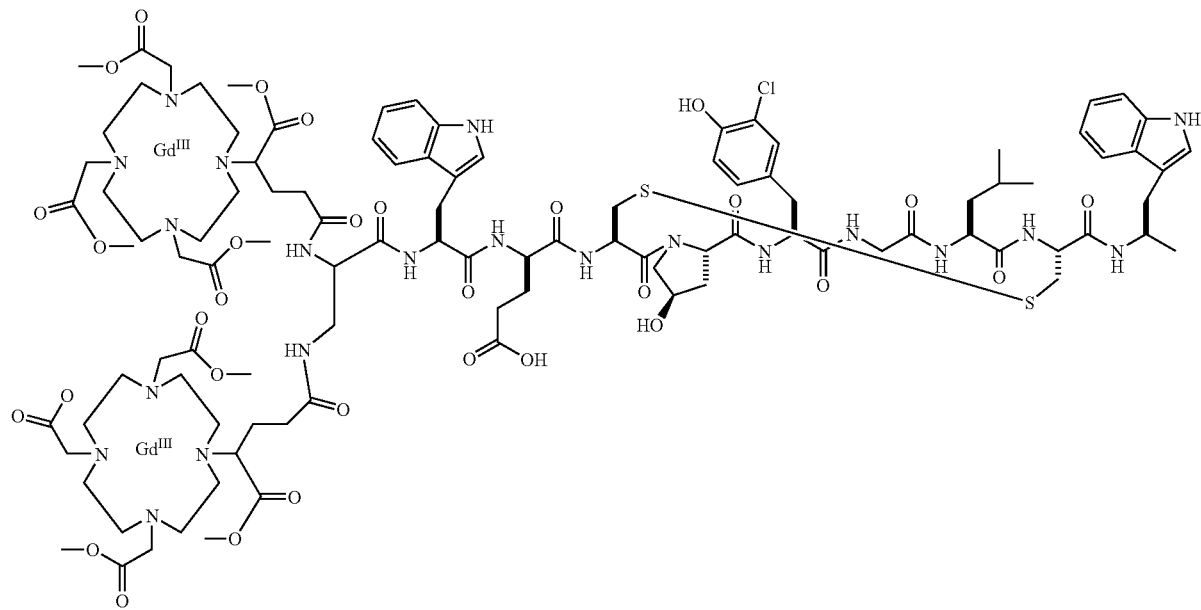

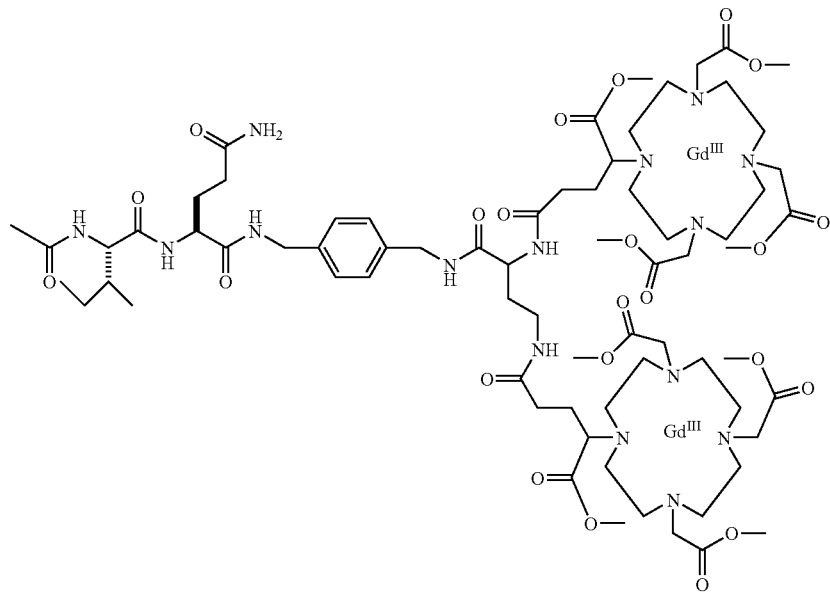
Structure IV:
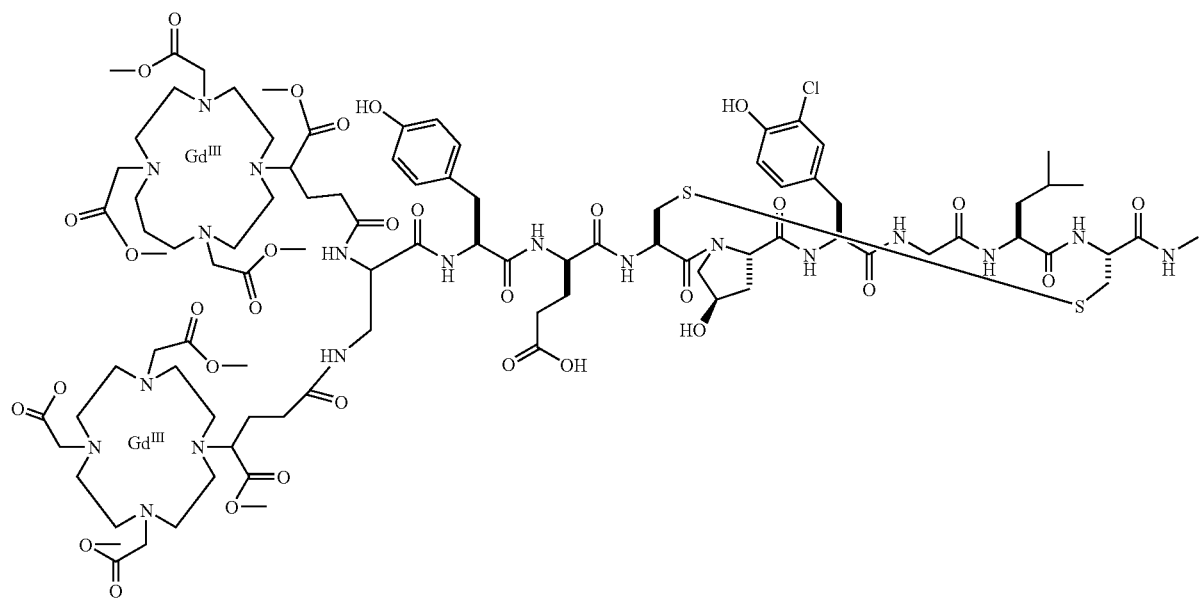

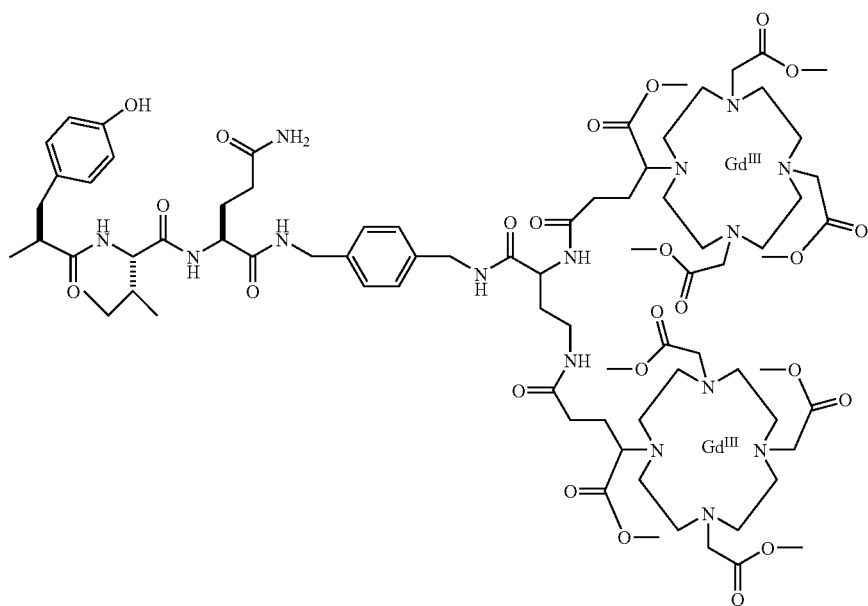
Structure V:
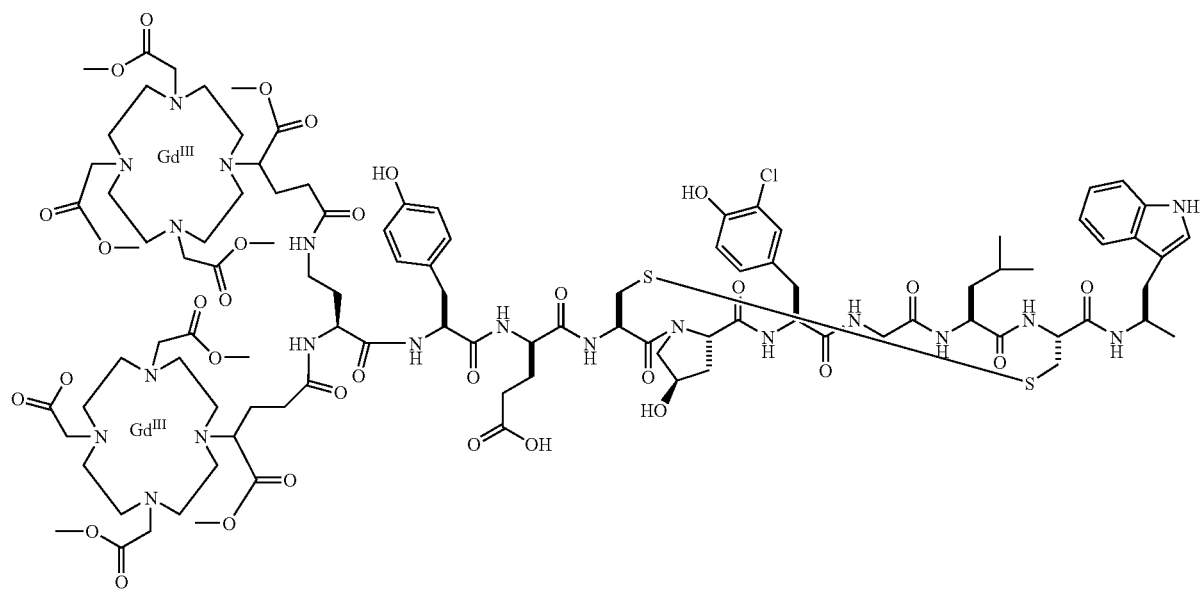

-continued
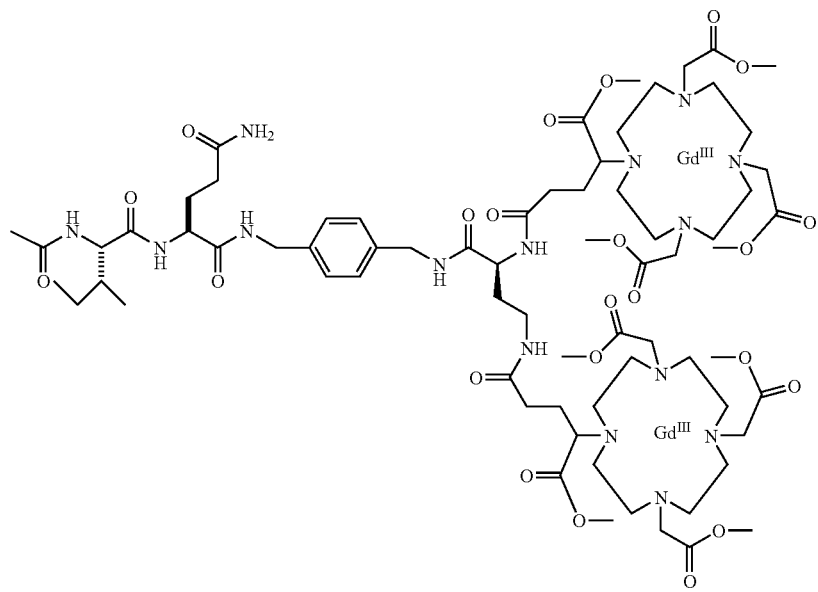
Structure VI:
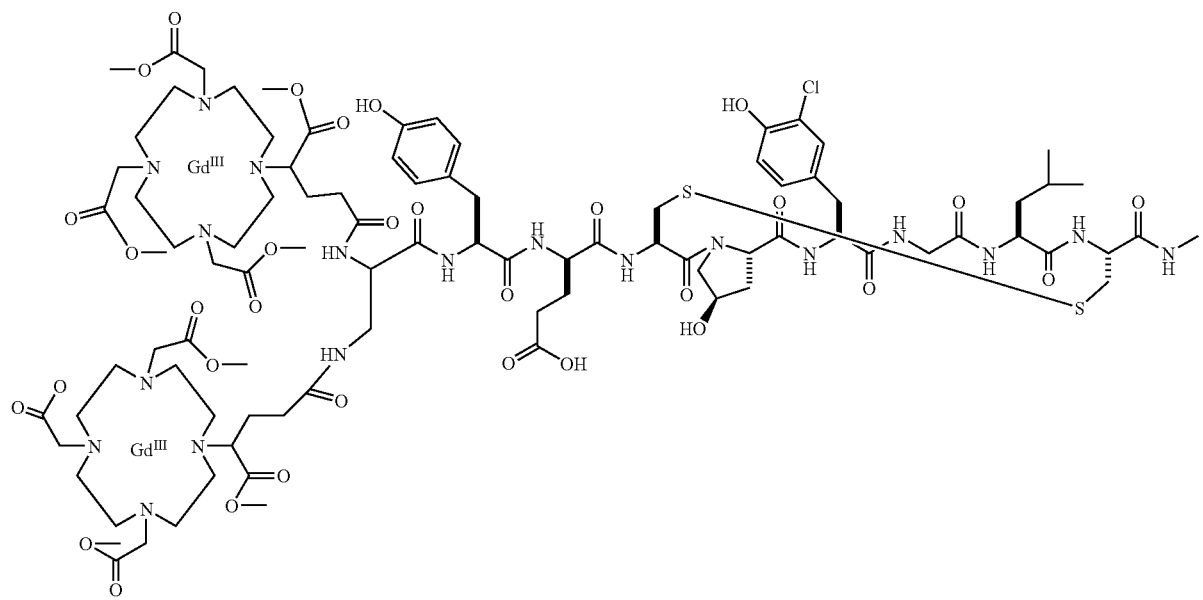

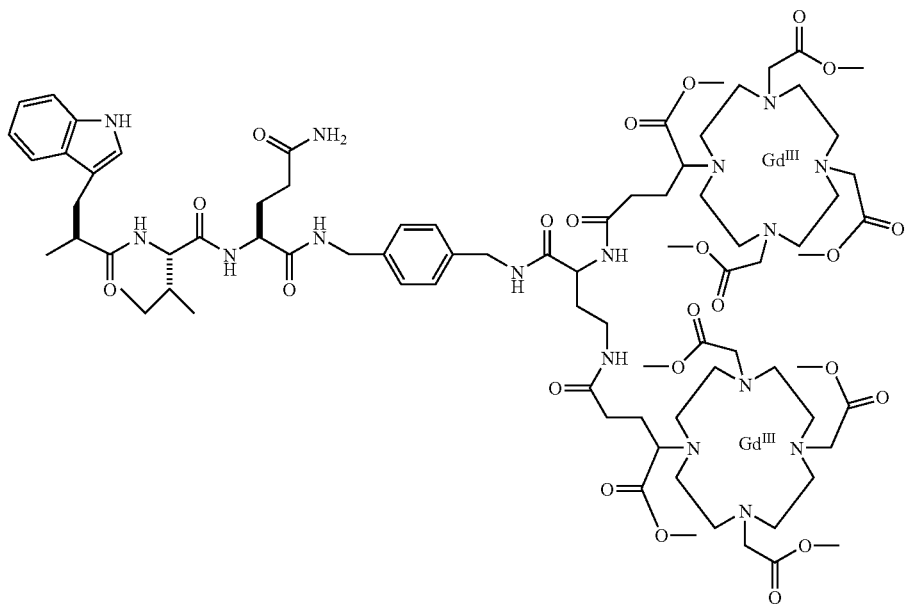
Structure VII:
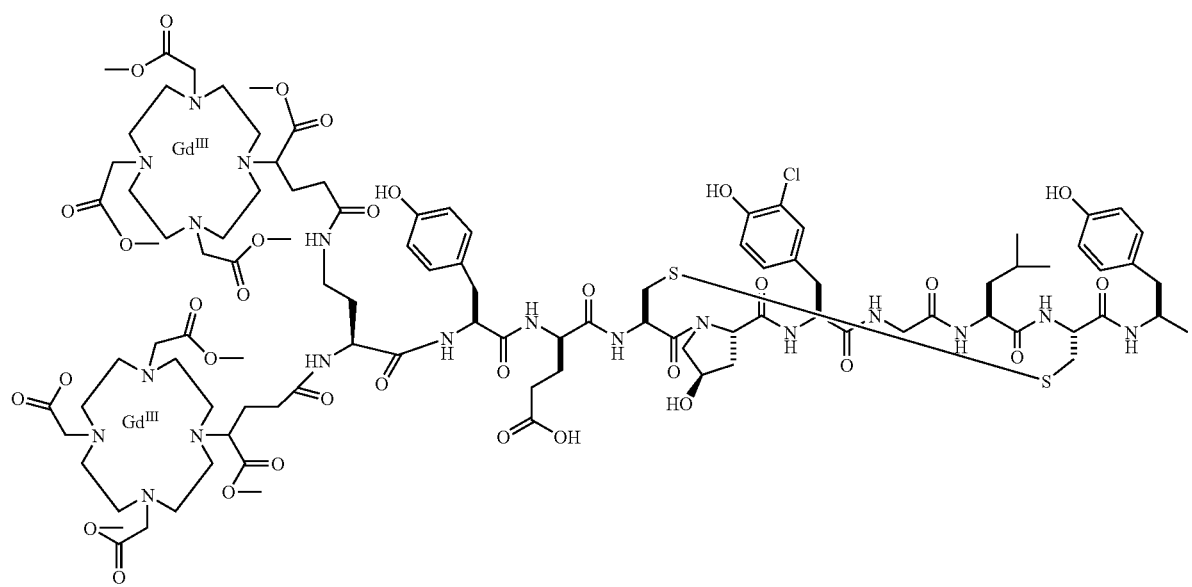

-continued
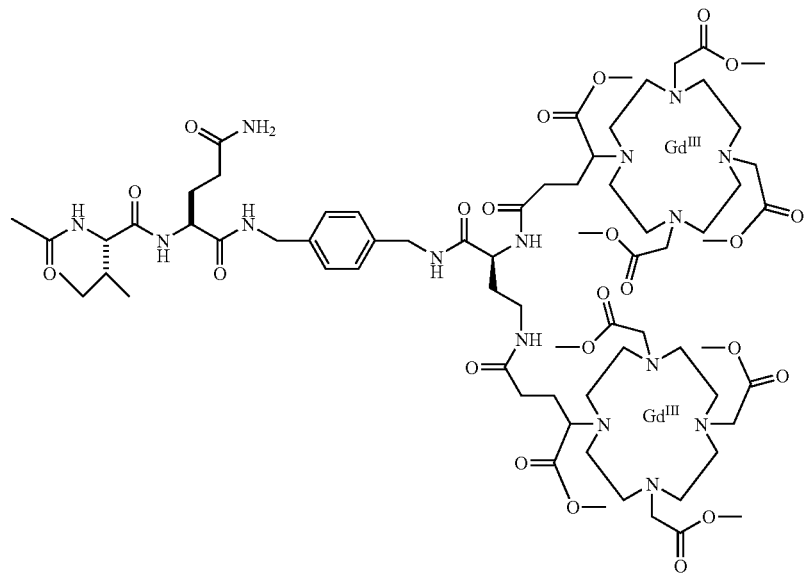
Structure VIII:
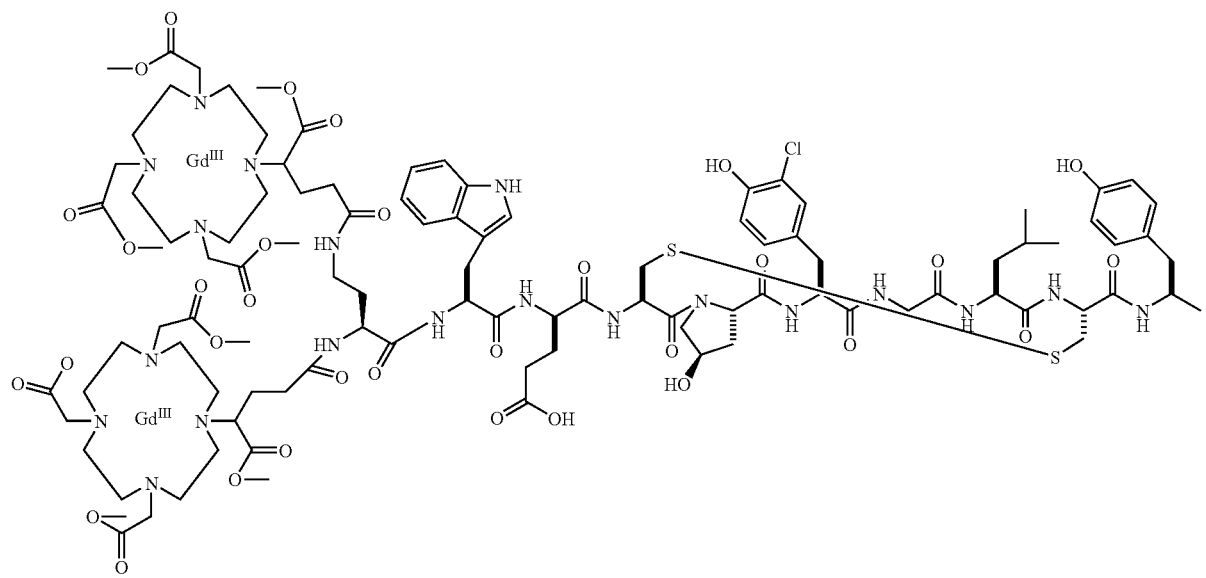

-continued
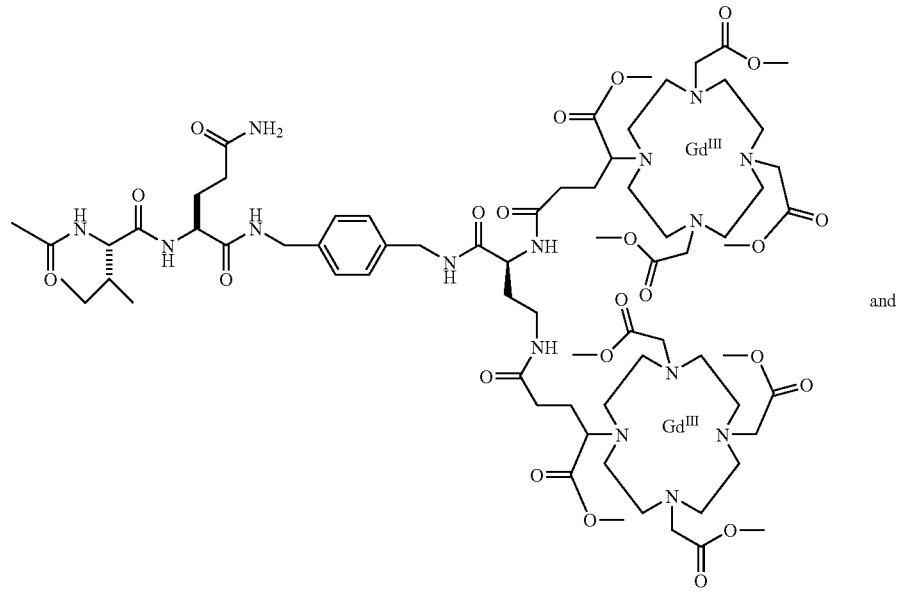
and
Structure IX:
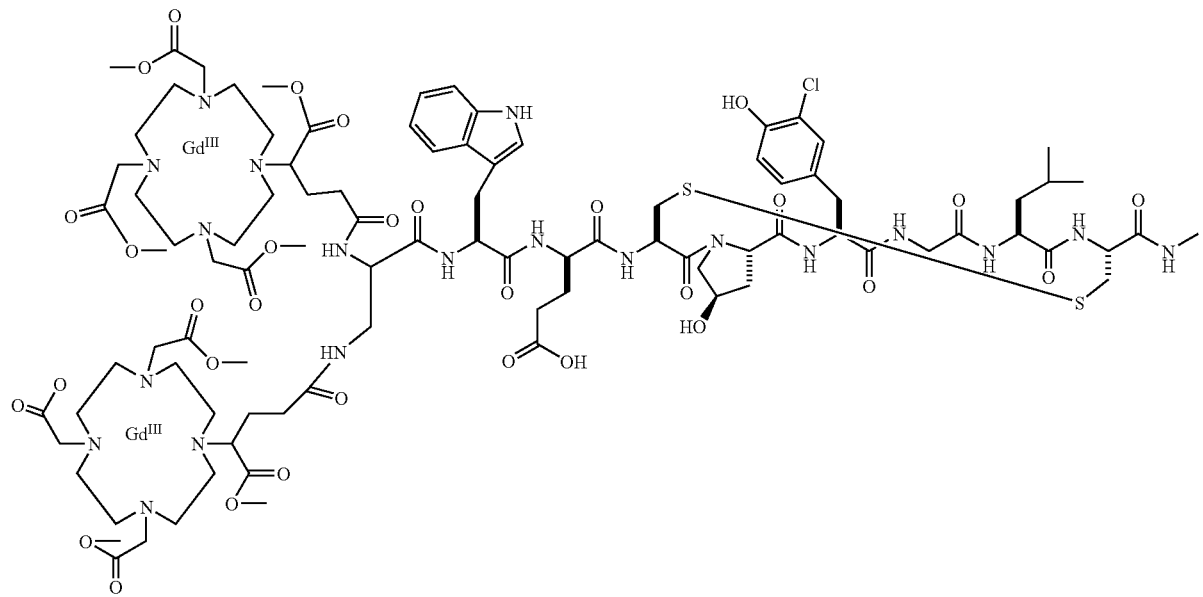

-continued

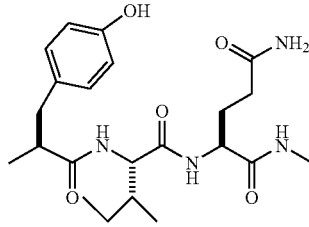
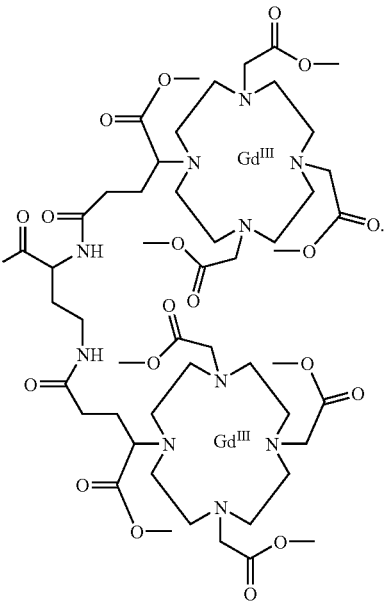

As noted previously, Structures I-IX above are disclosed in U.S. Provisional Application "Peptide-Based Multimeric Targeted Contrast Agents," by Zhang et al., filed Jul. 30, 2001, Ser. No. 60/308,721, and in "Peptide-Based Multimeric Targeted Contrast Agents" by Zhang et al., filed concurrently herewith, U.S. Ser. No. 11/564,648, both of which are incorporated by reference herein in their entirety.

According to the method, a vascular MRI contrast agent is also administered to the mammal. The vascular contrast agent is capable of providing contrast enhancement of the vascular system of the mammal. The vascular MRI contrast agent may be administered at a dose sufficient to result in a blood $T_1$ after administration of less than 300 ms. Alternatively, the vascular MRI contrast agent is administered at a dose sufficient to result in a blood $T_1$ after administration of less than 175 ms, or of less than 100 ms.

The vascular MRI contrast agent may be an extracellular MRI contrast agent. Examples of such extracellular MRI contrast agents include:

(Gd-DTPA)
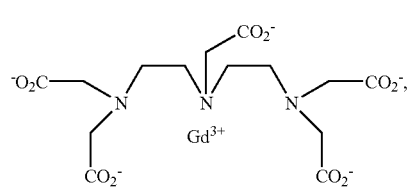

(Gd-DOTA)
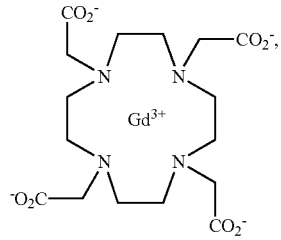

(Gd-DTPA-BMA)
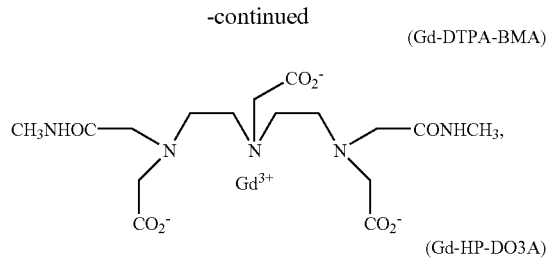

(Gd-HP-DO3A)
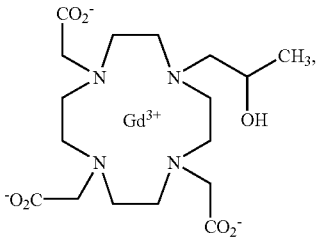

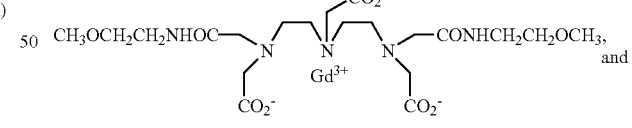
(gadoversetamide)

and

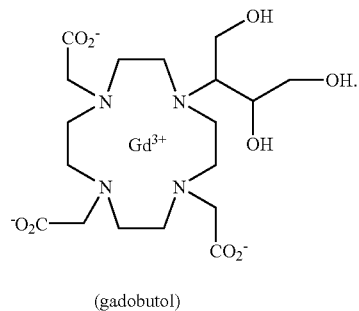
(gadobutrol)

Alternatively, the vascular MRI contrast agent may be an iron particle, including for example ultra-small particles of iron oxide (USPIOs) and monocrystalline iron oxide particles (MIONs).

In yet another embodiment, the vascular MRI contrast agent is a blood pool contrast agent. Some structures of blood pool contrast agents contemplated for use in the present invention include:

Gadomer-17, P760,

The vascular MRI contrast agent may also exhibit a specific affinity for a non-stationary biological component present within the mammal's vascular system. Examples of a non-stationary biological component present within the mammal's vascular system include proteins present in the blood and blood serum, e.g., human serum albumin, fibrinogen, alpha acid glycoprotein, globulins, and lipoproteins.

The targeted MRI contrast agent may be administered at a dose from about 0.001 to about 500 μmol/kg (e.g., about

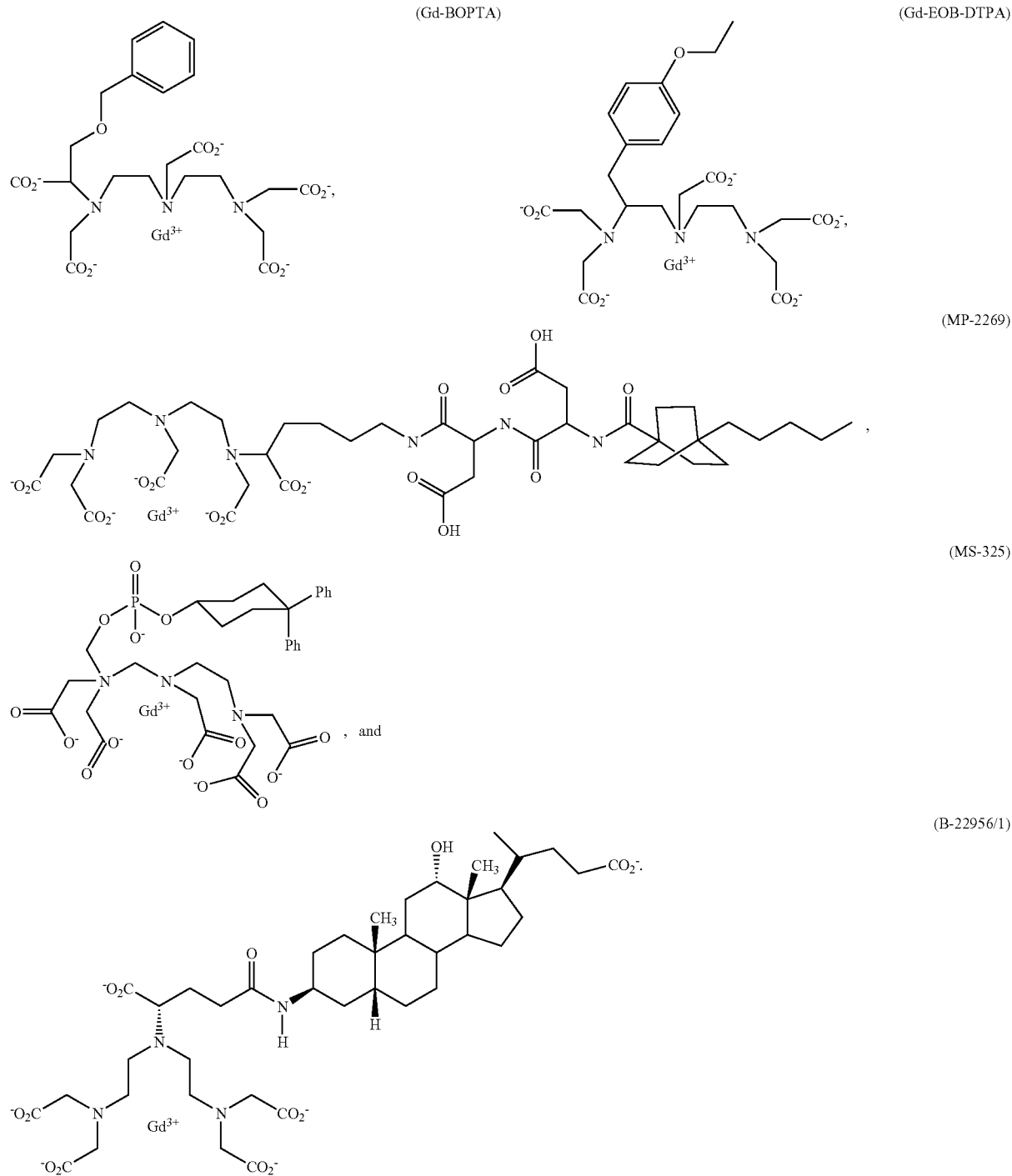

0.001 to about 50 µmol/kg or 0.001 to about 5 µmol/kg) and the vascular MRI contrast agent may be administered at a dose from about 0.01 to about 300 µmol/kg (e.g., about 0.01 to about 30 µmol/kg or about 0.01 to about 3 µmol/kg), respectively. In other embodiments, the targeted MRI contrast agent is administered at a dose from about from about 0.001 to about 50 µmol/kg and the vascular MRI contrast agent is administered at a dose from about 0.01 to about 30 µmol/kg. Alternatively, the targeted MRI contrast agent may be administered at a dose from about 0.001 to about 5 µmol/kg and the vascular MRI contrast agent is administered at a dose from about 0.01 to about 3 µmol/kg.

Both a vascular MRI data set which includes an image of the vascular system and a targeted MRI data set which includes an image of the stationary target are acquired. The targeted data set should be acquired at a time appropriate to provide an observable level of contrast enhancement of the stationary target, if present, relative to background blood and tissue enhancement. In some embodiments, the targeted MRI data set is acquired using a spoiled gradient echo sequence.

In one embodiment, the targeted contrast agent is administered prior to the vascular contrast agent, and the targeted MRI data set is acquired prior to the vascular MRI data set. Alternatively, the targeted contrast agent and the vascular contrast agent are administered simultaneously, and the vascular MRI data set is acquired prior to the targeted MRI data set. In one embodiment, the targeted and vascular data sets may be acquired in a single MRI session.

The targeted contrast agent and the vascular contrast agent may be administered within 2 hours of one another. Alternatively, the targeted contrast agent and the vascular contrast agent are administered within 30 min. of one another, or within 15 min. of one another. The vascular MRI contrast agent may be administered as a bolus or by infusion. If administered by infusion, an infusion time of less than 15 minutes may be used. In other embodiments, an infusion time of less than 10 minutes, or less than 3 minutes, is used.

The vascular and targeted MRI data sets can be compared to determine the presence of the stationary target within the vascular system, provided that the targeted MRI data set indicated the presence of the stationary target. The vascular and targeted MRI data sets may also be combined. For example, the vascular and targeted MRI data sets can be combined to produce a third MRI data set which includes an image of both the stationary target and the vascular system. The third data set is also capable of indicating the location and size of the stationary target, if present, within the vascular system. If desired, the third MRI data set may be displayed on a display device in order to indicate the location and size of the stationary target, if present, within the vascular system.

The data sets may be combined by registering spatially the targeted and vascular MRI data sets with respect to one another. The combining step may also include interpolating the spatial resolution of either the vascular or the targeted MRI data set so that the vascular and targeted MRI data sets are of equivalent spatial resolution. In one embodiment, for example, one can determine which of the vascular or targeted MRI data sets has the higher spatial resolution; and then interpolate the spatial resolution of the corresponding other data set to the higher spatial resolution. Additionally, the combining step can further include a direct calculation of modified image intensities resulting from a combination of individual values from the so registered, interpolated data elements from the vascular and targeted MRI data sets. In one embodiment, the direct calculation of modified image intensities includes variably weighting the individual values of the registered, interpolated data elements from the vascular and targeted MRI data sets.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the methods, materials, and examples are illustrative only and not intended to be limiting.

Commonly used chemical abbreviations that are not explicitly defined in this disclosure may be found in The American Chemical Society Style Guide, Second Edition; American Chemical Society, Washington, D.C. (1997); "2001 Guidelines for Authors," J. Org. Chem. 66(1), 24A (2001); and "A Short Guide to Abbreviations and Their Use in Peptide Science," J. Peptide Sci. 5, 465-471 (1999).

The details of one or more embodiments of the invention are set forth in the accompanying drawings and the description below. Other features, objects, and advantages of the invention will be apparent from the description and drawings, and from the claims.

DETAILED DESCRIPTION

Definitions

Figure 1:
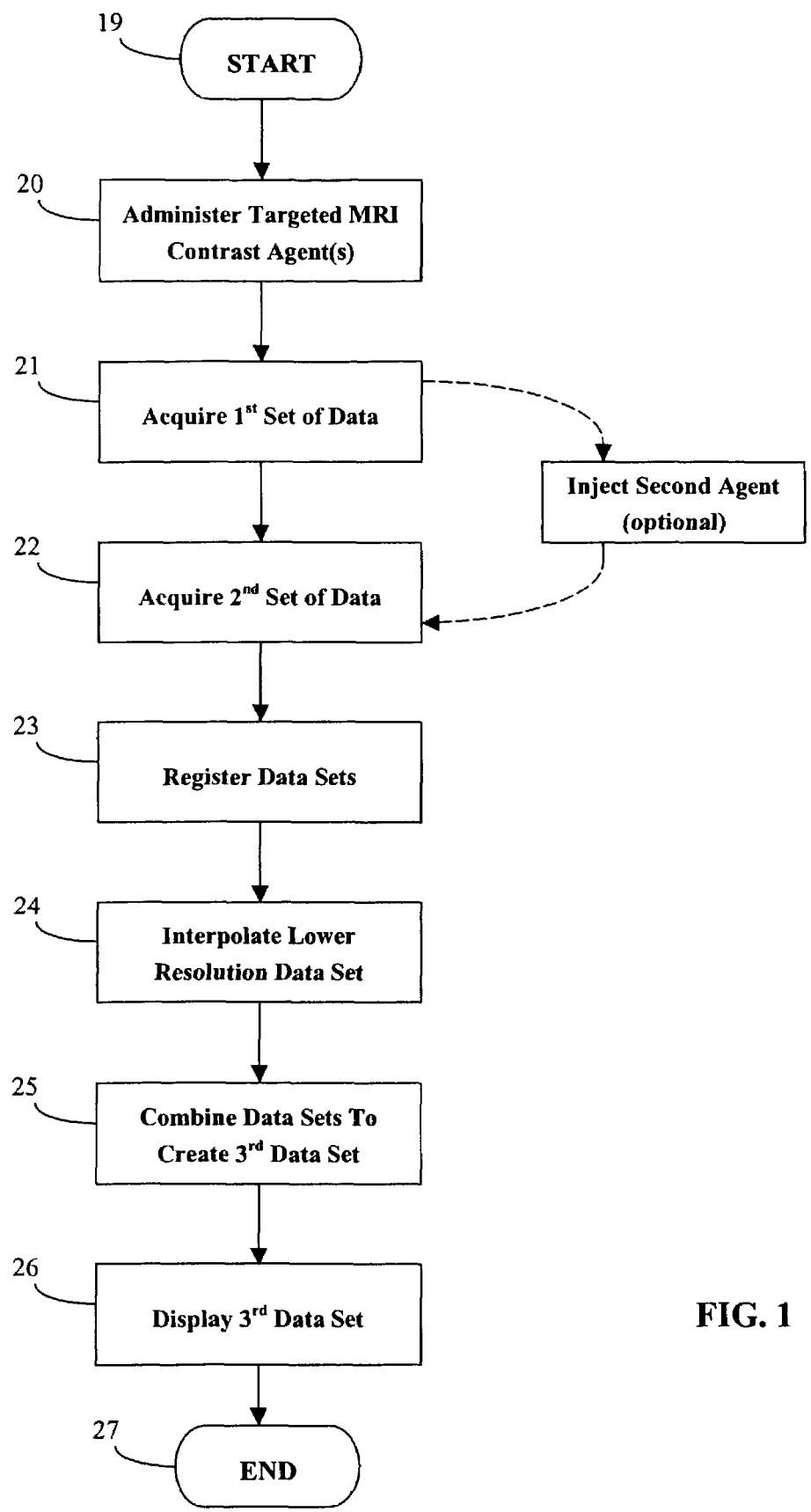
FIG. 1 is a flowchart representing one embodiment of the present invention.

Specific affinity—as used herein, specific affinity refers to the capacity of a contrast agent to be noncovalently bound to a particular stationary target, including one or more biological components which make up the stationary target, to a greater degree than other compounds. Specific affinity is often measured in terms of an equilibrium dissociation constant, $K_d$. Specific affinity, as used herein, expressly does not refer to the mechanism by which certain contrast agents (e.g, USPIOs or MIONs) are taken up by or phagocytosed by cells of the reticuloendothelial system (RES) and/or the mononuclear phagocytic system (MPS).

Stationary target—a stationary target, as used herein, is a biological component within the vascular system of a mammal that does not undergo significant translational motion in any of the X, Y, and Z axes that define its location within the vascular system during the MRI session. Any translational motion of the stationary target due to mammal breathing, intravascular blood flow, mammal body movement, or external pressure placed on the mammal or vascular system of the mammal should be excluded when evaluating any motion of the stationary target. At particular times, some stationary targets may be seen to be substantially fixed spatially within the vascular system, e.g, a thrombus.

Non-stationary target—a non-stationary target, as used herein, is a biological component within the vascular system of a mammal that undergoes significant translational or rotational motion in the X, Y, and Z axes that define its location at any one time.

Polypeptide—as used herein, polypeptide means a chain of amino acids longer than about 3 amino acids, which may include non-natural amino acids, and regardless of post-translational or post-synthetic modification or processing.

Biopolymer—as used herein, biopolymer means a polymeric substance usually naturally formed in a biological system. Certain biopolymers can be constructed from a defined set of building subunits and with common functionalities linking the subunits, e.g., a protein or polypeptide is usually constructed from a set of subunit amino acids (both natural and non-natural) with amide bonds linking the subunits.

Biological structure—as used herein, a biological structure is a physical structure present within the vascular system of a mammal, usually constructed from a homogenous or non-homogeneous assemblage, covalently or noncovalently linked, of biological components.

Blood Pool Contrast Agent—as used herein, the term blood pool contrast agent means a contrast agent that is retained in the blood pool volume for a period of time greater than that of an extracellular agent. The blood pool agent may be retained in the blood pool volume for a number of reasons, such as molecular size and weight, or due to specific affinity for some component in the blood pool or vascular system.

Extracellular Contrast Agent—as used herein, the term extracellular contrast agent refers to contrast agents that do not exhibit significant specific affinity for a biological component present within the vascular system, including biological structures or biopolymers present within the vascular system, and are not retained in the blood volume for a significant period of time.

As used herein, the term "Gd" is meant to convey the ionic form of the metal gadolinium; such an ionic form may be written herein as Gd(III), $Gd^{3+}$, gado, etc., with no difference in ionic form contemplated.

This invention relates to MRI-based methods and systems useful for diagnosing and clinically assessing the presence, location, and size of CVDs, e.g., thrombi and atherosclerotic lesions, within the vascular system. The use of the methods and systems of the present invention allows for improved anatomical information concerning CVDs to be obtained from vascular and targeted MRI images and allows the clinician to develop more effective treatment plans.

Use of a Targeted MRI Contrast Agent

Accordingly, it is one aspect of the invention to provide a method of determining the presence or absence of a stationary target within a vascular system of a mammal. In one embodiment, the method of the invention involves acquiring two MRI data sets after administration of a targeted MRI contrast agent. Generally, the targeted contrast agent is administered to a mammal (e.g., patient) suspected of having a CVD prior to acquiring the data sets.

The stationary target within the vascular system can be, for example, a tissue, a biological structure, a cell, a cell surface, and a biopolymer. Examples of biological structures include CVDs, such as a thrombus, an atherosclerotic plaque, an atherosclerotic lesion, a tumor, and a thromboembolism. Alternatively, the stationary target can be a biopolymer. Examples of biopolymers include lipids, lipoproteins, proteins, polypeptides, and polysaccharides. If the biopolymer is a protein, it can be a protein typically present at higher concentrations in CVDs, including, for example, fibrin and collagen.

According to one embodiment of the method, a targeted MRI contrast agent is administered to a mammal. The targeted MRI contrast agent has a specific affinity for the stationary target, and the targeted MRI contrast agent is also capable of providing contrast enhancement of both the stationary target and the vascular system of the mammal. In one embodiment, the targeted MRI contrast agent's specific affinity for the stationary target, expressed as a dissociation constant, is less than 50 µM. Alternatively, the targeted MRI contrast agent's specific affinity for the stationary target, expressed as a dissociation constant, is less than 5 µM, or less than 0.5 µM.

Some targeted MRI contrast agents contemplated for use in the present invention have a specific affinity for a stationary target, including a biological component or structure present in a CVD (e.g., a thrombus, plaque, or atherosclerotic lesion), and include the fibrin binding contrast agents described in WO 01/08712 and WO 01/09188 (incorporated herein by reference in their entirety); the fibrin targeted contrast agents described in Lanza et al., Acad. Radiol. 5(suppl 1): S173-S176 (1998) and Yu et al., Magnetic Resonance in Medicine 44: 867-872 (2000); the platelet targeted particle of Johansson et al., J. Mag. Res. Imaging 13: 615-618 (2001); the $\alpha_v\beta_3$ integrin targeted agent of Sipkins et al., Nature Medicine 4(5): 623-626 (1998); the ICAM-1 targeted agent of Sipkins et al., J. Neuroimmunol. 104: 1-9 (2000); macrophage targeting for plaque or infection as described by Moore et al., JMRI 7:1140-1145 (1997); anti-myosin agents for myocardium infarcts as described by Weissleder et al., Radiology 181: 245-249 (1991); lymphocyte specific agents of Kornguth et al., J. Neurosurg 66: 8980906 (1987); plaque targeting agents of Schmitz et al., Investigative Radiology 35(8): 460-471 (2000); and the plaque targeted agent of Ruehm et al., Circulation: 415-422 (Jun. 23, 2001).

In particular, some structures of targeted MRI contrast agents contemplated for use in the methods of the present invention include the following:

Structure I:
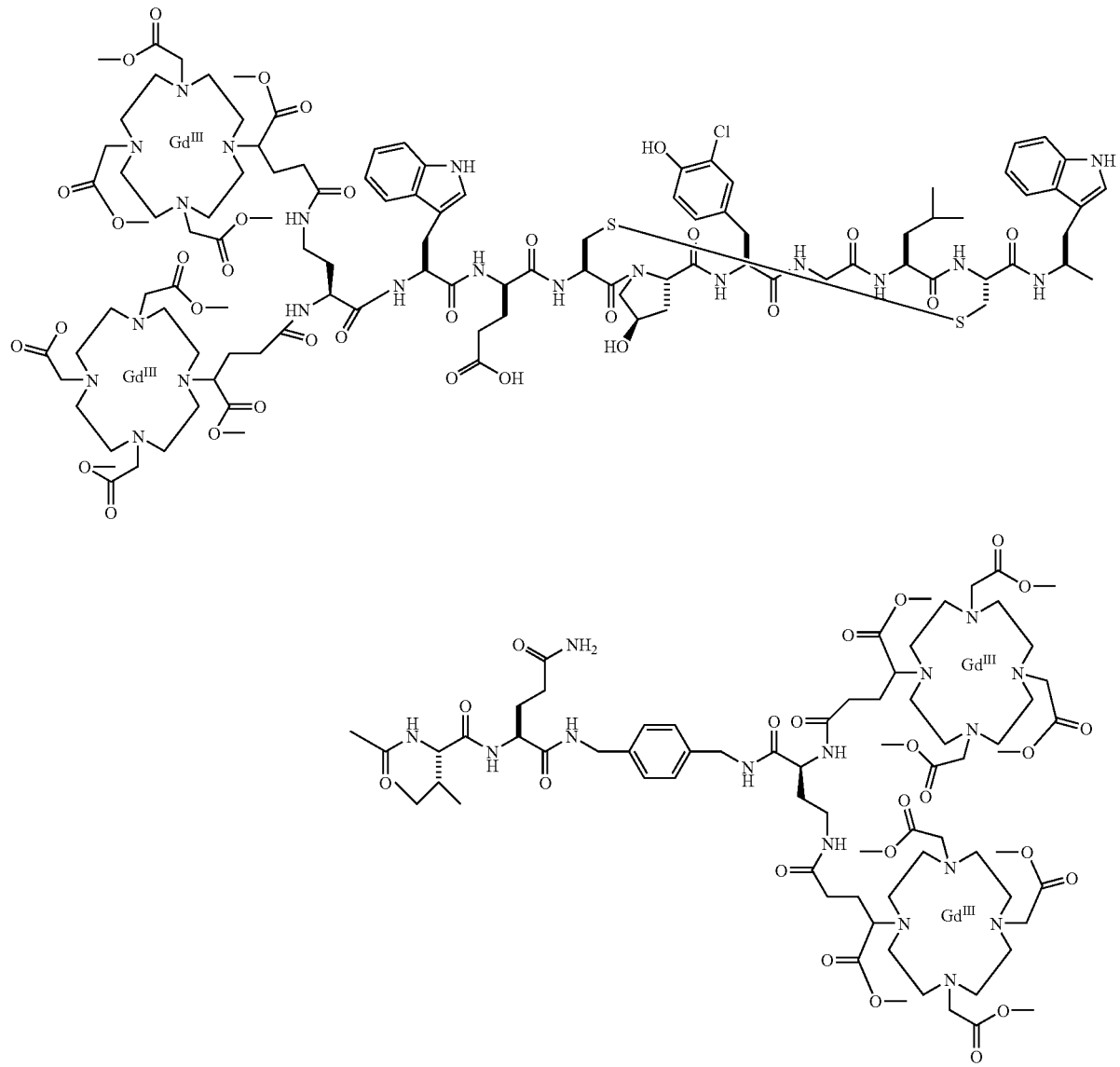

Structure II:
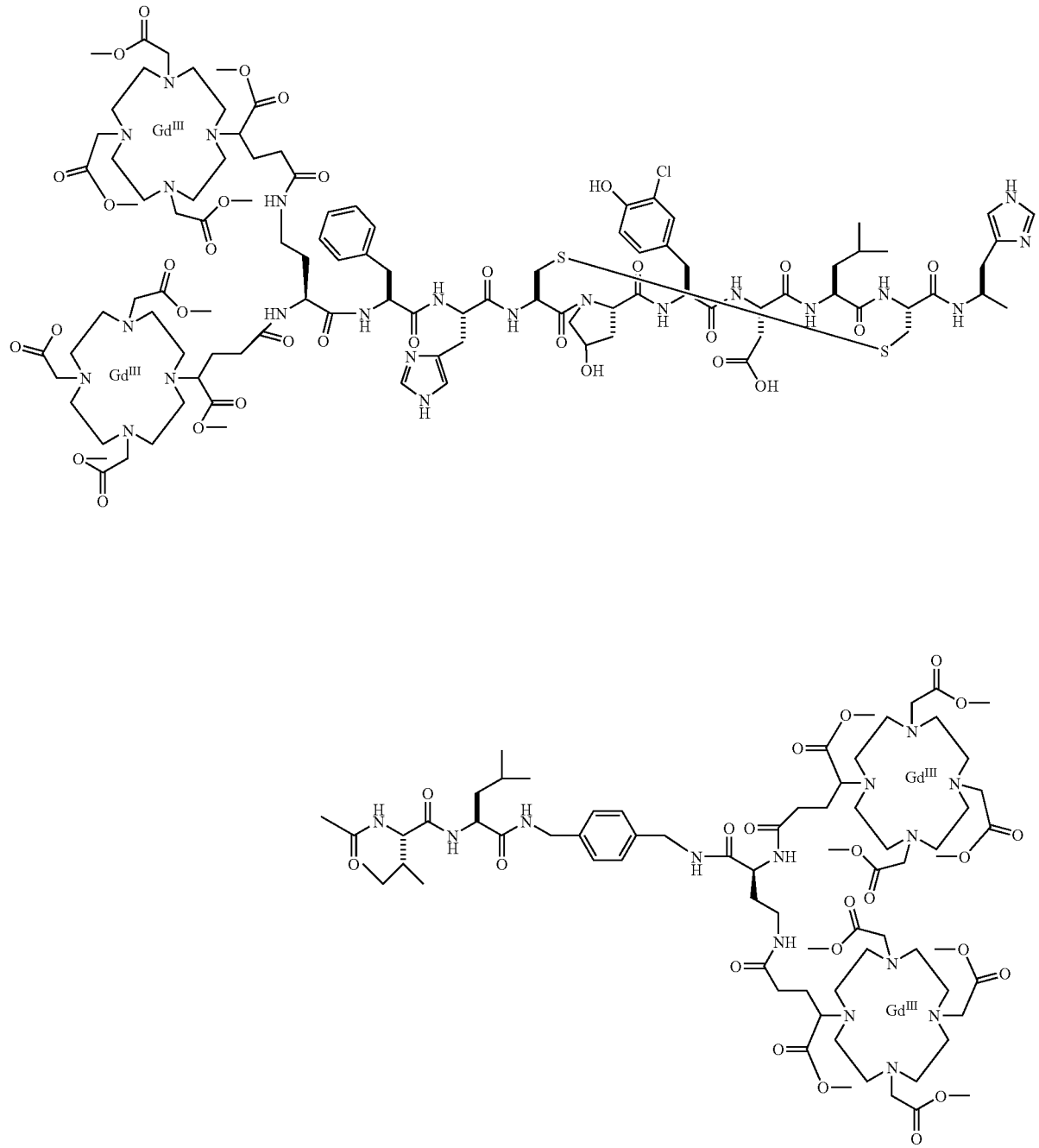

Structure III:
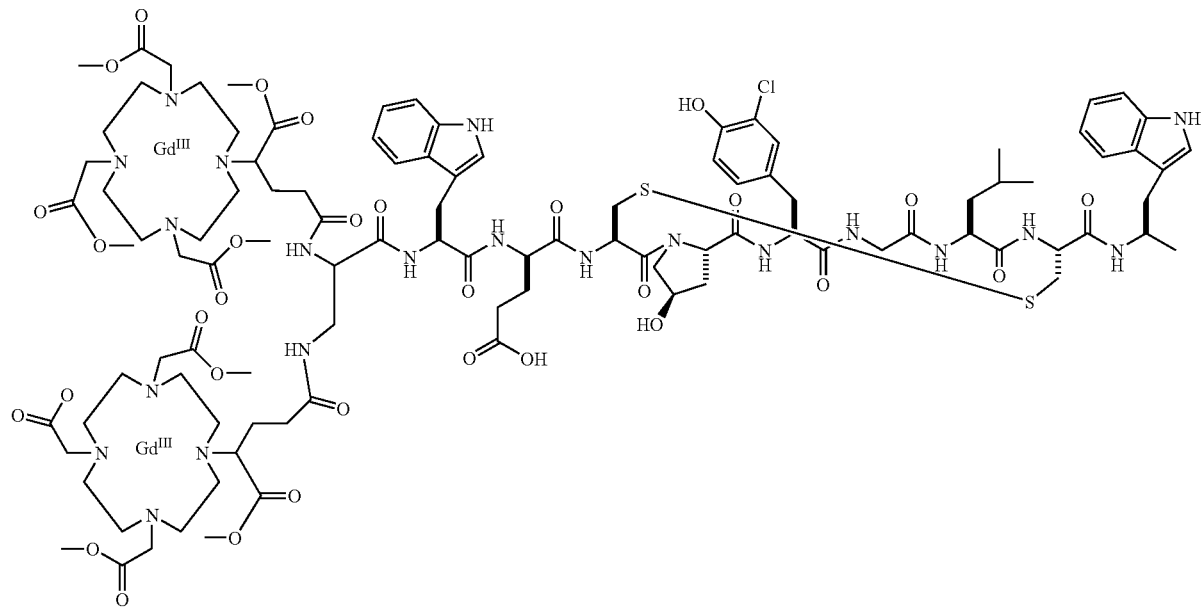
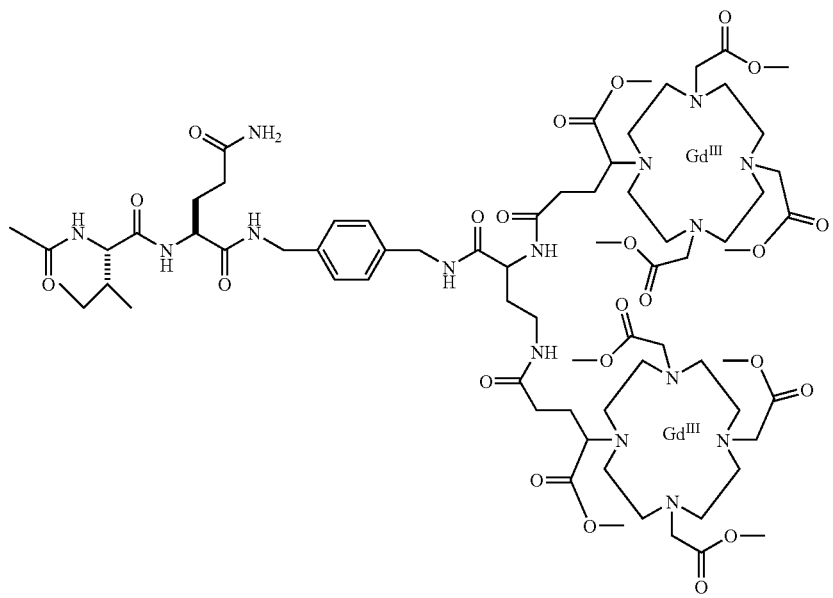

Structure IV:
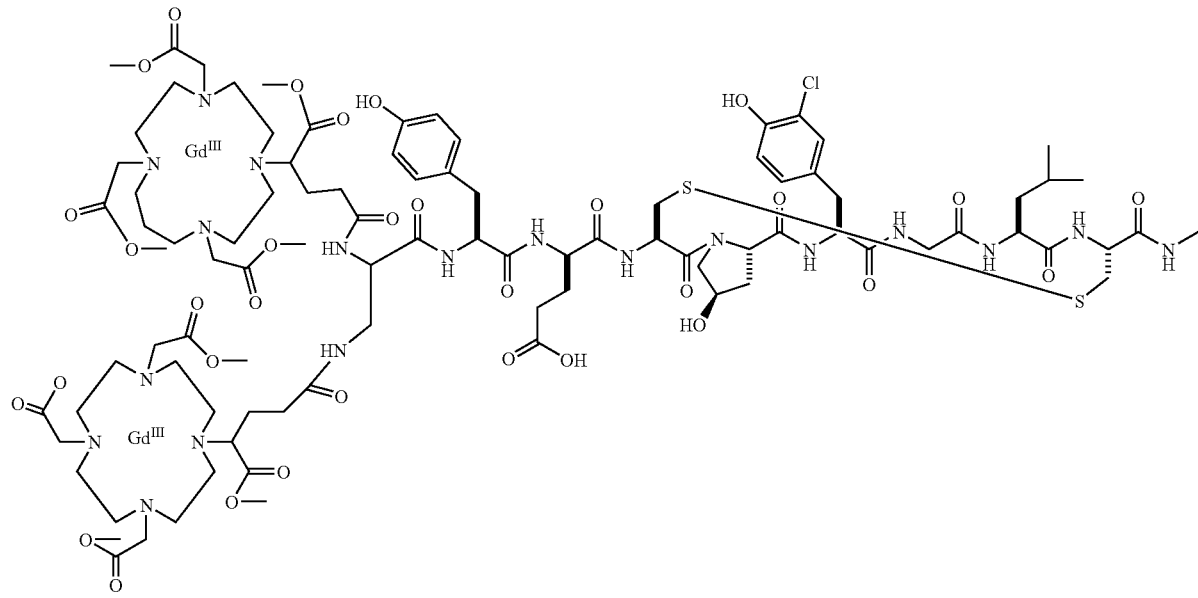
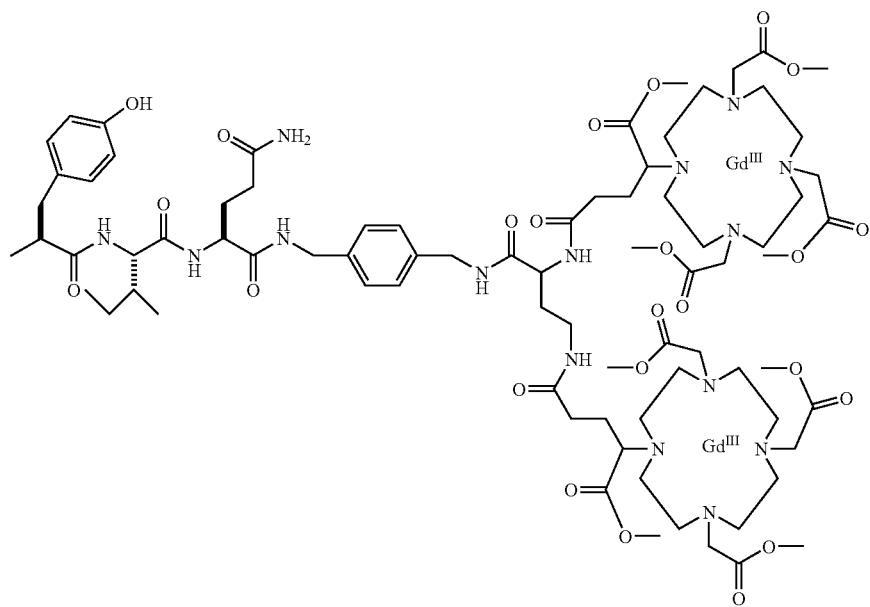

Structure V:
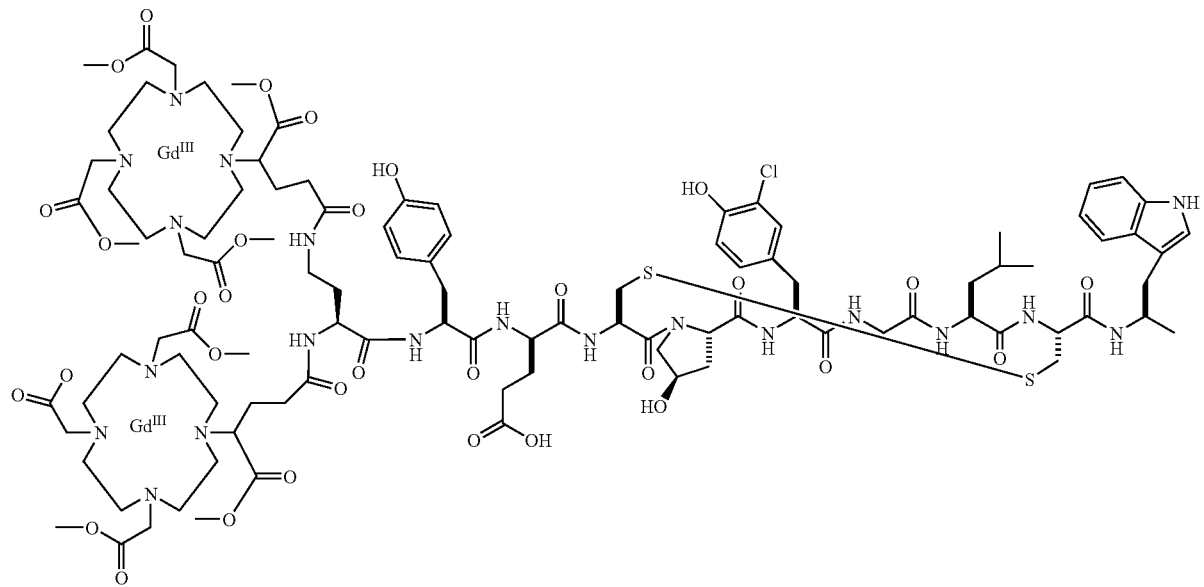
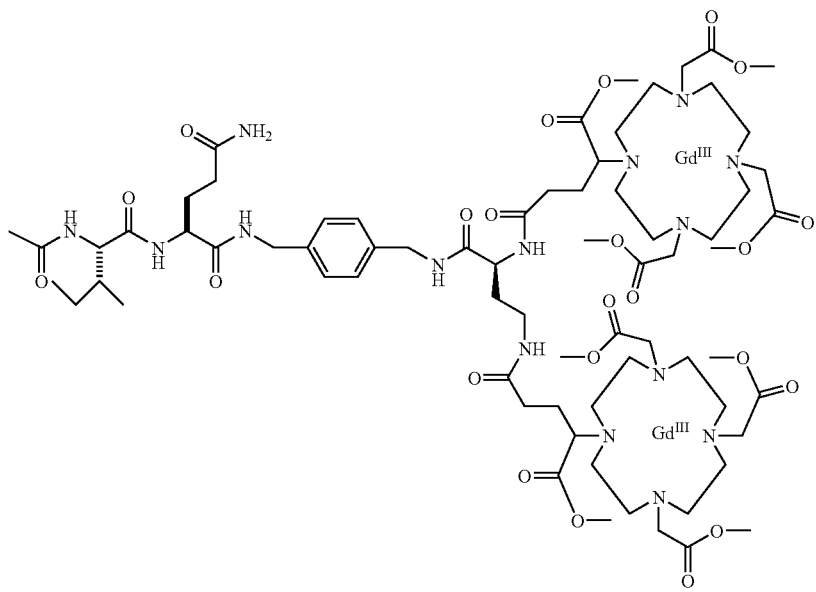

Structure VI:
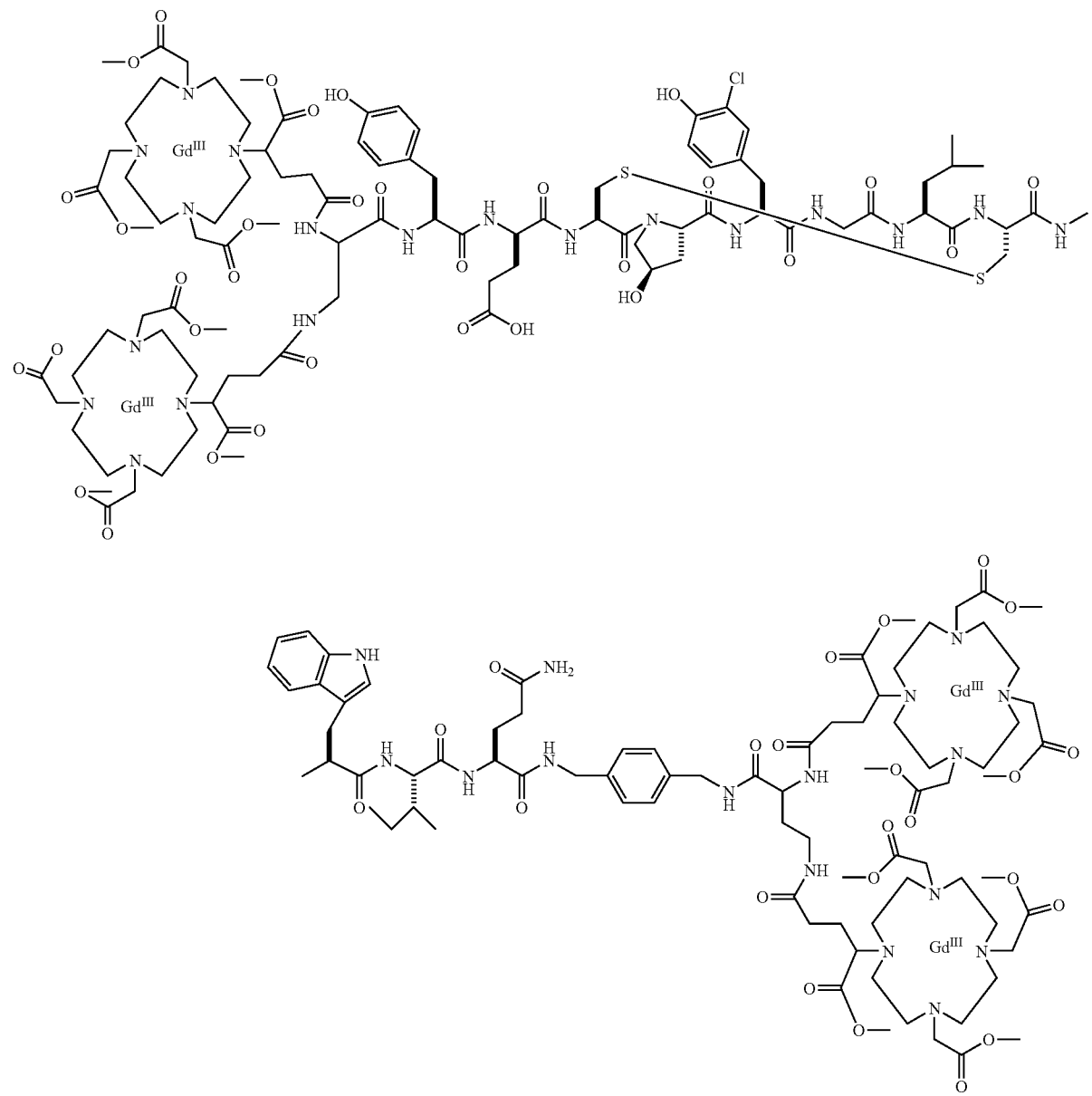

Structure VII:
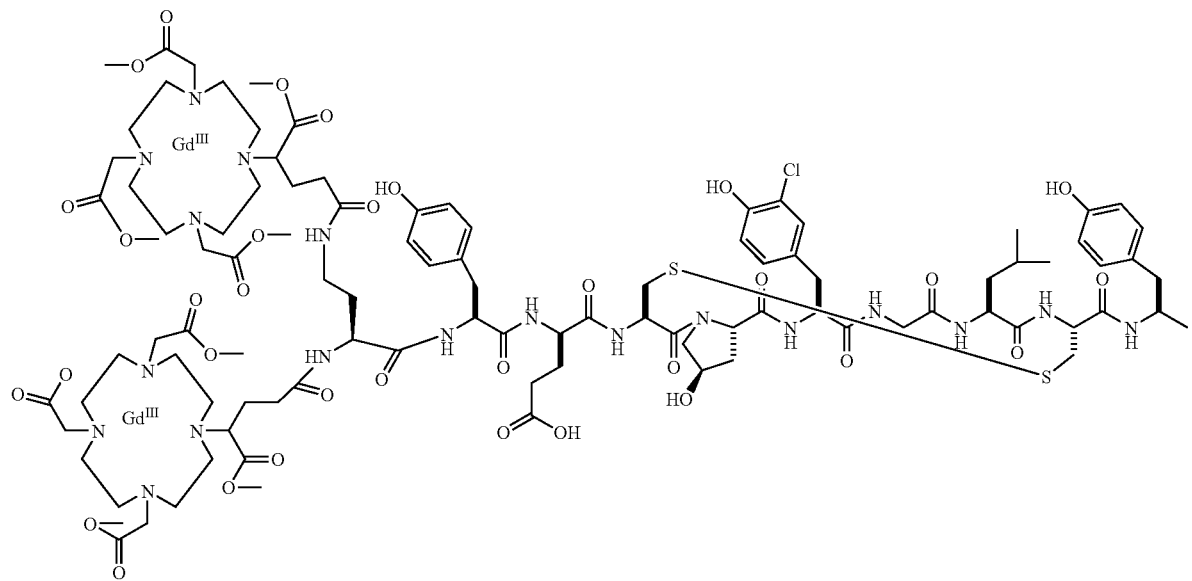
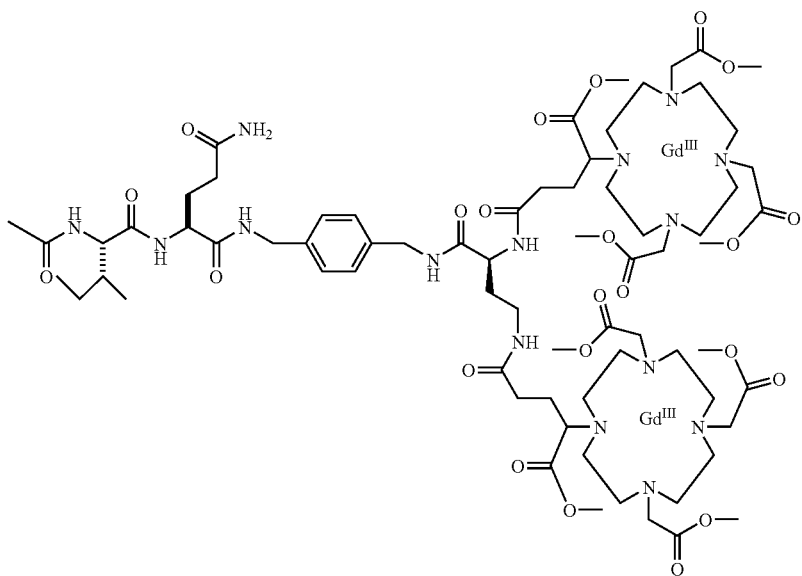

-continued
Structure VIII:
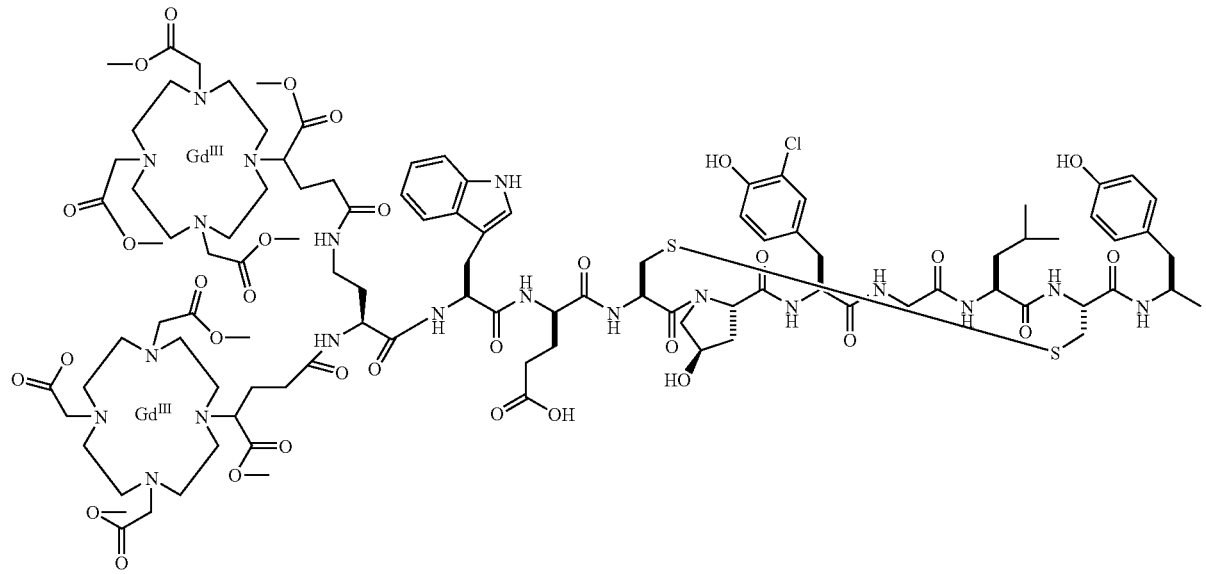
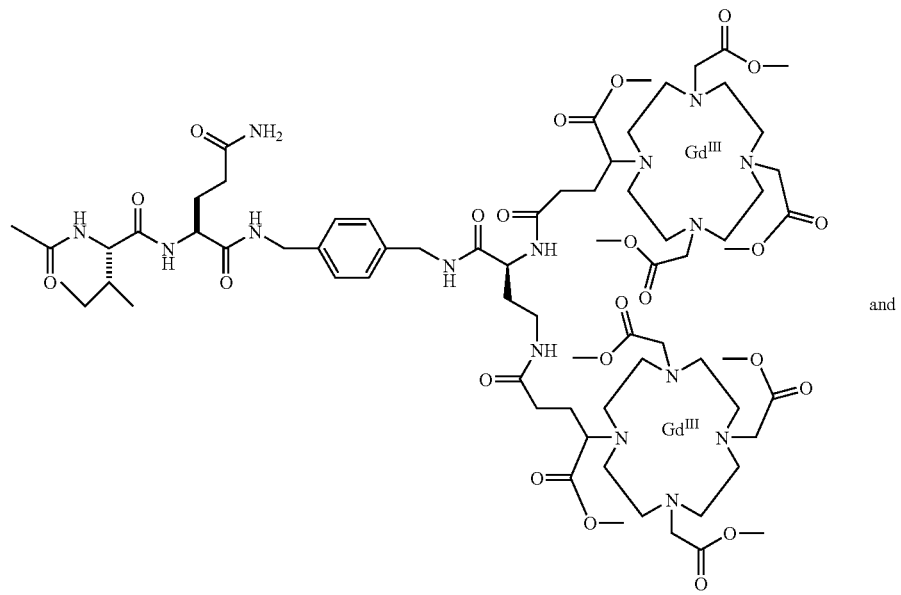
and

Structure IX:

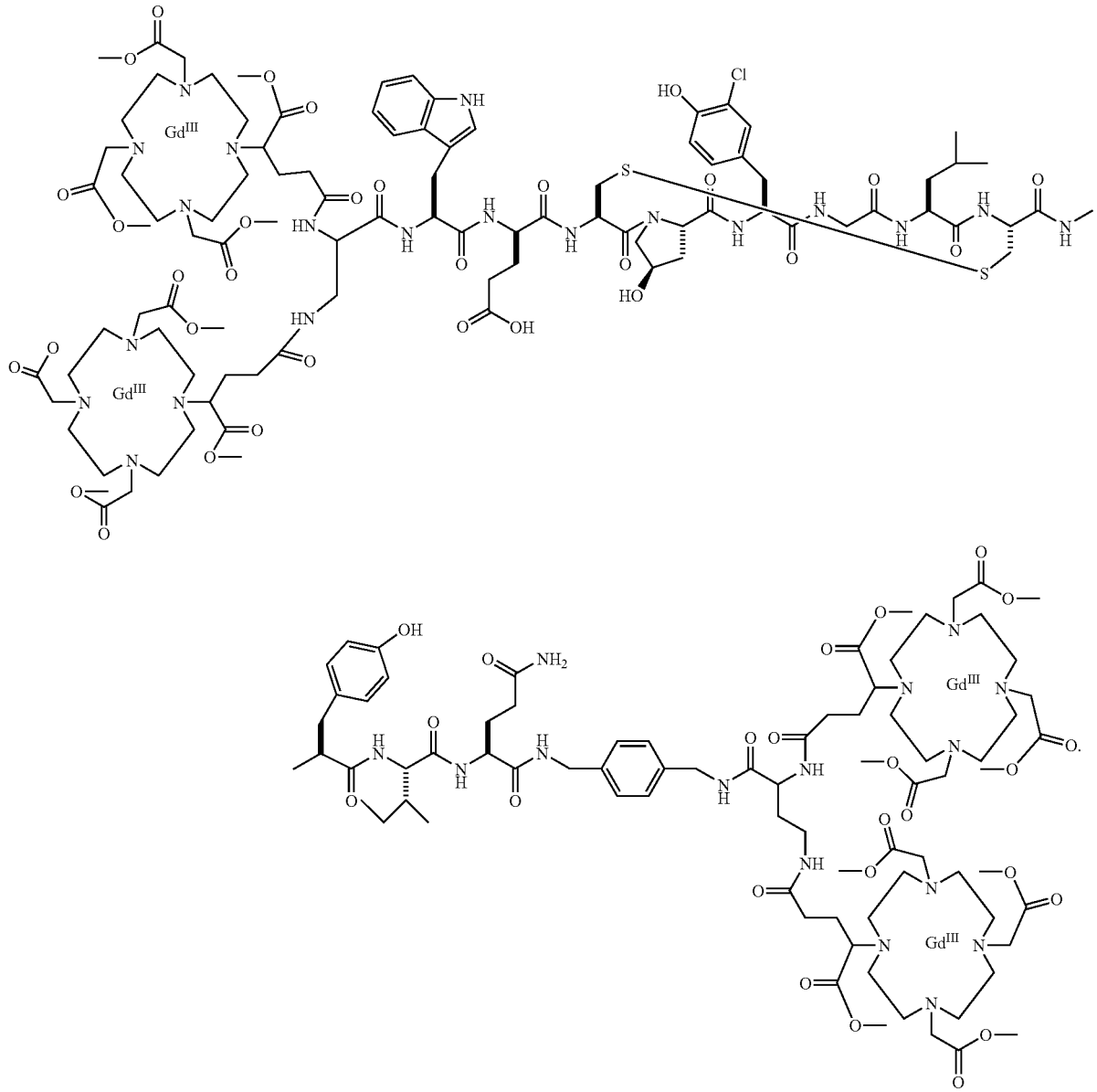

As indicated previously, Structures I-IX above are disclosed in U.S. Provisional Application "Peptide-Based Multimeric Targeted Contrast Agents," by Zhang et al., filed Jul. 30, 2001, Ser. No. 60/308,721, and in "Peptide-Based Multimeric Targeted Contrast Agents" by Zhang et al., filed concurrently herewith, U.S. Ser. No. 11/564,648, both of which are incorporated by reference herein in their entirety.

The dose of the targeted MRI contrast agent administered to the mammal may be typically much smaller than the usual dose of a MRI contrast agent used to image the vascular system. To obtain a sufficiently enhanced vascular image, the targeted MRI contrast agent should be administered at a dose sufficient to result in a blood $T_1$, i.e., the blood water proton relaxation time, of less than 500 ms. Alternatively, the targeted MRI contrast agent is administered at a dose sufficient to result in a blood $T_1$ after administration of less than 300 ms, or at a dose sufficient to result in a blood $T_1$ after administration of less than 175 ms. Typically, the targeted MRI contrast agent is administered at a dose from about 0.001 to about 500 µmol/kg. In other embodiments, the dose is from about 0.001 to about 50 µmol/kg, or from about 0.001. to about 5 µmol/kg.

At varying times after administering the targeted MRI contrast agent, a first MRI data set of an image of the vascular system is acquired. Subsequently, a second MRI data set of an image of the stationary target is acquired. The second MRI data set is acquired at a time appropriate to provide an observable level of contrast enhancement of the stationary target, if present, relative to background blood and tissue enhancement. The time in which to acquire the first and the second sets of data depends on the concentration of the targeted contrast agent in the blood, on the rate of penetration of the targeted contrast agent into the stationary target, and on the specific affinity of the targeted contrast agent for the stationary target. Such parameters, if not provided for the specific contrast agent used, can be determined by a preliminary optimization procedure involving administration of the agent and imaging the subject over time. In some embodiments, a preferred time to image the target will be when the signal intensity in the target is near its peak, or when there is maximum contrast enhancement relative to background blood and tissue enhancement.

Different MRI imaging acquisition parameters may be employed, dependent upon the area of the patient's body being visualized and on the desired view of the vascular system and the composition of the stationary target. These parameters may include the magnetic resonance (MR), pulse sequence specified in terms of the relaxation time, the repetition time (TR), the echo time (TE), the flip angle, the desired resolution and dimensions of the image, as well as the field of view.

The pulse sequence is a sequence of RF pulses used to disturb the orientation of the nuclei in the atoms being imaged. After the pulse sequence is passed through the patient, the nuclei fall back in line with the external magnetic field, and in doing so, reemit the radio-frequency energy as a signal that is detected by a receiver coil to ultimately produce the desired MRA image. The relaxation time is the time required for the nuclei to return to their normal positions. Several types of relaxation times are available, with each one resulting in different magnetization properties and conditions. Typical relaxation times include $T_1$, $T_2$, and $T_2^*$. Lastly, the repetition time (TR) specifies the time interval between applications of each RF pulse, the echo time (TE) is the time between the excitation pulse and the re-emitted echo, and the flip angle is the angle at which the nuclei shifts from its normal position.

The pulse sequence parameters should be chosen in order to specify a pulse sequence that makes the blood and vascular system appear bright. For contrast agents that make the $T_1$ of blood short (e.g, make the blood appear bright), these sequences can include, but are not limited to, $T_1$ weighted, spoiled gradient echo, or fast gradient echo. In one embodiment contemplated, the second MRI data set may be acquired using a spoiled gradient echo sequence. The choice of TR, TE, and flip angle are dependent upon the pulse sequence. For example, Prince (U.S. Pat. No. 5,417,213) describes special parameters for bright blood imaging. For contrast agents which make the blood appear dark because of magnetic susceptibility effects, such as certain iron particle based agents, an appropriate $T_2^*$ weighted imaging protocol should be used. It should be understood by one skilled in the art that many variations of pulse sequences may be used.

In one embodiment, the targeted MRI contrast agent is administered at a dose sufficient to result in a $T_1$ of the stationary target of less than 500 ms. Alternatively, the targeted MRI contrast agent is administered at a dose sufficient to result in a $T_1$ of the stationary target of less than 300 ms, or at a dose sufficient to result in a $T_1$ of the stationary target of less than 100 ms.

Generally, the vascular system and stationary target data sets are acquired within a short time period of one another. For example, the two data sets may be acquired during a single MRI session in which the subject mammal remains in the MRI scanner in the same position. In one embodiment, the single MRI session lasts for less than 6 hours. Alternatively, the single MRI session can last for less than 4 hours, or for less than 2 hours, or for less than 1 hour.

The first and second MRI data sets are then compared to determine the presence of the stationary target within the vascular system, provided that the second MRI data set had indicated the presence of the stationary target. In one embodiment, the first and second MRI data sets are displayed on a display device (e.g, side by side, or sequentially in either order) and visually compared.

Alternatively, the first and second MRI data sets can be combined to produce a third MRI data set that includes an image of both the stationary target and the vascular system. The first and second MRI data sets may be combined by registering spatially the first and second MRI data sets with respect to one another. The combining step may further include interpolating the spatial resolution of the first or the second MRI data set so that the first and second MRI data set are of equivalent spatial resolution. For example, one can determine which of the first and second data sets has the higher spatial resolution and interpolate the spatial resolution of the corresponding other data set to the higher spatial resolution. In addition, one can combine the data sets with a direct calculation of modified image intensities resulting from a combination of individual values from the so registered, interpolated data elements from the first and second data sets. In this regard, the direct calculation of modified image intensities may include variably weighting the individual values of the registered, interpolated data elements from the first and second data sets.

The third data set is capable of indicating the location of the stationary target, if present, within the vascular system. If desired, the third MRI data set may be displayed on a display device in order to indicate the location of the stationary target within the vascular system. The third MRI data set may also indicate the size and number of stationary targets within the vascular system.

A software method may be used to combine the stationary target and vascular system images together into a third MRI data set that includes the stationary target and the vascular system present in a single image. In one embodiment, the software method performs the following steps: (1) registering the first and second data sets with respect to each other, in such cases where the two data sets are not explicitly registered; (2) interpolating the lower resolution data set to the spatial resolution of the higher resolution data set, if the data sets are of different spatial resolutions; (3) creating a third data set that is a direct calculation of the modified image intensities resulting from the combination of individual values from the so registered, interpolated elements from the first and second data sets; and (4) displaying the third data set to produce a single image of the stationary target, its size and shape, and its location in relation to the vascular system image. The combined image thus aids in the visualization of the target, allowing diagnosis and further therapeutic intervention.

The registration step is performed to align anatomic structures represented within the image volumes which may or may not necessarily occupy identical regions in the separate image volumes. In cases where the images are registered implicitly (i.e., when the patient (mammal) has not moved and the MRI scans are performed in the same imaging session), there may not be a need to manipulate the data volumes for proper anatomic registration. However, in cases of patient movement or in cases where the image volumes are acquired in separate imaging sessions, registration is a necessary step. The specific method of registration of the two data sets is dependent on the method of generating the second data set. Specific algorithms to perform this registration are well documented in the literature and known to those skilled in the art. In case of sequential MR acquisitions, a simple transform using the information contained in the standard DICOM header may suffice. In other cases, registration using a commercially available package may be necessary to provide the desired accuracy. Similarly, in cases where interpolating the lower resolution data set to the spatial resolution of the higher resolution data set is necessary, any generally accepted algorithm for interpolation can he applicable.

After the two sets are interpolated to the same spatial resolution, they may be combined to create a third data set that is a direct calculation of the modified image intensities resulting from the combination of individual values from the registered and interpolated elements from the first and second data sets. The two data sets may be combined by using an algorithm such as the one described in U.S. patent application entitled "Magnetic Resonance Angiography Data" by Stefancik et al., Ser. No. 09/778,585, filed Feb. 7, 2001, incorporated herein by reference in its entirety, or other algorithms available for registering and superimposing two images generated by a MRI machine.

In addition to the particular methods and algorithms described above, there is a variety of other ways to meaningfully combine the data sets to produce images that may be medically useful. In addition to simply displaying the images side by side, they may be registered in space (to compensate for motion) using variance minimization techniques (e.g., Woods, R. P., S. R. Cherry, and J. C. Mazziotta, Rapid Automated Algorithm for Aligning and Reslicing PET Images. Journal of Computer Assisted Tomography, 1992. 16(4):620-633), or by aligning based on fiducial identification that is common to both the vascular system and targeted phases.

Alternatively, the data sets can be combined to produce a single composite image that includes both vascular system and stationary target information. This combination can be performed using grey-scale images by adding various weights of the two images together; for example, scaled to make the stationary target approximately twice as bright as the vascular image. One example of such variable weighting is the formula:

$$\text{Image}(x, y) = a(\text{Targeted-Image}(x, y)) + b(\text{Vascular-Image}(x, y)),$$

where a and b are chosen automatically based on histograms or semi-automatically using target selection from the underlying images. Alternatively, the combination of the data sets can use color maps to appropriately color code the stationary target image set information overlaid on the vascular image set.

The third data set is used as a landmark to indicate the location within the vascular system (e.g, within an artery or vein) the stationary target resides and its location with respect to anatomical landmarks such as vessel branch points. The third data set also may identify the number of stationary targets, their sizes, and their shapes. The third data set may be displayed to produce an accurate location of the target and its size and shape in conjunction within the portrayal of the vascular system.

Standard practice with MRI data is to review the data sets in their natural acquisition format, i.e., planar images of the individual acquisition slices, or to utilize a visualization algorithm to project the whole data volume into a set of representative two-dimensional images. The latter method of visualization has two primary algorithm methods in common use in MRI, the maximum intensity projection (MIP) and volume rendering (VR). Each of these algorithm methods calculates the displayed image of the data volume by methods well described in academic literature. These visualization methods are commonly available in most image review workstations.

For magnitude based images such as those commonly acquired in MRI, the displayed image is calculated by these algorithms using the magnitude of each voxel; thus the resulting displayed images are primarily reliant on the intensity differences within the MRI data volume. The combined data volume (third data set) is created to make the intensity differences between the relevant structures differentiable by these algorithms, allowing for an output image which simultaneously demonstrates the structures in question.

In addition to its specific affinity for the stationary target, the targeted MRI contrast agent may also exhibit a specific affinity for a non-stationary biological component present within the mammal's vascular system. The non-stationary biological component present within the mammal's vascular system can be, for example, a protein present within the vascular blood pool, such as human serum albumin, fibrinogen, alpha acid glycoprotein, globulins, and lipoproteins.

Referring to FIG. 1, a flowchart for using the systems and methods of the present invention to improve the visualization of a stationary target in the vascular system is set forth. At step 20, a targeted MRI contrast agent is administered to a patient suspect of having a CVD caused by a stationary target. The patient may receive the targeted agent while inside a MRI scanner, such as any MRI scanner from the ones developed by General Electric, Inc., Siemens, Philips, Marconi, and others. A computer system capable of generating two-dimensional representations of three-dimensional MRI data is also provided. Typical computer systems include General Electric's Advantage Windows, Siemens' 3D Virtuoso, and Syngo, Philips' Early Vision, Vital Image's Vitrea, and Algotec's ProVision.

After administering the targeted contrast agent to the patient, a first set of data is acquired at step 21 to produce an image of the vascular system. At step 22, a second set of data is acquired to produce an image of the stationary target itself, if one is present. The second set of data is acquired when the contrast enhancement of the stationary target should be at an observable level compared to the blood and tissue background.

At step 23, the first and the second data sets are registered with respect to each other in such cases where the two data sets are not explicitly registered. The specific method of registration of the two data sets is dependent on the method of generating the second data set. Specific algorithms to perform this registration are well documented in the literature and known to those skilled in the art. In case of sequential MR acquisitions, a simple transform using the information contained in the standard DICOM header may suffice. In other cases, registration using a commercially available package may be necessary to provide the desired accuracy.

At step 24, the lower resolution data set is interpolated to the spatial resolution of the higher resolution data set, if the data sets are of different spatial resolutions. Any generally accepted algorithm for interpolation may be applicable.

At step 25, the first and second data sets are combined to create a third data set that is a direct calculation of the modified image intensities of the first and second data sets. The two data sets may be combined by using an algorithm such as the one described in U.S. patent application entitled "Magnetic Resonance Angiography Data" by Stefancik et al., Ser. No. 09/778,585, filed Feb. 7, 2001, incorporated herein by reference in its entirety, or any other algorithm available for registering and superimposing two images generated by a MRI machine. Lastly, at step 26, the third data set is generated and displayed to indicate the location of the stationary target within the vascular system.

FIG. 1 also illustrates an alternative embodiment of a method of the present invention, wherein a second contrast agent (e.g., a vascular MRI contrast agent) is administered to the mammal (e.g., patient) at some point after the targeted MRI agent is administered. Such an embodiment may be used in cases where the specified dose of a targeted MRI contrast agent by itself is too low to elicit a sufficient change in blood $T_1$ necessary to obtain an acceptable vascular system image.

Use of a Targeted MRI Contrast Agent and a Vascular MRI Contrast Agent

It is another object of the invention to provide methods to determine the presence or absence of a stationary target within a vascular system of a mammal wherein both a targeted MRI contrast agent and a vascular MRI contrast agent are administered to a mammal, and wherein a vascular MRI and a targeted MRI data set are acquired. For example, in cases where the specified dose of a targeted MRI contrast agent is too low to elicit a sufficient change in blood $T_1$ necessary to obtain an acceptable vascular system image (see discussion above), then an additional vascular contrast agent may be administered either prior to, in addition to, or post-injection of the targeted contrast agent.

The order of administration of the two agents will vary and depends on the choice of contrast agents used. Variables include the rate of blood clearance of the vascular agent and the rate of stationary target binding by the targeted contrast agent. If the vascular contrast agent clears relatively slowly from the blood and the targeted agent localizes rapidly, then the vascular contrast agent should be administered second. If the vascular contrast agent clears rapidly from the blood and the targeted agent localizes in a relatively short period of time, then the two agents could be administered simultaneously. Alternatively, if the targeted agent takes a long time to localize, then the vascular contrast agent could be administered before the targeted contrast agent.

In some embodiments, it is preferable to acquire the data set corresponding to the targeted data set prior to the data set corresponding to the vascular system because it generally takes longer for the contrast enhanced vascular system to return to normal imaging ("brightness") levels than the time it takes for the stationary target to lose its contrast enhancement due to the presence of the targeted contrast agent.

The times in which to acquire the vascular and targeted sets of data depend on the concentration of the targeted contrast agent in the blood, on the rate of penetration of the targeted contrast agent into the target, and on the affinity of the targeted contrast agent for the target. The time to acquire the data set will usually be when the signal intensity in the stationary target is near its peak, or when the contrast enhancement relative to background blood and tissue is at an observable level, or at its highest level.

The stationary target data set may be acquired using a pulse sequence that exploits the short $T_1$ of the stationary target when the targeted agent is bound to it. For example, WO 01/08712 discloses using a spoiled gradient echo sequence with TR=36, TE=5, and flip angle of 30° to image a thrombus located in a rabbit jugular vein. If the targeted agent is based on an iron particle or some preparation which causes a shortening of $T_2$ or $T_2^*$, then an appropriate sequence is chosen to make the target hyper- or hypointense. For example, Schmitz et al. used a 3D fast low-angle-shot gradient echo sequence (TR=41, TE=11, and flip angle=15°) to image atherosclerotic plaques containing USPIOs.

The dose of the targeted contrast agent to be administered to the mammal (e.g., patient) may depend on the agent itself and its specific affinity for the stationary target, on the patient's health history, age, weight, sex, genetic makeup, and physical condition, and other factors, such as the presumed magnitude, location, and number of the stationary targets to be visualized. If the targeted contrast agent exhibits very high specific affinity for its target, then it may be administered at a relatively low dose. Dosages will ultimately be decided by medical personnel subsequent to experimental determinations of varying dosage followed by imaging as described herein. Suggested doses of a representative agent having affinity for a fibrin clot are described in WO 01/08712, incorporated by reference herein in its entirety, to visualize thrombi in the vascular system. In some embodiments, the targeted MRI contrast agent may be administered at a dose sufficient to result in a $T_1$ of the stationary target of less than 500 ms. In other embodiments, the targeted MRI contrast agent is administered at a dose sufficient to result in a $T_1$ of the stationary target of less than 300 ms, or of less than 100 ms.

The stationary target within the vascular system may be a tissue, a biological structure, a cell, a cell surface, or a biopolymer. In embodiments wherein the stationary target is a biological structure, the biological structure may be a structure associated with a CVD, e.g., such as a thrombus, an atherosclerotic plaque, an atherosclerotic lesion, a tumor, or a thromboembolism. Alternatively, the stationary target may be a biopolymer. Examples of biopolymers associated with CVDs are lipids, lipoproteins, proteins, polypeptides, and polysaccharides. If the stationary target is a biopolymer, the biopolymer is typically a protein present at high concentrations in CVDs, such as fibrin and collagen.

As above, the method includes administering a targeted MRI contrast agent to the mammal. The targeted contrast agent has a specific affinity for the stationary target and the targeted contrast agent is capable of providing contrast enhancement of the stationary target. The targeted MRI contrast agent exhibits a specific affinity for the stationary target. In some embodiments, the specific affinity of the targeted MRI contrast agent, expressed as a dissociation constant, is less than 50 µM. In other embodiments, the specific affinity is less than 5 µM. In still other embodiments, the specific affinity is less than 0.5 µM.

Suggested compounds or compositions for use as targeted contrast agents for use in the methods of the invention disclosed herein are those contrast agents identified in WO 01/08712, incorporated herein by reference in its entirety, and the compounds or compositions disclosed in U.S. Provisional Application "Peptide-Based Multimeric Targeted Contrast Agents" by Zhang et al., assigned to EPIX Medical Inc., filed Jul. 30, 2001, U.S. Ser. No. 60/308,721, and in "Peptide-Based Multimeric Targeted Contrast Agents" by Zhang et al., assigned to EPIX Medical Inc. and filed concurrently herewith, U.S. Ser. No. 11/564,648, both of which are incorporated herein by reference in their entirety.

Other targeted contrast agents contemplated for use in the present invention include fibrin targeted contrast agents as described in Lanza et al., Acad. Radiol. 5(suppl 1): S173-S176 (1998) and Yu et al., Magnetic Resonance in Medicine 44: 867-872 (2000); the platelet targeted particle of Johansson et al., J. Mag. Res. Imaging 13: 615-618 (2001); the $\alpha_v\beta_3$ integrin targeted agent of Sipkins et al., Nature Medicine 4(5): 623-626 (1998); the ICAM-1 targeted agent of Sipkins et al., J. Neuroimmunol. 104: 1-9 (2000); macrophage targeting for plaque or infection as described by Moore et al., JMRI 7:1140-1145 (1997); anti-myosin agents for myocardium infarcts as described by Weissleder et al., Radiology 181: 245-249 (1991); lymphocyte specific agents of Kornguth et al., J. Neurosurg 66: 8980906 (1987); plaque targeting agents of Schmitz et al., Investigative Radiology 35(8): 460-471 (2000); and the plaque targeted agent of Ruehm et al., Circulation: 415-422 (Jun. 23, 2001), all of which are incorporated herein by reference in their entirety.

Particular examples of targeted MRI contrast agents for use in the methods of the present invention include:
Structure I:
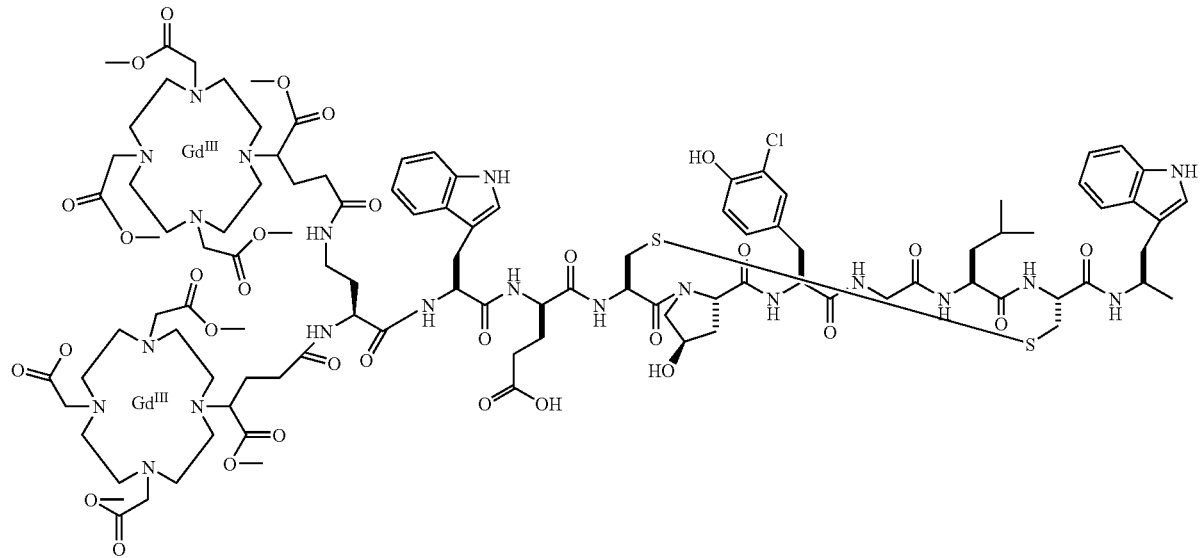
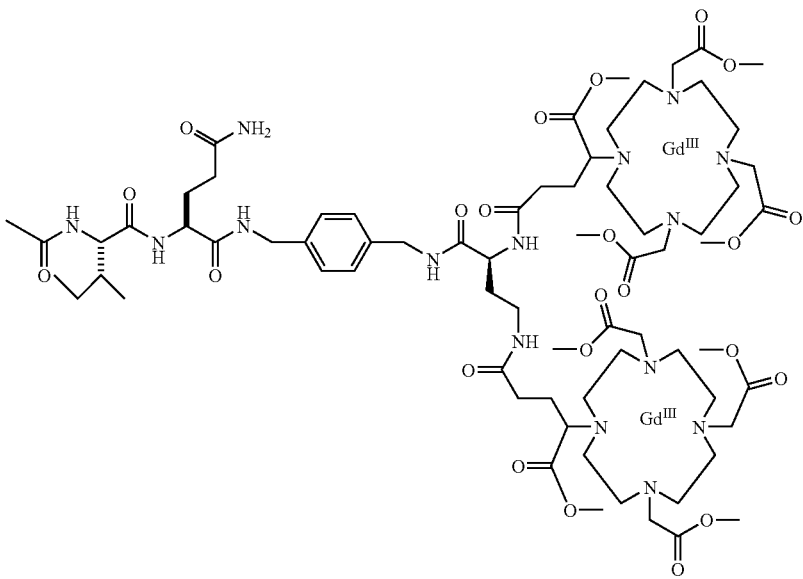

-continued
Structure II:
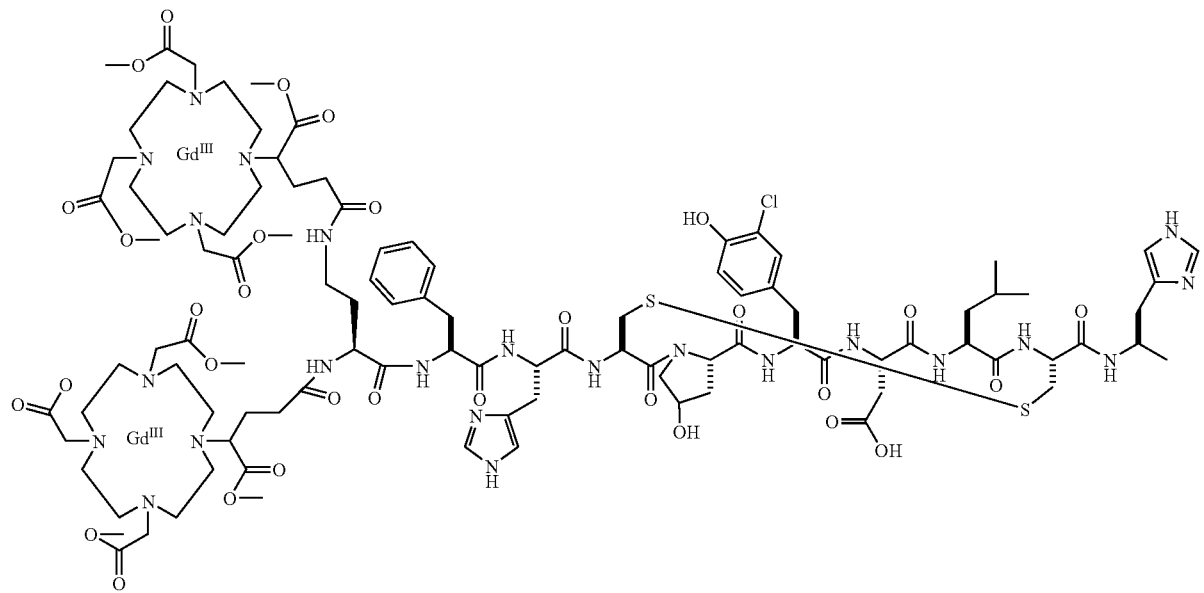
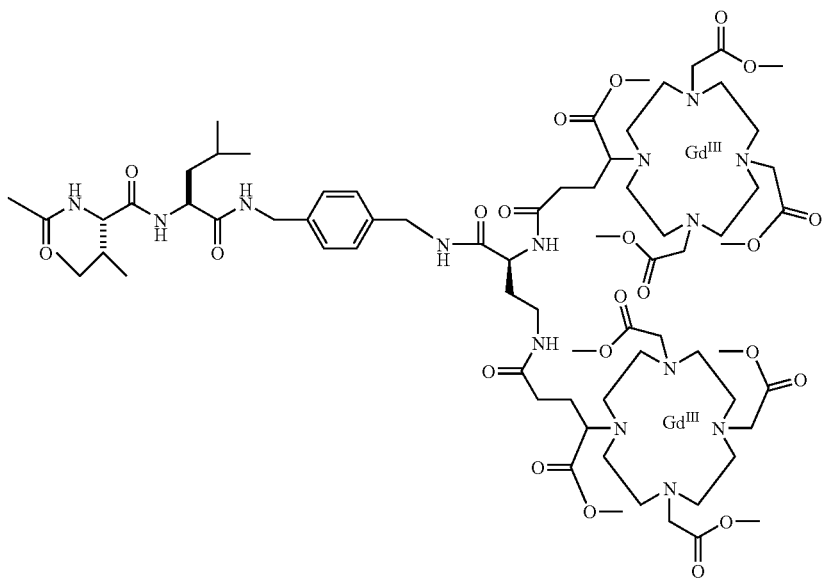

Structure III:
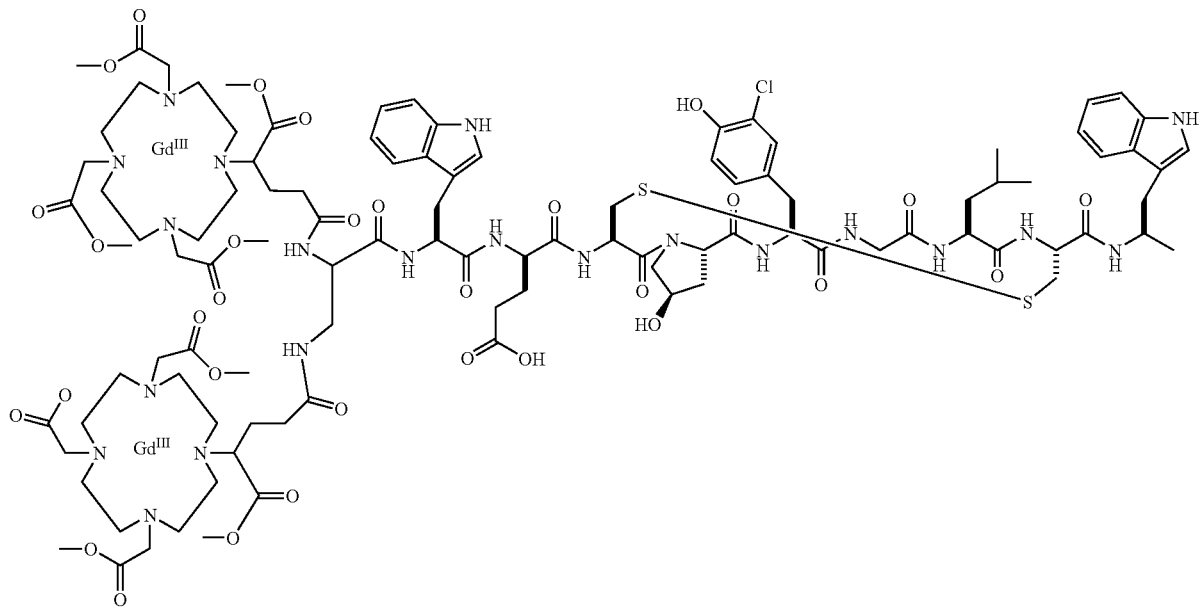
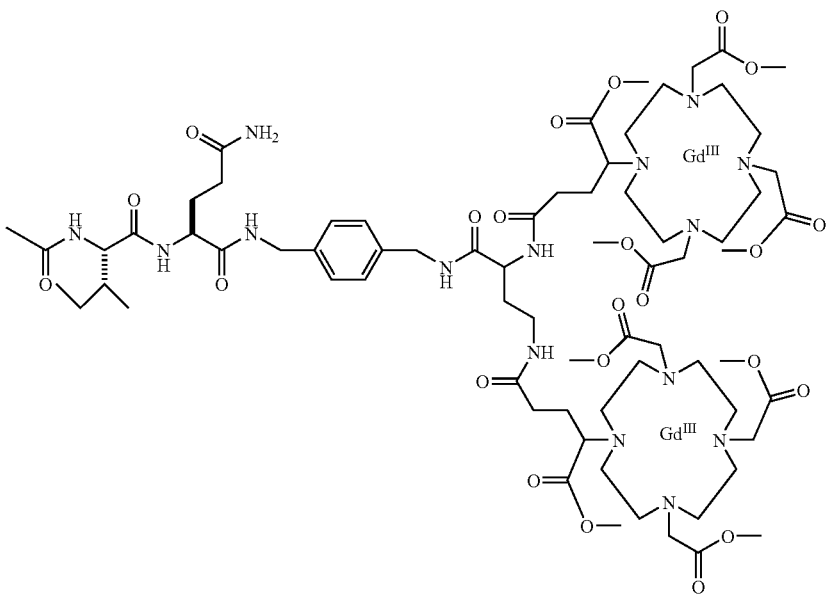

Structure IV:
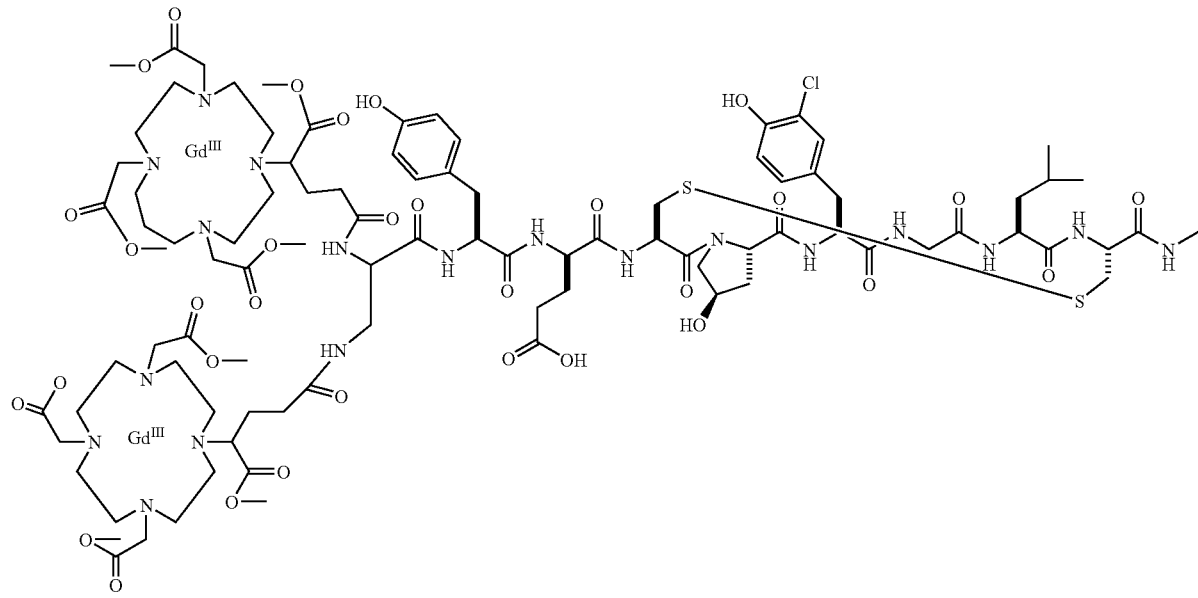
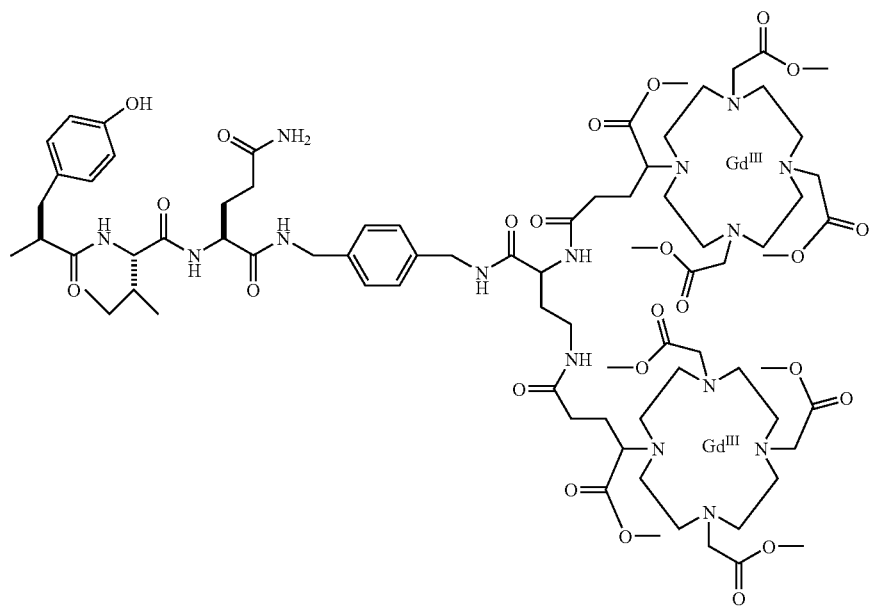

Structure V:
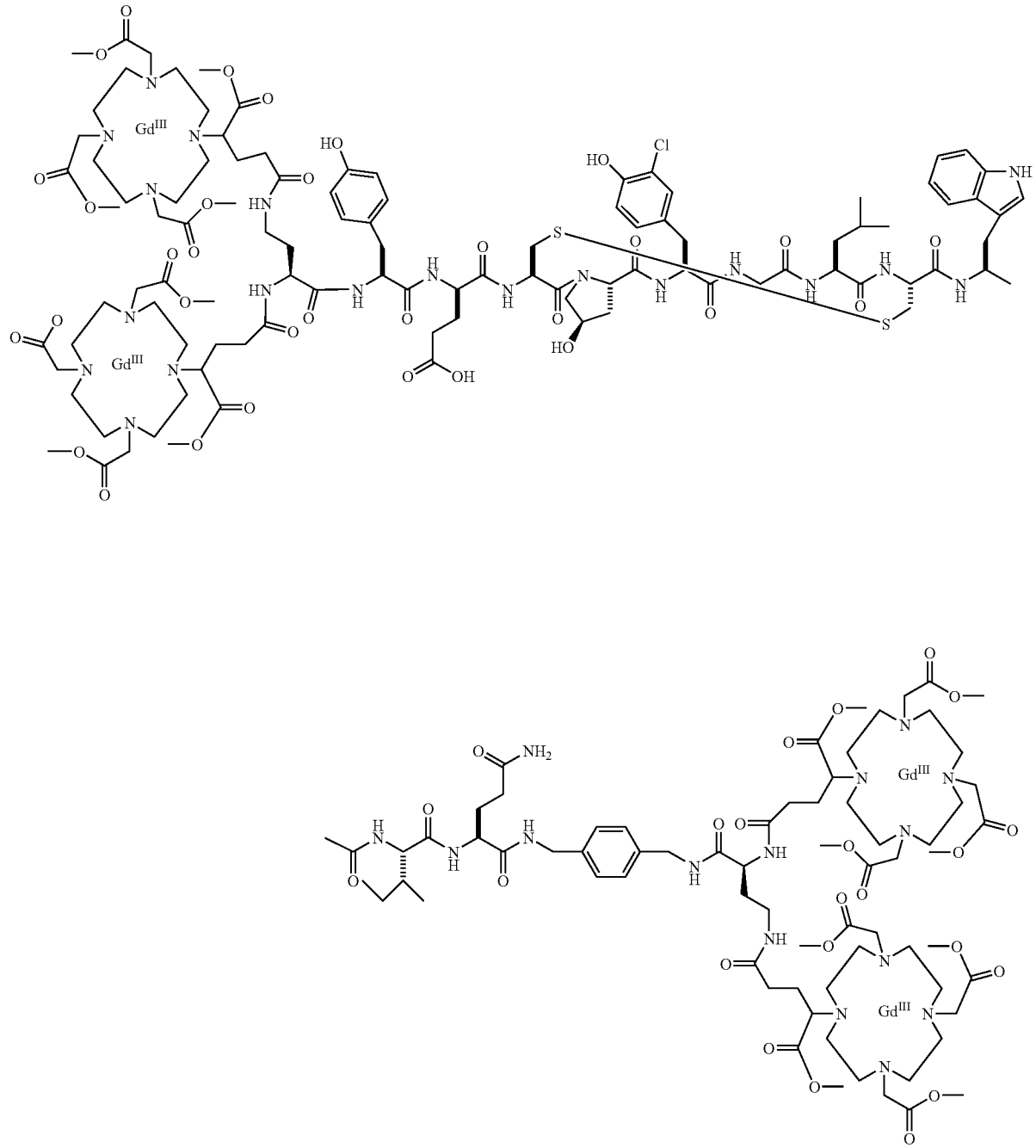

Structure VI:
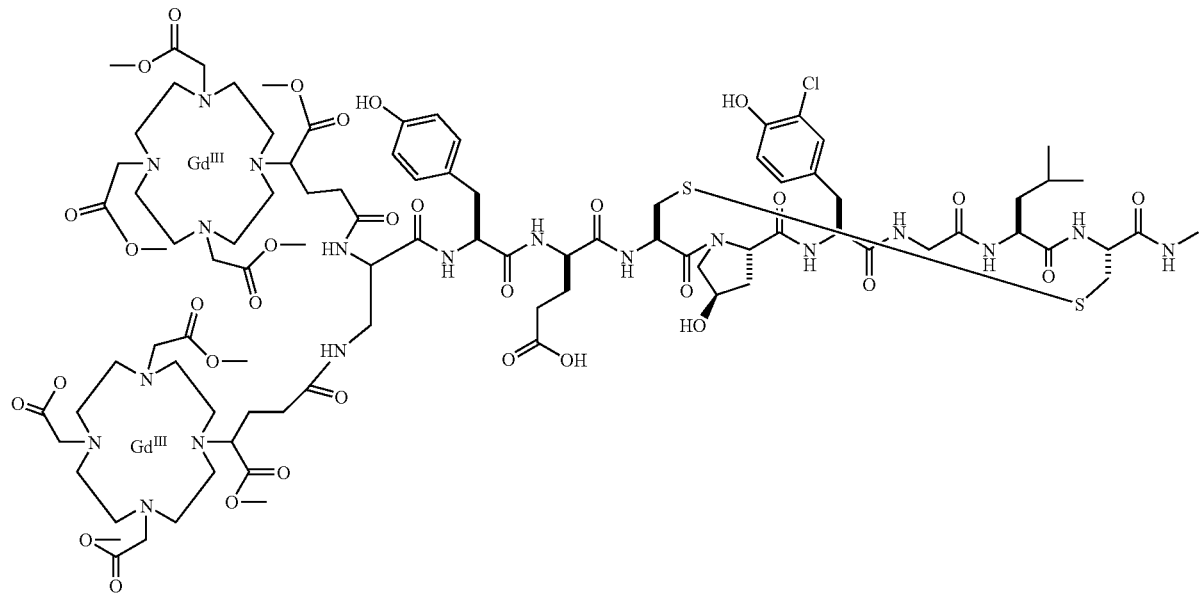
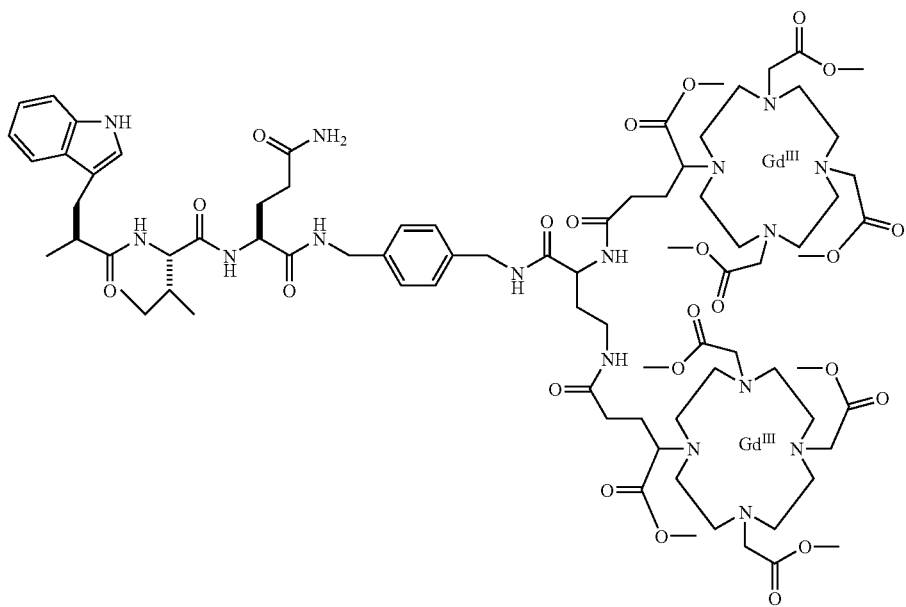

Structure VII:
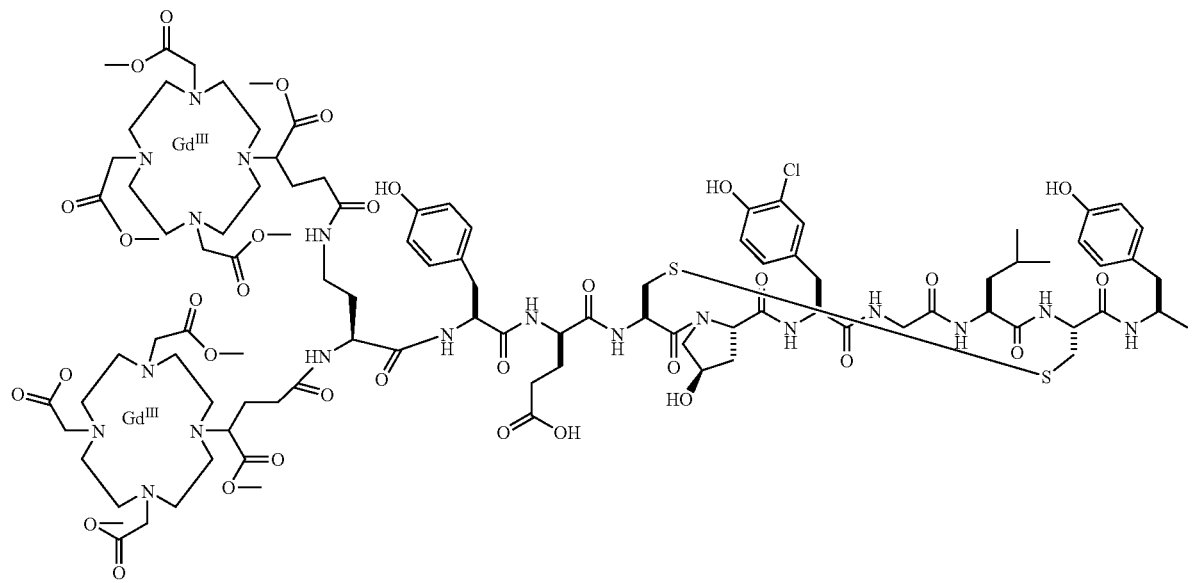
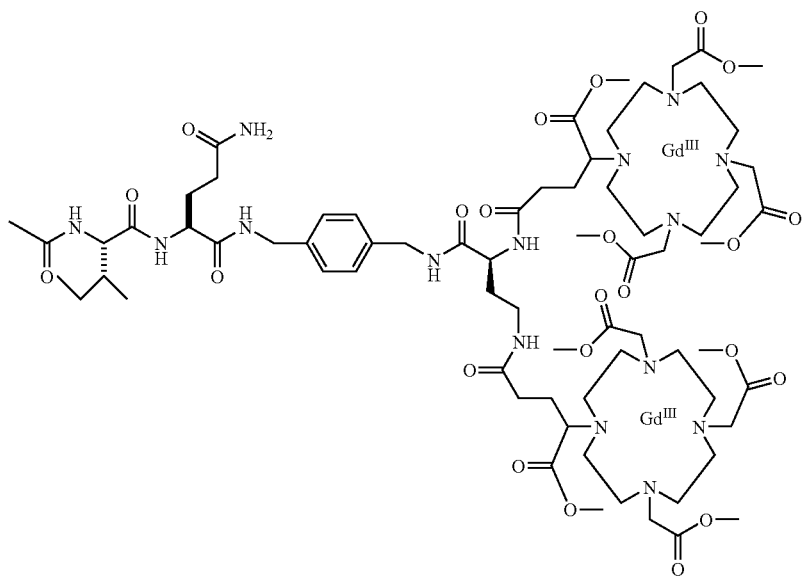

-continued
Structure VIII:
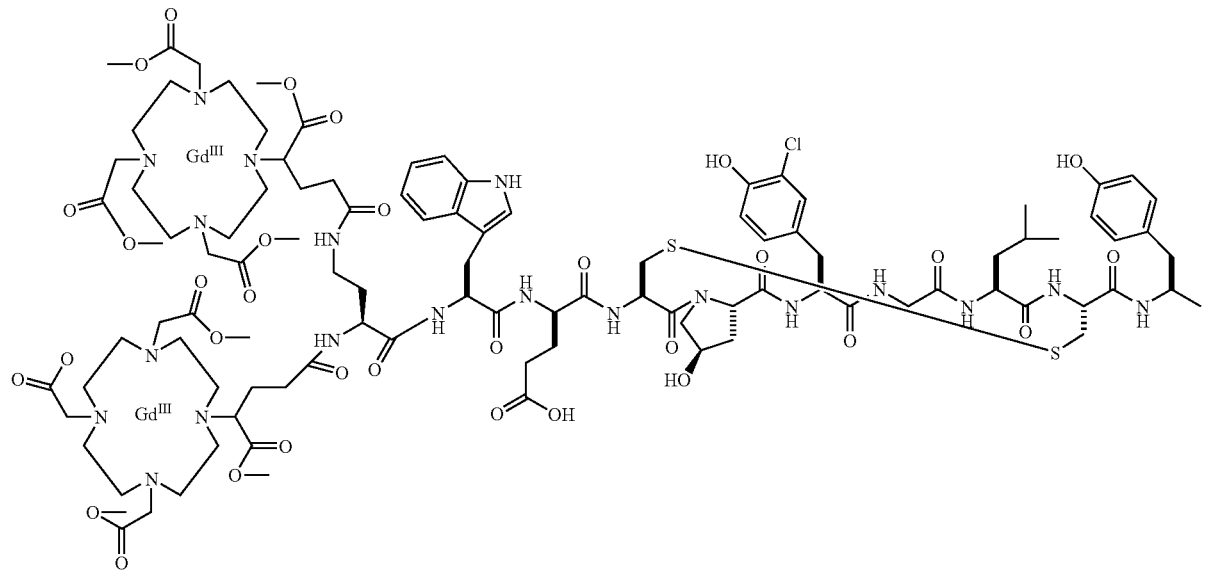
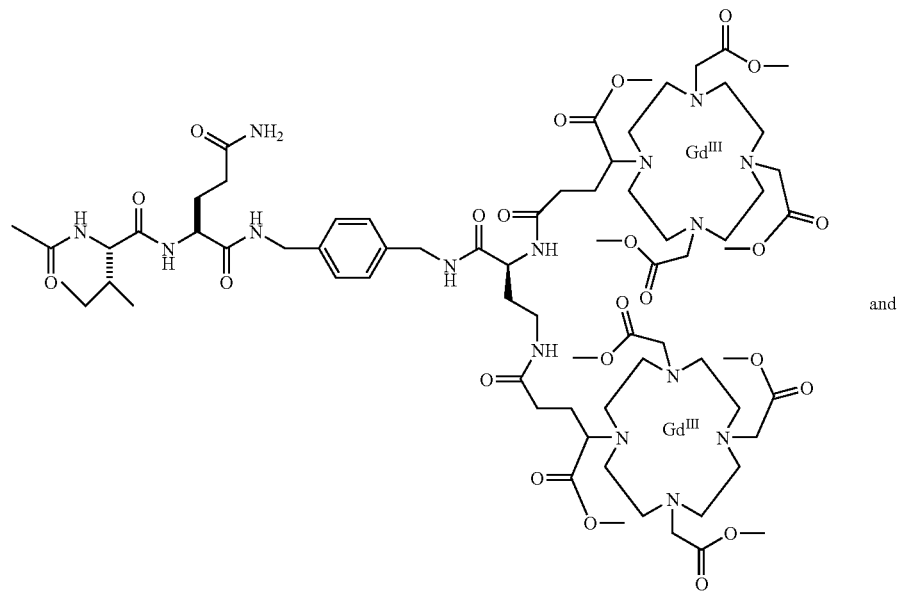 and

Structure IX:

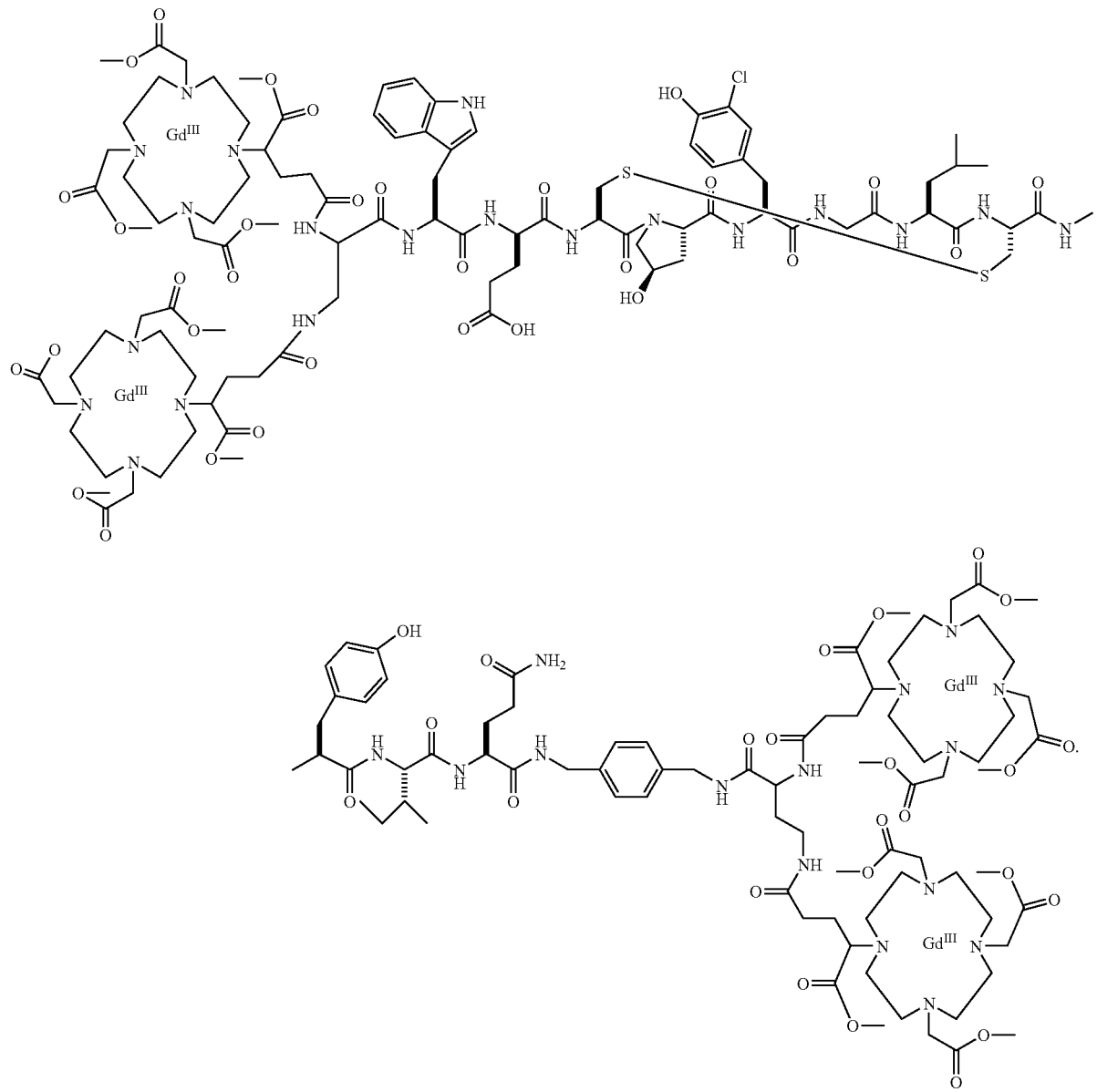

According to the method, a vascular MRI contrast agent is also administered to the mammal. The vascular contrast agent is capable of providing contrast enhancement of the vascular system of the mammal. In principle, MRI contrast agents suitable for use in imaging the vascular system include those that are currently commercially available or in clinical development, including extracellular contrast agents, particulate iron oxide contrast agents (e.g., USPIOs and MIONs), and blood pool contrast agents. Generally, contrast agents comprising gadolinium(III), cf. "Gadolinium(III) Chelates as MRI Contrast Agents: Structure, Dynamics, and Applications," P. Caravan et al. Chem. Rev. 99, 2293-2352 (1999), incorporated herein in its entirety by reference, are utilized because they are non-toxic in the large doses needed for imaging.

The vascular MRI contrast agent may be administered at a dose sufficient to result in a blood $T_1$ after administration of less than 300 ms. Alternatively, the vascular MRI contrast agent is administered at a dose sufficient to result in a blood $T_1$ after administration of less than 175 ms, or of less than 100 ms.

Some examples of extracellular contrast agents contemplated for use in the methods of the present invention include the agents known by those of skill in the art as ProHance™

(Bracco SpA) and Magnevist (Schering AG). Some structures of extracellular MRI contrast agents contemplated for use in the present invention include:

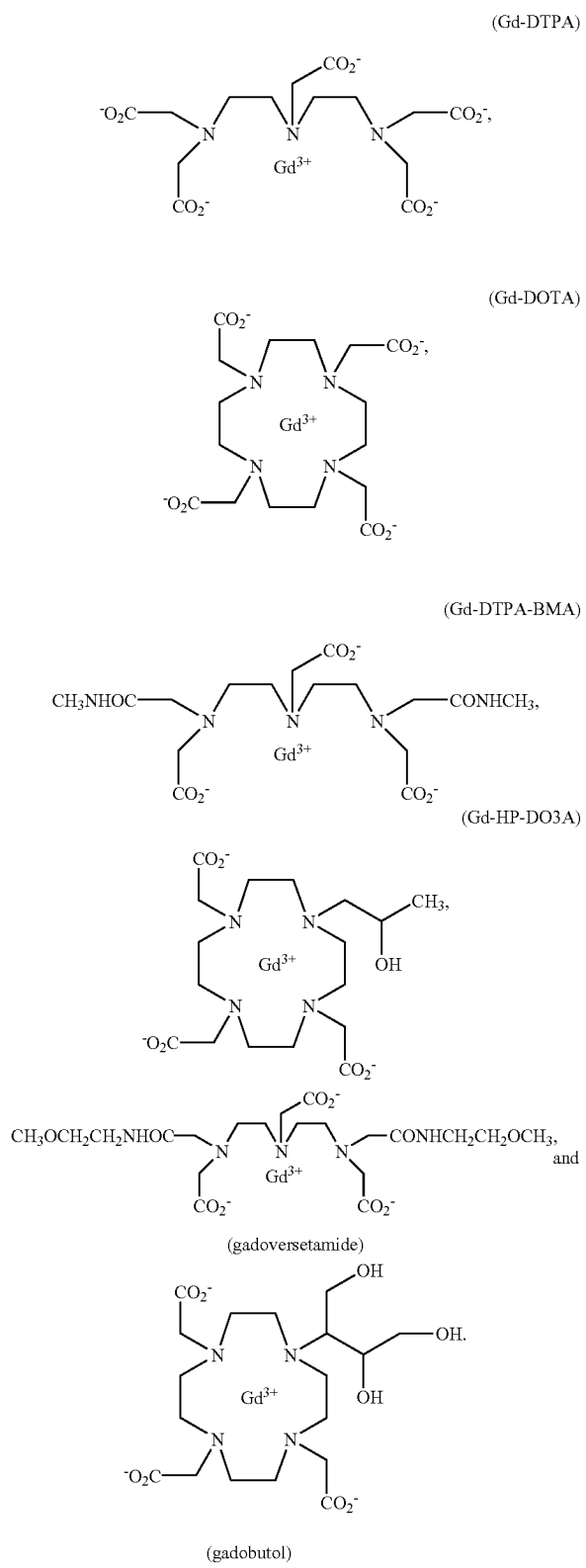

While gadolinium-based agents are generally contemplated, an iron oxide particle contrast agent also may be used to enhance (via negative contrast) the vascular system. Such agents include ultra small particles of iron oxide (USPIOs) or monocrystalline iron oxide particles (MIONs). These latter agents are iron oxide particles taken up by both the reticuloendothelial system (RES) and the mononuclear phagocytic system (MPS), resulting in a distribution in the liver, spleen, lung, and in active areas of macrophage activity, such as atherosclerotic lesions. Examples include the agent Ferridex™ (Advanced Magnetics, Inc.).

With respect to blood pool contrast agents contemplated for use in the methods of the present invention, examples include agents that are commercially sold or in development or clinical trials, including MultiHance™ (Bracco SpA); MS-325 (EPIX Medical Inc.); Eovist™ (Schering AG), and the contrast agents disclosed in U.S. Pat. Nos. 5,798,092 and 5,695,739; and 5,733,528.

It should be noted that the blood pool is a moving mobile tissue with a large total volume, e.g, about a 3 liter plasma volume in adult humans. The blood pool is also filtered through other organs such as the liver, kidney, spleen, and lungs, which affects its volume and distribution as well as the size of the blood vessels which can be imaged in those organs. While both extracellular and blood pool contrast agents will distribute throughout the vascular space, neither are designed to directly image a stationary target in the vascular system of a mammal, and generally do not exhibit specific affinity for a stationary target. For general information on "blood pool" MRI contrast agents, see "Blood Pool Contrast Agents for Cardiovascular MR Imaging" by L. J. M. Kroft et al. JMRI 10, 395-403 (1999), incorporated herein by reference, and "The Future of Contrast-Enhanced Magnetic Resonance Angiography: Are Blood Pool Agents Needed?" by A. Mühler Invest. Radiol. 33, 709-714 (1998), also incorporated herein by reference.

Other examples of blood pool contrast agents contemplated for use in the present invention include MP-2269 (Mallinckrodt, Inc.) and the contrast agents disclosed in U.S. Pat. No. 5,888,576; the contrast agents disclosed in PCT publication numbers WO 95/28179 and WO 96/23526, incorporated herein by reference in their entirety; P760 (Geurbet); Gadomer-17™ (Schering AG) and the contrast agents disclosed in U.S. Pat. Nos. 5,876,698, 5,820,849, 5,681,543, 5,650,136, and 5,364,614; Clariscan™ (Nycomed Amersham) and the contrast agents disclosed in PCT publications WO 96/09840 and WO 9725073; and B22956/1 (Bracco SpA) and the contrast agents disclosed in PCT publications WO 00/30688, WO 98/05625, WO 98/05626, WO 95/32741, WO 98/38738, WO 95/32741, and U.S. Pat. No. 5,649,537.

In particular, structures of certain blood pool contrast agents contemplated for use in the present invention include:

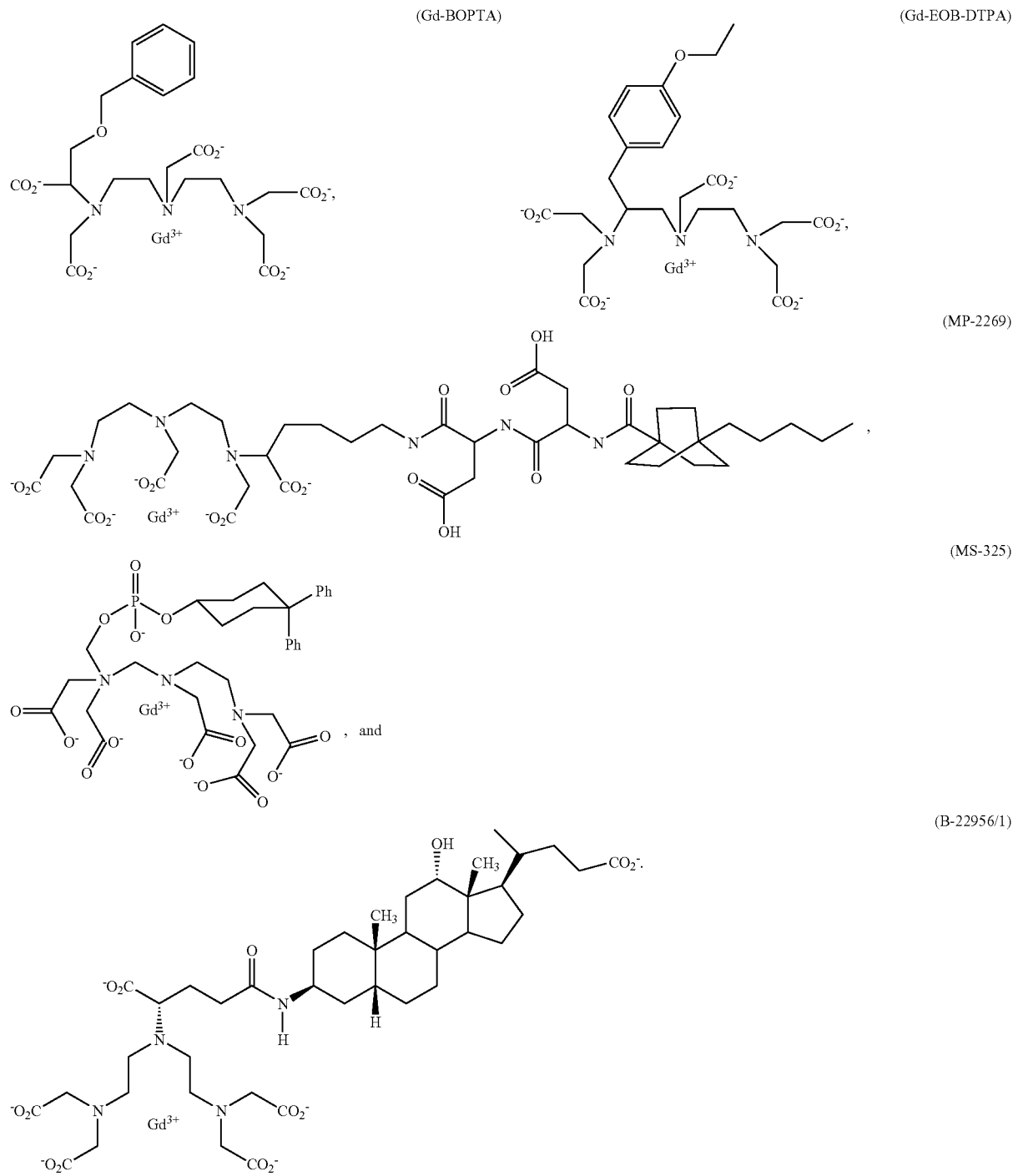

The vascular MRI contrast agent also may exhibit a specific affinity for a non-stationary biological component present within the mammal's vascular system. Examples of a non-stationary biological component present within the mammal's vascular system include proteins present in the blood and blood serum, e.g., human serum albumin, fibrinogen, alpha acid glycoprotein, globulins, and lipoproteins.

The dose of the vascular MRI agent may be affected by the method of injection and the rate of clearance of the agent from the blood pool. For example, a bolus injection (a single injection which is then distributed throughout the blood pool over time) or an injection at a rapid rate in a short time period typically results in a blood concentration of the vascular contrast agent that decreases with a bi-exponential decay. Because the $T_1$ or $T_2$ change is a function of the concentration of the contrast agent, large changes in $T_1$ or $T_2$ generally result when the contrast agent concentration is highest, resulting in a large degree of contrast. As a result, a convenient time to image the blood pool (and thus the vascular system) is shortly after administration of the vascular MRI agent when the blood concentration is high and clearance is minimal. For example, during a "dynamic" contrast MRA, imaging is performed immediately post bolus injection of a contrast agent designed to image the blood pool, e.g., MS-325.

Generally, the targeted MRI contrast agent may be administered at a dose from about 0.001 to about 500 µmol/kg (e.g., about 0.001 to about 50 µmol/kg or about 0.001 to about 5 µmol/kg) and the vascular MRI contrast agent may be administered at a dose from about 0.01 to about 300 µmol/kg (e.g., about 0.01 to about 30 µmol/kg or about 0.01 to about 3 µmol/kg), respectively. In other embodiments, the targeted MRI contrast agent is administered at a dose from about 0.001 to about 50 µmol/kg and the vascular MRI contrast agent is administered at a dose from about 0.01 to about 30 µmol/kg. Alternatively, the targeted MRI contrast agent may be administered at a dose from about 0.001 to about 5 µmol/kg and the vascular MRI contrast agent is administered at a dose from about 0.01 to about 3 µmol/kg.

In the method, both a vascular MRI data set comprising an image of the vascular system and a targeted MRI data set are acquired. The targeted data set should be acquired at a time appropriate to provide an observable level of contrast enhancement of the stationary target, if present, relative to background blood and tissue enhancement. In some embodiments, the targeted MRI data set is acquired using a spoiled gradient echo sequence.

In one embodiment, the targeted contrast agent is administered prior to the vascular contrast agent, and the targeted MRI data set is acquired prior to the vascular MRI data set. Alternatively, the targeted contrast agent and the vascular contrast agent are administered simultaneously, and the vascular MRI data set is acquired prior to the targeted MRI data set. The targeted and vascular data sets may be acquired in a single MRI session where the mammal (e.g., patient) remains in the MRI machine.

The targeted contrast agent and the vascular contrast agent may be administered within 2 hours of one another. Alternatively, the targeted contrast agent and the vascular contrast agent are administered within 30 min. of one another, or within 15 min. of one another. The vascular MRI contrast agent may be administered as a bolus or by infusion. If administered by infusion, an infusion time of less than 15 minutes may be used. In other embodiments, an infusion time of less than 10 minutes, or less than 3 minutes, is used.

The vascular and targeted MRI data sets can be compared to determine the presence of the stationary target within the vascular system, provided that the targeted MRI data set indicated the presence of the stationary target. The vascular and targeted MRI data sets also may be combined. For example, the vascular and targeted MRI data sets can be combined to produce a third MRI data set which includes an image of both the stationary target and the vascular system. The third data set is also capable of indicating the location and size of the stationary target, if present, within the vascular system. If desired, the third MRI data set may be displayed on a display device in order to indicate the location and size of the stationary target, if present, within the vascular system.

The data sets may be combined by registering spatially the targeted and vascular MRI data sets with respect to one another. The combining step also may include interpolating the spatial resolution of either the vascular or the targeted MRI data set so that the vascular and targeted MRI data sets are of equivalent spatial resolution. In one embodiment, for example, one can determine which of the vascular or targeted MRI data sets has the higher spatial resolution; and then interpolate the spatial resolution of the corresponding other data set to the higher spatial resolution. Additionally, the combining step can include a direct calculation of modified image intensities resulting from a combination of individual values from the so registered, interpolated data elements from the vascular and targeted MRI data sets. In one embodiment, the direct calculation of modified image intensities includes variably weighting the individual values of the registered, interpolated data elements from the vascular and targeted MRI data sets.

Display of the Data

Standard practice with MR data is to review the data sets in their natural acquisition format, i.e., planar images of the individual acquisition slices, or to utilize a visualization algorithm to project the whole data volume into a set of representative two-dimensional images. The latter method of visualization has two primary methods in common use in MRI, the maximum intensity projection (MIP) and volume rendering (VR). Each of these algorithms calculates the displayed image of the data volume by methods well described in academic literature. These visualization methods are commonly available in most image review workstations.

For magnitude based images such as those commonly acquired in MRI, the displayed image is calculated by these algorithms using the magnitude of each voxel; thus the resulting displayed images are primarily reliant on the intensity differences within the MRI data volume. The combined data volume (third data set) is created to make the intensity differences between the relevant structures differentiable by these algorithms, allowing for an output image which simultaneously demonstrates the structures in question.

In particular, one example of a display format is a standard grayscale MIP where the stationary target has the highest general intensity, the vascular system has a medium general intensity, and the surrounding tissues have lower general intensity. An extension of this approach would be to add color-coding to specific intensity bands, allowing for a discrimination of the structures based on their color and intensity or exclusively their color, versus the intensity differences in the grayscale MIP. Another display method is a VR representation of the data which has the stationary target having the highest intensity, the vascular system having a medium general intensity, and the surrounding tissues having the lower general intensity. Permutations on the VR representation include color-coding some or all of the intensity regions for a different visualization and/or controlling the alpha channel (opaqueness) of specific intensity bands. Controlling color and/or alpha are common VR settings and are well known to those skilled in the art.

A third example of display of the data set is planar visualization of the acquisition slices. In this case, the images displayed would be a sequence of images representing the anatomic region acquired. The intensity of the combined image could again be separated into high, medium, and low intensity for each of the primary structures to be visualized. Color coding and/or contrast/intensity manipulation will provide different embodiments of the displayed image result.

A fourth example of displaying the output data is known as the multi-planar reformat (MPR). MPR generally displays the image data in planar format; however, thickness, orientation, and spacing of the visualized region and the method of combining the component voxels into the output image can vary. MPR can utilize the intensity differences and color coding concepts outlined above to provide images with the stationary target component, the vascular system component, and the surrounding tissues with differentiable colors and/or intensities in a manner highly similar to that outlined in the previous three examples.

EXAMPLES

Example 1

In Vivo Protocol for Use of a Vascular Agent Followed by a Targeted Agent

One procedure for in vivo imaging of a stationary target within the vascular system (e.g., a thrombus) with a vascular agent (e.g., an extracellular contrast agent or a blood pool agent), and a targeted contrast agent is as follows: A 600 g guinea pig (Hartley male) is anaesthetized. An incision is made in the throat and one of the jugular veins is isolated. A 1 cm section of the jugular vein is isolated with vascular clamps. Freshly drawn blood from the animal (50 µL) is mixed with human thrombin (50 µL, 4 units) and injected into the clamped segment of the vein. Four minutes after injection, the clamps are removed and the thrombus is allowed to age for 30 minutes. GdDTPA (Magnevist®), 100 µmol/kg, an extracellular contrast agent, is injected and the throat area of the guinea pig is imaged using the following pulse sequence on a GE Medical Systems 1.5T MRI: T1-weighted SPGR, TE=3.1, TR=22, flip angle=40°. (Alternatively, a blood pool contrast agent is injected.) There is some enhancement of the vasculature immediately after injection of GdDTPA, but no enhancement of the thrombus after GdDTPA injection. After 30 minutes, GdDTPA has cleared from the blood and a stationary target (thrombus) targeted MRI agent is injected at a dose of 6 µmol/kg. The thrombus appears bright relative to the blood and vascular system and this bright image slowly fades over time to 60 minutes post-injection of the targeted agent. The data, which are implicitly registered, are combined and visualized using an Algotec Provision workstation to show the location of the enhanced thrombus within the vascular system as follows:

Using the Archives Manager, the vascular image series is selected, then the stationary target image series is selected as Series 1 and Series 2, respectively.
Under the 'Processing' menu, select 'Combine Images'.
In the pop-up menu, choose 2 for 'Images to Combine'.
In the pop-up menu, enter appropriate values for Series 1 and Series 2.
Perform the image combination and save the images in the desired location

Example 2

In Vivo Protocol for Use of a Targeted MRI Contrast Agent to Image the Vascular System and the Stationary Target The procedure for in vivo imaging of the vascular system and a stationary target thrombus with a thrombus-targeted contrast agent is as follows: A 600 g guinea pig (Hartley male) is anaesthetized. An incision is made in the throat and one of the jugular veins is isolated. A 1 cm section of the jugular vein is isolated with vascular clamps. Freshly drawn blood from the animal (50 µL) is mixed with human thrombin (50 µL, 4 units) and injected into the clamped segment of the vein. Four minutes after injection, the clamps are removed and the thrombus is allowed to age for 30 minutes. A thrombus-targeted contrast agent as described herein (10 µmol/kg, 40 µmol Gd/kg) is delivered via a catheter in the carotid artery and the animal is imaged using the following pulse sequence on a GE Medical Systems 1.5T MRI: T1-weighted SPGR, TE=3.1, TR=22, flip angle=27°. Initially the blood appears brighter than the thrombus. With time the signal in the blood decays, whereas the signal intensity in the thrombus persists such that the thrombus appears bright relative to the blood. The early phase vascular system data and the data acquired later showing thrombus enhancement, which are implicitly registered, are combined and visualized using an Algotec Provision workstation to show the position of the enhanced thrombus within the vascular system as above.

Example 3

Figure 2A:
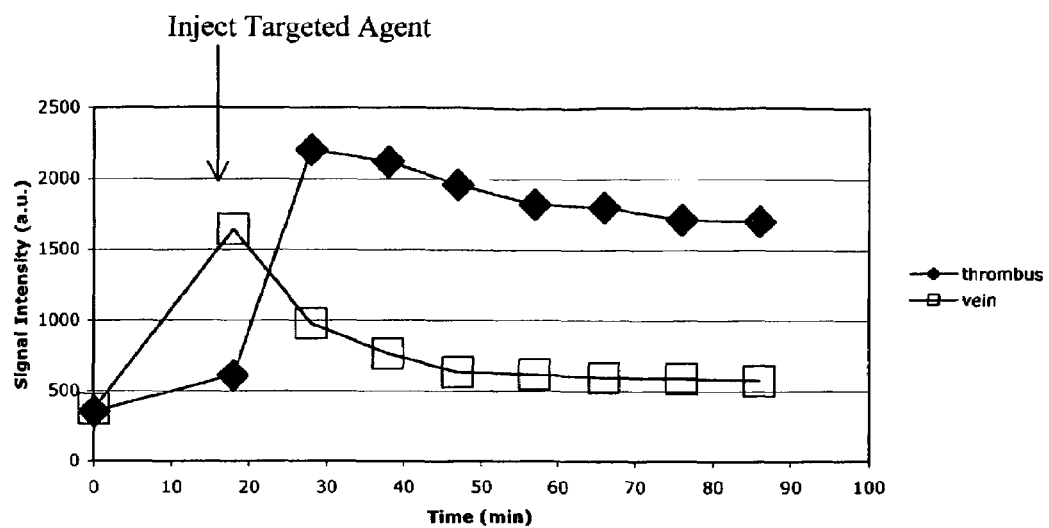
FIG. 2A is a graph showing the signal intensity (arbitrary units, a.u.) of targeted contrast agent present in the vascular system (e.g., vein) or bound to the stationary target (e.g., thrombus) versus time when a dose of the targeted contrast agent appropriate to enhance both the stationary target and the vascular system (e.g., vein) is administered to the patient.

Analysis of Signal Intensity in the Vascular System and at the Stationary Target Upon Use of a Targeted Agent Alone FIG. 2A demonstrates the signal intensity (a function of concentration) at a stationary target and in the vascular system versus time when a targeted contrast agent is used to image both the vascular system and the stationary target. The graph shows that immediately after injection of the targeted contrast agent, there was not a significant concentration of contrast agent present at the stationary target thrombus, followed by a period of time when the concentration of targeted contrast agent at the stationary target increased. This time period depends on the rate of penetration of the agent into the stationary target and the specific affinity of the agent for the stationary target. The concentration of the targeted agent at the stationary target then decreased. Thus the signal intensity at the stationary target rose, reached a maximum, and then fell. One preferred time to acquire an image of the stationary target would be when the signal intensity in the stationary target is near its peak and signal intensity from the targeted agent in other surrounding tissues is minimal.

In reality the targeted contrast agent is present in the blood (vascular system, e.g., vein) and at the stationary target simultaneously. If an imaging data set is acquired at a short time after injection, then the signal intensity of the blood will be comparable to, or greater than, the signal intensity of the stationary target. The graph demonstrates this signal enhancement of the vascular system prior to significant enhancement of the stationary target. This earlier data set would give an angiogram—an image of the vascular system. Since the stationary target in such an image may be obscured by the bright blood surrounding it, this image alone would not be an optimal image for detecting the stationary target. If a second imaging data set were to be acquired at a time when the signal in the blood approached baseline levels, but the signal intensity in the stationary target were still high, as shown in the graph, then the stationary target to vascular system contrast should be high. The second imaging data set would image the stationary target. By comparing the two data sets, the relationship between the target and the vascular system would be better ascertained.

Example 4

Figure 2B:
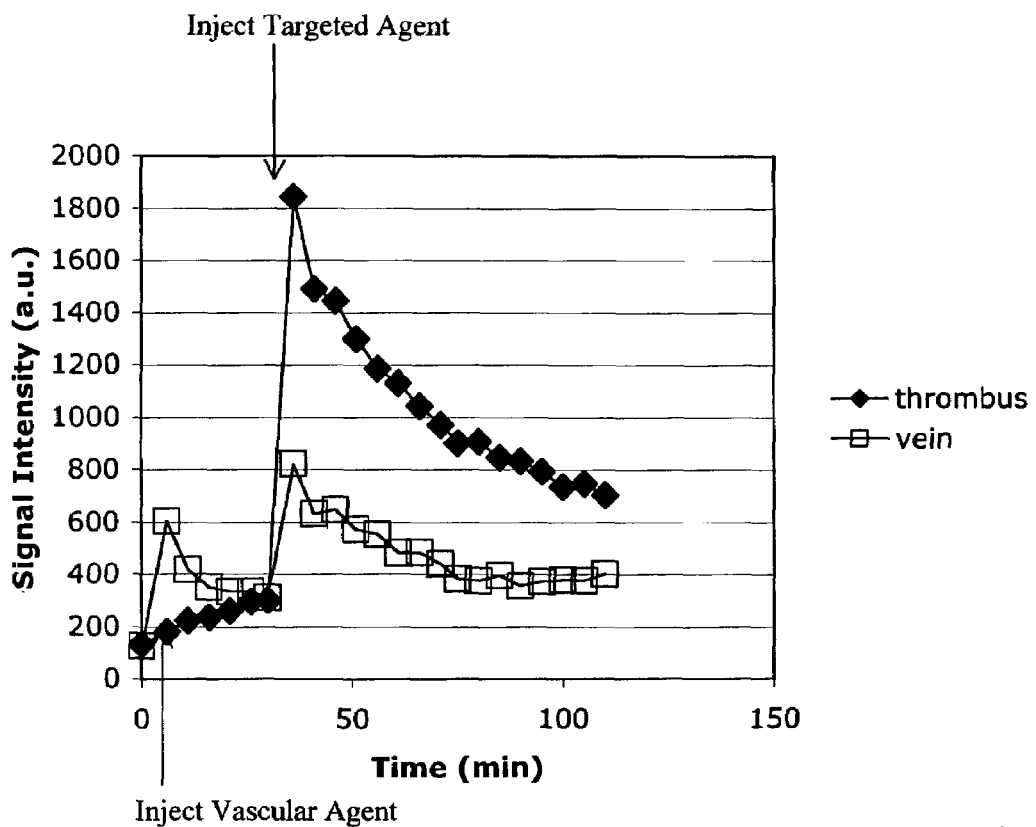
FIG. 2B is a graph showing the signal intensity (arbitrary units, a.u.) versus time for the vascular system and a stationary target when the vascular contrast agent is administered before the targeted contrast agent.

Analysis of Signal Intensity in the Vascular System and at the Stationary Target Upon Use of a Vascular Agent Followed by a Targeted Agent FIG. 2B demonstrates a graph showing the signal intensity (a function of concentration) at a stationary target and in the vascular system versus time when a targeted contrast agent is administered to the patient following the administration of a vascular agent. The graph shows that immediately upon injection of the targeted contrast agent, there is no significant intensity of the stationary target (thrombus) due to the targeted contrast agent being present at the stationary target, followed by a period of time when the concentration of targeted contrast agent at the stationary target increased. This period of time depends on the rate of penetration of the agent into the stationary target and the specific affinity of the targeted agent for the stationary target. After this point, the targeted agent concentration at the stationary target decreased. Thus, the signal intensity of the stationary target rose, reached a maximum, and then fell. One preferred time to image the stationary target would be when the signal intensity in the stationary target is near its peak and signal intensity from the targeted agent in other surrounding tissues is minimal.

In reality, the targeted contrast agent is present in the vascular system (e.g., vein) and at the stationary target simultaneously. Due to the low dose of targeted contrast agent administered, however, the signal intensity of the blood may be too low to produce a clear image of the vascular system. An extracellular or blood pool vascular contrast agent may be administered to the patient prior to, in conjunction with, or after administering the targeted contrast agent to the patient in order to provide an image of the vascular system. In the graph shown, the vascular agent is administered prior to injection of the targeted contrast agent. An image of the vascular system may be acquired while the signal intensity of the vascular system is enhanced due to the presence of the vascular agent. After clearance of the vascular agent and concomitant reduced signal enhancement of the vascular system, the targeted agent was then injected to image the stationary target.

Example 5

Embodiment of a Method of Combination of Data Sets

Figure 3:
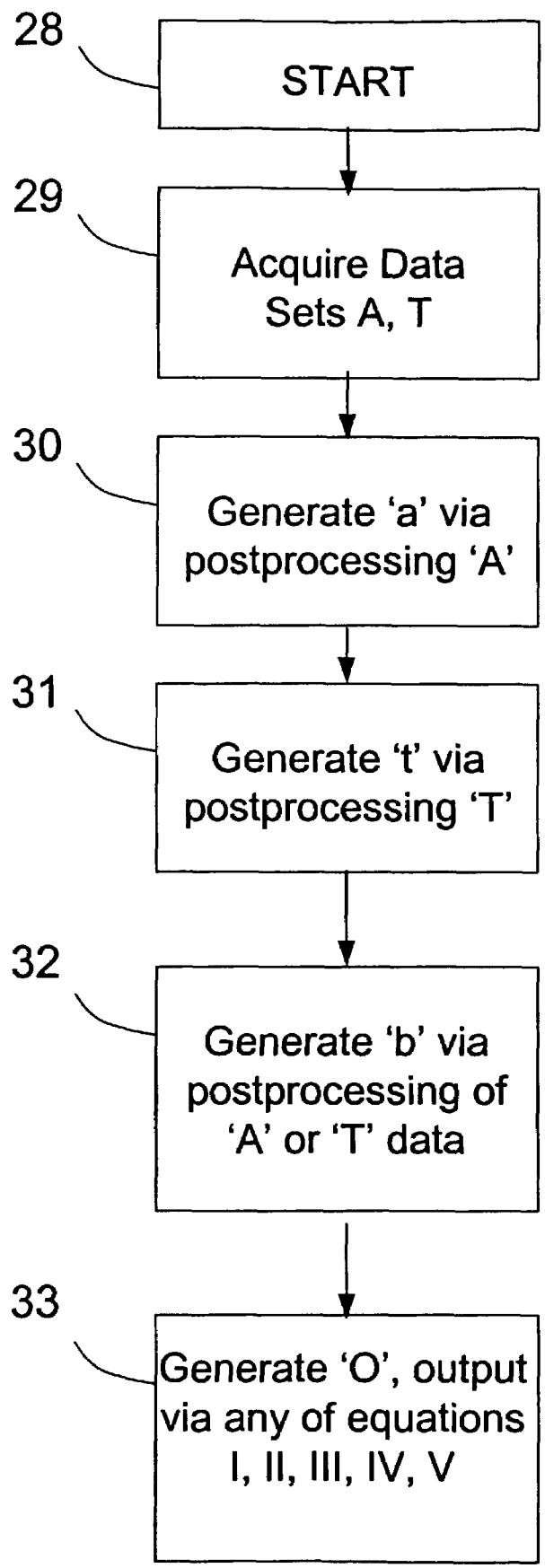
FIG. 3 is a flow chart illustrating one embodiment of a method of combining MRI data sets of the present invention.

Referring now to FIG. 3, a flowchart for combining the data set corresponding to the vascular contrast image and the data set corresponding to the targeted contrast image to generate a third data set is described. The mathematical symbols referred to in the flowchart are as follows:

A: Data set representing the contrast enhanced vascular system.
T: Data set representing the contrast enhanced stationary target (e.g., thrombus).
O: An output data set.
$\alpha, \beta$: Scaling factors for the data sets which are combined to generate the output data set O.
a: A subset of A consisting exclusively of the contrast enhanced vascular system signal. This subset can be determined by any desired post-processing method.
t: A subset of T consisting exclusively of the contrast enhanced stationary target (e.g., thrombus) signal. This subset can be determined by any desired post-processing method.
b: A subset of either A or T consisting of the structures exclusive of either the stationary target or the vascular system. This subset can be determined by any desired post-processing method.

Each of the sets a, b, t, A, T, and O have the same dimensions, i.e., they have been interpolated and registered as described above if necessary.

At step 30, the subset a is generated and at step 31, the subset t is generated. At step 32, the subset b is generated.

Next, at step 33, when both the first and second data sets are independent MRI scans, an output data set O is then produced according to the following equations:

$$O = \alpha A + \beta T \quad \text{(I)}$$

$$O_i = \max(\alpha A, \beta T) \quad \text{(II)}$$

In these equations, $\alpha$ and $\beta$ are predetermined variable weighting factors. In equation I the output data set O is generated by ordinary set arithmetic. In Equation II, the output set O is generated by taking only the value at each coordinate in space with the highest $T_1$, i.e., the "maximum" signal.

In equation I, the values $\alpha$ and $\beta$ are preferably in the range $1 > \alpha, \beta > 0$, and preferably $\alpha + \beta = 1$. This ranging of the weighting factors will allow the output data set to be of the same approximate magnitude of intensity as the contributing data sets, and is done only to ensure that the output data set will not have any significant representation errors. More elaborate measures to ensure proper output representation may be necessary should the data sets utilize maximum representational range for the stored variable type. Typically in MR imaging DICOM data sets will not require this level of dynamic range manipulation, thus the $\alpha, \beta$ representations will suffice for most cases.

In equation II, the values $\alpha$ and $\beta$ are preferably both equal to unity in which case the resultant data set O has a unified representation of the contrast enhanced stationary target (e.g., thrombus) and contrast enhanced vascular system (e.g., blood pool) in a single image. $\alpha$ and $\beta$ can be manipulated to compensate for base intensity differences between the two data sets A and T to ensure that the max operation yields the proper outcome of presenting a data set with the vascular system (blood pool) and stationary target (thrombus) represented.

When one or both of the first and second data sets is derived from the source data sets by a post-processing algorithm, an output data set O is then produced according to any of the following equations:

$$O = \alpha A \pm \gamma t \quad \text{(III)}$$

$$O = \alpha a + \beta T \quad \text{(IV)}$$

$$O = \alpha a + \beta t + \gamma t \quad \text{(V)}$$

Similar to the case above, in these equations, $\alpha, \beta$, and $\gamma$ are relative weighting factors. Preferred values are in the range $1 > \alpha, \beta, \gamma > 0$ and preferably $\alpha + \beta + \gamma = 1$. For Equation (III), the addition of a weighted stationary target (e.g., thrombus) 'mask' data set to the data set containing the vascular system information will, when properly implemented, result in a data set in which the stationary target (e.g., thrombus) and the vascular system are differentiable from each other and the surrounding tissue via intensity differences. Equation (IV) is significantly similar to Equation (III), except that the vascular information is added to the stationary target (e.g., thrombus) containing data set in its entirety. Equation (V) represents creation of the output data set from the three segmented components of the original imaged region. Proper weighting of each of the three components will produce an output data set in which maximum differentiability with respect to intensity differences of the three components will be possible.

Example 6

In Vivo Detection of a Stationary Target Using a Targeted MRI Agent Followed by a Vascular MRI Agent A 2.5 kg female New Zealand White rabbit was anesthetized with a cocktail of Ketamine (50 mg/kg), Aceapromazine (2.5 mg/kg), and Rompon (5 mg/kg), and anesthesia maintained with sodium pentobarbital (approx.35 mg/kg as needed). An i.v. catheter (24 g) was placed into the ear vein and the ear artery. The jugular vein and carotid artery were isolated. A stenosis was created in the carotid artery by placing an 18 g needle on top of the vessel and then suturing it into place with 3-0 suture. The needle was then removed. A 5 mm portion of the artery was then segmented off distally to the stenosis with microvascular clips. The artery was crushed twice along the 5 mm section. The proximal vascular clip was released to allow blood flow into the section for circa 3 sec. The clip was reapplied and the artery was crushed twice again along the 5 mm section. After 4 minutes, the clips were removed. A 5 mm segment of the jugular vein was isolated with microvascular clips. A thrombus was created by injecting 100 μL of a 3.7 units thrombin, 0.06 M $CaCl_2$, rabbit whole blood mixture. After 4 minutes, the clips were removed.

The thrombi were allowed to age for 50 minutes. A 1.0 mL solution of a 5 mM targeted contrast agent (Structure III, 2 μmol/kg) was administered via the ear vein. After 30 minutes, the animal was placed inside a General Electric Signa LxCVi 1.5 tesla scanner and a first MRI data set and image were obtained using a 3D RF spoiled gradient echo sequence (SPGR) with the following parameters TR=39 ms, TE=3.1 ms, flip angle=40 degrees, field of view=8 cm, acquisition bandwith=31.25 kHz. Chemical fat saturation was applied as well as 40 cm spatial inferior and superior saturation bands. After an additional 30 minutes, the vascular agent Gd-DTPA-BSA, 3 mL of 80 mM Gd solution (80 μmol Gd/kg), was injected. The same sequence was used to acquire a second MRI data set and image.

Figure 4A:
FIG. 4A is an MRI image of a stationary target (here, a thrombus) enhanced by the binding of a targeted MRI contrast agent.
Figure 4B:
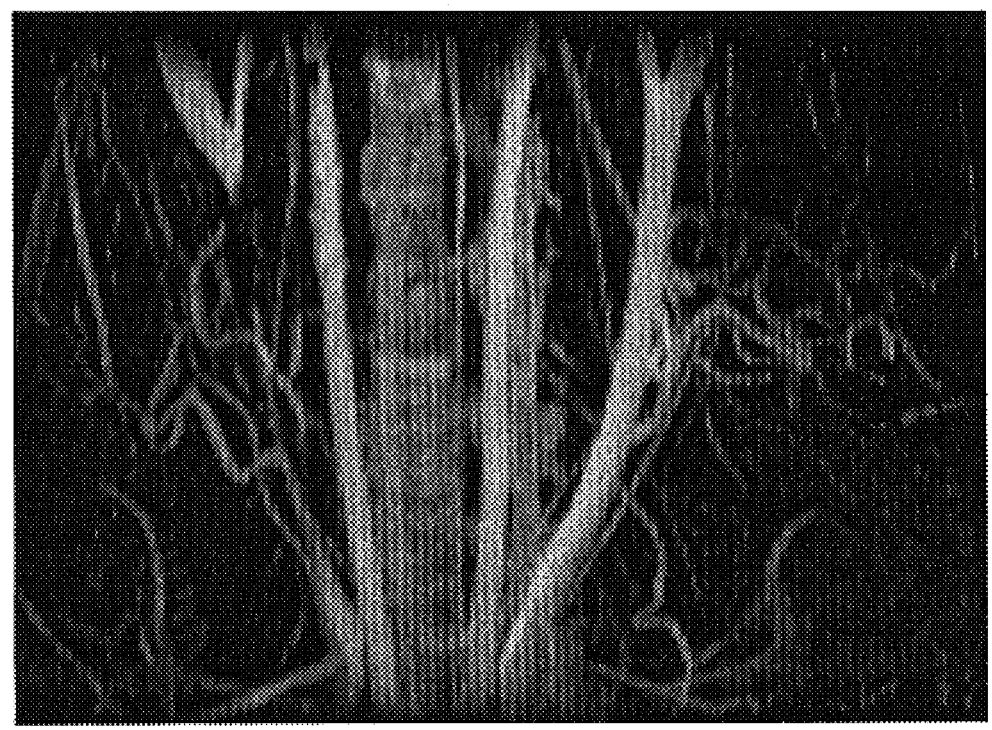
FIG. 4B is an MRI image of the vascular system enhanced by the administration of a vascular contrast agent.
Figure 5:
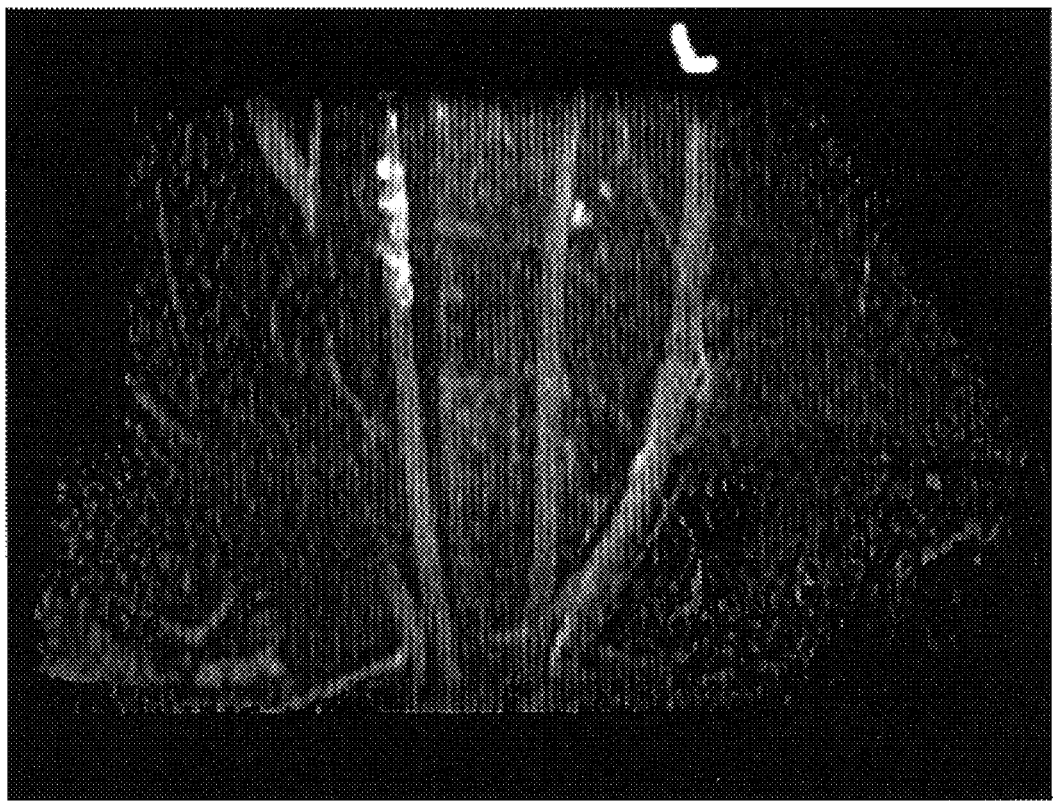
FIG. 5 is an embodiment of a combined third data set from the data sets in FIG. 4A and FIG. 4B, demonstrating an image of both the stationary target and the vascular system and indicating the location of the stationary target within the vascular system.

FIG. 4A shows the maximum intensity projection (MIP) of the first image. There is a region of brightness in the upper left hand quadrant of the MIP. FIG. 4B shows the MIP of the second image acquired immediately after injection of the vascular agent Gd-DTPA-BSA. In this MIP, the blood vessels, such as the carotid arteries and jugular veins, of the throat and neck area of the rabbit are readily visible. FIG. 5 is an image created from combining the data sets represented in FIGS. 4A and 4B. As these two images are of the same resolution and the two scans are of the same anatomic location, the combined image corresponds to eqn. (I) O=0.2A+0.8T. In the combined image of FIG. 5, it is apparent that the bright region enhanced by the thrombus targeted agent corresponds with the animal's right carotid artery, suggesting that there is a thrombus in the animal's right carotid artery.

Example 7

In Vivo Detection of a Stationary Target Using a Targeted MRI Agent Alone

A 3.1 kg female New Zealand White rabbit was anesthetized with a cocktail of Ketamine (50 mg/kg), Aceapromazine (2.5 mg/kg), and Rompon (5 mg/kg), and anesthesia maintained with sodium pentobarbital (approx.35 mg/kg as needed). An i.v. catheter (24 g) was placed into the ear vein and the ear artery. The jugular vein and carotid artery were isolated. A stenosis was created in the carotid artery by placing an 18 g needle on top of the vessel and then suturing it into place with 3-0 suture. The needle was then removed. A 5 mm portion of the artery was then segmented off distally to the stenosis with microvascular clips. The artery was then crushed twice along the 5 mm section. The proximal vascular clip was released to allow blood flow into the section for ca. 3 sec. The clip was reapplied and artery was crushed twice again along the 5 mm section. After 4 minutes, the clips were removed. A 5 mm segment of the jugular vein was isolated with microvascular clips. A thrombus was created by injecting 100 μL of a 3.7 units thrombin, 0.06 M $CaCl_2$, rabbit whole blood mixture. After 4 minutes, the clips were removed.

The thrombi were allowed to age for 45 minutes. The animal was placed inside a General Electric Signa LxCVi 1.5 tesla scanner and imaged using a 3D RF spoiled gradient echo sequence (SPGR) with the following parameters TR=39 ms, TE=3.1 ms, flip angle=40 degrees, field of view=8 cm, acquisition bandwith=31.25 kHz. Chemical fat saturation was applied as well as 40 mm spatial inferior and superior saturation bands. After one scan prior to injection, a 1.5 mL solution of a 4.2 mM targeted contrast agent solution (2 μmol/kg, Structure I) was administered via the ear vein, and the image sequence was repeated to obtain a first MRI data set. After allowing the blood concentration to decrease for 35 minutes, the animal was imaged again using the same sequence to obtain a second MRI data set.

Figure 6A:
FIG. 6A is an MRI image of the vascular system enhanced by the administration of a targeted contrast agent.
Figure 6B:
FIG. 6B is an MRI image of a stationary target (here, a thrombus) enhanced by the binding of a targeted MRI contrast agent.
Figure 7:
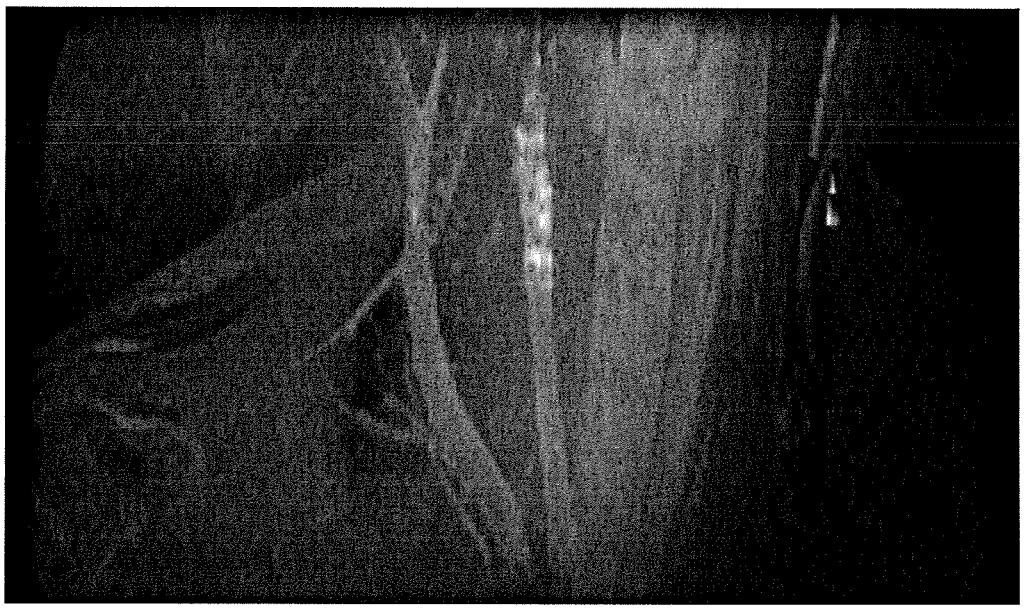
FIG. 7 is an embodiment of a combined third data set from the data sets in FIG. 6A and FIG. 6B, demonstrating an image of both the stationary target and the vascular system and indicating the location of the stationary target within the vascular system.

FIG. 6A shows the maximum intensity projection (MIP) of the first MRI data set. There is an enhancement of the blood vessels and one can identify the carotid arteries and jugular veins. FIG. 6B is the MIP of the second MRI data set where one can no longer see the blood vessels, but one can see a bright region in the upper middle region of the image from the targeted contrast agent. FIG. 7 is an image created from the 1:1 (i.e. eqn. (I): O=0.5A+0.5T) combination of the first and second MRI data sets (e.g., those embodied in the FIGS. 6A and 6B images, respectively), where it is apparent that the bright region observed in FIG. 6B corresponds to a stationary target in the animal's right carotid artery, suggesting that there is a thrombus in the animal's right carotid artery.

Example 8

Vascular and Stationary Target MR Images Acquired Post-Injection of a Targeted MRI Contrast Agent A 3.0 kg female New Zealand White rabbit was anesthetized with a cocktail of Ketamine (50 mg/kg), Aceapromazine (2.5 mg/kg), and Rompon (5 mg/kg), and anesthesia maintained with sodium pentobarbital (approx.35 mg/kg as needed). An i.v. catheter (24 g) was placed into the ear vein and the ear artery. The jugular vein and carotid artery were isolated. A stenosis was created in the carotid artery by placing an 18 g needle on top of the vessel and then suturing it into place with 3-0 suture. The needle was then removed. A 5 mm portion of the artery was segmented off distally to the stenosis with microvascular clips. The artery was crushed twice along the 5 mm section. The proximal vascular clip was released to allow blood flow into the section for ca. 3 sec. The clip was reapplied and the artery was crushed twice again along the 5 mm section. After 4 minutes, the clips were removed. A 5 mm segment of the jugular vein was isolated with microvascular clips. A thrombus was created by injecting 100 μL of a 3.7 units thrombin, 0.06 M CaCl$_2$, rabbit whole blood mixture. After 4 minutes, the clips were removed.

The thrombi were allowed to age for 40 minutes. The animal was placed inside a General Electric Signa LxCVi 1.5 tesla scanner and imaged using a 3D RF spoiled gradient echo sequence (SPGR) with the following parameters TR=39 ms, TE=3.1 ms, flip angle=40 degrees, field of view=8 cm, acquisition bandwith=31.25 kHz. Chemical fat saturation was applied as well as 40 mm spatial inferior and superior saturation bands. After one scan the targeted contrast agent ((10 μmol/kg), 4.0 mL solution of a 7.6 mM solution of Structure 23, as set forth in U.S. Provisional Application "Peptide-Based Multimeric Targeted Contrast Agents," by Zhang et al., filed Jul. 30, 2001, Ser. No. 60/308,721, and in "Peptide-Based Multimeric Targeted Contrast Agents," by Zhang et al., filed concurrently herewith, U.S. Ser. No. 11/564,648) was administered via the ear vein. The image sequence was repeated over the next 80 minutes. Region of interest (ROI) analysis was performed on selected axial slices for the thrombus and the normal jugular vein.

Prior to injection, the thrombus and the blood were isointense in the MR image. The first image acquired post-injection of the targeted contrast image showed the blood to be enhanced relative to the pre-injection image by a factor of 4.4. The thrombus was also enhanced relative to the pre-injection image. The second scan post injection demonstrated that the thrombus was enhanced relative to the blood by a factor of 2.2. The thrombus remained brighter than the blood for the duration of the study (ca. 3-fold brighter). In summary, the first image post injection of the targeted contrast agent (the vascular system MRI image) showed the blood vessels to be bright. Over time the subsequent image(s) (the stationary MRI images) demonstrated a decreased blood signal, and the stationary target (e.g. thrombus) appeared bright due to a greater signal compared to the blood.

Example 9

A Stationary Target MR Image Acquired After the Injection of a Targeted MRI Contrast Agent, Followed by the Administration of a Vascular MRI Contrast Agent and the Acquisition of a Vascular MR Image A 3.1 kg female New Zealand White rabbit was anesthetized with a cocktail of Ketamine (50 mg/kg), Aceapromazine (2.5 mg/kg), and Rompon (5 mg/kg) and anesthesia maintained with sodium pentobarbital (approx.35 mg/kg as needed). An i.v. catheter (24 g) was placed into the ear vein and the ear artery. The jugular vein and carotid artery are isolated. A stenosis was created in the carotid artery by placing an 18 g needle on top of the vessel and then suturing it into place with 3-0 suture. The needle was then removed. A 5 mm portion of the artery was then segmented off distally to the stenosis with microvascular clips. The artery was crushed twice along the 5 mm section. The proximal vascular clip was released to allow blood flow into the section for ca. 3 sec. The clip was reapplied and artery was crushed twice again along the 5 mm section. After 4 minutes, the clips were removed. A 5 mm segment of the jugular vein was isolated with microvascular clips. A thrombus was created by injecting 100 μL of a 3.7 units thrombin, 0.06 M CaCl$_2$, rabbit whole blood mixture. After 4 minutes, the clips were removed.

The thrombi were allowed to age for 45 minutes. The animal was placed inside a General Electric Signa LxCVi 1.5 tesla scanner and imaged using a 3D RF spoiled gradient echo sequence (SPGR) with the following parameters TR=39 ms, TE=3.1 ms, flip angle=40 degrees, field of view=8 cm, acquisition bandwith=31.25 kHz. Chemical fat saturation was applied as well as 40 mm spatial inferior and superior saturation bands. After one scan prior to injection of the targeted MRI contrast agent, a 1.5 mL solution of a 4.2 mM Structure I (see above) solution (2 μmol/kg) was administered via the ear vein. The image sequence was repeated over the next 80 minutes. After 80 minutes, the blood pool vascular MRI contrast agent Gd-DTPA-BSA, 3 mL of 80 mM Gd solution (80 μmol Gd/kg), was injected. The same sequence was used to acquire an additional image. Region of interest (ROI) analysis was performed on selected axial slices for the thrombus and the normal jugular vein.

The thrombus and the blood were isointense prior to injection of the targeted contrast agent. The first image acquired post injection showed significant enhancement of the thrombus clot (e.g., a bright spot) and slight enhancement of the blood, which decreased rapidly. Compared to the blood, the thrombus was 2-3 fold brighter. After injection of the blood pool agent, the signal intensity of both the blood and thrombus increased dramatically, providing a detailed view of the vascular system. Comparing and combining the two images provided for a detailed analysis of the stationary targets (thrombi) and their location.

Example 10

A Vascular MR Image Obtained After the Administration of an Extracellular Vascular MRI Contrast Agent, Followed by the Administration of a Targeted MRI Contrast Agent and the Acquisition of a Stationary MR Image A 600 g guinea pig (Hartley male) was anaesthetized with a cocktail of Ketamine (50 mg/kg), Aceapromazine (2.5 mg/kg), and Rompon (5 mg/kg), and anesthesia maintained with sodium pentobarbital (approx.35 mg/kg as needed). An incision was made in the throat and one of the jugular veins was isolated. A 1 cm section of the jugular vein was isolated with vascular clamps. Freshly drawn blood from the animal (50 μL) was mixed with human thrombin (50 uL, 4 units) and injected into the clamped segment of the vein. Four minutes after injection, the clamps were removed and the thrombus was allowed to age for 30 minutes.

The animal was placed inside a General Electric Signa LxCVi 1.5 tesla scanner and imaged using a 3D RF spoiled gradient echo sequence (SPGR) with the following parameters TR=22 ms, TE=3.1 ms, flip angle=40 degree, field of view=8 cm, acquisition bandwith=31.25 kHz. After one scan, an extracellular vascular MRI contrast agent, GdDTPA (Magnevist®), 100 μmol/kg, was injected via a catheter in the carotid artery. The image sequence was repeated 5 times over the next 30 minutes to acquire the vascular MRI data set. After 30 minutes, 5 μmol/kg of a thrombus targeted MRI contrast agent (Structure 32, as set forth in U.S. Provisional Application "Peptide-Based Multimeric Targeted Contrast Agents," by Zhang et al., filed Jul. 30, 2001, Ser. No. 60/308,721, and in "Peptide-Based Multimeric Targeted Contrast Agents," by Zhang et al., filed concurrently herewith, U.S. Ser. No. 11/564,648) was injected. The same sequence was used over the next 80 minutes to acquire the targeted MRI data set. Region of interest (ROI) analysis was performed on selected axial slices for the thrombus and the normal jugular vein.

In the vascular MR image, there was enhancement (4-fold) of the vascular system, with no observable enhancement of the thrombus. The thrombus appeared bright relative to the blood in the stationary MR image, and this bright image slowly faded over time out to 80 minutes post injection of the targeted contrast agent.

A number of embodiments of the invention have been described. Nevertheless, it will be understood that various modifications may be made without departing from the spirit and scope of the invention. Accordingly, other embodiments are within the scope of the following claims.

What is claimed is:

1. A method of determining the presence or absence of a thrombus, an atherosclerotic plaque, an atherosclerotic lesion, a tumor, or a thromboembolism within a vascular system of a mammal comprising:

a) administering a targeted MRI contrast agent to the mammal, the targeted MRI contrast agent having a specific affinity for the thrombus, the atherosclerotic plaque, the atherosclerotic lesion, the tumor, or the thromboembolism, and the targeted MRI contrast agent further capable of providing contrast enhancement of the thrombus, the atherosclerotic plaque, the atherosclerotic lesion, the tumor, or the thromboembolism and the vascular system of the mammal;

b) acquiring a first MRI data set comprising an image of the vascular system; and c) acquiring a second MRI data set, the second MRI data set acquired at a time appropriate to provide an observable level of contrast enhancement of the thrombus, the atherosclerotic plaque, the atherosclerotic lesion, the tumor, or the thromboembolism, if present, relative to background blood and tissue enhancement;

wherein the targeted MRI contrast agent is selected from the group consisting of:

Structure I:

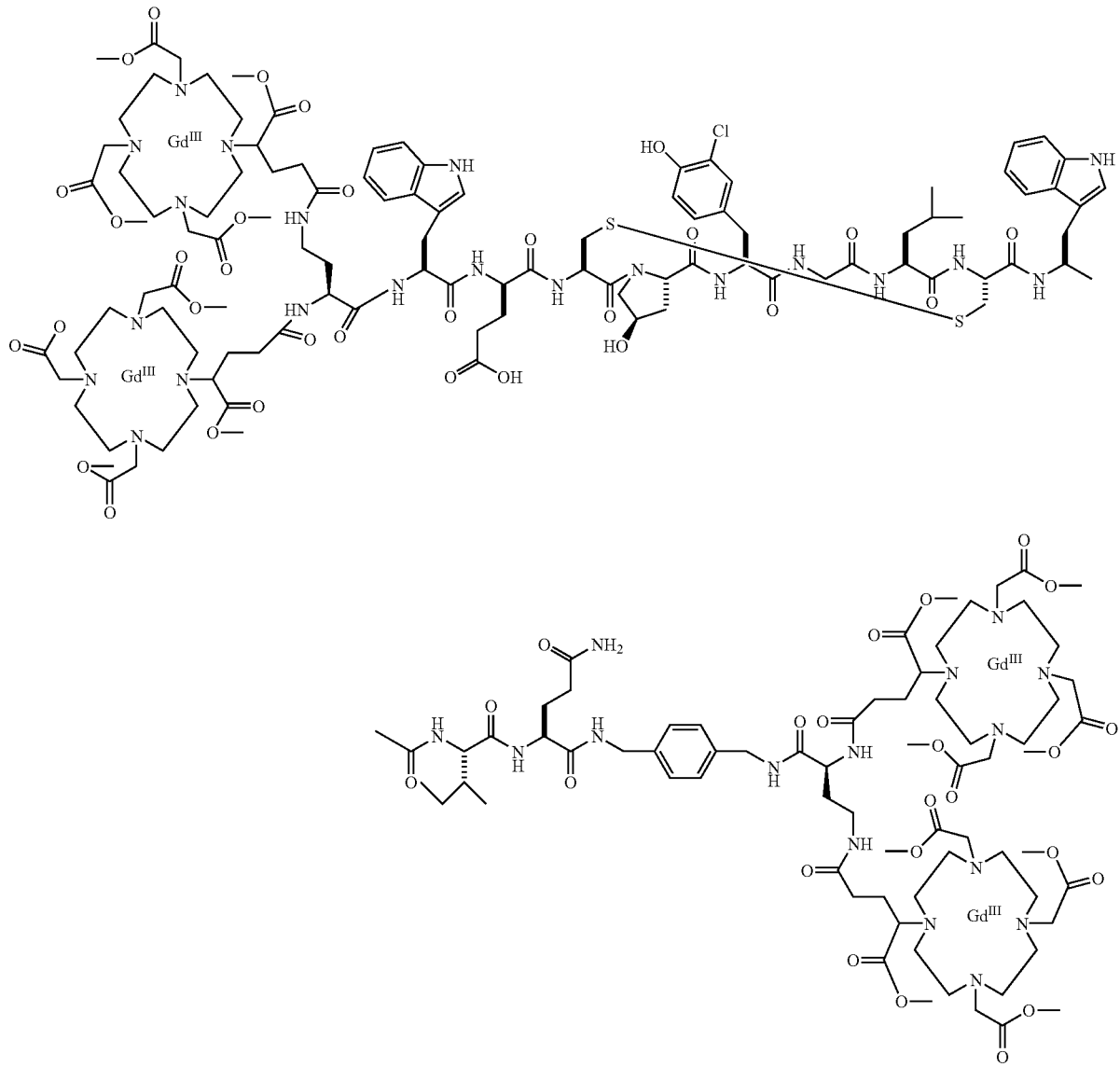

-continued
Structure II:
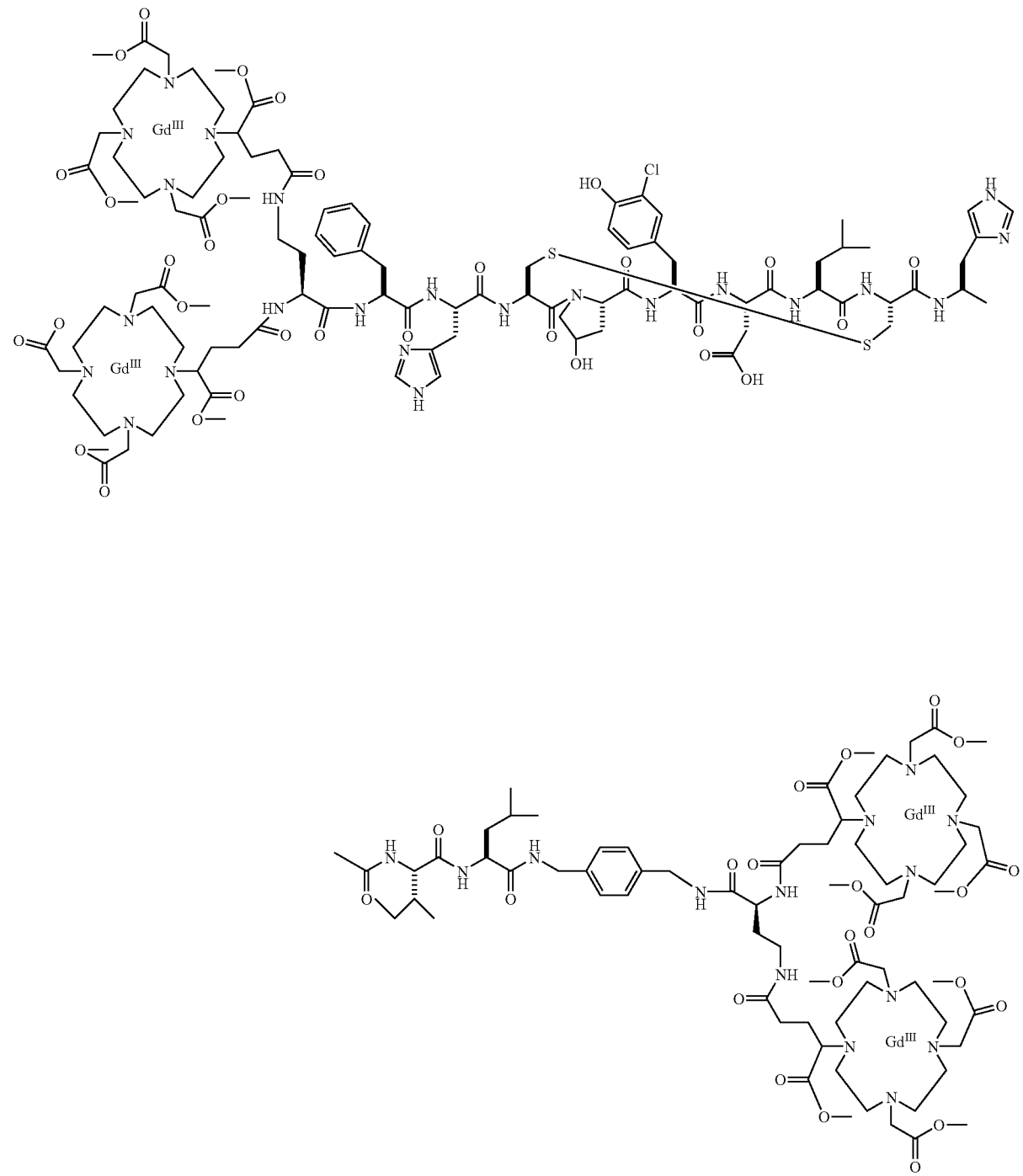

Structure III:
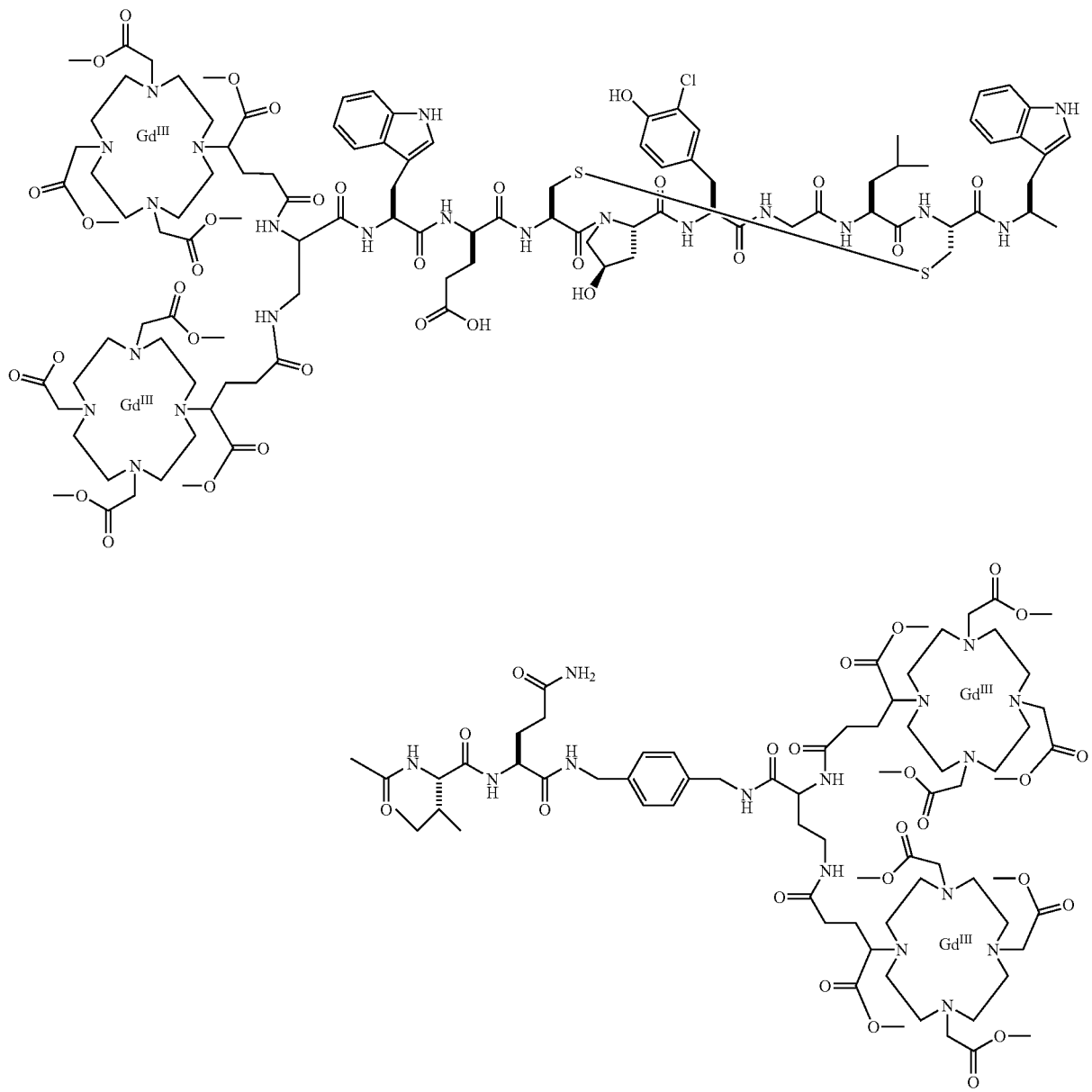

Structure IV:
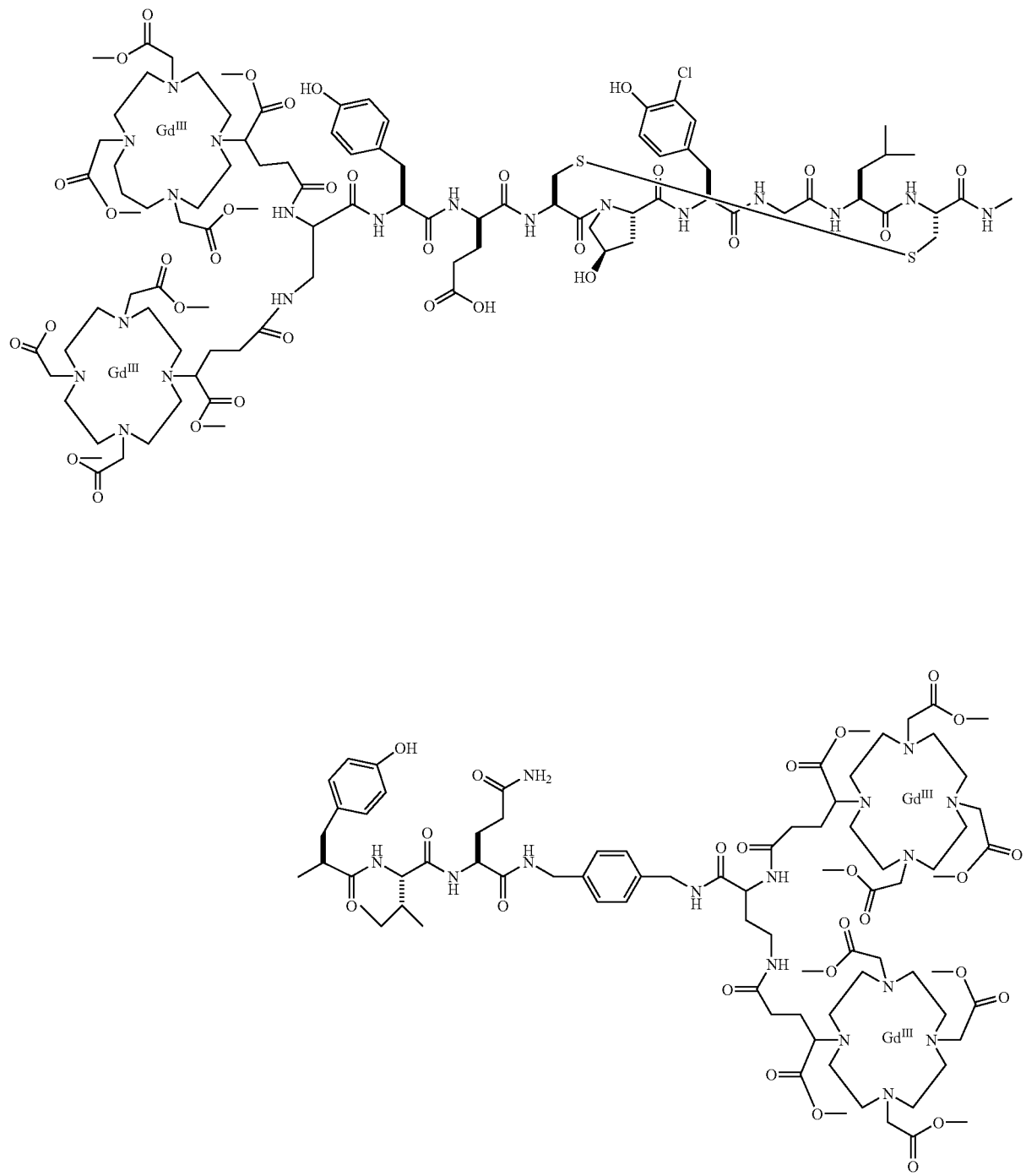

Structure V:
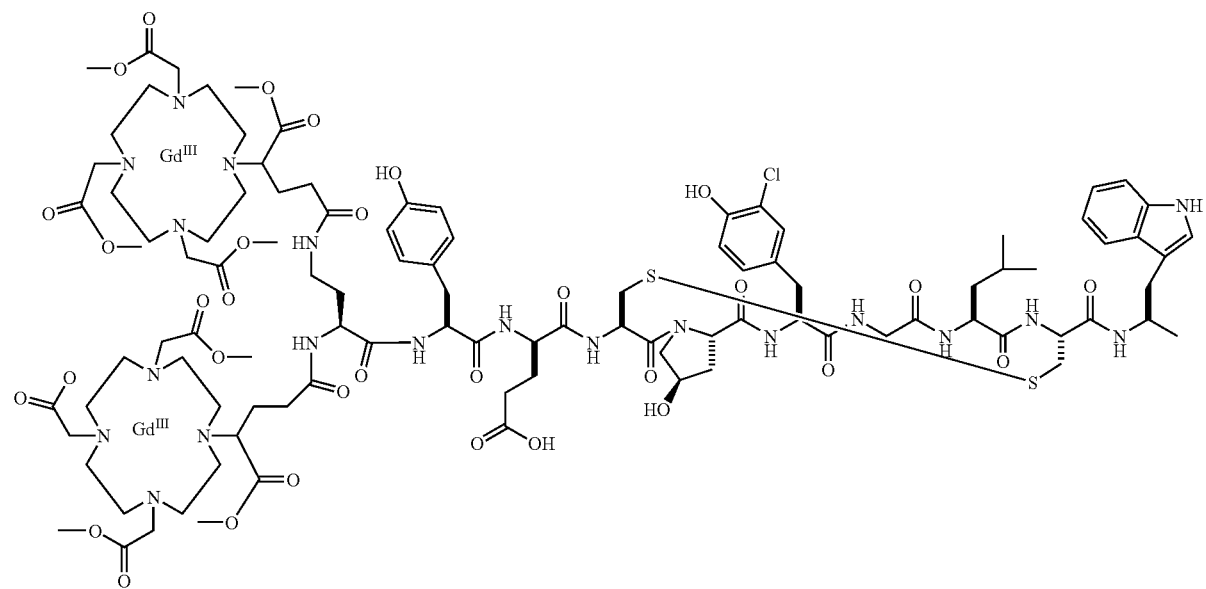
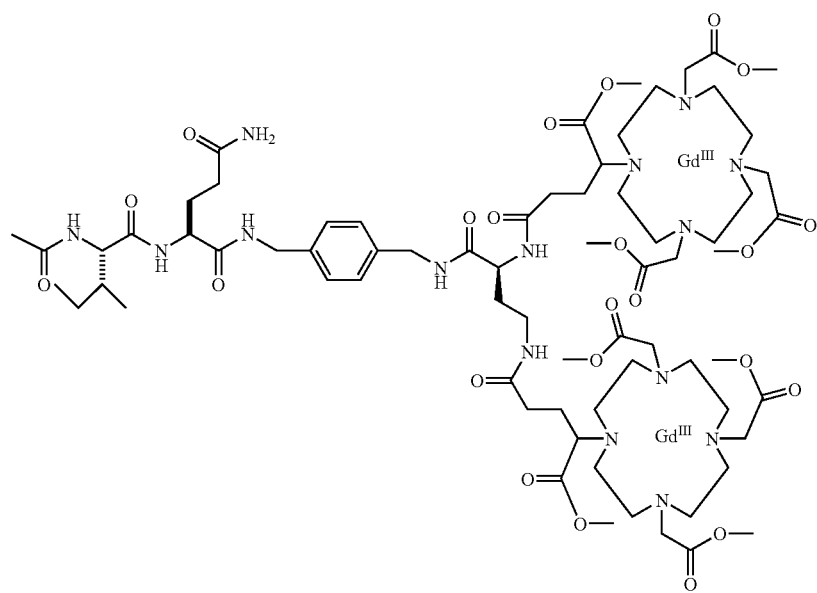

-continued
Structure VI:
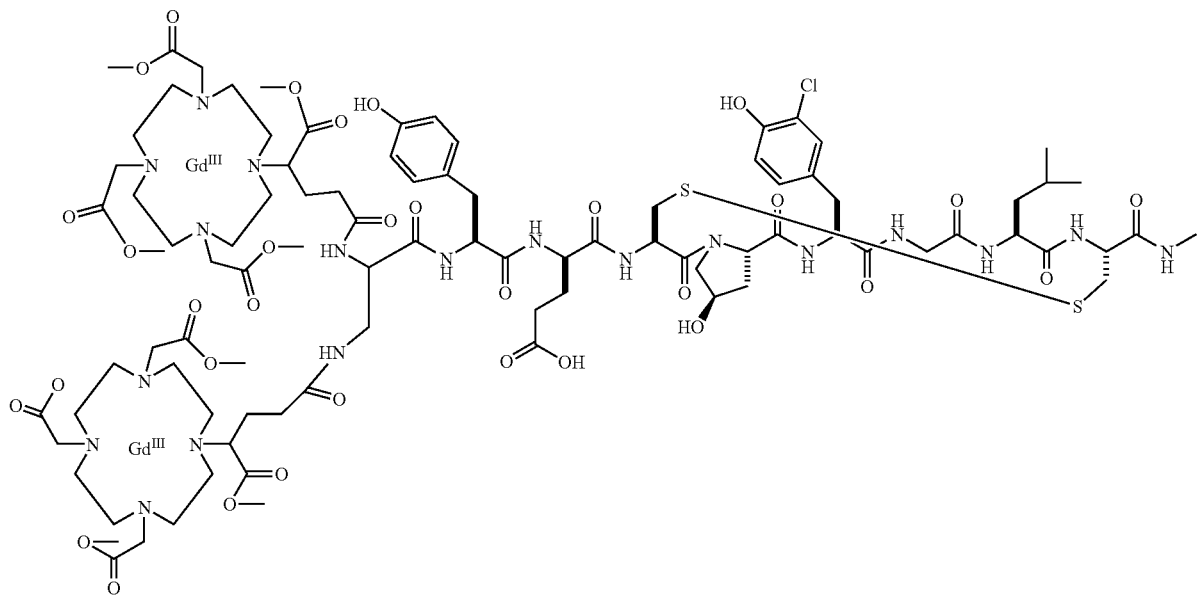
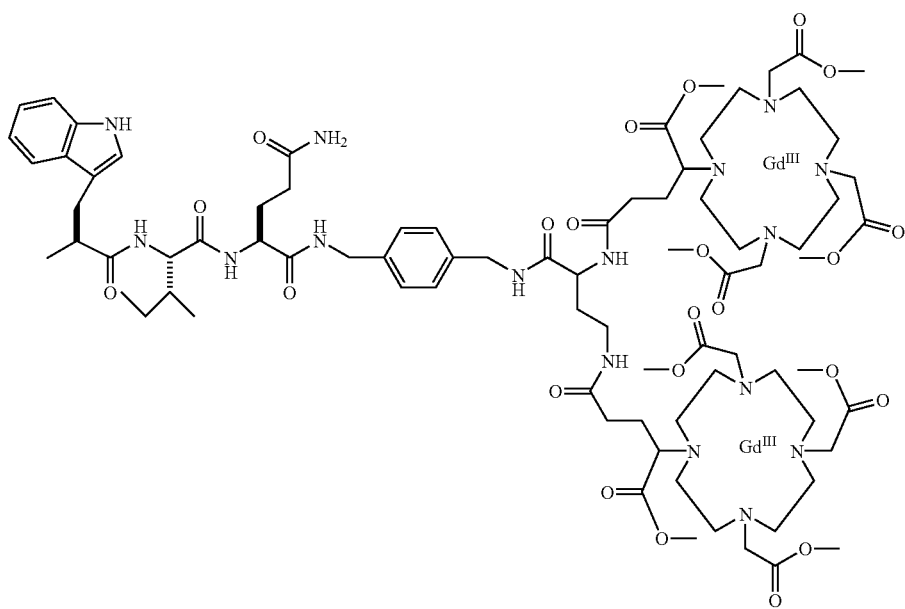

-continued
Structure VII:
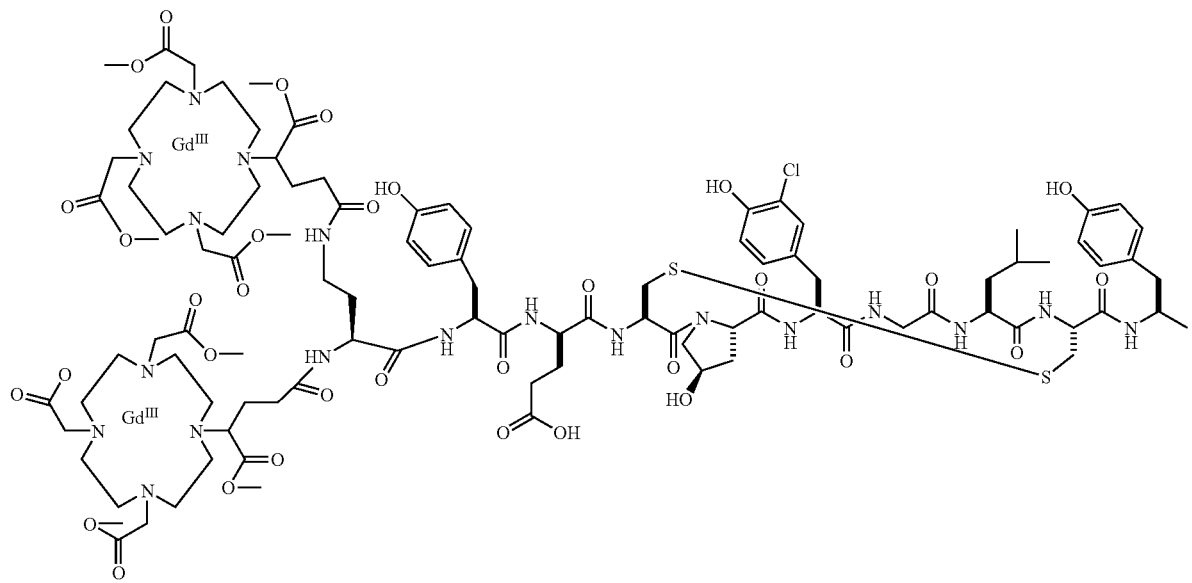
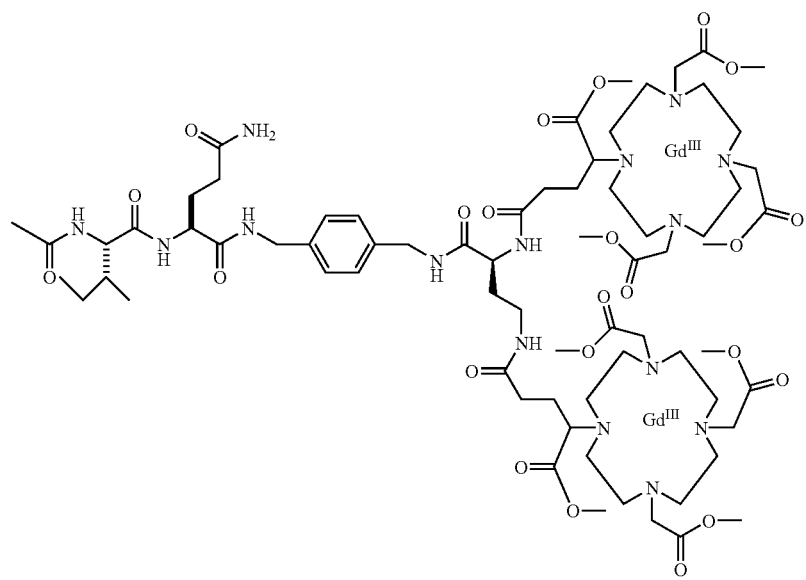

Structure VIII:
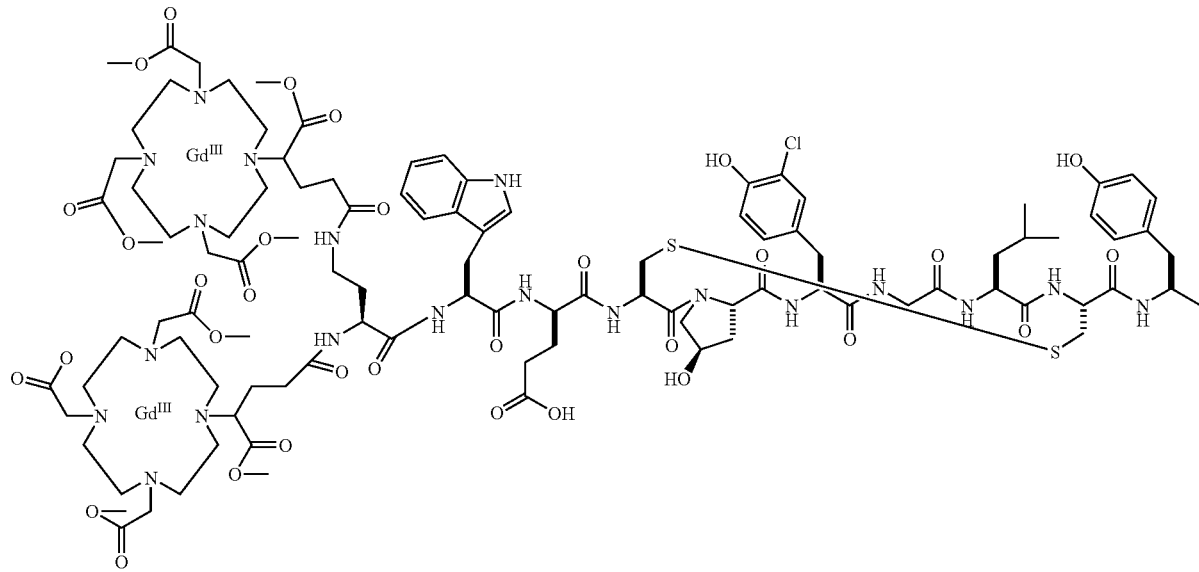
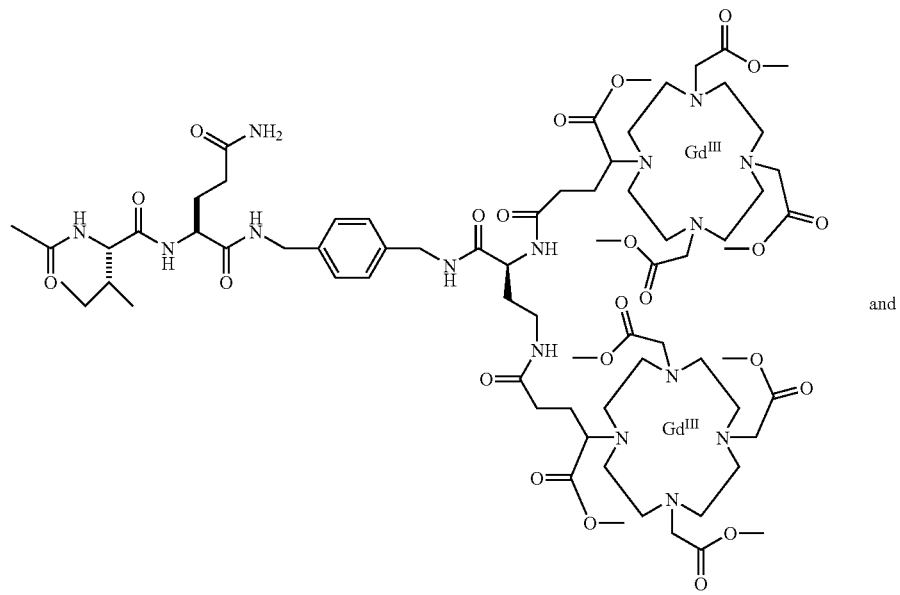
and

Structure IX:

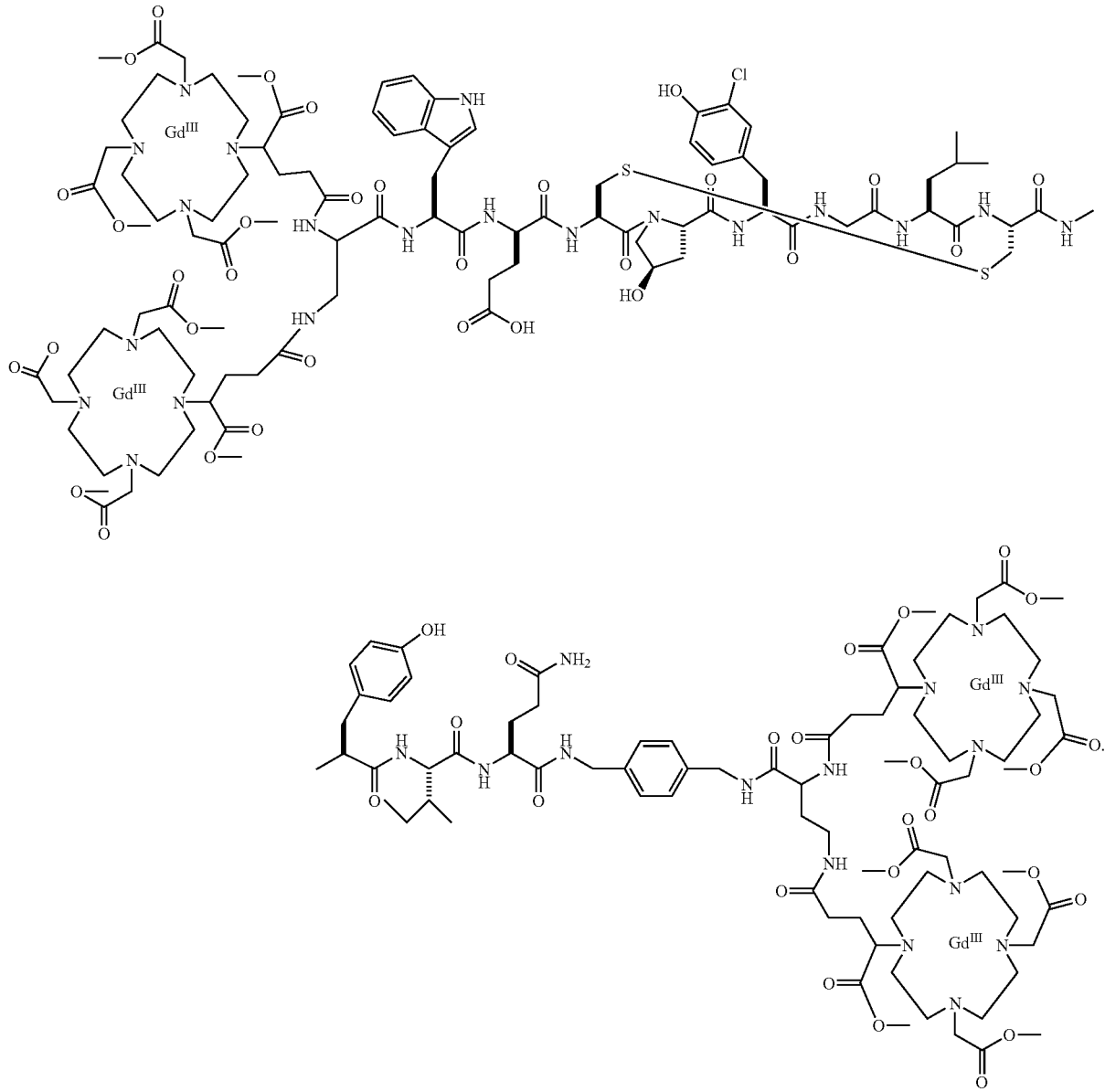

2. The method according to claim 1, further comprising comparing the first and second MRI data sets to determine the presence of the thrombus, the atherosclerotic plaque, the atherosclerotic lesion, the tumor, or the thromboembolism within the vascular system, provided that the second MRI data set indicates the presence of the thrombus, the atherosclerotic plaque, the atherosclerotic lesion, the tumor, or the thromboembolism.

3. The method according to claim 2, wherein the comparing step comprises combining the first and second MRI data sets to produce a third MRI data set, the third MRI data set comprising an image of both the thrombus, the atherosclerotic plaque, the atherosclerotic lesion, the tumor, or the thromboembolism and the vascular system, and the third data set capable of indicating the location of the thrombus, the atherosclerotic plaque, the atherosclerotic lesion, the tumor, or the thromboembolism, if present, within the vascular system.

4. The method according to claim 3, further comprising displaying the third MRI data set on a display device in order to indicate the location of the thrombus, the atherosclerotic plaque, the atherosclerotic lesion, the tumor, or the thromboembolism, if present, within the vascular system.

5. The method according to claim 3, wherein the third MRI data set is further capable of indicating the size of the thrombus, the atherosclerotic plaque, the atherosclerotic lesion, the tumor, or the thromboembolism within the vascular system.

6. The method according to claim 3, wherein the combining step comprises registering spatially the first and second MRI data sets with respect to one another.

7. The method according to claim 3, wherein the combining step further comprises interpolating the spatial resolution of either the first or the second MRI data set so that the first and second MRI data set are of equivalent spatial resolution.

8. The method according to claim 7, wherein said interpolating step comprises:
   determining which of the first and second data sets has the higher spatial resolution;
   and
   interpolating the spatial resolution of the corresponding other data set to the data set determined to have the higher spatial resolution.

9. The method according to claim 7, wherein said combining step further comprises a direct calculation of modified image intensities resulting from a combination of individual values from registered, interpolated data elements from the first and second data sets.

10. The method according to claim 9, wherein the direct calculation of modified image intensities includes variably weighting the individual values of the registered, interpolated data elements from the first and second data sets.

11. The method according to claim 1, wherein the targeted MRI contrast agent is administered at a dose sufficient to result in a blood $T_1$ after administration of less than 500 ms.

12. The method according to claim 11, wherein the targeted MRI contrast agent is administered at a dose sufficient to result in a blood $T_1$ after administration of less than 300 ms.

13. The method according to claim 12, wherein the targeted MRI contrast agent is administered at a dose sufficient to result in a blood $T_1$ after administration of less than 175 ms.

14. The method according to claim 1, wherein the targeted MRI contrast agent further exhibits a specific affinity for a non-stationary biological component present within the mammal's vascular system.

15. The method according to claim 14, wherein the non-stationary biological component present within the mammal's vascular system is selected from the group consisting of human serum albumin, fibrinogen, alpha acid glycoprotein, globulins, and lipoproteins.

16. The method according to claim 15, wherein the non-stationary biological component present within the mammal's vascular system is human serum albumin.

17. The method according to claim 1, wherein the targeted MRI contrast agent is administered at a dose sufficient to result in a $T_1$ of the thrombus, the atherosclerotic plaque, the atherosclerotic lesion, the tumor, or the thromboembolism of less than 500 ms.

18. The method according to claim 17, wherein the targeted MRI contrast agent is administered at a dose sufficient to result in a $T_1$ of the thrombus, the atherosclerotic plaque, the atherosclerotic lesion, the tumor, or the thromboembolism of less than 300 ms.

19. The method according to claim 18, wherein the targeted MRI contrast agent is administered at a dose sufficient to result in a $T_1$ of the thrombus, the atherosclerotic plaque, the atherosclerotic lesion, the tumor, or the thromboembolism of less than 100 ms.

20. The method according to claim 1, wherein the targeted MRI contrast agent is administered at a dose from about 0.001 to about 500 µmol/kg.

21. The method according to claim 20, wherein the dose is from about 0.001 to about 50 µmol/kg.

22. The method according to claim 21, wherein the dose is from about 0.001. to about 5 µmol/kg.

23. The method according to claim 1, wherein the targeted MRI contrast agent's specific affinity for the thrombus, the atherosclerotic plaque, the atherosclerotic lesion, the tumor, or the thromboembolism, expressed as a dissociation constant, is less than 50 µM.

24. The method according to claim 23, wherein the targeted MRI contrast agent's specific affinity for the thrombus, the atherosclerotic plaque, the atherosclerotic lesion, the tumor, or the thromboembolism, expressed as a dissociation constant, is less than 5 µM.

25. The method according to claim 24, wherein the targeted MRI contrast agent's specific affinity for the thrombus, the atherosclerotic plaque, the atherosclerotic lesion, the tumor, or the thromboembolism, expressed as a dissociation constant, is less than 0.5 µM.

26. The method according to claim 1, wherein the second MRI data set is acquired using a spoiled gradient echo sequence.

27. The method according to claim 1, wherein the first and second MRI data sets are acquired in a single MRI session.

28. The method according to claim 27, wherein the single MRI session lasts for less than 6 hours.

29. The method according to claim 28, wherein the single MRI session lasts for less than 4 hours.

30. The method according to claim 29, wherein the single MRI session lasts for less than 2 hours.

31. The method according to claim 30, wherein the single MRI session lasts for less than 1 hour.

32. A method of determining the presence or absence of a thrombus, an atherosclerotic plaque, an atherosclerotic lesion, a tumor, or a thromboembolism within a vascular system of a mammal comprising:
   a) administering a targeted MRI contrast agent to the mammal, the targeted contrast agent having a specific affinity for the thrombus, the atherosclerotic plaque, the atherosclerotic lesion, the tumor, or the thromboembolism and the targeted contrast agent capable of providing contrast enhancement of the thrombus, the atherosclerotic plaque, the atherosclerotic lesion, the tumor, or the thromboembolism;
   b) administering a vascular MRI contrast agent to the mammal, the vascular contrast agent capable of providing contrast enhancement of the vascular system of the mammal;
   c) acquiring a vascular MRI data set comprising an image of the vascular system; and
   d) acquiring a targeted MRI data set, the targeted data set acquired at a time appropriate to provide an observable level of contrast enhancement of the thrombus, the atherosclerotic plaque, the atherosclerotic lesion, the tumor, or the thromboembolism, if present, relative to background blood and tissue enhancement;
wherein the targeted MRI contrast agent is selected from the group consisting of:

Structure I:
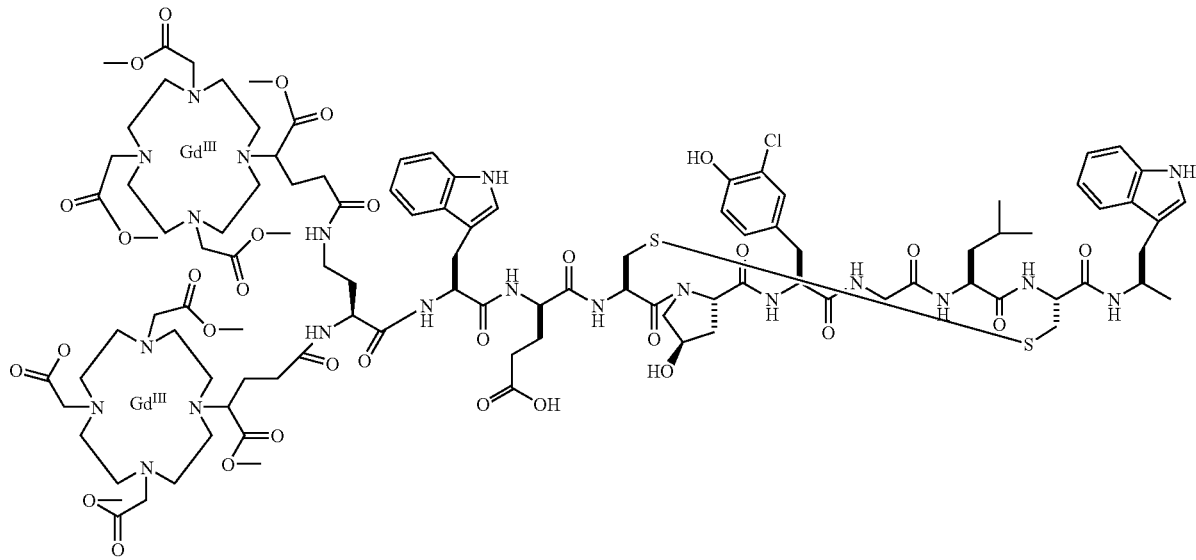
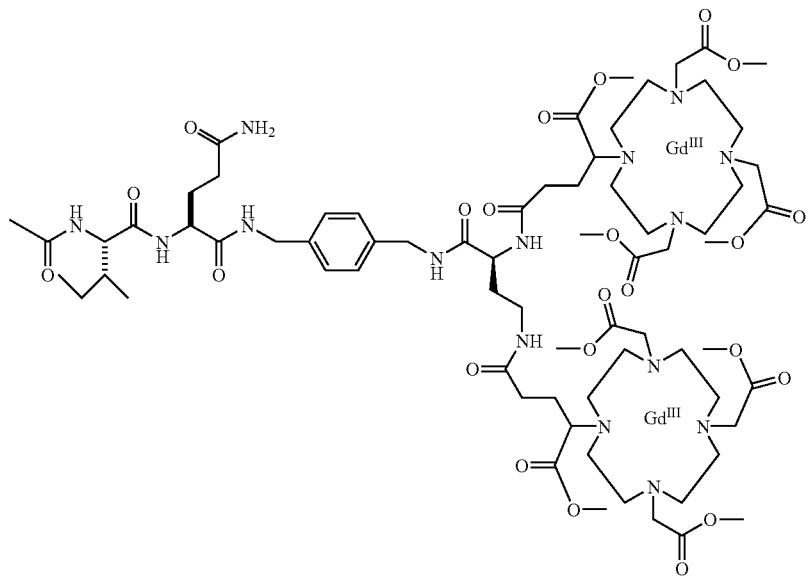

Structure II:
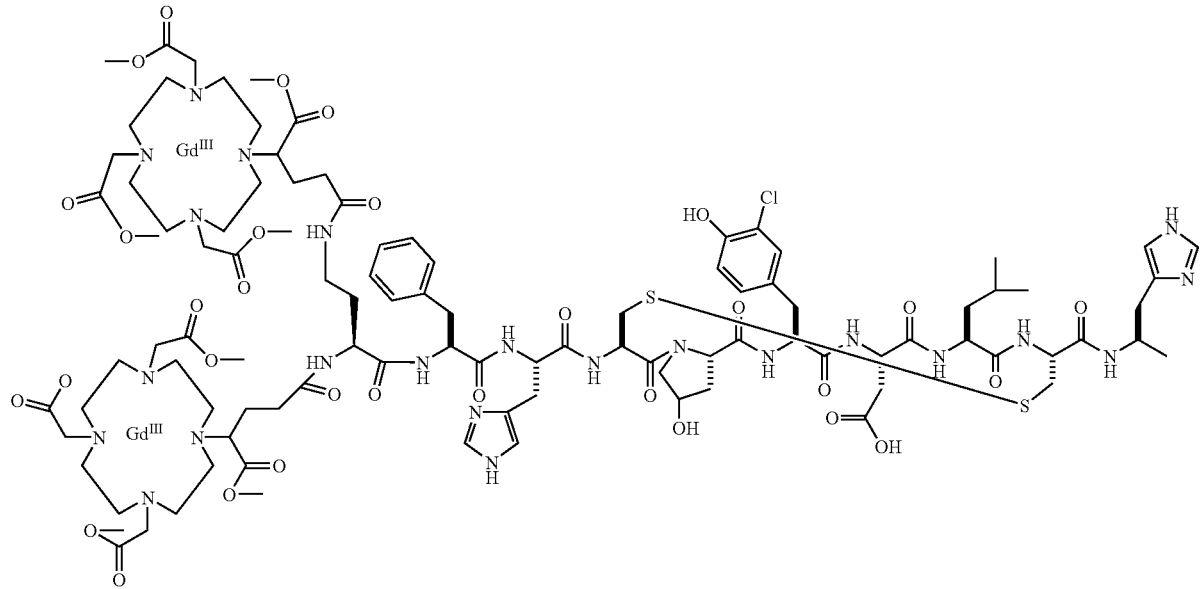
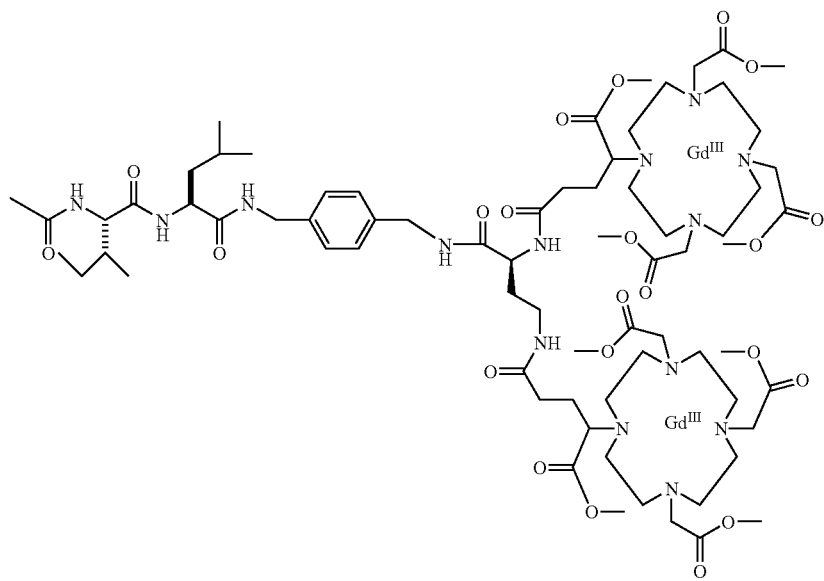

-continued
Structure III:
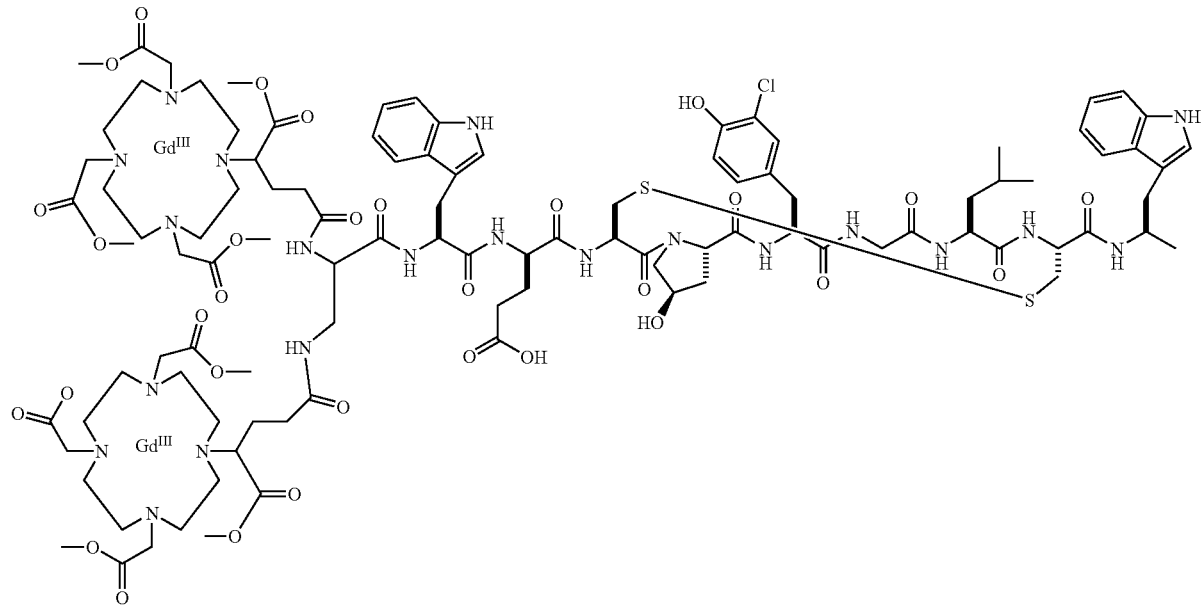
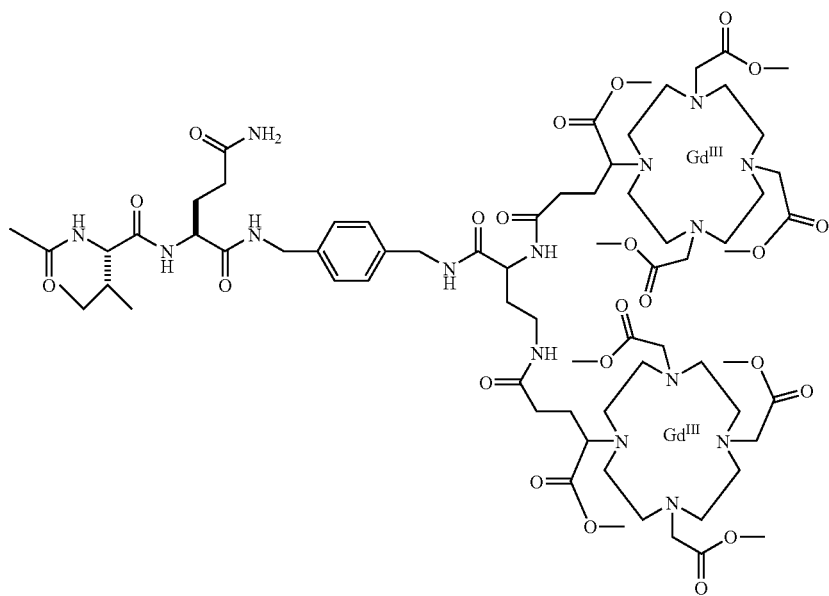

Structure IV:
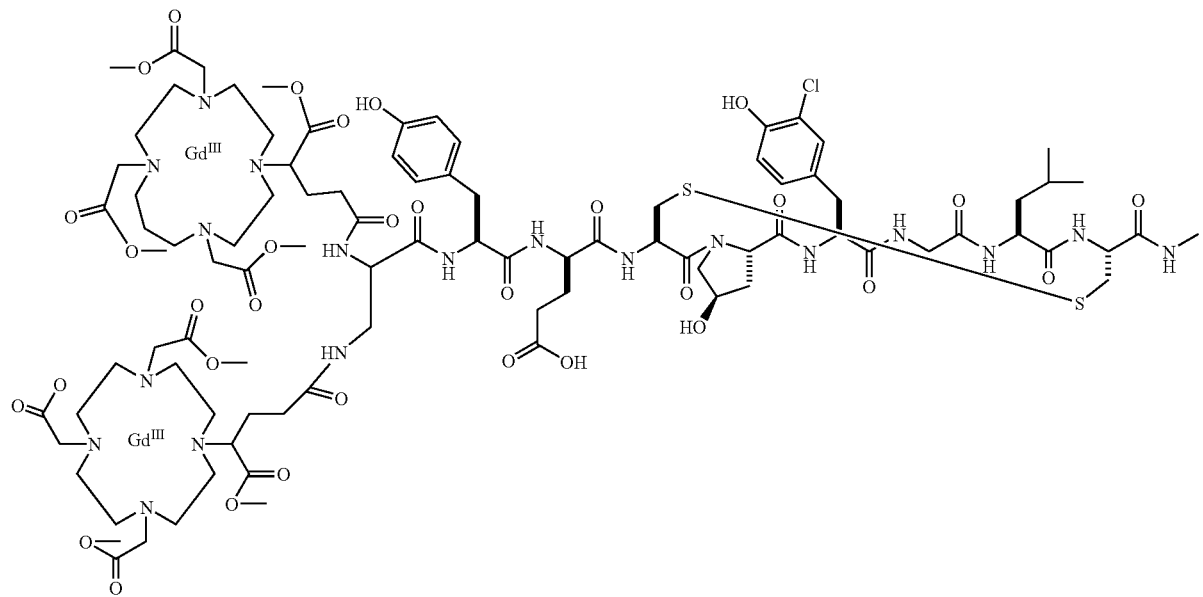
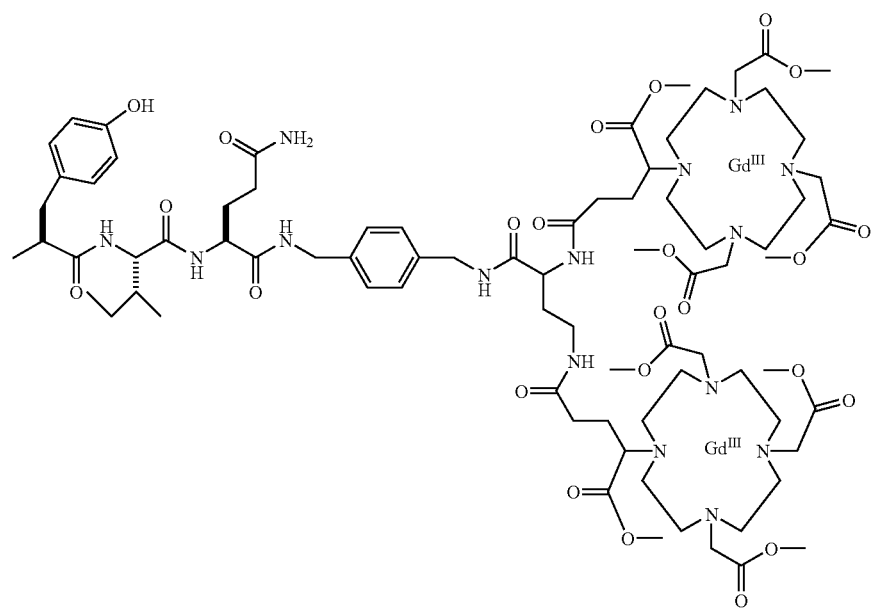

Structure V:
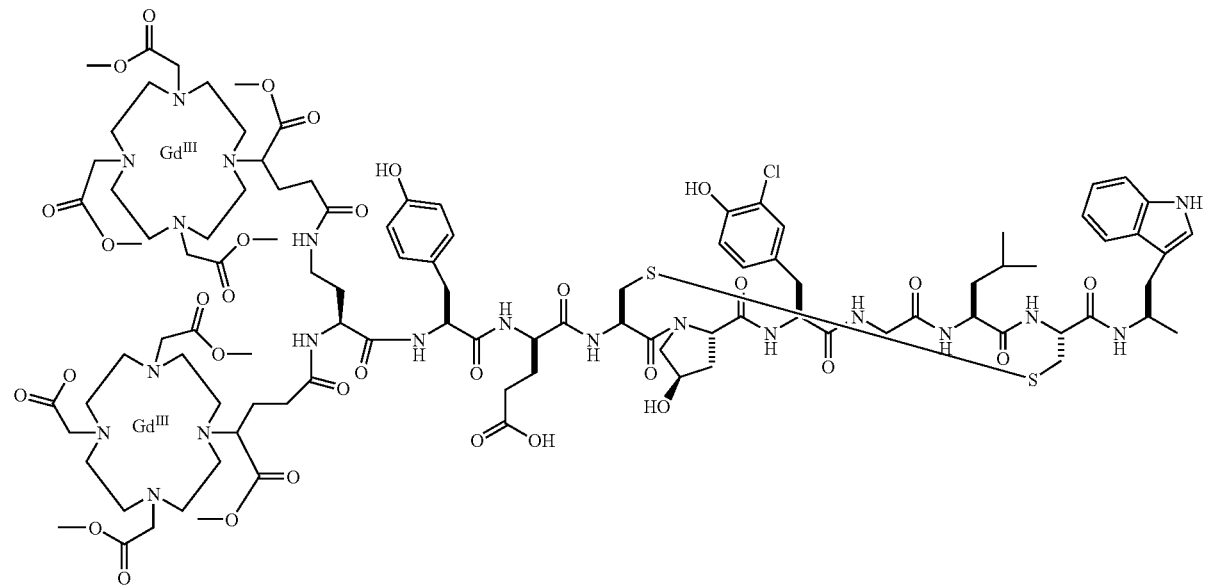
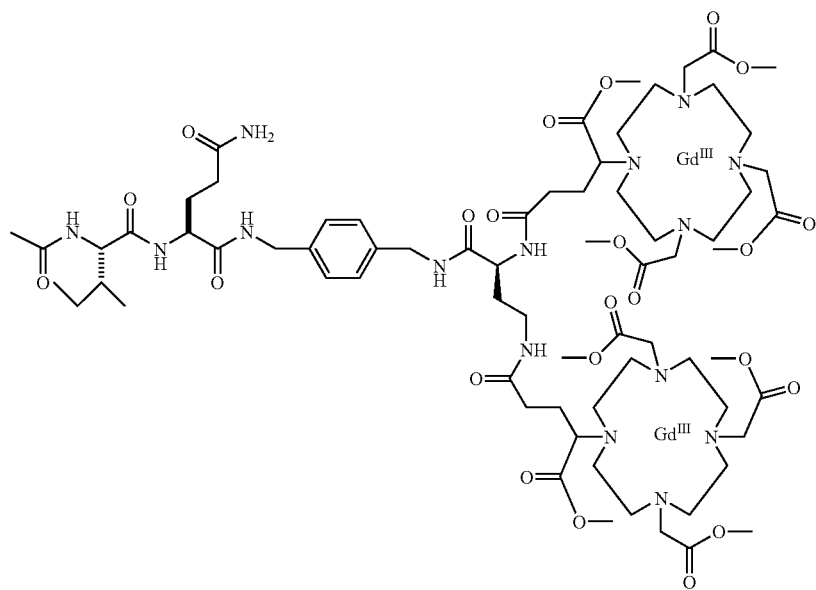

Structure VI:
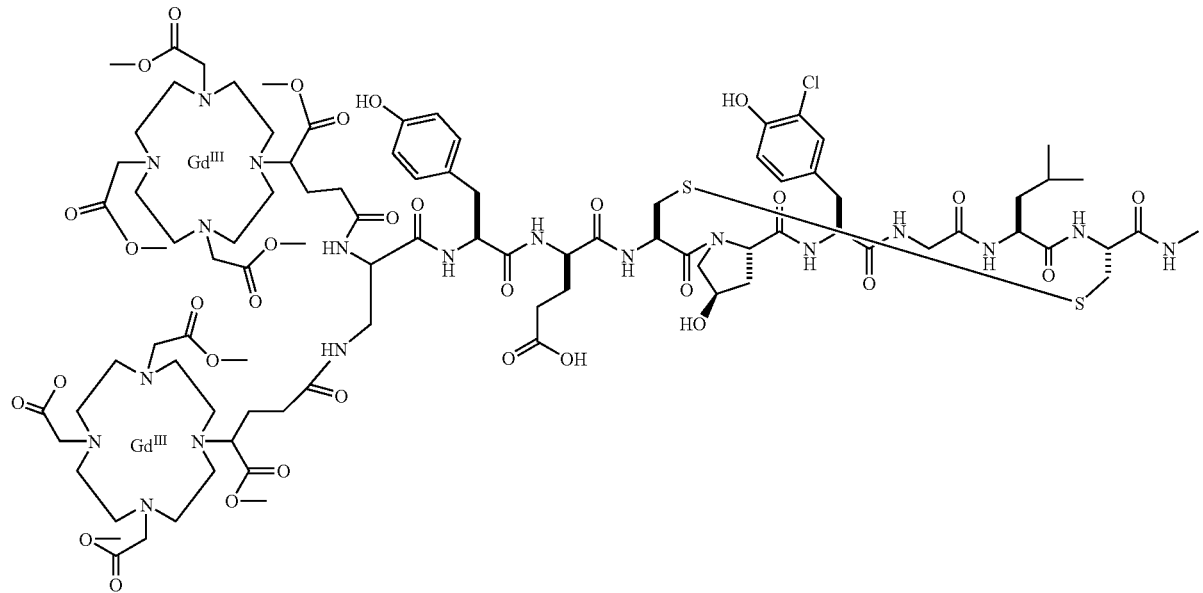
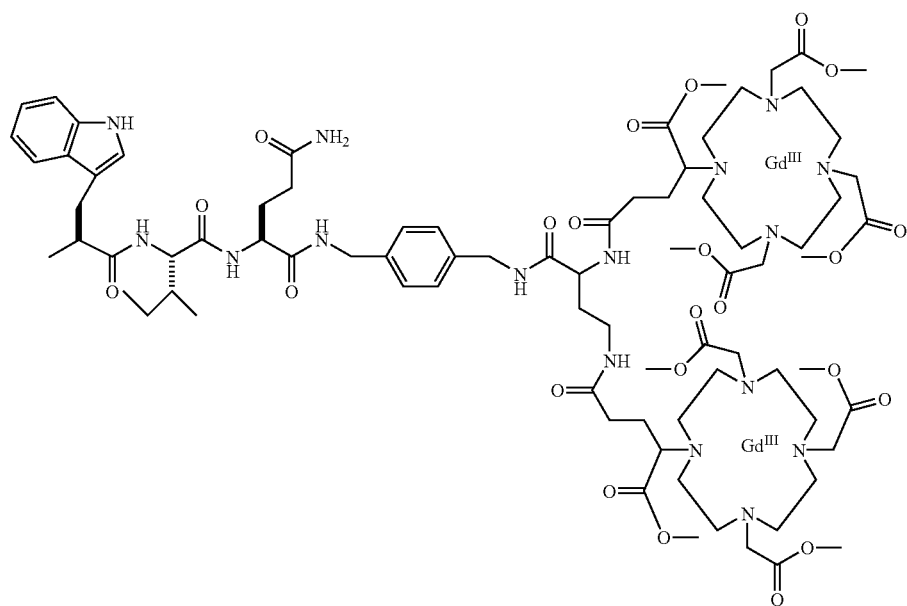

Structure VII:
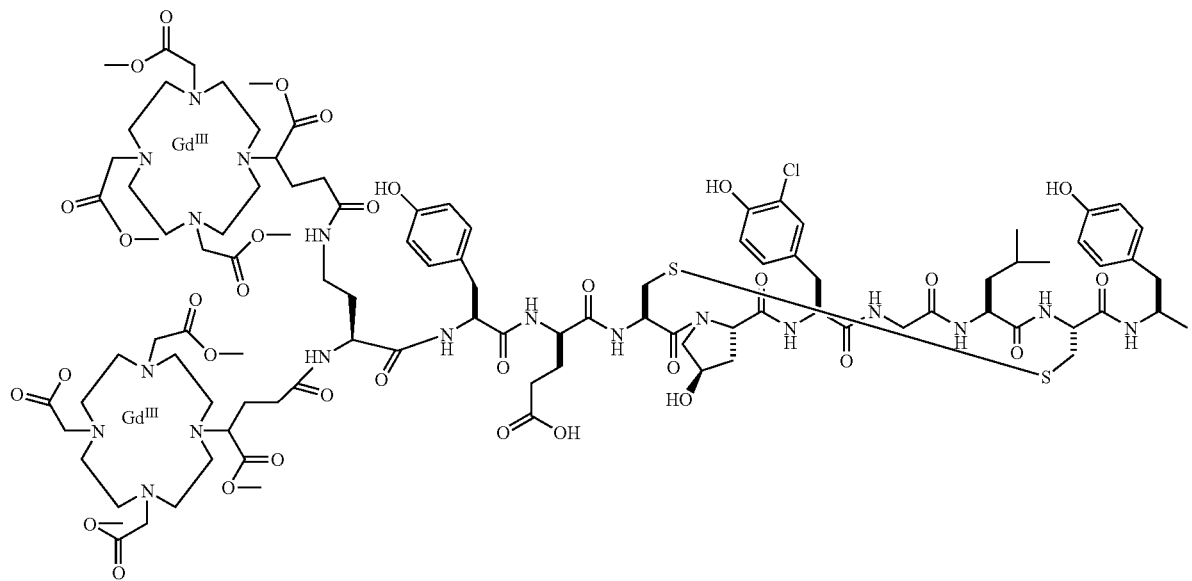
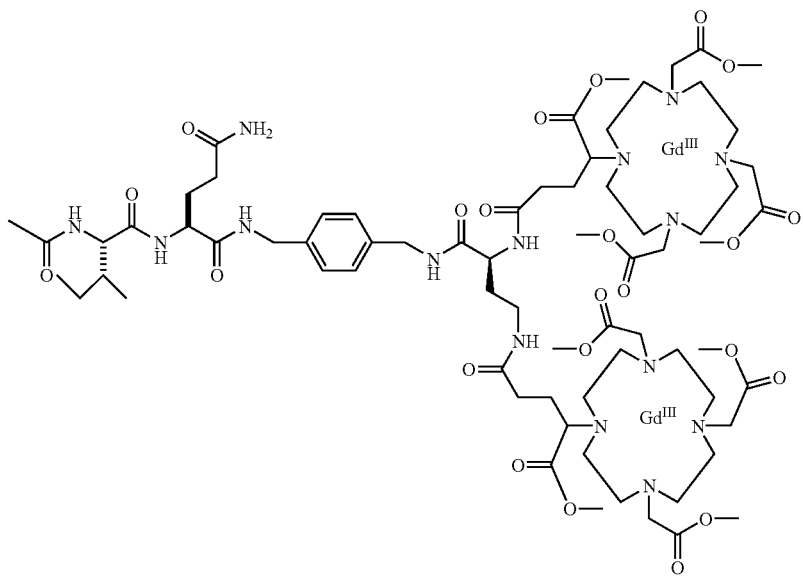

Structure VIII:
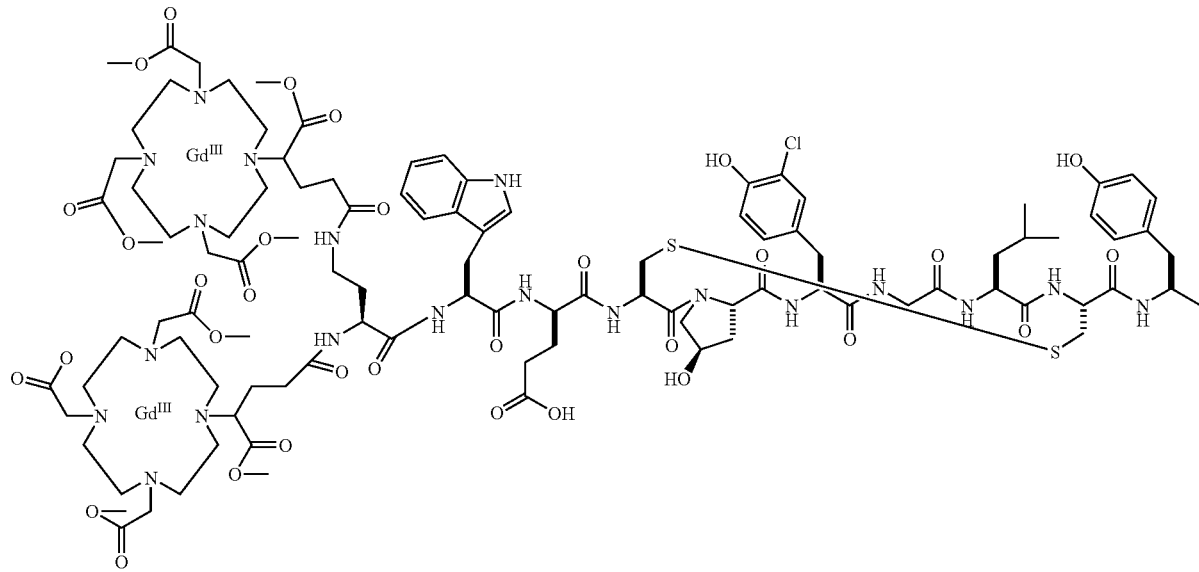
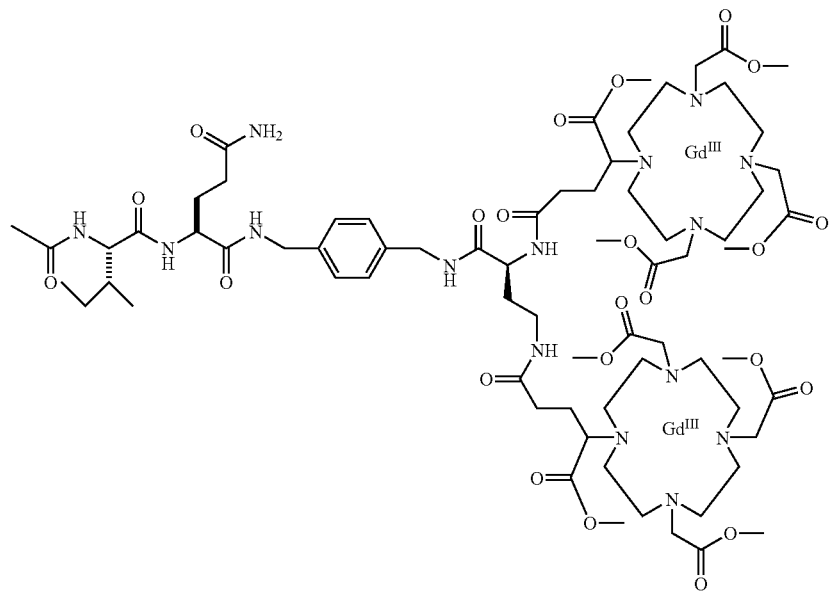
and

Structure IX:

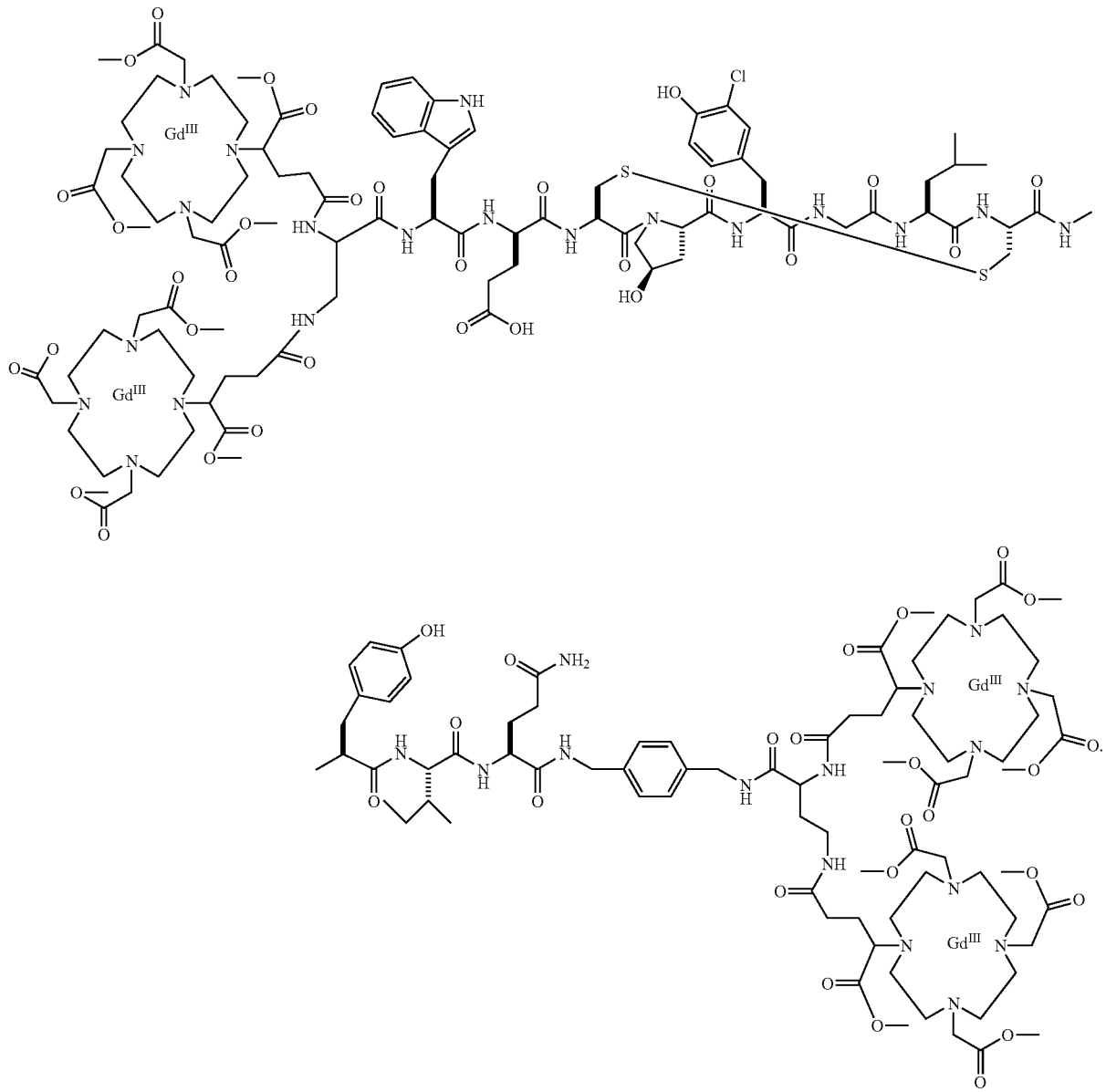

33. The method according to claim 32, further comprising comparing the vascular and targeted MRI data sets to determine the presence of the thrombus, the atherosclerotic plaque, the atherosclerotic lesion, the tumor, or the thromboembolism within the vascular system, provided that the targeted MRI data set indicates the presence of the thrombus, the atherosclerotic plaque, the atherosclerotic lesion, the tumor, or the thromboembolism.

34. The method according to claim 33, wherein the comparing step comprises combining the vascular and targeted MRI data sets to produce a third MRI data set, the third data set comprising an image of both the thrombus, the atherosclerotic plaque, the atherosclerotic lesion, the tumor, or the thromboembolism and the vascular system, and the third data set capable of indicating the location of the thrombus, the atherosclerotic plaque, the atherosclerotic lesion, the tumor, or the thromboembolism, if present, within the vascular system.

35. The method according to claim 34, further comprising displaying the third MRI data set on a display device in order to indicate the location of the thrombus, the atherosclerotic plaque, the atherosclerotic lesion, the tumor, or the thromboembolism, if present, within the vascular system.

36. The method according to claim 34, wherein the third MRI data set is further capable of indicating the size of the thrombus, the atherosclerotic plaque, the atherosclerotic lesion, the tumor, or the thromboembolism within the vascular system.

37. The method according to claim 34, wherein the combining step comprises registering spatially the targeted and vascular MRI data sets with respect to one another.

38. The method according to claim 34, wherein the combining step further comprises interpolating the spatial resolution of either the vascular or the targeted MRI data set so that the vascular and targeted MRI data sets are of equivalent spatial resolution.

39. The method according to claim 38, wherein the interpolating step comprises:
determining which of the vascular or targeted MRI data sets has the higher spatial resolution; and
interpolating the spatial resolution of the corresponding other data set to the data set determined to have the higher spatial resolution.

40. The method according to claim 38, wherein the combining step further comprises a direct calculation of modified image intensities resulting from a combination of individual values from registered, interpolated data elements from the vascular and targeted MRI data sets.

41. The method according to claim 40, wherein the direct calculation of modified image intensities includes variably weighting the individual values of the registered, interpolated data elements from the vascular and targeted MRI data sets.

42. The method according to claim 32, wherein the targeted contrast agent is administered prior to the vascular contrast agent, and wherein the vascular MRI data set is acquired prior to the targeted MRI data set.

43. The method according to claim 32, wherein the targeted contrast agent and the vascular contrast agent are administered simultaneously, and wherein the targeted MRI data set is acquired prior to the vascular MRI data set.

44. The method according to claim 32, wherein the targeted contrast agent and the vascular contrast agent are administered within 2 hours of one another.

45. The method according to claim 44, wherein the targeted contrast agent and the vascular contrast agent are administered within 30 min. of one another.

46. The method according to claim 45, wherein the targeted contrast agent and the vascular contrast agent are administered within 15 min. of one another.

47. The method according to claim 32, wherein the targeted MRI data set and the vascular MRI data set are acquired in a single MRI session.

48. The method according to claim 32, wherein the vascular MRI contrast agent is administered at a dose sufficient to result in a blood $T_1$ after administration of less than 300 ms.

49. The method according to claim 48, wherein the vascular MRI contrast agent is administered at a dose sufficient to result in a blood $T_1$ after administration of less than 175 ms.

50. The method according to claim 48, wherein the vascular MRI contrast agent is administered at a dose sufficient to result in a blood $T_1$ after administration of less than 100 ms.

51. The method according to claim 32, wherein the vascular MRI contrast agent is an extracellular MRI contrast agent selected from the group consisting of:

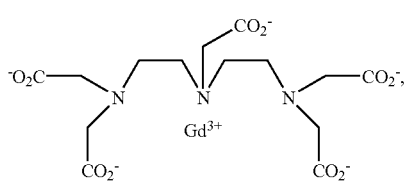
(Gd-DTPA)

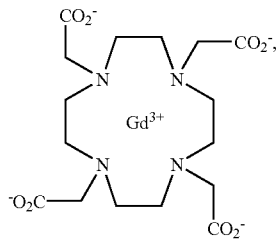
(Gd-DOTA)

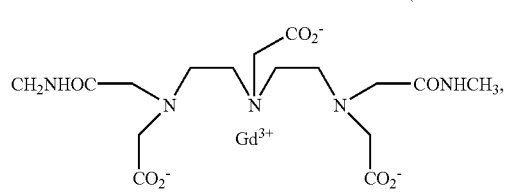
(Gd-DTPA-BMA)

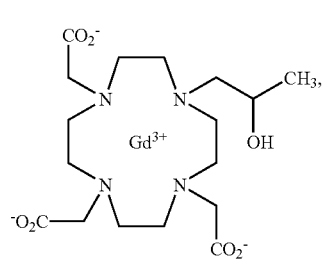
(Gd-HP-DO3A)

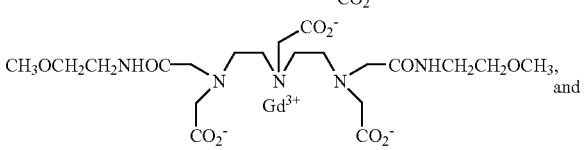
(gadoversetamide)

and

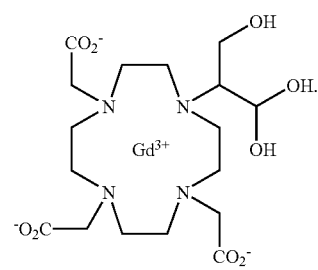
(gadobutol)

52. The method according to claim 32, wherein the vascular MRI contrast agent is selected from the group consisting of ultra-small particles of iron oxide (USPIOs) and monocrystalline iron oxide particles (MIONs).

53. The method according to claim 32, wherein the vascular MRI contrast agent is a blood pool contrast agent.

54. The method according to claim 53, wherein the vascular MRI blood pool contrast agent is selected from the group consisting of:

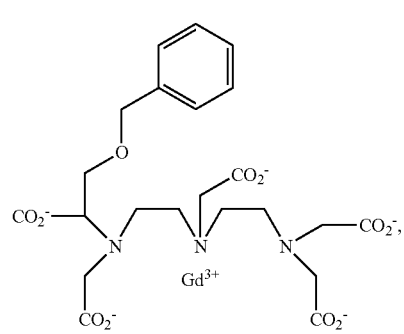
(Gd-BOPTA)

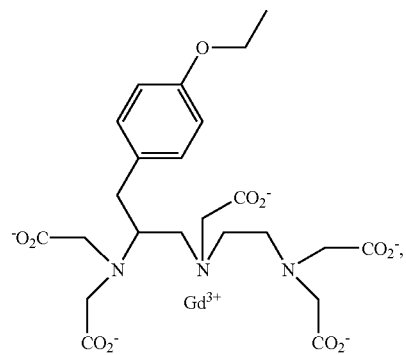
(Gd-EOB-DTPA)

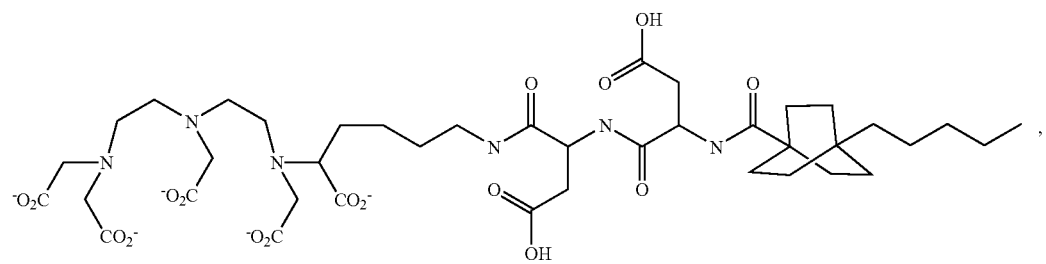
(MP-2269)

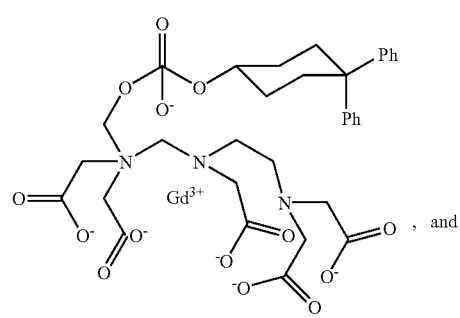
(MS-325)

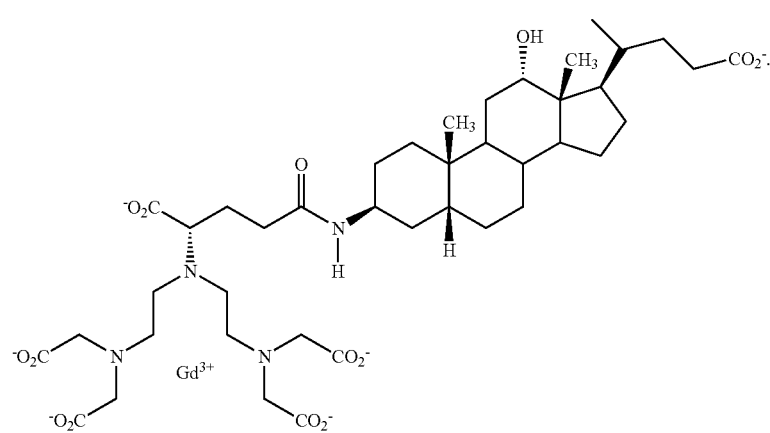
(B-22956/1)

55. The method according to claim 32, wherein the vascular MRI contrast agent further exhibits a specific affinity for a non-stationary biological component present within the mammal's vascular system.

56. The method according to claim 55, wherein the non-stationary biological component present within the mammal's vascular system is selected from the group consisting of human serum albumin, fibrinogen, alpha acid glycoprotein, globulins, and lipoproteins.

57. The method according to claim 56, wherein the non-stationary biological component present within the mammal's vascular system is human serum albumin.

58. The method according to claim 32, wherein the targeted MRI contrast agent is administered at a dose sufficient to result in a $T_1$ of the stationary target of less than 500 ms.

59. The method according to claim 58, wherein the targeted MRI contrast agent is administered at a dose sufficient to result in a $T_1$ of the stationary target of less than 300 ms.

60. The method according to claim 59, wherein the targeted MRI contrast agent is administered at a dose sufficient to result in a $T_1$ of the stationary target of less than 100 ms.

61. The method according to claim 32, wherein the targeted MRI contrast agent is administered at a dose from about 0.001 to about 500 μmol/kg and the vascular MRI contrast agent is administered at a dose from about 0.01 to about 300 μmol/kg.

62. The method according to claim 61, wherein the targeted MRI contrast agent is administered at a dose from about 0.001 to about 50 μmol/kg and the vascular MRI contrast agent is administered at a dose from about 0.01 to about 30 μmol/kg.

63. The method according to claim 62, wherein the targeted MRI contrast agent is administered at a dose from about 0.001 to about 5 μmol/kg and the vascular MRI contrast agent is administered at a dose from about 0.01 to about 3 μmol/kg.

64. The method according to claim 32, wherein the targeted MRI contrast agent's specific affinity for the thrombus, the atherosclerotic plaque, the atherosclerotic lesion, the tumor, or the thromboembolism, expressed as a dissociation constant, is less than 50 μM.

65. The method according to claim 64, wherein the targeted MRI contrast agent's specific affinity for the thrombus, the atherosclerotic plaque, the atherosclerotic lesion, the tumor, or the thromboembolism, expressed as a dissociation constant, is less than 5 μM.

66. The method according to claim 65, wherein the targeted MRI contrast agent's specific affinity for the thrombus, the atherosclerotic plaque, the atherosclerotic lesion, the tumor, or the thromboembolism, expressed as a dissociation constant, is less than 0.5 μM.

67. The method according to claim 32, wherein the targeted MRI data set is acquired using a spoiled gradient echo sequence.

68. The method according to claim 32, wherein the vascular MRI contrast agent is administered as a bolus.

69. The method according to claim 32, wherein the vascular MRI contrast agent is administered by infusion, with an infusion time of less than 15 minutes.

70. The method according to claim 69, wherein the infusion time is less than 10 minutes.

71. The method according to claim 70, wherein the infusion time is less than 3 minutes.

* * * * *

UNITED STATES PATENT AND TRADEMARK OFFICE
CERTIFICATE OF CORRECTION

| | | |
|---|---|---|
| PATENT NO. | : 7,412,279 B2 | Page 1 of 29 |
| APPLICATION NO. | : 10/209416 | |
| DATED | : August 12, 2008 | |
| INVENTOR(S) | : Robert M. Weisskoff | |

It is certified that error appears in the above-identified patent and that said Letters Patent is hereby corrected as shown below:

Columns 3-4, please delete the chemical figure shown after "Structure I" and insert
--

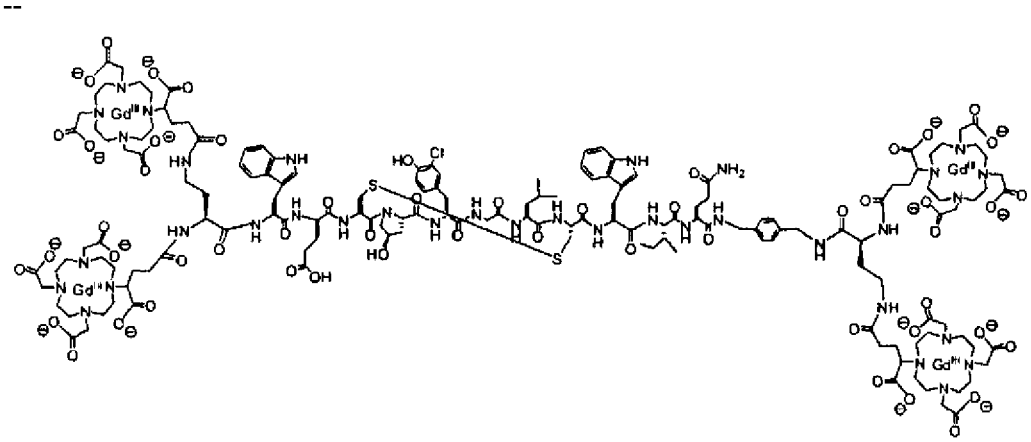

-- therefor;

Columns 5-6, please delete the chemical figure shown after "Structure II" and insert
--

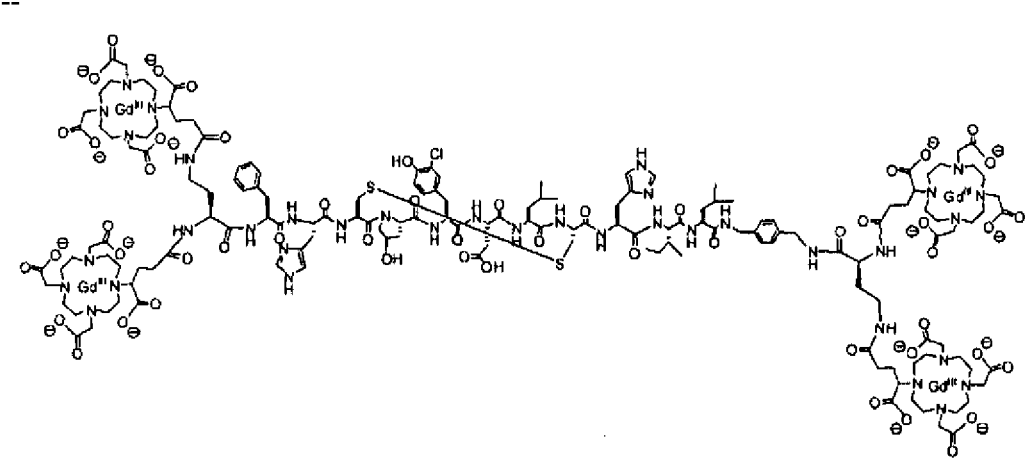

-- therefor;

UNITED STATES PATENT AND TRADEMARK OFFICE
CERTIFICATE OF CORRECTION

PATENT NO. : 7,412,279 B2  Page 2 of 29
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 7-8, please delete the chemical figure shown after "Structure III" and insert
--

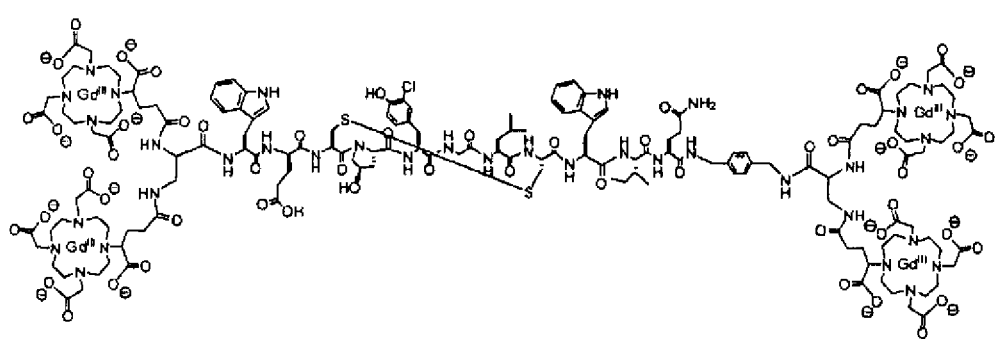

-- therefor;

Columns 9-10, please delete the chemical figure shown after "Structure IV" and insert
--

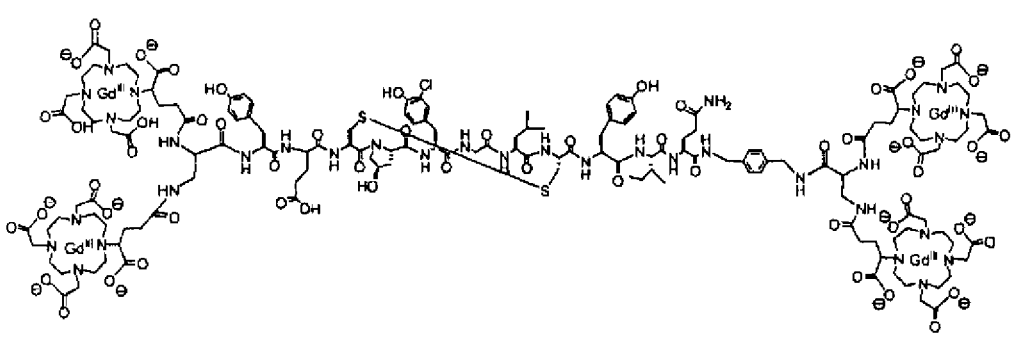

-- therefor;

UNITED STATES PATENT AND TRADEMARK OFFICE
CERTIFICATE OF CORRECTION

PATENT NO. : 7,412,279 B2  Page 3 of 29
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 11-12, please delete the chemical figure shown after "Structure V" and insert --

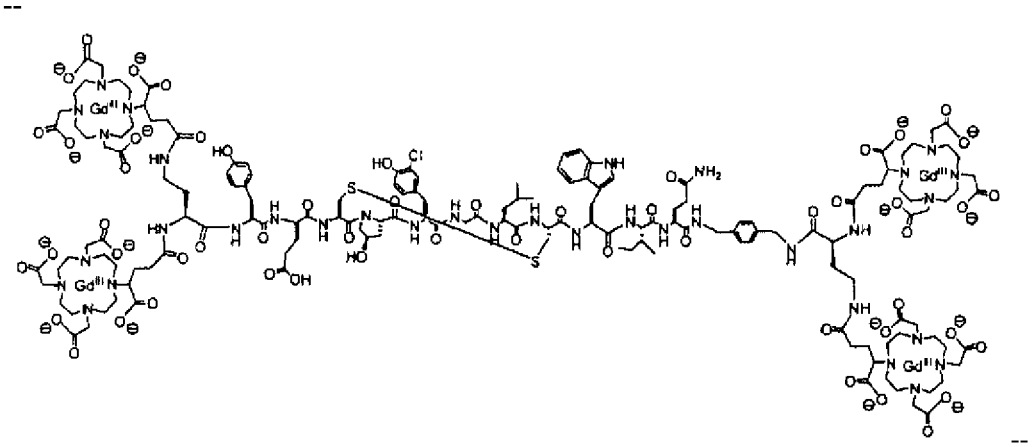

-- therefor;

Columns 13-14, please delete the chemical figure shown after "Structure VI" and insert --

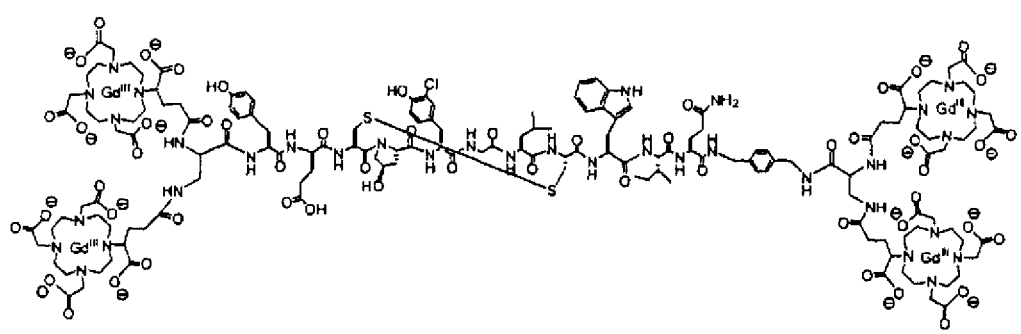

-- therefor;

UNITED STATES PATENT AND TRADEMARK OFFICE
CERTIFICATE OF CORRECTION

PATENT NO. : 7,412,279 B2  Page 4 of 29
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 15-16, please delete the chemical figure shown after "Structure VII" and insert
--

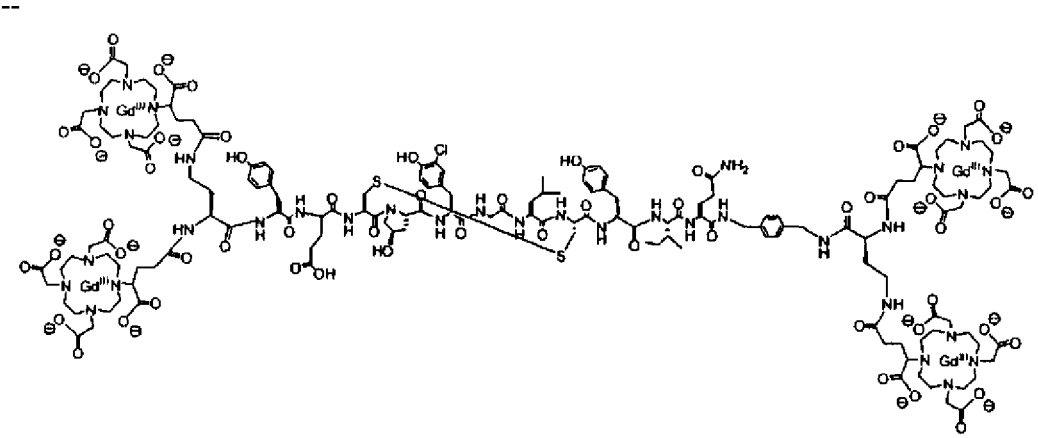

-- therefor;

Columns 17-18, please delete the chemical figure shown after "Structure VIII" and insert
--

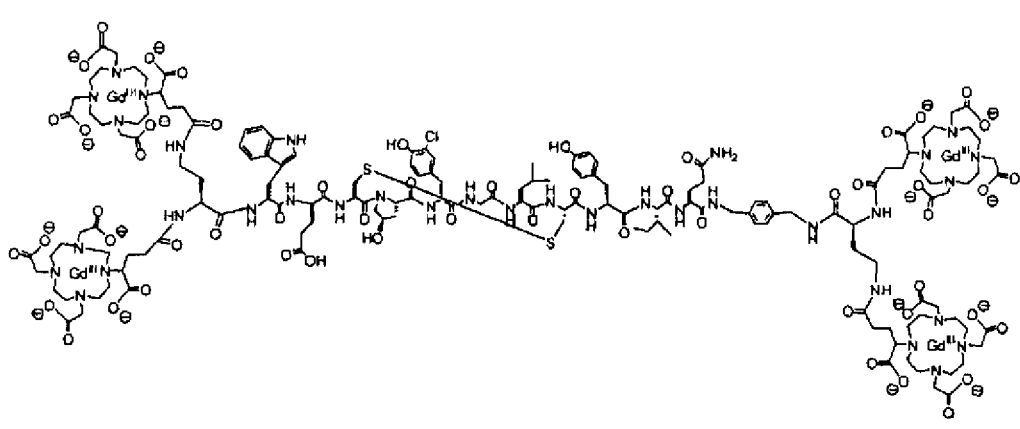

-- therefor;

UNITED STATES PATENT AND TRADEMARK OFFICE
CERTIFICATE OF CORRECTION

PATENT NO. : 7,412,279 B2
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 19-20, please delete the chemical figure shown after "Structure IX" and insert --

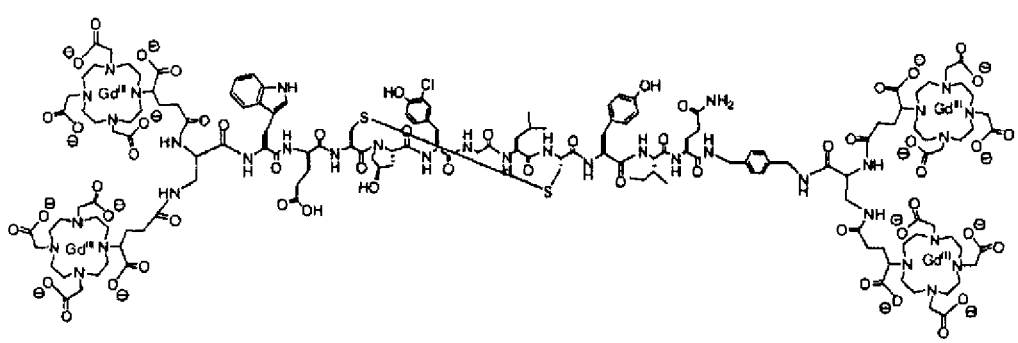

-- therefor;

Columns 21-24, please delete the chemical figure shown after "Structure I" and insert --

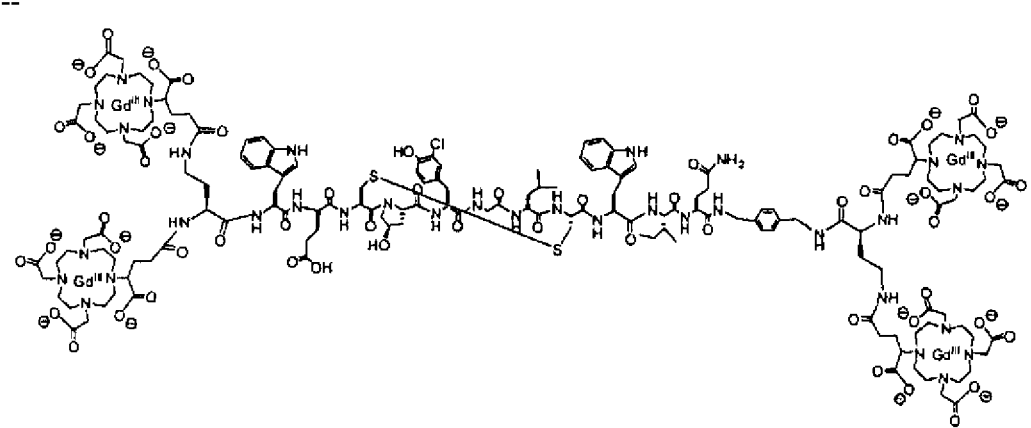

-- therefor;

UNITED STATES PATENT AND TRADEMARK OFFICE
CERTIFICATE OF CORRECTION

PATENT NO. : 7,412,279 B2
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 23-26, please delete the chemical figure shown after "Structure II" and insert --

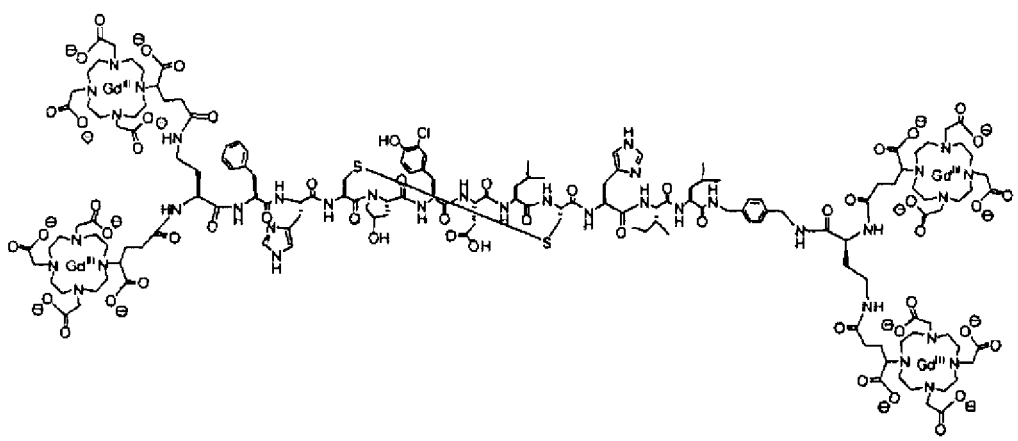

-- therefor;

Columns 25-28, please delete the chemical figure shown after "Structure III" and insert --

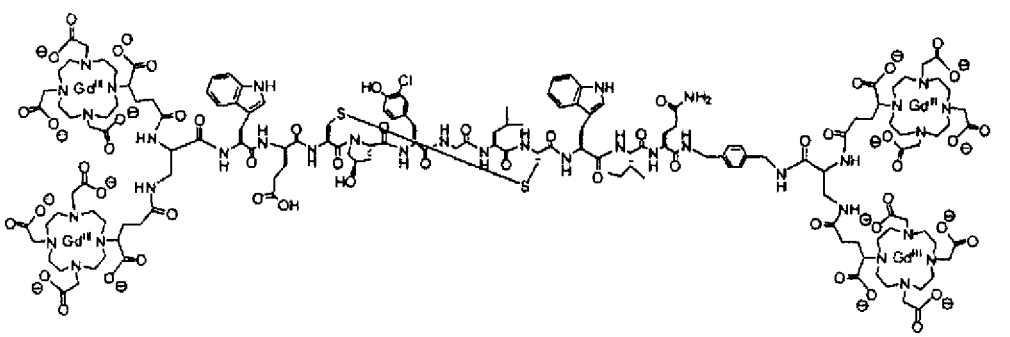

-- therefor;

UNITED STATES PATENT AND TRADEMARK OFFICE
CERTIFICATE OF CORRECTION

PATENT NO. : 7,412,279 B2  Page 7 of 29
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 27-30, please delete the chemical figure shown after "Structure IV" and insert --

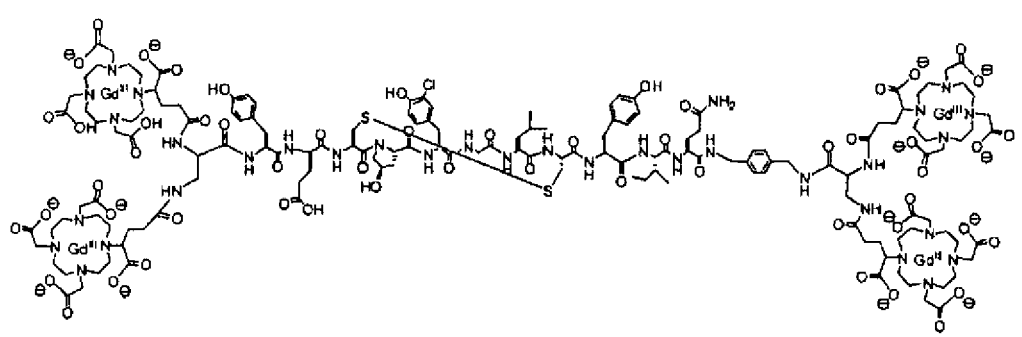

-- therefor;

Columns 29-32, please delete the chemical figure shown after "Structure V" and insert --

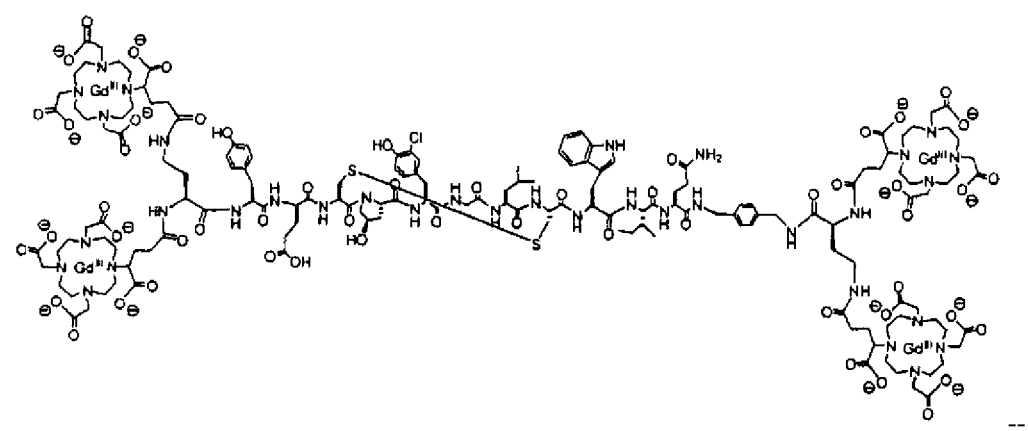

-- therefor;

UNITED STATES PATENT AND TRADEMARK OFFICE
CERTIFICATE OF CORRECTION

PATENT NO.         : 7,412,279 B2                                    Page 8 of 29
APPLICATION NO.    : 10/209416
DATED              : August 12, 2008
INVENTOR(S)        : Robert M. Weisskoff It is certified that error appears in the above-identified patent and that said Letters Patent is hereby corrected as shown below:

Columns 31-34, please delete the chemical figure shown after "Structure VI" and insert --

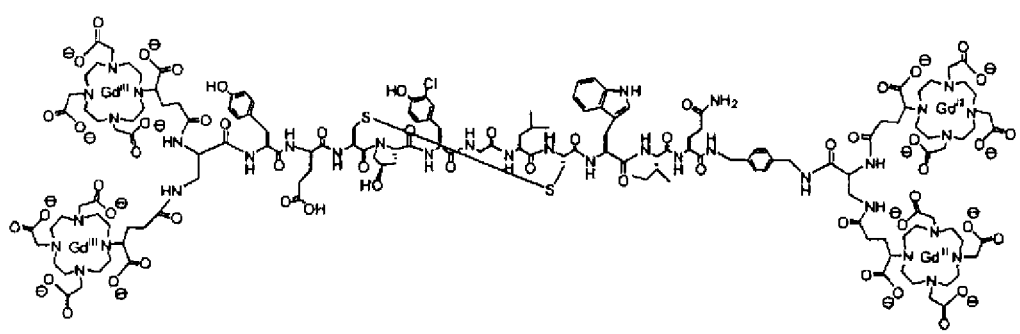

-- therefor;

Columns 33-36, please delete the chemical figure shown after "Structure VII" and insert --

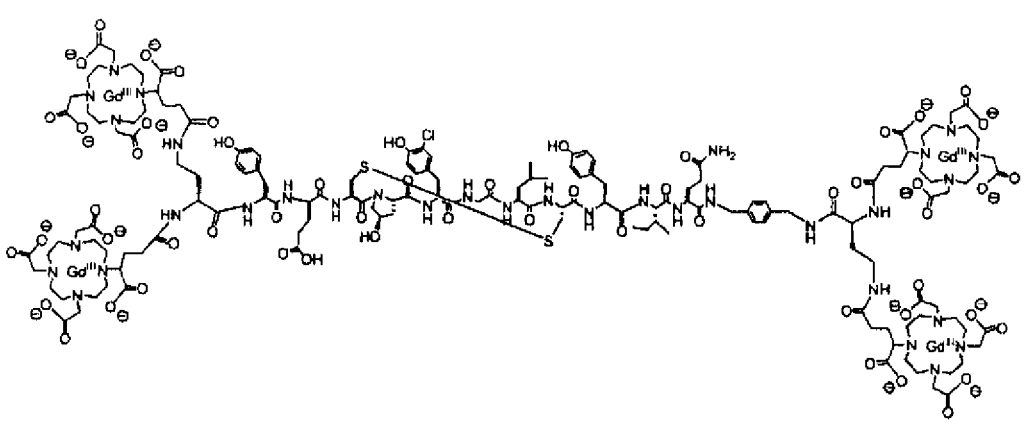

-- therefor;

UNITED STATES PATENT AND TRADEMARK OFFICE
CERTIFICATE OF CORRECTION

PATENT NO. : 7,412,279 B2
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 35-38, please delete the chemical figure shown after "Structure VIII" and insert --

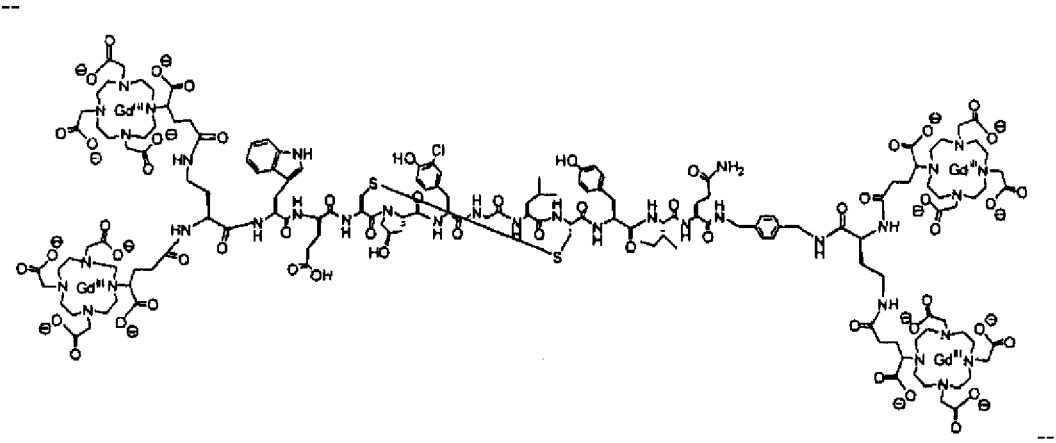

therefor;

Columns 37-40, please delete the chemical figure shown after "Structure IX" and insert --

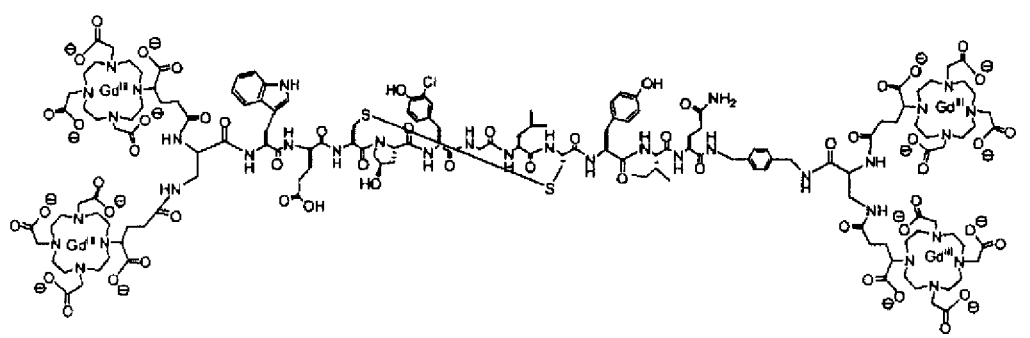

therefor;

UNITED STATES PATENT AND TRADEMARK OFFICE
CERTIFICATE OF CORRECTION

PATENT NO.        : 7,412,279 B2
APPLICATION NO.   : 10/209416
DATED             : August 12, 2008
INVENTOR(S)       : Robert M. Weisskoff It is certified that error appears in the above-identified patent and that said Letters Patent is hereby corrected as shown below:

Column 41, please delete the chemical figure shown after "(MS-325)" and insert
--
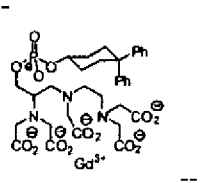
-- therefor;

Columns 47-48, please delete the chemical figure shown after "Structure I" and insert
--
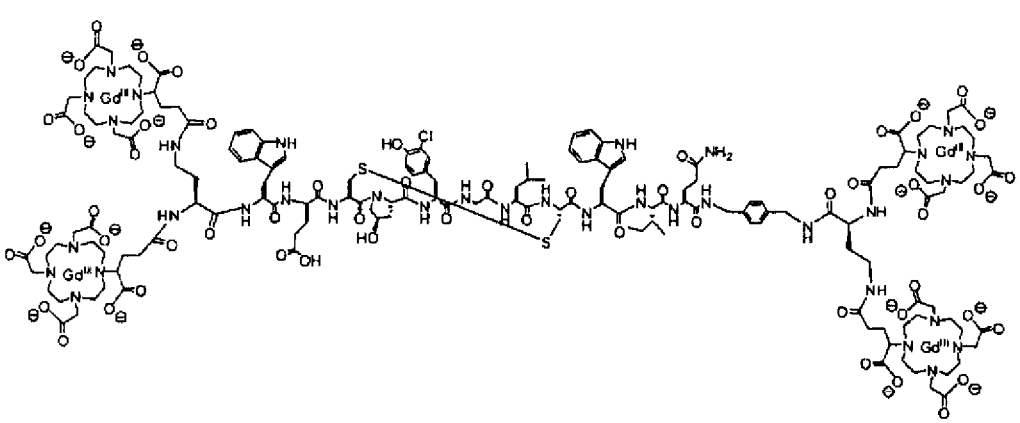
-- therefor;

UNITED STATES PATENT AND TRADEMARK OFFICE
CERTIFICATE OF CORRECTION

PATENT NO. : 7,412,279 B2 Page 11 of 29
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 49-50, please delete the chemical figure shown after "Structure II" and insert
--

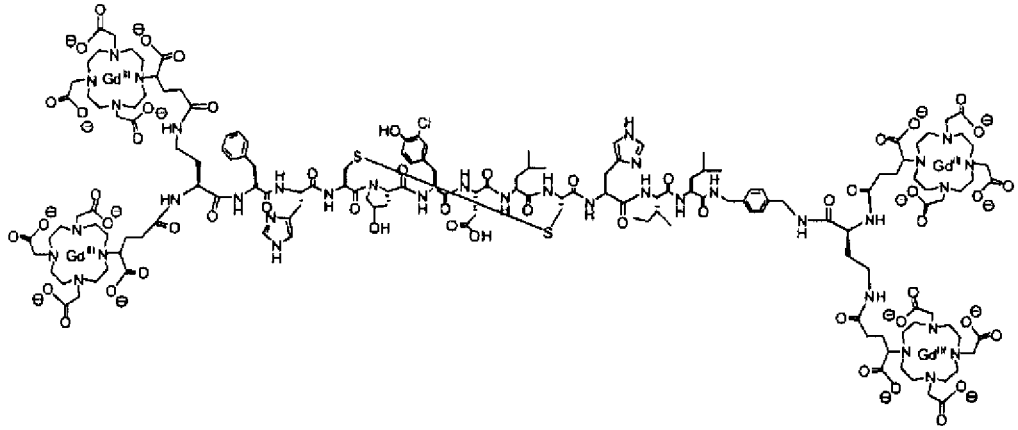

therefor;

Columns 51-52, please delete the chemical figure shown after "Structure III" and insert
--

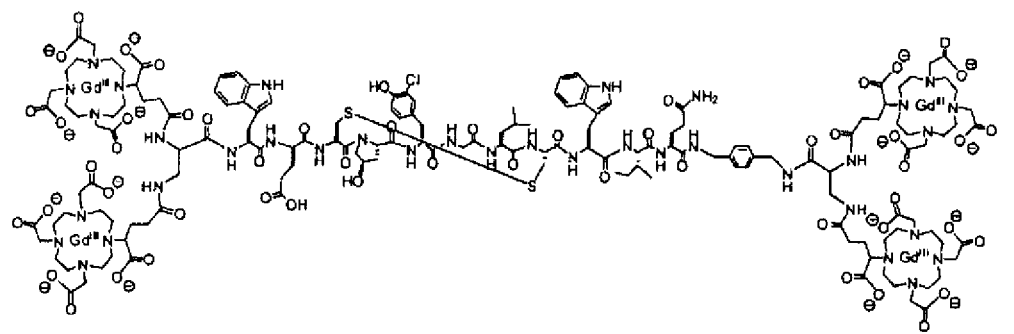

therefor;

UNITED STATES PATENT AND TRADEMARK OFFICE
CERTIFICATE OF CORRECTION

PATENT NO. : 7,412,279 B2
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 53-54, please delete the chemical figure shown after "Structure IV" and insert --

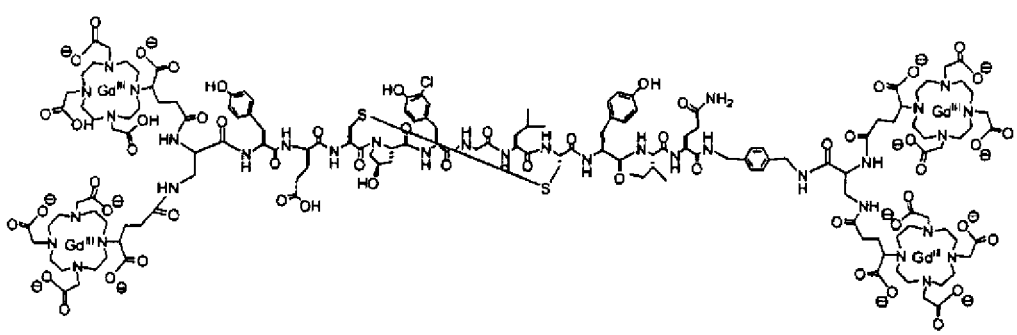

-- therefor;

Columns 55-56, please delete the chemical figure shown after "Structure V" and insert --

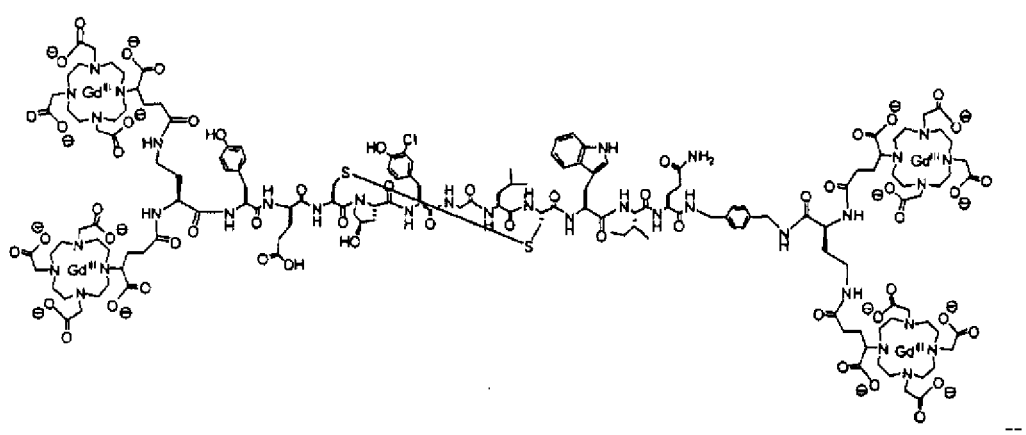

-- therefor;

UNITED STATES PATENT AND TRADEMARK OFFICE
CERTIFICATE OF CORRECTION

PATENT NO. : 7,412,279 B2 Page 13 of 29
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 57-58, please delete the chemical figure shown after "Structure VI" and insert --

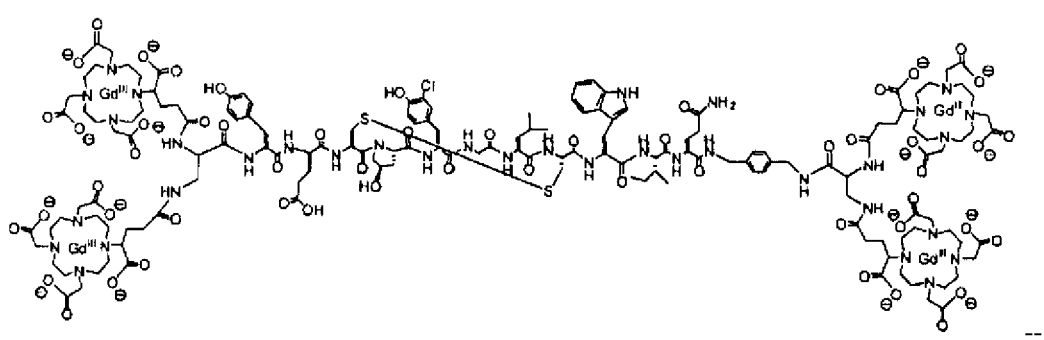

-- therefor;

Columns 59-60, please delete the chemical figure shown after "Structure VII" and insert --

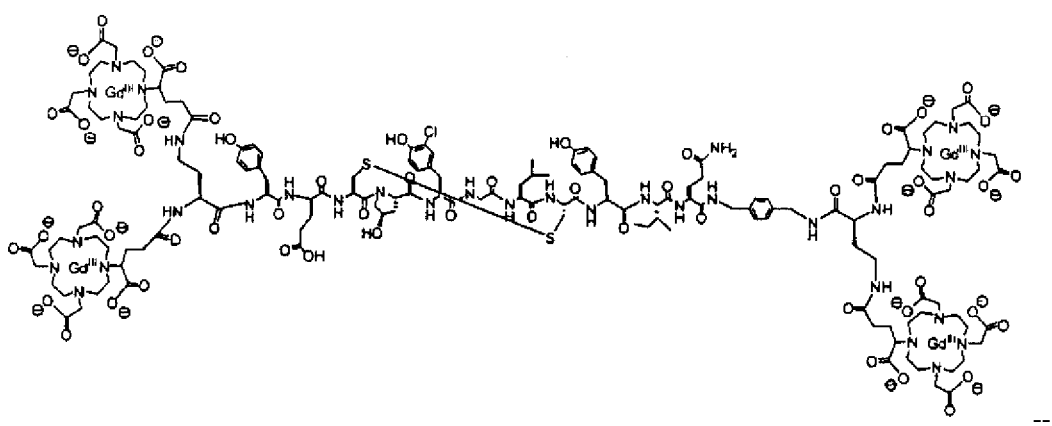

-- therefor;

UNITED STATES PATENT AND TRADEMARK OFFICE
CERTIFICATE OF CORRECTION

PATENT NO.          : 7,412,279 B2
APPLICATION NO.  : 10/209416
DATED                    : August 12, 2008
INVENTOR(S)          : Robert M. Weisskoff It is certified that error appears in the above-identified patent and that said Letters Patent is hereby corrected as shown below:

Columns 61-62, please delete the chemical figure shown after "Structure VIII" and insert --

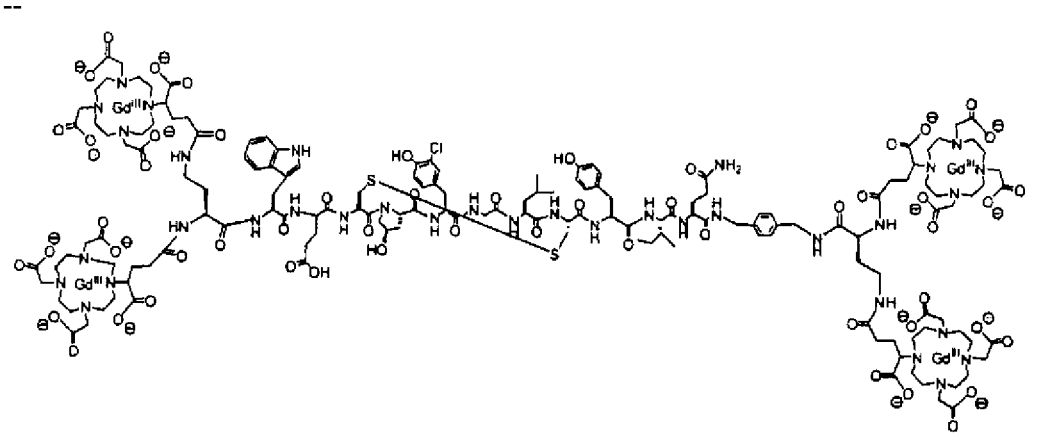

-- therefor;

Columns 63-64, please delete the chemical figure shown after "Structure IX" and insert --

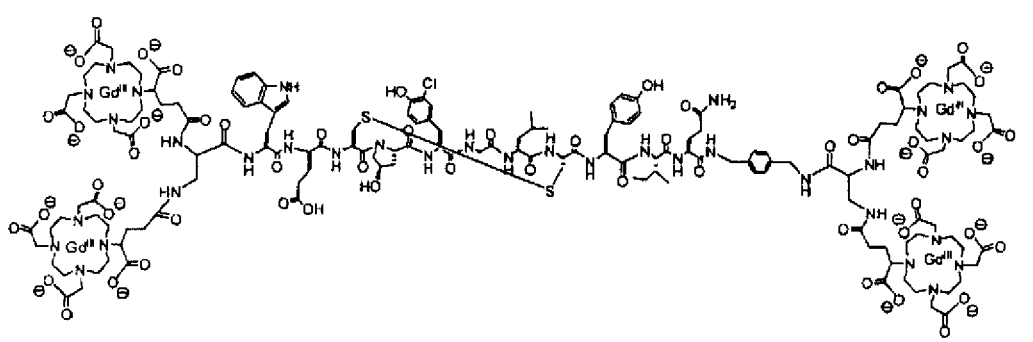

-- therefor;

UNITED STATES PATENT AND TRADEMARK OFFICE
CERTIFICATE OF CORRECTION

PATENT NO. : 7,412,279 B2
APPLICATION NO. : 10/209416
DATED : August 12, 2008
INVENTOR(S) : Robert M. Weisskoff Page 15 of 29

It is certified that error appears in the above-identified patent and that said Letters Patent is hereby corrected as shown below:

Columns 71-72, please delete the chemical figure shown after "Structure I" and insert --

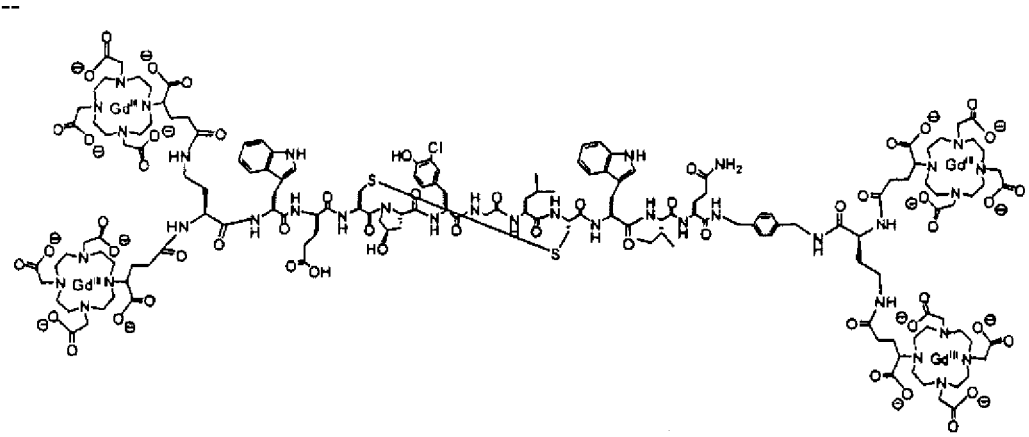

-- therefor;

Columns 73-74, please delete the chemical figure shown after "Structure II" and insert --

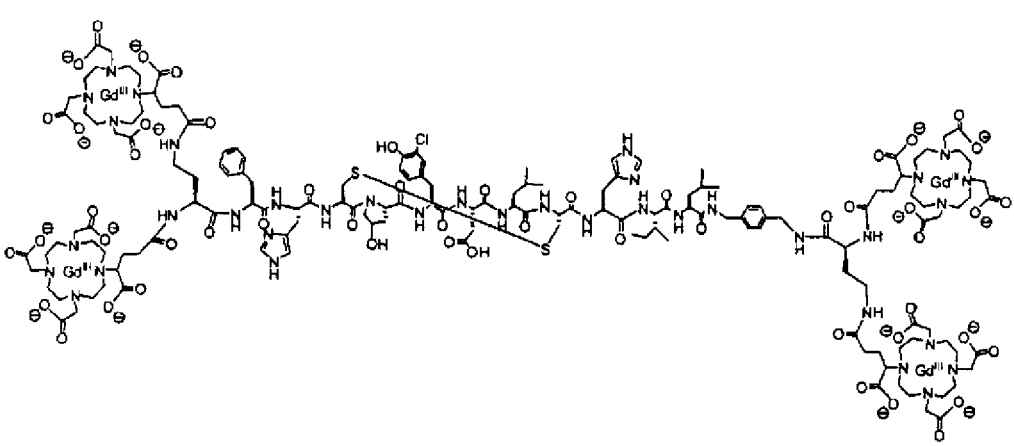

-- therefor;

UNITED STATES PATENT AND TRADEMARK OFFICE
CERTIFICATE OF CORRECTION

PATENT NO.        : 7,412,279 B2
APPLICATION NO.   : 10/209416
DATED             : August 12, 2008
INVENTOR(S)       : Robert M. Weisskoff It is certified that error appears in the above-identified patent and that said Letters Patent is hereby corrected as shown below:

Columns 75-76, please delete the chemical figure shown after "Structure III" and insert --

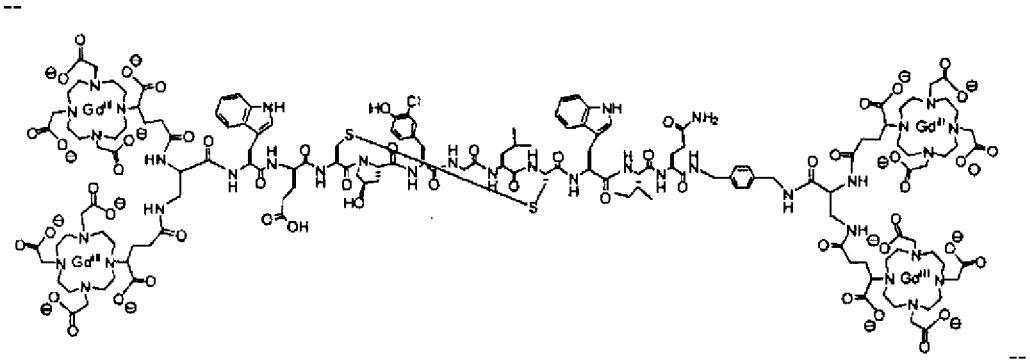

-- therefor;

Columns 77-78, please delete the chemical figure shown after "Structure IV" and insert --

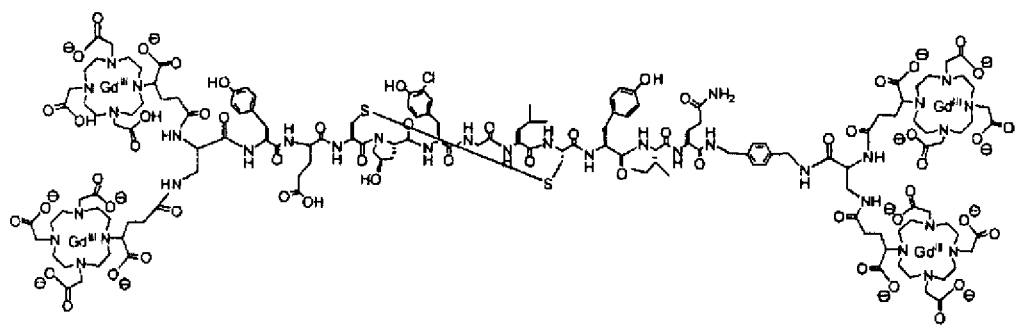

-- therefor;

UNITED STATES PATENT AND TRADEMARK OFFICE
CERTIFICATE OF CORRECTION

PATENT NO.        : 7,412,279 B2
APPLICATION NO.   : 10/209416
DATED             : August 12, 2008
INVENTOR(S)       : Robert M. Weisskoff It is certified that error appears in the above-identified patent and that said Letters Patent is hereby corrected as shown below:

Columns 79-80, please delete the chemical figure shown after "Structure V" and insert --

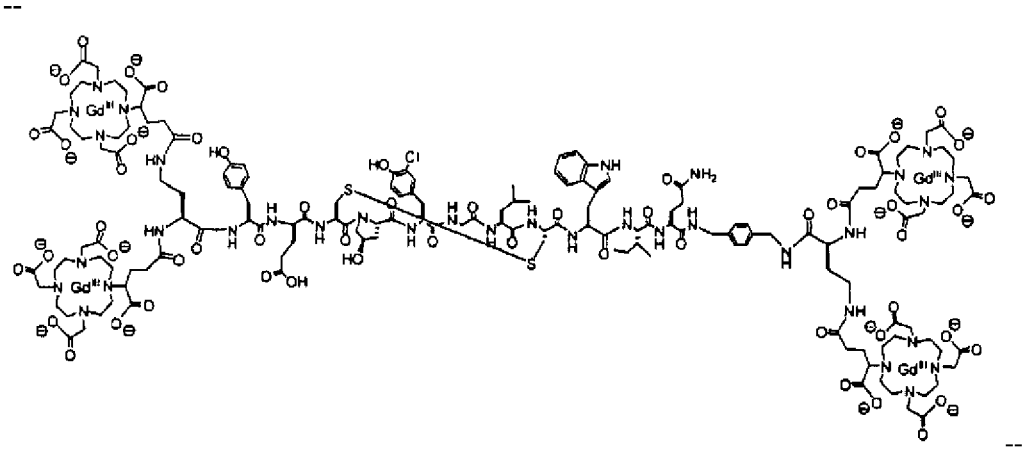

-- therefor;

Columns 81-82, please delete the chemical figure shown after "Structure VI" and insert --

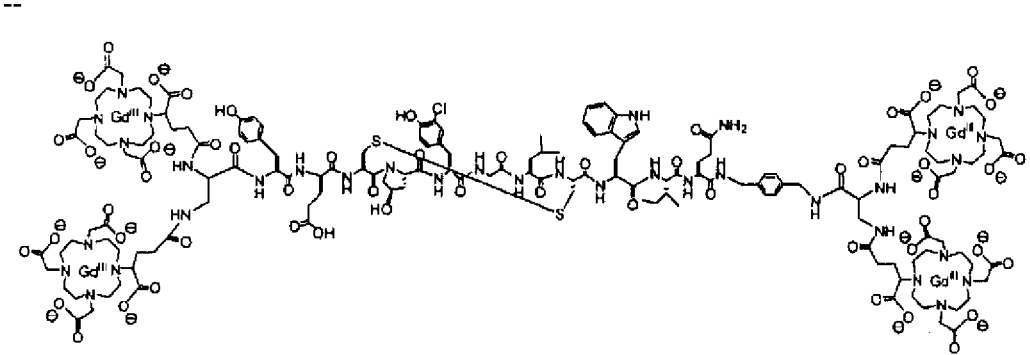

-- therefor;

UNITED STATES PATENT AND TRADEMARK OFFICE
CERTIFICATE OF CORRECTION

PATENT NO. : 7,412,279 B2
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 83-84, please delete the chemical figure shown after "Structure VII" and insert --

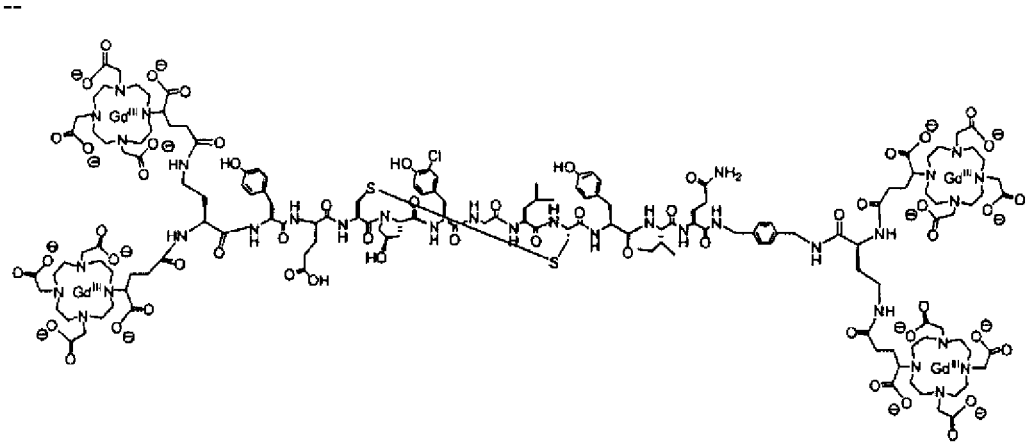

-- therefor;

Columns 85-86, please delete the chemical figure shown after "Structure VIII" and insert --

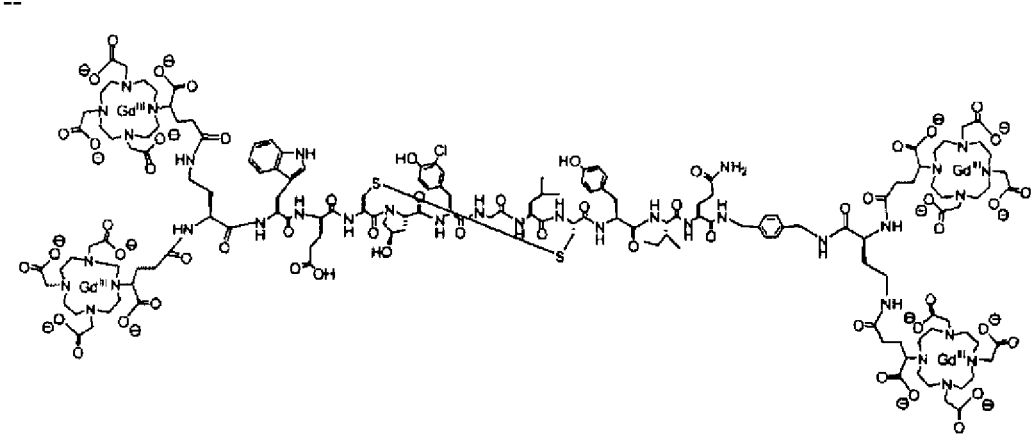

-- therefor;

UNITED STATES PATENT AND TRADEMARK OFFICE
CERTIFICATE OF CORRECTION

PATENT NO.         : 7,412,279 B2
APPLICATION NO.    : 10/209416
DATED              : August 12, 2008
INVENTOR(S)        : Robert M. Weisskoff It is certified that error appears in the above-identified patent and that said Letters Patent is hereby corrected as shown below:

Columns 87-88, please delete the chemical figure shown after "Structure IX" and insert --

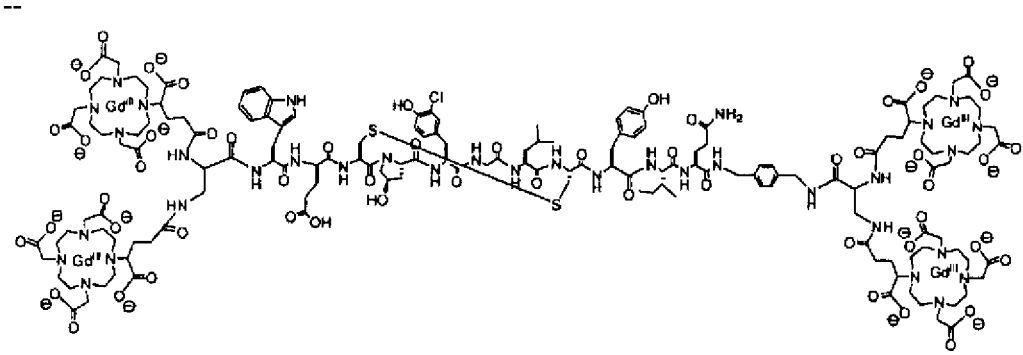

-- therefor;

Column 91, please delete the chemical figure shown after "(MS-325)" and insert --

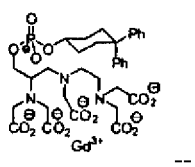

-- therefor;

UNITED STATES PATENT AND TRADEMARK OFFICE
CERTIFICATE OF CORRECTION

PATENT NO. : 7,412,279 B2
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 103-104, Claim 1, please delete the chemical figure shown after "Structure I" and insert
--
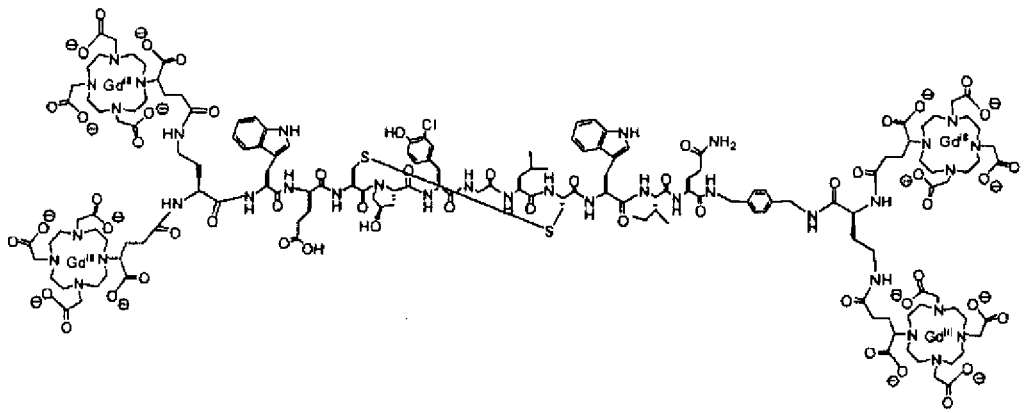
-- therefor;

Columns 105-106, Claim 1, please delete the chemical figure shown after "Structure II" and insert
--
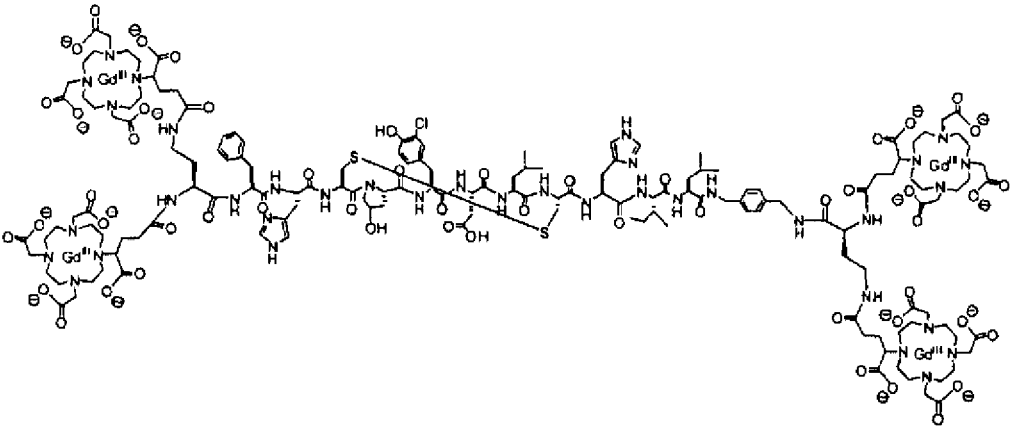
-- therefor;

UNITED STATES PATENT AND TRADEMARK OFFICE
CERTIFICATE OF CORRECTION

PATENT NO. : 7,412,279 B2  Page 21 of 29
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 107-108, Claim 1, please delete the chemical figure shown after "Structure III" and insert
--

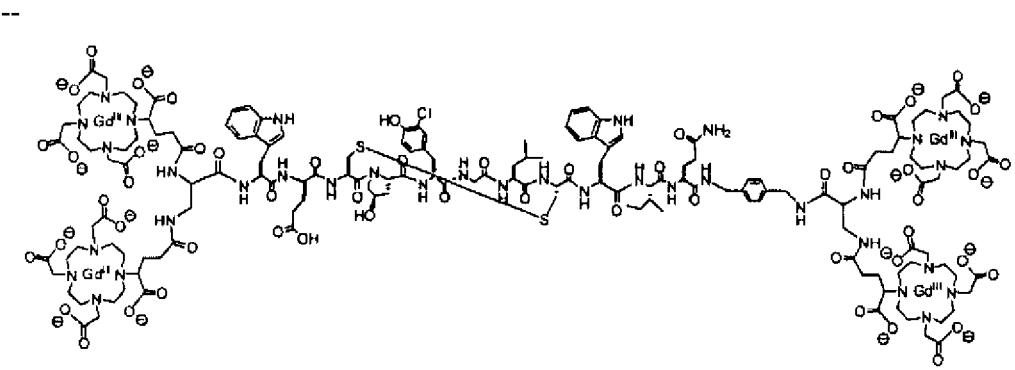

-- therefor;

Columns 109-110, Claim 1, please delete the chemical figure shown after "Structure IV" and insert
--

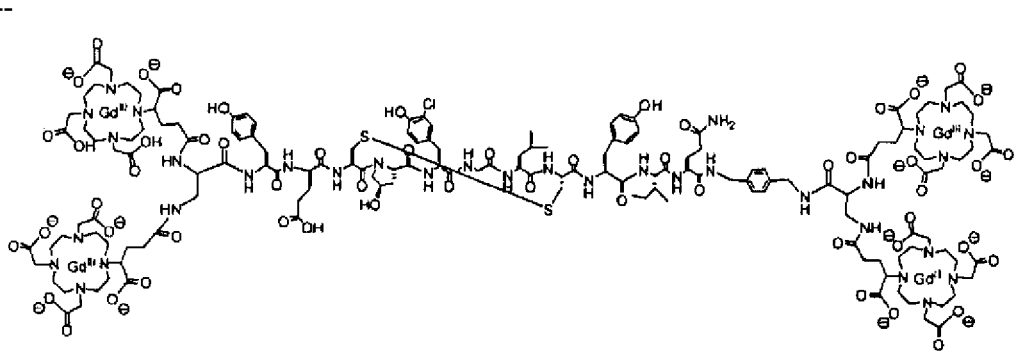

-- therefor;

UNITED STATES PATENT AND TRADEMARK OFFICE
CERTIFICATE OF CORRECTION

PATENT NO. : 7,412,279 B2
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 111-112, Claim 1, please delete the chemical figure shown after "Structure V" and insert
--
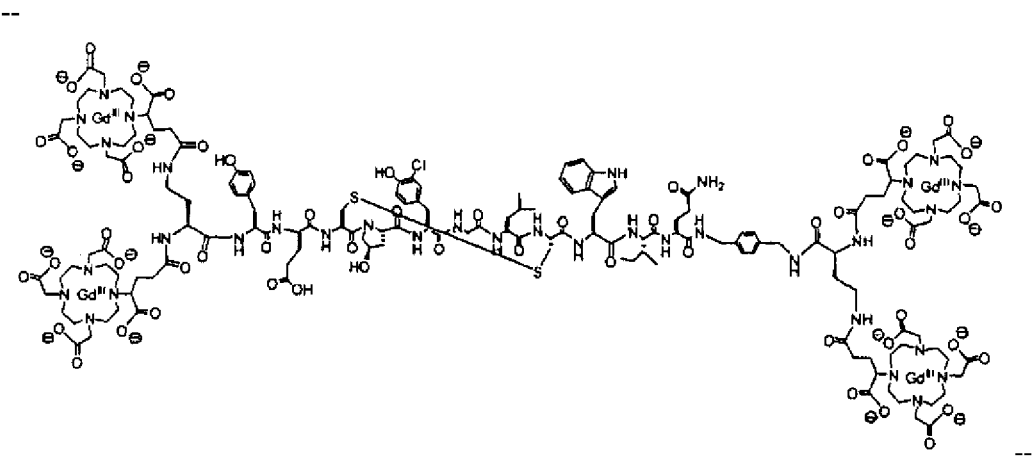
-- therefor;

Columns 113-114, Claim 1, please delete the chemical figure shown after "Structure VI" and insert
--
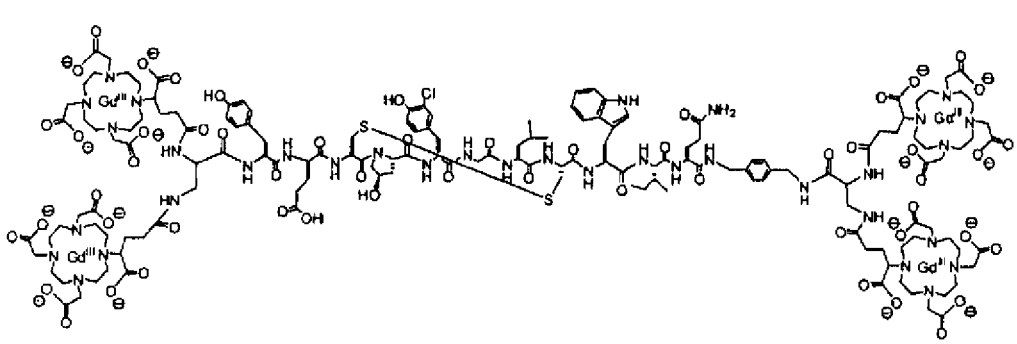
-- therefor;

UNITED STATES PATENT AND TRADEMARK OFFICE
CERTIFICATE OF CORRECTION

PATENT NO. : 7,412,279 B2
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 115-116, Claim 1, please delete the chemical figure shown after "Structure VII" and insert
--

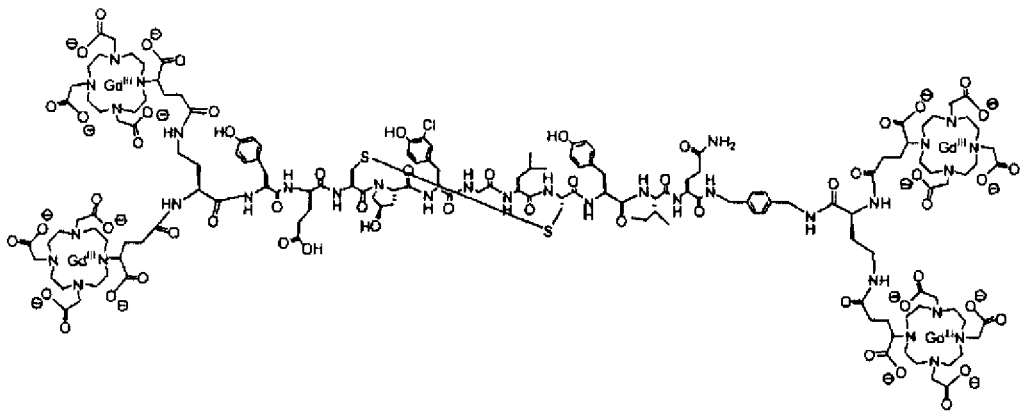

therefor;

Columns 117-118, Claim 1, please delete the chemical figure shown after "Structure VIII" and insert
--

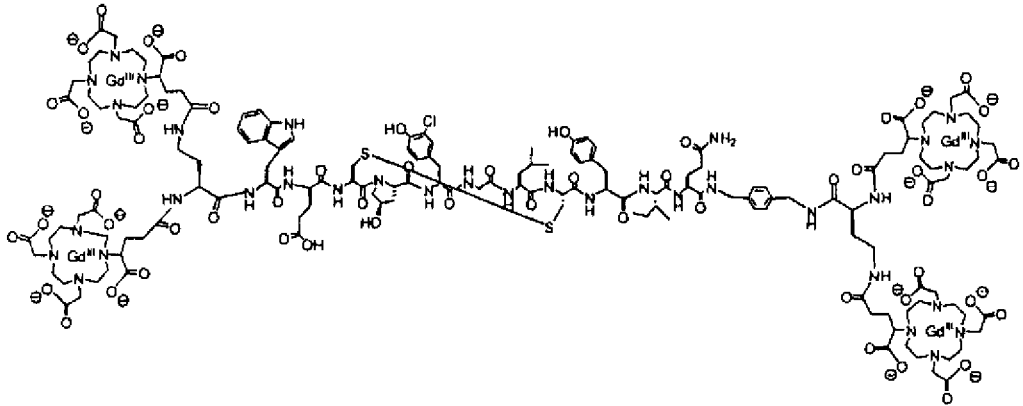

-- therefor;

UNITED STATES PATENT AND TRADEMARK OFFICE
CERTIFICATE OF CORRECTION

PATENT NO.        : 7,412,279 B2
APPLICATION NO.   : 10/209416
DATED             : August 12, 2008
INVENTOR(S)       : Robert M. Weisskoff It is certified that error appears in the above-identified patent and that said Letters Patent is hereby corrected as shown below:

Columns 119-120, Claim 1, please delete the chemical figure shown after "Structure IX" and insert
--

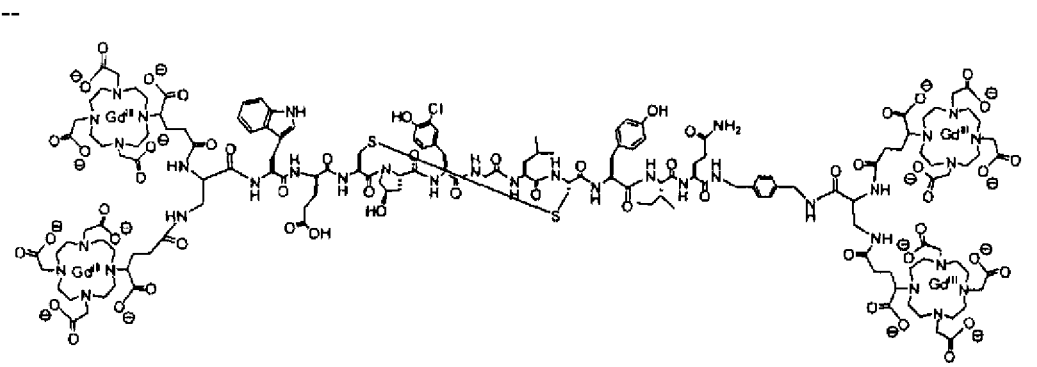

-- therefor;

Columns 123-124, Claim 32, please delete the chemical figure shown after "Structure I" and insert
--

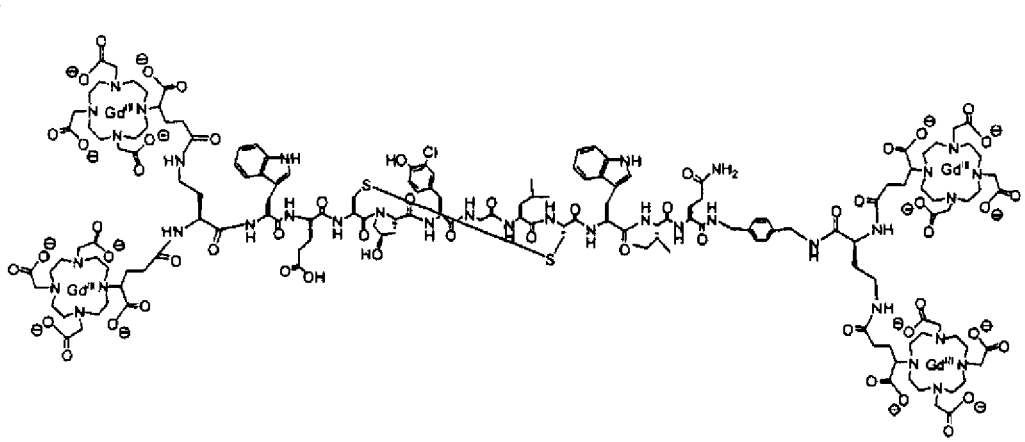

-- therefor;

UNITED STATES PATENT AND TRADEMARK OFFICE
CERTIFICATE OF CORRECTION

PATENT NO. : 7,412,279 B2
APPLICATION NO. : 10/209416
DATED : August 12, 2008
INVENTOR(S) : Robert M. Weisskoff Page 25 of 29

It is certified that error appears in the above-identified patent and that said Letters Patent is hereby corrected as shown below:

Columns 125-126, Claim 32, please delete the chemical figure shown after "Structure II" and insert
--

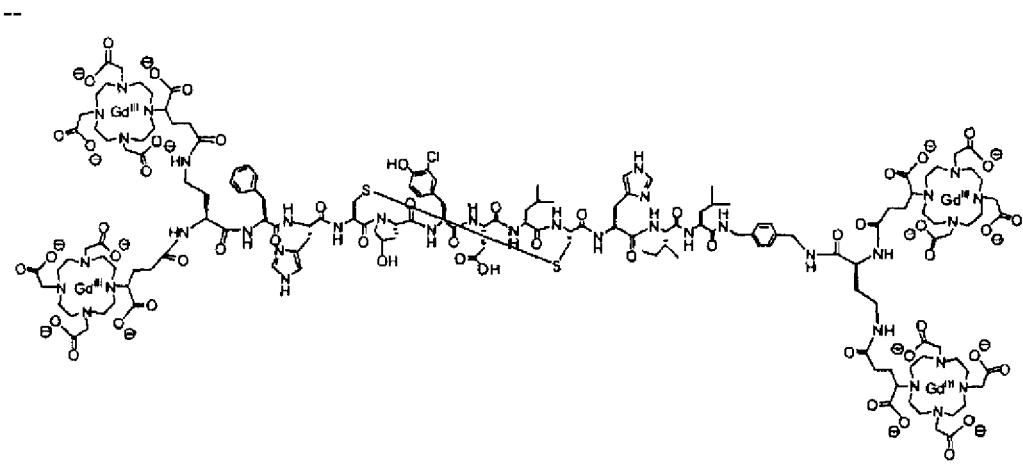

-- therefor;

Columns 127-128, Claim 32, please delete the chemical figure shown after "Structure III" and insert
--

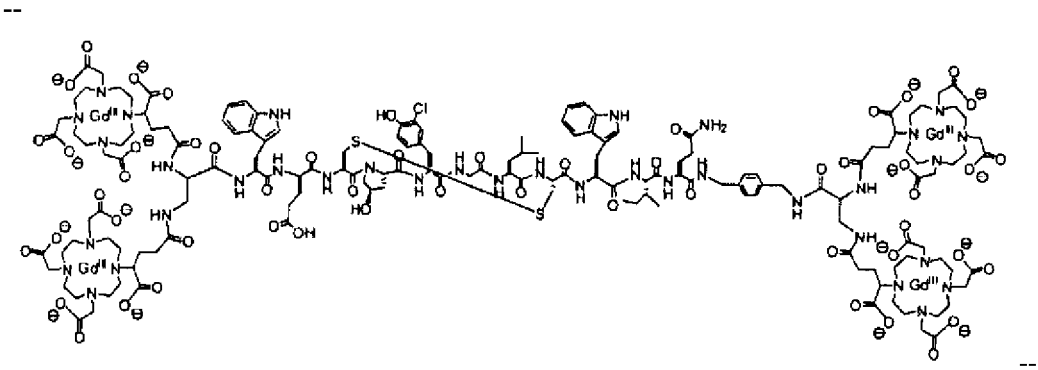

-- therefor;

UNITED STATES PATENT AND TRADEMARK OFFICE
CERTIFICATE OF CORRECTION

PATENT NO. : 7,412,279 B2
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 129-130, Claim 32, please delete the chemical figure shown after "Structure IV" and insert
--

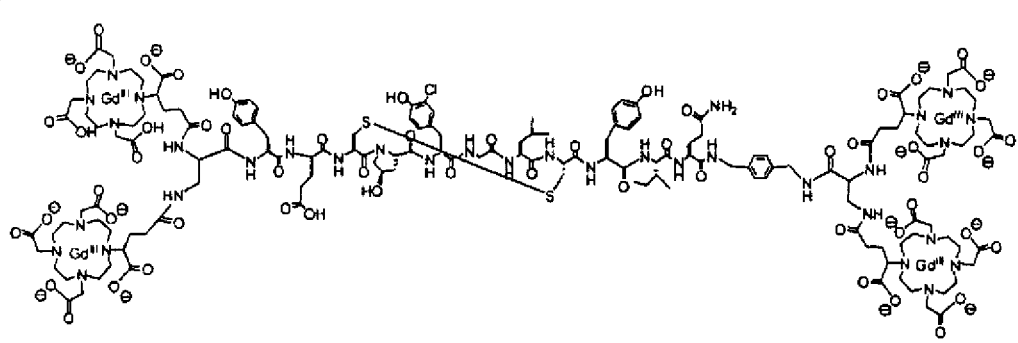

-- therefor;

Columns 131-132, Claim 1, please delete the chemical figure shown after "Structure V" and insert
--

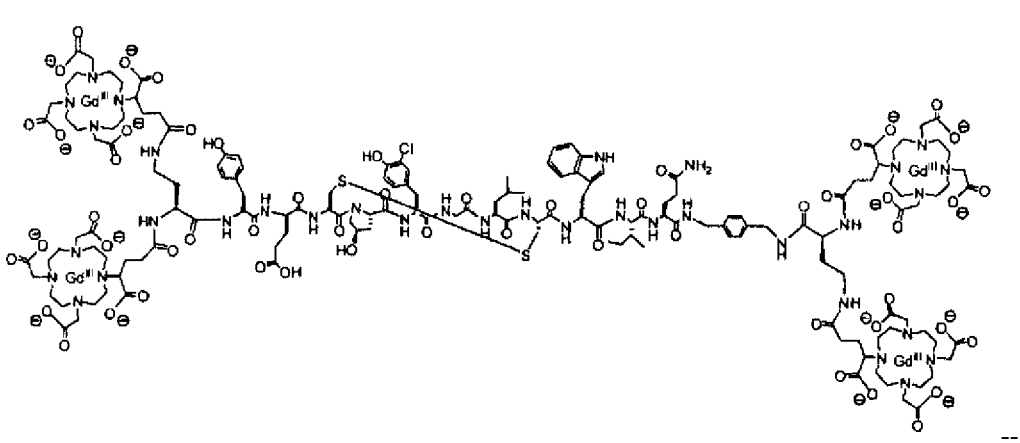

-- therefor;

UNITED STATES PATENT AND TRADEMARK OFFICE
CERTIFICATE OF CORRECTION

PATENT NO.         : 7,412,279 B2
APPLICATION NO.    : 10/209416
DATED              : August 12, 2008
INVENTOR(S)        : Robert M. Weisskoff It is certified that error appears in the above-identified patent and that said Letters Patent is hereby corrected as shown below:

Columns 133-134, Claim 32, please delete the chemical figure shown after "Structure VI" and insert
--
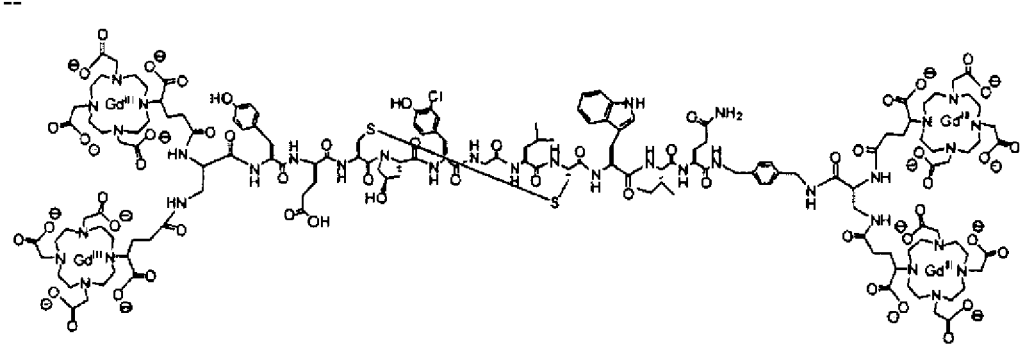
-- therefor;

Columns 135-136, Claim 32, please delete the chemical figure shown after "Structure VII" and insert
--
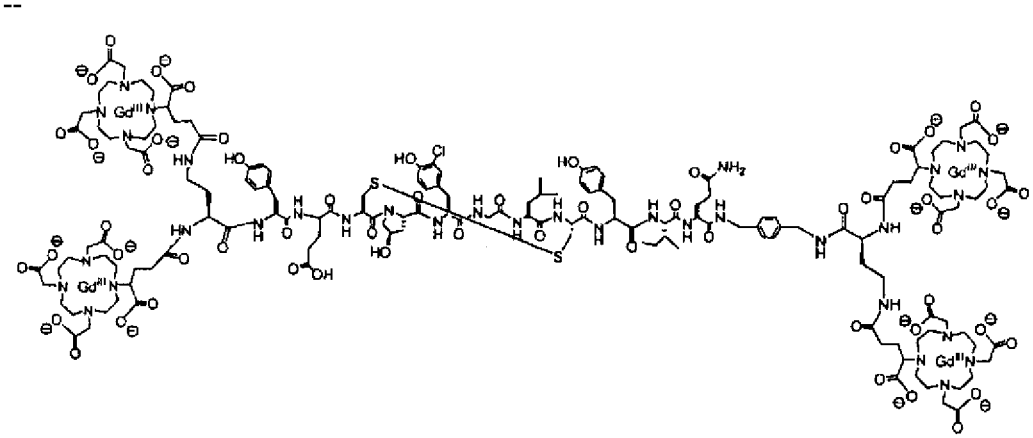
-- therefor;

UNITED STATES PATENT AND TRADEMARK OFFICE
CERTIFICATE OF CORRECTION

PATENT NO. : 7,412,279 B2
APPLICATION NO. : 10/209416
DATED : August 12, 2008
INVENTOR(S) : Robert M. Weisskoff It is certified that error appears in the above-identified patent and that said Letters Patent is hereby corrected as shown below:

Columns 137-138, Claim 32, please delete the chemical figure shown after "Structure VIII" and insert
--

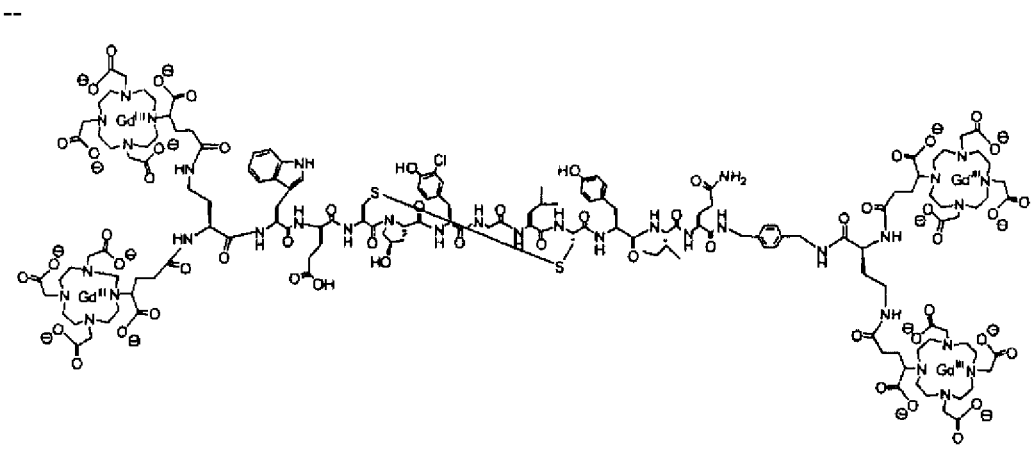

-- therefor;

Columns 139-140, Claim 32, please delete the chemical figure shown after "Structure IX" and insert
--

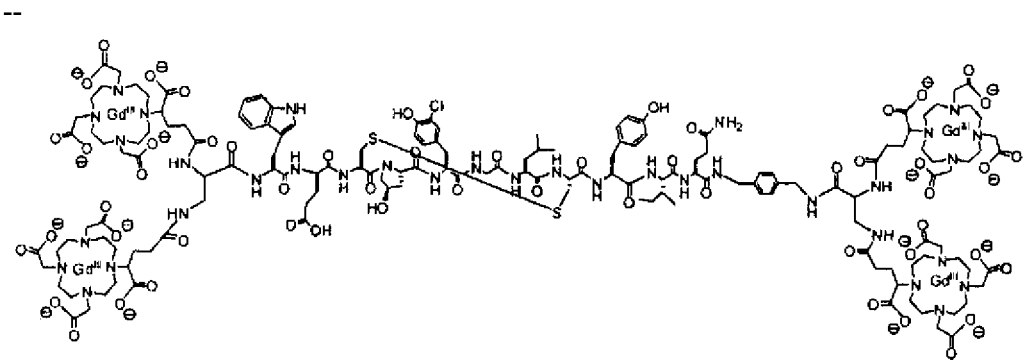

-- therefor;

UNITED STATES PATENT AND TRADEMARK OFFICE
CERTIFICATE OF CORRECTION

PATENT NO. : 7,412,279 B2
APPLICATION NO. : 10/209416
DATED : August 12, 2008
INVENTOR(S) : Robert M. Weisskoff It is certified that error appears in the above-identified patent and that said Letters Patent is hereby corrected as shown below:

Column 142, line 17 (Claim 51), please delete the chemical figure shown after "(Gd-DTPA-BMA)" and insert
--
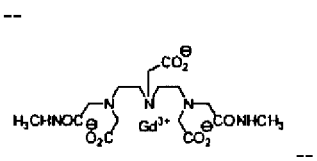
-- therefor;

Column 143, Claim 54, please delete the chemical figure shown after "(MS-325)" and insert
--
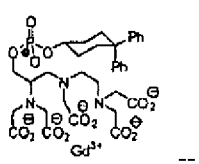
-- therefor.

Signed and Sealed this

Thirty-first Day of March, 2009

JOHN DOLL
*Acting Director of the United States Patent and Trademark Office*